US006887863B2

(12) United States Patent
Craig et al.

(10) Patent No.: US 6,887,863 B2
(45) Date of Patent: May 3, 2005

(54) HYDRAZIDE AND ALKOXYAMIDE ANGIOGENESIS INHIBITORS

(75) Inventors: Richard A. Craig, Racine, WI (US); Megumi Kawai, Libertyville, IL (US); Linda M. Lynch, Pleasant Prairie, WI (US); Jyoti R. Patel, Libertyville, IL (US); George S. Sheppard, Wilmette, IL (US); Jieyi Wang, Lake bluff, IL (US); Fan Yang, Highwood, IL (US); Nwe Ba-Maung, Niles, IL (US); Xenia Beebe Searle, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/782,502

(22) Filed: Feb. 19, 2004

(65) Prior Publication Data

US 2004/0167126 A1 Aug. 26, 2004

Related U.S. Application Data

(63) Continuation of application No. 09/833,917, filed on Apr. 12, 2001, now abandoned.
(60) Provisional application No. 60/197,262, filed on Apr. 14, 2000.

(51) Int. Cl.[7] ........................ A61K 31/33; A61K 31/16; A61K 31/20
(52) U.S. Cl. ........................ 514/183; 514/614; 514/615; 514/558
(58) Field of Search ................................ 514/183, 614, 514/615, 558

(56) References Cited

U.S. PATENT DOCUMENTS 5,977,408 A * 11/1999 Levin et al. ................ 562/622

FOREIGN PATENT DOCUMENTS

| DE | 9831710 | 1/2000 |
| EP | 266950 | 5/1988 |
| WO | 99/42436 | 8/1999 |
| WO | 99/57098 | 11/1999 |

OTHER PUBLICATIONS

Castro–Pichel, et al., "Synthesis & antiviral & cystatic activities," Nucleos. & Nucleit. 9(7):985–1000 (1990).

Griffith, E.C., "Methionine aminopeptidase (type 2) is the common target for angiogenesis inhibitors AGM–1470 and ovalicin," Chemistry and Biology 4(6):461–471 (1997).

Sin, Ny; "The anti–angiogenic agent fumagillin covalently binds and inhibits the methionine aminopeptidase, MetAP–2," Proc. National Academy of Science USA 94:6099–6103 (1997).

* cited by examiner

Primary Examiner—Richard L. Raymond
Assistant Examiner—Sudhaker B. Patel
(74) Attorney, Agent, or Firm—B. Gregory Donner

(57) ABSTRACT

Compounds having the formula

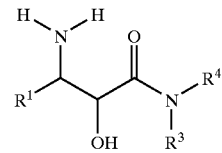

are methionine aminopeptidase type 2 (MetAP2) inhibitors and are useful for inhibiting angiogenesis. Also disclosed are MetAP2-inhibiting compositions and methods of inhibiting angiogenesis in a mammal.

40 Claims, No Drawings

HYDRAZIDE AND ALKOXYAMIDE ANGIOGENESIS INHIBITORS

CROSS-REFERENCE TO RELATED APPLICATIONS

This application is a continuation of U.S. patent application Ser. No. 09/833,917, filed Apr. 12, 2001 now abandoned, which claims priority to U.S. provisional patent application 60/197,262, filed Apr. 14, 2000.

TECHNICAL FIELD

The present invention relates to substituted hydrazides and N-alkoxyamides which are useful for preventing angiogenesis, methods of making the compounds, compositions containing the compounds, and methods of treatment using the compounds.

BACKGROUND OF THE INVENTION

Angiogenesis, the fundamental process by which new blood vessels are formed, is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions, these molecules appear to maintain the microvasculature in a quiescent state (i.e., one of no capillary growth) for prolonged periods which may last for as long as weeks or in some cases, decades. When necessary, however, (such as during wound repair), these same cells undergo rapid proliferation and turnover within a 5 day period. (*The Journal of Biological Chemistry*, 267: 10931–10934 (1987), *Science*, 235: 442–447 (1987)).

Although angiogenesis is a highly regulated process under normal conditions, many diseases (characterized as "angiogenic diseases") are driven by persistent unregulated angiogenesis. For example, ocular angiogenesis has been implicated as the most common cause of blindness and dominates approximately 20 eye diseases. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (*Cancer Research*, 46: 467–473 (1986), *Journal of the National Cancer Institute*, 82: 4–6 (1989)).

Because the pivotal role played by angiogenesis in tumor formation, metastasis, other disease conditions such as arthritis, inflammation, macular degeneration of age, and diabetic retinopathy, agents which inhibit angiogenesis have been the subject of active current research for their clinical potential.

In *Proc. Natl. Acad. Sci. USA*, 94: 6099–6103 (1997) and *Chemistry and Biology*, 4(6): 461–471 (1997) it is reported that both AGM-1470 and ovalicin, a sequiterpene isolated from the fungus *Pseudorotium ocalis* have been found to covalently inactivate a common bifunctional protein, type 2-methionine aminopeptidase (MetAP2) and is concluded that MetAP2 plays a critical role in the proliferation of endothelial cells and may serve as a promising target for the development of new anti-angiogenic drugs. The literature has thus established a casual link between inhibition of MetAP2 and the resultant inhibition of endothelial cell proliferation and angiogenesis. There is a need for discovery of new agents which inhibit MetAP2 for their potential as new drugs in combating angiogenesis and disease conditions which depend upon angiogenesis for their development.

SUMMARY OF THE INVENTION

In its principle embodiment, the present invention provides a compound of formula

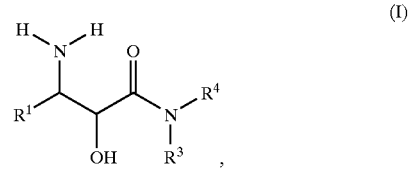

or a therapeutically acceptable salt or prodrug thereof, wherein $R^1$ is selected from the group consisting of alkyl, aryl, arylalkyl, cycloalkyl, (cycloalkyl)alkyl, (heterocycle)alkyl, and $R^5$S-(alkylene)-;

wherein each group is drawn with its right-hand end being the end that is attached to the parent molecular moiety;

$R^3$ is selected from the group consisting of hydrogen, alkyl, and arylalkyl;

$R^4$ is selected from the group consisting of —$NR^6R^7$, and —$OR^8$;

wherein each group is drawn with its left-hand end being the end that is attached to the parent molecular moiety;

$R^5$ is selected from the group consisting of alkyl, aryl, arylalkyl, cycloalkyl, and (cycloalkyl)alkyl;

$R^6$ and $R^7$ are independently selected from the group consisting of hydrogen, alkanoyl, alkenyl, alkenyloxyalkyl, alkoxyalkyl, alkoxycarbonylalkyl, alkyl, alkylsulfanylalkyl, aryl, arylalkanoyl, arylalkoxyalkyl, arylalkoxycarbonyl, arylalkyl, aryloxyalkyl, (aryl)oyl, arylsulfonyl, carboxyalkyl, cycloalkyl, (cycloalkyl)alkyl, (cycloalkyl)alkanoyl, (cycloalkyl)oyl, haloalkanoyl, haloalkyl, heterocycle, (heterocycle)alkanoyl, (heterocycle)oyl, hydroxyalkyl, a nitrogen protecting group, and —C(O)$NR^9R^{10}$; or $R^6$ and $R^7$ together are arylalkylidene; or $R^6$ and $R^7$, together with the nitrogen atom to which they are attached, form a heterocycle;

$R^8$ is selected from the group consisting of hydrogen, alkanoylalkyl, alkenyl, alkoxycarbonylalkyl, alkyl, amidoalkyl, aryl, arylalkyl, arylalkoxycarbonylalkyl, (aryl)oylalkyl, carboxyalkyl, and (cycloalkyl)alkyl; and $R^9$ and $R^{10}$ are independently selected from the group consisting of hydrogen, alkyl and aryl.

In another embodiment, the present invention provides a compound of formula (II)

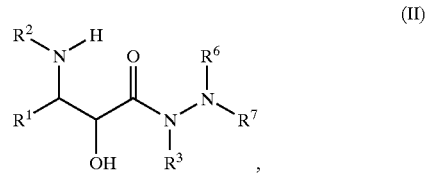

or a therapeutically acceptable salt or prodrug thereof, wherein $R^1$, $R^3$, $R^6$, and $R^7$ are as previously defined.

In a preferred embodiment, the present invention provides a compound of formula (II) wherein $R^1$ is $R^5$S-(alkylene)-, $R^3$ is hydrogen, one of $R^6$ and $R^7$ is hydrogen, and the other is (aryl)oyl.

In another embodiment, the present invention provides a compound of formula (III)

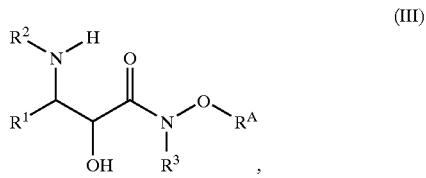

(III)

or a therapeutically acceptable salt or prodrug thereof, wherein $R^1$ and $R^3$ are as previously defined and $R^A$ is selected from the group consisting of aryl, alkyl, and arylalkyl.

In another embodiment, the present invention provides a pharmaceutical composition comprising a compound of formula (I) or a therapeutically acceptable salt or prodrug thereof, in combination with a therapeutically acceptable carrier.

In another embodiment, the present invention provides a method of inhibiting angiogenesis in a mammal in recognized need of such treatment comprising adminstering to the mammal a therapeutically acceptable amount of a compound of formula (I).

DETAILED DESCRIPTION OF THE INVENTION

Compounds of the present invention comprise hydrazines and hydroxylamines substituted with substituted 2-hydroxy-3-amino alkanoic acids.

Compounds of the present invention exist as stereoisomers, wherein asymmetric or chiral centers are present. These compounds are designated by the symbols "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers are designated (RS). Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Because carbon-carbon double bonds may exist in the present compounds, the invention contemplates various geometric isomers and mixtures thereof resulting from the arrangement of substituents around these carbon-carbon double bonds. These substituents are designated as being in the E or Z configuration wherein the term "E" represents higher order substituents on opposite sides of the carbon-carbon double bond, and the term "Z" represents higher order substituents on the same side of the carbon-carbon double bond.

When used throughout this specification and the appended claims, the following terms have the meanings indicated:

The term "alkanoyl" refers to an alkyl group attached to the parent molecular moiety through a carbonyl group. The alkanoyl groups of this invention can be unsubstituted or substituted with one, two, or three substituents independently selected from the group consisting of alkoxycarbonyl, alkylsulfanyl, amino, and hydroxy.

The term "alkanoylalkyl" refers to an alkanoyl group attached to the parent molecular moiety through an alkyl group.

The term "alkenyl" refers to a monovalent straight or branched chain groups having from two to fourteen carbon atoms containing at least one carbon-carbon double bond.

The term "alkenyloxy" refers to an alkenyl group attached to the parent molecular moiety through an oxygen atom.

The term "alkenyloxyalkyl" refers to an alkenyloxy group attached to the parent molecular moiety through an alkyl group.

The term "alkoxy" refers to an alkyl group attached to the parent molecular moiety through an oxygen atom.

The term "alkoxyalkyl" refers to an alkoxy group attached to the parent molecular moiety through an alkyl group.

The term "alkoxycarbonyl" refers to an alkoxy group attached to the parent molecular moiety through a carbonyl group.

The term "alkoxycarbonylalkyl" refers to an alkoxycarbonyl group attached to the parent molecular moiety through an alkyl group.

The term "alkyl" refers to a monovalent group derived from a straight or branched chain saturated hydrocarbon having from one to fourteen carbons by the removal of a single hydrogen atom.

The term "alkylene" refers to a saturated divalent hydrocarbon group derived from a straight or branched chain saturated hydrocarbon having from one to fourteen carbons by the removal of two hydrogen atoms.

The term "alkylsulfanyl" refers to an alkyl group attached to the parent molecular moiety through a sulfur atom.

The term "alkylsulfanylalkyl" refers to an alkylsulfanyl group attached to the parent molecular moiety through an alkyl group.

The term "alkylsulfonyl" refers to an alkyl group attached to the parent molecular moiety through a sulfonyl group.

The term "amido" refers to an amino group attached to the parent molecular moiety through a carbonyl group.

The term "amidoalkyl" refers to an amido group attached to the parent molecular moiety through an alkyl group.

The term "amino" refers to —$NR^aR^b$, wherein $R^a$ and $R^b$ are independently selected from the group consisting of hydrogen, unsubstituted alkanoyl, alkoxycarbonylalkyl, alkyl, aryl, arylalkyl, (aryl)oyl, cycloalkyl, and (cycloalkyl)alkyl. The aryl and the aryl part of the arylalkyl and the (aryl)oyl can be unsubstituted or substituted with one, two, three, four, or five substituents independently selected from the group consisting of alkoxy, alkoxycarbonyl, cyano, halo, haloalkoxy, haloalkyl, and nitro.

The term "aminoalkoxy" refers to an amino group attached to the parent molecular moiety through an alkoxy group.

The term "aminoalkyl" refers to an amino group attached to the parent molecular moiety through an alkyl group.

The term "aminosulfonyl" refers to an amino group attached to the parent molecular moiety through a sulfonyl group.

The term "aryl" refers to phenyl, naphthyl, dihydronaphthyl, tetrahydronaphthyl, indanyl, and indenyl. Aryl groups having an unsaturated or partially saturated ring fused to an aromatic ring can be attached through either the saturated or unsaturated part of the group. The aryl groups of this invention can be unsubstituted or substituted with one, two, three, four, or five substituents independently selected from the group consisting of alkanoyl, alkoxy, alkoxyalkyl, alkoxycarbonyl, alkyl, alkylsulfonyl, alkylsulfanyl, alkylsulfanylalkyl, amino, aminoalkoxy, aminoalkyl, aminosulfonyl, carboxy, cyano, (cycloalkyl)alkylsulfanyl, cycloalkylsulfanyl, halo, haloalkoxy, haloalkyl, haloalkylsulfanyl, (heterocycle)alkenyl, hydroxy, hydroxyalkoxy, nitro, oxo, and thioxo. The aryl groups of this invention can be further substituted with an additional aryl group or an arylalkyl, arylalkylsulfanyl, aryloxy, aryloxyalkyl, heterocycle, or (heterocycle)alkenyl group, wherein the aryl, the aryl part of the arylalkyl, the arylalkylsulfanyl, the aryloxy, and the aryloxyalkyl, the heterocycle, and the heterocycle part of the (heterocycle)alkenyl can be further substituted with one, two, three, four, or five substituents independently selected from the group consisting of alkanoyl, alkoxy, alkoxycarbonyl, alkyl, carboxy, cyano, haloalkoxy, haloalkyl, and nitro.

The term "arylalkanoyl" refers to an aryl group attached to the parent molecular moiety through an alkanoyl group.

The term "arylalkoxy" refers to an aryl group attached to the parent molecular moiety through an alkoxy group.

The term "arylalkoxyalkyl" refers to an arylalkoxy group attached to the parent molecular moiety through an alkyl group.

The term "arylalkoxycarbonyl" refers to an arylalkoxy group attached to the parent molecular moiety through a carbonyl group.

The term "arylalkoxycarbonylalkyl" refers to an arylalkoxycarbonyl group attached to the parent molecular moiety through an alkyl group.

The term "arylalkyl" refers to an aryl group attached to the parent group through an alkyl group. The alkyl part of the arylalkyl can be unsubstituted or substituted with a cyano group.

The term "arylalkylidene" refers to =CHR$^c$, wherein R$^c$ is aryl.

The term "arylalkylsulfanyl" refers to an arylalkyl group attached to the parent molecular moiety through a sulfur atom.

The term "aryloxy" refers to an aryl group attached to the parent molecular moiety through an oxygen atom.

The term "aryloxyalkyl" refers to an aryloxy group attached to the parent molecular moiety through an alkyl group. The alkyl part of the aryloxyalkyl can be unsubstituted or substituted with a hydroxy group.

The term "(aryl)oyl" refers to an aryl group attached to the parent molecular moiety through a carbonyl group.

The term "(aryl)oylalkyl" represnts an (aryl)oyl group attached to the parent molecular moiety through an alkyl group.

The term "arylsulfonyl" refers to an aryl group attached to the parent molecular moiety through a sulfonyl group.

The term "carbonyl" refers to —C(O)—.

The term "carboxy" refers to —CO$_2$H.

The term "carboxyalkyl" refers to a carboxy group attached to the parent molecular moiety through an alkyl group.

The term "cyano" refers to —CN.

The term "cycloalkyl" refers to a monovalent saturated cyclic hydrocarbon having from three to ten carbon atoms.

The term "cycloalkylalkanoyl" refers to a cycloalkyl group attached to the parent molecular moiety through an alkanoyl group.

The term "(cycloalkyl)alkyl" refers to a cycloalkyl group attached to the parent molecular moiety through an alkyl group.

The term "(cycloalkyl)alkylsulfanyl" refers to a (cycloalkyl)alkyl group attached to the parent molecular moiety through a sulfur atom.

The term "(cycloalkyl)oyl" refers to a cycloalkyl group attached to the parent molecular moiety through a carbonyl group.

The term "cycloalkylsulfanyl" refers to a cycloalkyl group attached to the parent molecular moiety through a sulfur atom.

The term "halo" or "halogen" refers to F, Cl, Br, or I.

The term "haloalkanoyl" refers to a haloalkyl group attached to the parent molecular moiety through a carbonyl group.

The term "haloalkoxy" refers to a haloalkyl group attached to the parent molecular moiety through an oxygen atom.

The term "haloalkyl" refers to an alkyl group substituted by one, two, three, or four halogen atoms.

The term "haloalkylsulfanyl" refers to a haloalkyl group attached to the parent molecular moiety through a sulfur atom.

The term "heterocycle" refers to a five-, six- or seven-membered ring containing one, two or three heteroatoms independently selected from the group consisting of nitrogen, oxygen and sulfur. The five-membered ring has zero to two double bonds and the six- and seven-membered rings have zero to three double bonds. The term "heterocycle" also includes bicyclic groups in which the heterocycle ring is fused to a phenyl group or a cycloalkyl group. The heterocycle groups of the present invention can be attached through a carbon atom or a nitrogen atom in the group. Examples of heterocycles include, but are not limited to, benzodioxolyl, benzothiazolyl, benzothienyl, chromenyl, dihydropyridazinyl, furyl, isoxazolyl, morpholinyl, piperazinyl, piperidinyl, pyrazinyl, pyrazolyl, pyridazinyl, pyridinyl, pyrimidinyl, pyrrolidinyl, pyrrolyl, quinolinyl, quinoxolinyl, tetrahydrobenzothienyl, tetrahydrofuryl, thiazolidinyl, thiazolyl, thienyl, and the like. The heterocycle groups of this invention can be unsubstituted or substituted with one, two, three, or four, substituents independently selected from the group consisting of alkanoyl, alkoxy, alkoxyalkyl, alkoxycarbonyl, alkyl, alkylsulfanylalkyl, amino, aminosulfonyl, carboxy, halo, haloalkoxy, haloalkyl, hydroxy, nitro, oxo, and thioxo. The heterocycle groups of this invention can be further substituted with an aryl, arylalkyl, aryloxy, aryloxycarbonyl, or (heterocycle)alkenyl group, wherein the aryl, the aryl portion of the aryloxy, the arylalkyl, and the aryloxycarbonyl, and the heterocycle portion of the (heterocycle)alkenyl can be further substituted with one, two, three, four, or five substituents independently selected from the group consisting of alkanoyl, alkoxy, alkoxycarbonyl, alkyl, carboxy, cyano, haloalkoxy, haloalkyl, and nitro.

The term "(heterocycle)alkanoyl" refers to a heterocycle group attached to the parent molecular moiety through an alkanoyl group.

The term "(heterocycle)alkenyl" refers to a heterocycle group attached to the parent molecular moiety through an alkenyl group.

The term "(heterocycle)alkyl" refers to a heterocycle group attached to the parent molecular moiety through an alkyl group.

The term "(heterocycle)oyl" refers to a heterocycle group attached to the parent molecular moiety through a carbonyl group.

The term "hydroxy" refers to —OH.

The term "hydroxyalkoxy" refers to a hydroxyalkyl group attached to the parent molecular moiety through an oxygen atom.

The term "hydroxyalkyl" refers to an alkyl group substituted with one, two, or three hydroxy groups.

The term "nitro" refers to —NO$_2$.

The term "nitrogen protecting group" refers to groups intended to protect an amino group against undersirable reactions during synthetic procedures. Common N-protecting groups comprise acyl groups such as formyl, acetyl, propionyl, pivaloyl, tert-butylacetyl, 2-chloroacetyl, 2-bromoacetyl, trifluoroacetyl, trichloroacetyl, phthalyl, ortho-nitrophenoxyacetyl, α-chlorobutyryl, benzoyl, 4-chlorobenzoyl, 4-bromobenzoyl, and 4-nitrobenzoyl; sulfonyl groups such as benzenesulfonyl, and para-toluenesulfonyl; carbamate forming groups such as benzyloxycarbonyl, para-chlorobenzyloxycarbonyl, p-methoxybenzyloxycarbonyl, tert-butyloxycarbonyl (Boc), benzyloxycarbonyl (Cbz), and the like.

The term "oxo" refers to (=O).

The term "sulfonyl" refers to —SO$_2$—.

The term "thioxo" refers to (=S).

The compounds of the present invention can exist as therapeutically acceptable salts. The term "therapeutically acceptable-salt," as used herein, represents salts or zwitterionic forms of the compounds of the instant invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formatin of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

In accordance with methods of treatment and pharmaceutical compositions of the invention, the compounds can be administered alone or in combination with other anti-angiogenesis agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally adminstered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The anti-angiogenesis effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefor.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

Assays for the inhibition of catalytic activities of MetAP2 were performed in 96-well microtiter plates. Compounds to be tested were dissolved in dimethyl-sulfoxide at 10 mM and diluted ten-fold in assay buffer (50 mM HEPES, pH 7.4, 100 mM NaCl). Ten microliters of solution of each compound to be tested for inhibition were introduced into each cell of the plate. Zero inhibition of enzyme activity was taken to be the result obtained in cells in which 10 mL of assay buffer was placed. A mixture totaling 90 mL per well and made up of of 84 mL of assay buffer containing 100 mM $MnCl_2$, 1 mL of L-amino acid oxidase (Sigma Catalog No. A-9378, ~11 mg/mL), 1 mL of horseradish peroxidase (Sigma Catalog No. P-845 1, dissolved in assay buffer at a concentration of 10 mg/mL), 1 mL of the tripeptide Met-Ala-Ser (Bachem) dissolved in assay buffer at concentration of 50 mM, 1 mL of ortho-dianisidine (Sigma Catalog No. D-1954, freshly made solution in water at a concentration of 10 mg/mL), and MetAP1 at final concentration of 6 mg/ml or MetAP2 at a final concentration of 1.5 mg/mL was rapidly mixed and added to each cell containing test or control compound. The absorbence at 450 nanometers was measured every 20 seconds over a period of twenty minutes using an automatic plate reader (Molecular Devices, CA, USA). The Vmax in mOD/min, calculated for each well, was used to represent MetAP1 or MetAP2 activity. The $IC_{50}$ for each inhibitor was obtained by plotting the remaining activity versus inhibitor concentrations. All of the compounds of the invention displayed $IC_{50}$'s below 15 $\mu$M. Preferred compounds of the invention displayed $IC_{50}$'s below 1 $\mu$M, and most preferred compounds displayed $IC_{50}$'s below 0.1 $\mu$M. Thus, the compounds are useful for treating diseases caused or exacerbated by angiogenesis.

Synthetic Methods

Abbreviations which have been used in the descriptions of the scheme and the examples that follow are: THF for tetrahydrofuran, PDC for pyridinium dichromate, DMSO for dimethylsulfoxide, DME for 1,2-dimethoxyethane, DCC for 1,3-diicyclohexylcarbodiimide, DIC for 1,3-diisopropylcarbodiimide, HOBT for 1-hydroxybenzotriazole, HOAT for 1-hydroxy-7-azabenzotriazole, EDCI for 1-(3-dimethylaminopropyl)-3-ethylcarbodiimide hydrochloride, PyBOP for benzotriazol-1-yloxytripyrrolidinophosphonium hexafluorophosphate, DBU for 1,8-diazabicyclo(5.4.0)undec-7-ene, NMM for N-methylmorpholine, DMA for N,N-dimethylacetamide, NMP for N-methylpyrrolidinone, BOC-ON for (2-(tert-butoxycarbonyloxyimino)-2-phenylacetonitrile, and DMF for N,N dimethylformaide.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups $R^1$, $R^3$, $R^4$, $R^5$, and $R^6$ are defined above. It will be readily apparent to one of ordinary skill in the art that the compounds defined above can be synthesized by substitution of the appropriate reactants and agents in the syntheses shown below.

Scheme 1

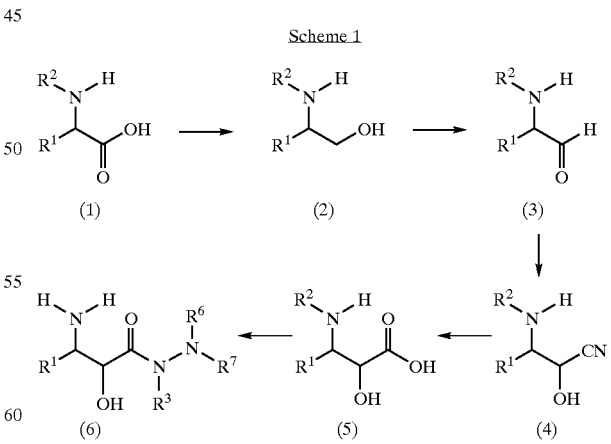

As shown in Scheme 1, compounds of formula (1) ($R^2$ is a nitrogen protecting group) can be converted to compounds of formula (2) by treatment with a reducing agent. Representative reducing agents include sodium borohydride, calcium borohydride, lithium borohydride, zinc borohydride, lithium aluminum hydride, borane, sodium cyanoborohydride, diisobutylaluminum hydride, and sodium bis(2-methoxyethoxy)aluminum hydride (Red-Al®). Examples of solvents used in these reactions include toluene, dichloromethane, ethanol, THF, dioxane, diethyl ether, or mixtures thereof. The reaction temperature is about −78° C. to 60° C. and depends on the method chosen. Reaction times are typically about 0.5 to 24 hours. Compounds of formula (2) can be converted to compounds of formula (3) by treatment with an oxidizing reagent. Representative oxidizing agents include Dess-Martin periodinane, PDC, $MnO_2$, DMSO/oxalyl chloride, and DMSO/$SO_3$-pyridine/triethylamine. Examples of solvents used in these reactions include DMSO, dichloromethane, chloroform, and THF. The reaction temperature is about −78° C. to 60° C. and depends on the method chosen. Reaction times are typically about 0.5 to 24 hours.

Conversion of compounds of formula (3) to compounds of formula (4) can be accomplished by the addition of sodium bisulfite, followed by the addition of sodium cyanide or potassium cyanide. Examples of solvents used in these reactions include water, ethyl acetate, and acetonitrile. The reaction temperature is about −10° C. to 60° C. and depends on the method chosen. Reaction times are typically about 2–36 hours. Compounds of formula (4) can be converted to compounds of formula (5) by hydrolysis with aqueous acid or by hydrolysis with aqueous base followed by acidification. Representative aqueous acids include HBr, HCl, HOAc, and $H_2SO_4$, and representative aqueous bases include NaOH, KOH, and $Ba(OH)_2$. Examples of solvents used in these reactions include dioxane, water, ethylene glycol, and DME. The reaction temperature is about 25° C. to 150° C. and depends on the method chosen. Reaction times are typically about 2–36 hours.

Conversion of compounds of formula (5) to compounds of formula (6) can be accomplished by coupling with substituted hydrazines ($HNR^3NR^6R^7$) in the presence of a carbonyl activating group such as DCC, DIC, HOBT, HOAT, EDCI, and PyBOP, and base. Representative bases include NMM, diisopropylethylamine, and DBU. Examples of solvents used in these reactions include dichloromethane, chloroform, DMA, THF, and NMP. The reaction temperature is about −10° C. to 60° C. and depends on the method chosen. Reaction times are typically about 2–72 hours.

A method for the preparation of compounds of formula (11) is shown in Scheme 2. Aldehydes of formula (7) can be reacted with compounds of formula (8) ($R^d$ is alkyl or arylalkyl) in the presence of a base and lithium bromide to provide compounds of formula (9). Examples of bases include triethylamine and diisopropylethylamine. Representative solvents include THF, diethyl ether, and methyl tert-butyl ether. The reaction is conducted at about 25 to about 30° C. for about 12 to about 24 hours.

Compounds of formula (9) can be treated with an appropriately substituted amine or amide in the presence of tert-butylhypochlorite and base, then treated with potassium osmate dihydrate and hydroquinidine 1,4-phathalazinediyl diether to provide compounds of formula (10) ($R^2$ is a nitrogen protecting group). Examples of bases include sodium hydroxide, potassium hydroxide, and lithium hydroxide. Representative solvents include water, 1-propanol, isopropanol, acetonitrile, and mixtures thereof. The reaction is typically conducted at about 0 to about 30° C. for about 30 minutes to about 4 hours.

Conversion of compounds of formula (10) to compounds of formula (5) can be accomplished by treatment with hydrogen peroxide in the presence of hydroxide such as lithium hydroxide. Examples of solvents include THF, water, and mixtures thereof. The reaction is conducted at about 0 to about 25° C. for about 1 to about 6 hours.

Compounds of formula (5) can be converted to compounds of formula (12) (Re is aryl, arylalkyl, cycloalkyl, (cycloalkyl)alkyl, heterocycle, or (heterocycle)alkyl) either by the methods desribed in Schemes 1 and 3, or by sequentially coupling the carboxylic acid with hydrazine and then coupling with an appropriately substituted carboxylic acid. Conditions for these couplings are similar to those described in Scheme 1 and are known to those of ordinary skill in the art.

Scheme 2

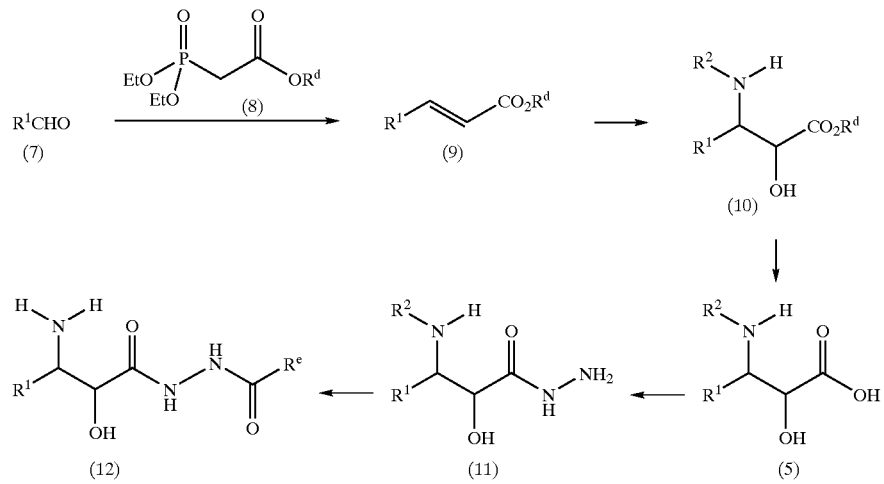

Scheme 3

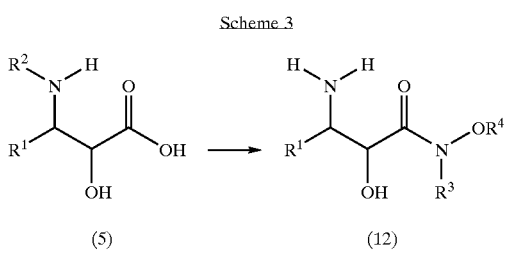

As shown in Scheme 3, compounds of formula (5) (made as described in Scheme 1) can be converted to compounds of formula (12) by coupling with substituted hydroxylamines (HNR$^3$OR$^4$) in the presence of a carbonyl activating group such as DCC, DIC, HOBT, HOAT, EDCI, and PyBOP, and base. Representative bases include NMM, diisopropylethylamine, and DBU. Examples of solvents used in these reactions include dichloromethane, chloroform, DMA, THF, and DMF. The reaction temperature is about −10° C. to 60° C. and depends on the method chosen. Reaction times are typically about 2–72 hours. In a preferred embodiment, compounds of formula (5) are treated with HOBT, NMM, EDCI, and a substituted hydroxylamine in dichloromethane/DMF at room temperature for 16 hours to provide compounds of formula (12).

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 4.01 (developed by Advanced Chemistry Development, Inc., Toronto, ON, Canada) or were given names which appeared to be consistent with ACD nomenclature.

EXAMPLE 1

(2RS,3R)-3-amino-N'-benzyl-4-cyclohexyl-2-hydroxybutanohydrazide

EXAMPLE 1A tert-butyl (1R)-2-cyclohexyl-1-(hydroxymethyl) ethylcarbamate

A solution of (2R)-2-((tert-butoxycarbonyl)amino)-3-cyclohexylpropanoic acid (30.4 g, 112 mmol) in toluene (300 mL) at 0° C. was treated with sodium bis(2-methoxyethoxy)aluminum hydride (Red-Al®) (115 mmol) over 45 minutes. The mixture was stirred for 30 minutes, warmed to room temperature, stirred for 1 hour, treated with aqueous Rochelle salt, and extracted with diethyl ether. The extract was washed with brine and aqueous NaHCO$_3$, dried (MgSO$_4$), filtered, and concentrated to provide the desired product.

EXAMPLE 1B tert-butyl (1R)-2-cyclohexyl-1-formylethylcarbamate

A solution of Example 1A (25.8 g,100 mmol), sulfur trioxide pyridine complex (79.6 g, 500 mmol), and triethylamine (69.7 mL, 500 mmol) in DMSO (70 mL) at room temperature was stirred for 30 minutes, cooled to 0° C., treated with water and saturated aqueous KHSO$_4$, and extracted with ethyl acetate. The extract was washed with saturated aqueous KHSO$_4$ and brine, dried (MgSO$_4$), filtered, and concentrated to provide the desired product.

EXAMPLE 1C (2RS,3R)-3-((tert-butoxycarbonyl)amino)-4-cyclohexyl-2-hydroxybutanoic acid A solution of Example 1B (19.7 g, 77.1 mmol) and sodium bisulfite (8.0 g, 77.1 mmol) in water (500 mL) at 5° C. was stirred for 24 hours, warmed to room temperature, treated with a solution of potassium cyanide (5.1 g, 78.8 mmol) in ethyl acetate (350 mL), and stirred for 5 hours. The aqueous phase was separated and extracted with ethyl acetate. The combined extracts were washed with water and brine, dried (MgSO$_4$), filtered, and concentrated to provide tert-butyl (1R)-2-cyano-1-(cyclohexylmethyl)-2-hydroxyethylcarbamate.

The concentrate was dissolved in dioxane (150 mL), treated with 12N HCl (150 mL), heated to reflux, stirred for 21 hours, and cooled to room temperature. The mixture was concentrated, dissolved in a mixture of water (30 mL) and acetone (200 mL), adjusted to pH 5.5 with 1N NaOH, treated with acetone (3.5 L), and cooled to 0° C. for 4 hours. The resulting precipitate was collected by filtration and dried to provide (3R)-3-amino-4-cyclohexyl-2-hydroxybutanoic acid.

A solution of the acid, BOC-ON (1.2 eq.), and triethylamine (2 eq.) in 1:1 water/dioxane at 45° C. was stirred for 15 hours, treated with 10% aqueous KHSO$_4$, and extracted with ethyl acetate. The extract was washed with water and brine, dried (MgSO$_4$), filtered, and concentrated to provide the desired product.

EXAMPLE 1D (2RS,3R)-3-amino-N'-benzyl-4-cyclohexyl-2-hydroxybutanohydrazide

A solution of Example 1C (50 mg, 0.17 mmol), 1-hydroxybenzotriazole hydrate (30 mg, 0.22 mmol), and N-methylmorpholine (0.07 mL, 0.63 mmol) in 5:1/dichloromethane:N,N-dimethylacetamide (2 mL) at 0° C. was treated with 1,3-diisopropylcarbodiimide (0.03 mL, 0.21 mmol), and stirred for 5 minutes. The solution was treated with 1-benzylhydrazine dihydrochloride (0.05 g, 0.25 mmol), stirred for 2 hours, and warmed to room temperature over 44 hours. The reaction was washed with 2N HCl and saturated NaHCO$_3$, and concentrated. The concentrate was purified by silica gel chromatography with 3:1/hexanes:ethyl acetate then 1:1/hexanes:ethyl acetate, then dissolved in 4N HCl in dioxane (1 mL), stirred for 1 hour, and concentrated, then purified by HPLC to provide the desired product.

MS (APCI) m/e 306 (M+H)$^+$; $^1$H NMR (300 MHz, CD$_3$OD) δ 7.43–7.26 (m, 5H), 4.13 (d, 1H), 4.01 (s, 2H), 3.53 (m, 1H), 3.39 (s, 1H), 1.80–1.67 (m, 5H), 1.57–1.51 (m, 1H), 1.46–1.17 (m, 5H), 1.00–0.90 (m, 1H).

EXAMPLE 2

(2RS,3R)-3-amino-N'-benzyl-4-cyclohexyl-2-hydroxybutanohydrazide

The desired product was prepared by substituting diphenylhydrazine for 1-benzylhydrazine dihydrochloride in Example 1.

MS (APCI) m/e 368 (M+H)⁺; ¹H NMR (300 MHz, CD₃OD) δ 7.32–7.26 (m, 4H), 7.16–7.13 (m, 4H), 7.06–7.01 (m, 2H), 4.26 (d, 1H), 3.52 (m, 1H), 1.72–1.12 (m, 13H).

EXAMPLE 3

(2RS,3R)-3-amino-N'-(7-chloro-4-quinolinyl)-4-cyclohexyl-2-hydroxybutanohydrazide The desired product was prepared by substituting 7-chloro-4-hydrazinoquinoline for 1-benzylhydrazine dihydrochloride in Example 1.

MS (APCI) m/e 377 (M+H)⁺; ¹H NMR (300 MHz, CD₃OD) δ 8.51 (d, 1H), 8.35 (d, 1H), 7.96 (d, 1H), 7.76 (dd, 1H), 6.96 (d, 1H), 4.47 (d, 1H), 3.70 (m, 1H), 1.86–0.98 (m, 13H).

EXAMPLE 4

(2RS,3R)-3-amino-4-cyclohexyl-2-hydroxy-N'-(2-phenylethyl)butanohydrazide

The desired product was prepared by substituting 1-(2-phenethyl)hydrazine for 1-benzylhydrazine dihydrochloride in Example 1.

MS (APCI) m/e 320 (M+H)⁺; ¹H NMR (300 MHz, CD₃OD) δ 7.30–7.21 (m, 5H), 4.16 (d, 1H), 3.59 (m, 1H), 3.09 (t, 2H), 2.82 (t, 2H), 1.81–0.91 (m, 13H).

EXAMPLE 5

(2RS,3R)-3-amino-4-cyclohexyl-2-hydroxy-N'-methyl-N'-phenylbutanohydrazide

The desired product was prepared by substituting 1-methyl-1-phenylhydrazine for 1-benzylhydrazine dihydrochloride in Example 1.

MS (APCI) m/e 306 (M+H)⁺; ¹H NMR (300 MHz, CD₃OD) δ 7.21–7.26 (m, 2H), 6.82–6.91 (m, 3H), 4.28 (d, 1H), 3.63 (m, 1H), 3.16 (s, 3H), 1.68–1.88 (m, 6H), 1.48–1.58 (m, 2H), 1.19–1.38 (m, 3H), 0.92–1.08 (m, 2H).

EXAMPLE 6

N'-((2RS,3R)-3-amino-4-cyclohexyl-2-hydroxybutanoyl)-1-naphthohydrazide

The desired product was prepared by substituting 1-naphthohydrazide for 1-benzylhydrazine dihydrochloride in Example 1.

MS (APCI) m/e 370 (M+H)⁺; ¹H NMR (300 MHz, CD₃OD) δ 8.37 (m, 1H), 8.05 (d, 1H), 7.95 (m, 1H), 7.77 (dd, 1H), 7.57 (m, 3H), 4.42 (d, 1H), 3.77 (m, 1H), 1.90–0.97 (m, 13H).

EXAMPLE 7

(2RS,3R)-3-amino-4-cyclohexyl-2-hydroxy-N'-(4-methylphenyl)butanohydrazide

The desired product was prepared by substituting 1-(4-methylphenyl)hydrazine for 1-benzylhydrazine dihydrochloride in Example 1.

MS (APCI) m/e 306 (M+H)⁺; ¹H NMR (300 MHz, CD₃OD) δ 7.01 (d, 2H), 6.76 (d, 2H), 4.27 (d, 1H), 3.61 (m, 1H), 2.23 (s, 3H), 1.85–1.64 (m, 6H), 1.54–1.42 (m, 2H), 1.36–1.15 (m, 3H), 1.06–0.89 (m, 2H).

EXAMPLE 8

2-((2RS,3R)-3-amino-4-cyclohexyl-2-hydroxybutanoyl)-N-(4-iodophenyl)hydrazinecarboxamide The desired product was prepared by substituting N-(4-iodophenyl)hydrazinecarboxamide for 1-benzylhydrazine dihydrochloride in Example 1.

MS (APCI) m/e 461 (M+H)⁺; ¹H NMR (300 MHz, CD₃OD) δ 7.59 (d, 2H), 7.23 (d, 2H), 4.33 (d, 1H), 3.68 (m, 1H), 1.85–1.65 (m, 6H), 1.59–1.19 (m, 5H), 1.09–0.93 (m, 2H).

EXAMPLE 9

N'-((2RS,3R)-3-amino-4-cyclohexyl-2-hydroxybutanoyl)-2,4,6-trimethylbenzenesulfonohydrazide The desired product was prepared by substituting 2,4,6-trimethylbenzenesulfonohydrazide for 1-benzylhydrazine dihydrochloride in Example 1.

MS (APCI) m/e 398 (M+H)⁺; ¹H NMR (300 MHz, CD₃OD) δ 7.01 (s, 2H), 4.01 (d, 1H), 3.36 (m, 1H), 2.67 (s, 6H), 2.29 (s, 3H), 1.78–1.65 (m, 4H), 1.47–1.20 (m, 7H), 1.00–0.78 (m, 2H).

EXAMPLE 10 ethyl (2-((2RS,3R)-3-amino-4-cyclohexyl-2-hydroxybutanoyl)hydrazino)acetate

The desired product was prepared by substituting ethyl hydrazinoacetate for 1-benzylhydrazine dihydrochloride in Example 1.

MS (APCI) m/e 302 (M+H)⁺; ¹H NMR (300 MHz, CD₃OD) δ 4.20 (q, 2H), 4.18 (d, 1H), 3.62 (d, 2H), 3.60 (m, 1H), 1.82–1.57 (m, 7H), 1.56–1.20 (m, 4H), 1.28 (t, 3H), 1.05–0.90 (m, 2H).

EXAMPLE 11

(2RS,3R)-3-amino-4-cyclohexyl-2-hydroxy-N'-(4-methoxyphenyl)butanohydrazide

The desired product was prepared by substituting 1-(4-methoxyphenyl)hydrazine for 1-benzylhydrazine dihydrochloride in Example 1.

MS (APCI) m/e 322 (M+H)⁺; ¹H NMR (300 MHz, CD₃OD) δ 6.82 (m, 4H), 4.27 (d, 1H), 3.72 (s, 3H), 3.61 (m, 1H), 1.85–1.62 (m, 6H), 1.55–1.18 (m, 5H), 1.08–0.90 (m, 2H).

EXAMPLE 12

(2RS,3R)-3-amino-4-cyclohexyl-2-hydroxy-N'-(1-naphthyl)butanohydrazide

The desired product was prepared by substituting 1-(1-naphthyl)hydrazine for 1-benzylhydrazine dihydrochloride in Example 1.

MS (APCI) m/e 342 (M+H)⁺; ¹H NMR (300 MHz, CD₃OD) δ 8.06 (m, 1H), 7.82 (m, 1H), 7.48 (m, 2H), 7.41–7.29 (m, 2H), 6.91 (dd, 1H), 4.38 (d, 1H), 3.68 (m, 1H), 1.89–1.66 (m, 6H), 1.60–1.47 (m, 2H), 1.19–1.31 (m, 3H), 1.09–0.92 (m, 2H).

EXAMPLE 13 benzyl 2-((2RS,3R)-3-amino-4-cyclohexyl-2-hydroxybutanoyl)hydrazinecarboxylate

EXAMPLE 13A benzyl 2-((2RS,3R)-3-((tert-butoxycarbonyl)amino)-4-cyclohexyl-2-hydroxybutanoyl)hydrazinecarboxylate A solution of Example 1C (1.10 g, 3.65 mmol) in dichloromethane at 0° C. was treated with dicyclohexylcarbodiimide (0.83 g, 4.02 mmol), stirred for 30 minutes, treated with benzyl carbazate (0.69 g, 4.02 mmol), warmed to room temperature, and stirred for 32 hours. The mixture was filtered, and concentrated, and the concentrate was purified by flash column chromatography on silica gel with ethyl acetate in hexanes to provide the desired product.

EXAMPLE 13B benzyl 2-((2RS,3R)-3-amino-4-cyclohexyl-2-hydroxybutanoyl)hydrazinecarboxylate EXAMPLE 13A (0.09 g, 0.2 mmol) was treated with 4N HCl in dioxane, stirred for 4 hours, concentrated, and precipitated from diethyl ether to provide the desired product.

MS (APCI) m/e 350 (M+H)$^+$; $^1$H NMR (300 MHz, DMSO-d$_6$) δ 10.23 (m, 1H), 10.08 (m, 1H), 9.32 (m, 1H), 7.85 (m, 2H), 7.38 (m, 5H), 6.51 (m, 1H), 5.18 (s, 1H), 5.10 (s, 1H), 4.07 (m, 1H), 3.69 (m, 1H), 3.49 (m 1H), 3.23 (m, 1H), 1.63 (m, 5H), 1.47 (m, 3H), 1.19 (m, 2H).

EXAMPLE 14

(2RS,3R)-3-amino-N'-((E)-(4-chlorophenyl)methylidene)-4-cyclohexyl-2-hydroxybutanohydrazide

EXAMPLE 14A tert-butyl (1R,2RS)-1-(cyclohexylmethyl)-3-hydrazino-2-hydroxy-3-oxopropylcarbamate A solution of Example 13A (0.37 g, 0.82 mmol) in methanol (15mL) was treated with Pd-carbon (0.05 g), stirred under a hydrogen atmosphere for 16 hours, filtered, and concentrated to provide the desired product.

EXAMPLE 14B (2RS,3R)-3-amino-N'-((E)-(4-chlorophenyl)methylidene)-4-cyclohexyl-2-hydroxybutanohydrazide A solution of Example 14A (0.064 g, 0.20 mmol) in ethanol (3 mL) was treated with pyridine (2 mL) and 4-chlorobenzaldehyde (0.033 mL, 0.23 mmol), heated to 85° C., stirred for 16 hours, and concentrated. The concentrate was purified by flash column chormatography on silica gel with ethyl acetate in hexanes, and the purified concntrate was treated with 4N HCl in dioxane, stirred for 4 hours, concentrated, precipitated from diethyl ether, and collected by filtration to provide the desired product.

MS (APCI) m/e 336 (M–H)$^-$; $^1$H NMR (300 MHz, DMSO-d$_6$) δ 11.60 (m, 1H), 8.42 (m, 1H), 7.83 (m, 2H), 7.71 (m, 2H), 7.53 (m, 2H), 6.61 (m, 1H), 4.18 (m, 1H), 4.12 (m, 1H), 3.70 (m, 1H), 1.66 (m, 5H), 1.43 (m, 3H), 1.19 (m, 2H).

EXAMPLE 15 ethyl 3-(2-((2RS,3R)-3-amino-4-cyclohexyl-2-hydroxybutanoyl)hydrazino)-3-oxopropanoate A solution of Example 14A (0.096 g, 0.30 mmol) in dichloromethane (8 mL) at 0° C. was treated with N-methylmorpholine (0.094 mL, 0.67 mmol) and ethyl-3-chloro-3-oxo propionate (0.049 mL, 0.38 mmol), stirred for 30 minutes, warmed to room temperature and stirred for 16 hours. The mixture was treated with dichloromethane, washed sequentially with 0.5M HCl, water, and brine, dried (MgSO$_4$), filtered, and concentrated. The concentrate was purified by flash column chromatography on silica gel with ethyl acetate in hexanes, and the purified concentrate was treated with 4N HCl in dioxane, stirred for 4 hours, concentrated, precipitated from diethyl ether, and collected by filtration to provide the desired product.

MS (APCI) m/e 330 (M+H)$^+$; $^1$H NMR (300 MHz, DMSO-d$_6$) δ 10.24 (m, 1H), 7.71 (m, 2H), 6.53 (m, 1H), 4.10 (m, 5H), 3.70 (m, 1H), 3.49 (m, 2H), 3.37 (m, 1H), 1.65 (m, 5H), 1.43 (m, 3H), 1.20 (m, 5H).

EXAMPLE 16 benzyl 2-((2RS,3S)-3-amino-4-((cyclohexylmethyl)sulfanyl)-2-hydroxybutanoyl)hydrazinecarboxylate

EXAMPLE 16A (2S)-2-((tert-butoxycarbonyl)amino)-3-((cyclohexylmethyl)sulfanyl)propanoic acid A solution of D-cysteine hydrochloride (4.78 g, 39.4 mmol) in liquid ammonia (250 mL) at –70° C. was slowly treated with sodium (3.78 g, 161 mmol), stirred for 30 minutes, treated with (bromomethyl)cyclohexane (6.33 mL, 45.4 mmol), warmed to room temperature, and stirred until the ammonia evaporated. The residue was treated with water (75 mL), isopropanol (50 mL) and di-tert-butyl dicarbonate (9.97 mL, 43.3 mmol), stirred for 24 hours, and concentrated. The concentrate was dissolved in water (150 mL), cooled to 0° C., adjusted to pH<7 with 3N HCl, and extracted with diethyl ether. The combined extracts were washed with brine, dried (MgSO$_4$), filtered, and concentrated to provide the desired product.

MS (APCI) m/e 318 (M+H)$^+$.

EXAMPLE 16B (2RS,3R) 3-(tert-butoxycarbonylamino)-2-hydroxy-4-(cyclohexylmethylthio)butanoic acid The desired product was prepared by substituting Example 16A for (2R)-2-((tert-butoxycarbonyl)amino)-3-cyclohexylpropanoic acid in Examples 1A–1C.

MS (APCI) m/e 346 (M+H)$^+$.

EXAMPLE 16C benzyl 2-((2RS,3S)-3-amino-4-((cyclohexylmethyl)sulfanyl)-2-hydroxybutanoyl)hydrazinecarboxylate The desired product was prepared by substituting Example 16B for Example 1C in Example 13.

MS (APCI) m/e 396 (M+H)$^+$; $^1$H NMR (300 MHz, DMSO-d$_6$) δ 9.32 (m, 1H), 7.97 (m, 2H), 7.38 (m, 5H), 6.63 (m, 1H), 5.10 (m, 2H), 4.23 (m, 1H), 3.69 (m, 3H), 2.43 (m, 2H), 1.83–1.58 (m, 6H), 1.18 (m, 5H).

EXAMPLE 17 benzyl 2-((2RS,3S)-3-amino-2-hydroxy-4-(propylsulfanyl)butanoyl)hydrazinecarboxylate

EXAMPLE 17A

N-(tert-butoxycarbonyl)-S-propyl-D-cysteine

The desired product was prepared by substituting 1-bromopropane for (bromomethyl)cyclohexane in Example 16.

MS (APCI) m/e 264 (M+H)$^+$.

EXAMPLE 17B (2RS,3R) 3-(tert-butoxycarbonylamino)-2-hydroxy-4-(propylthio)butanoic acid The desired product was prepared by substituting Example 17A for (2R)-2-((tert-butoxycarbonyl)amino)-3-cyclohexylpropanoic acid in Examples 1A–1C.

MS (APCI) m/e 294 (M+H)$^+$.

EXAMPLE 17C benzyl 2-((2RS,3S)-3-amino-2-hydroxy-4-(propylsulfanyl)butanoyl)hydrazinecarboxylate The desired product was prepared by substituting Example 17B for Example 1C in Example 13.

MS (APCI) m/e 342 (M+H)$^+$; $^1$H NMR (300 MHz, DMSO-d$_6$) δ 9.30 (m, 1H), 8.12 (m, 2H), 7.38 (m, 5H), 6.63 (m, 1H), 5.10 (m, 2H), 4.28 (m, 1H), 3.70 (m, 2H), 3.49 (m, 1H), 2.84 (m, 1H), 2.48 (m, 1H), 1.52 (m, 2H), 0.95 (m, 3H).

EXAMPLE 18

(2RS,3R)-3-amino-4-cyclohexyl-2-hydroxy-N'-(2,2,2-trifluoroethyl)butanohydrazide The desired product was prepared by substituting 1-(2,2,2-trifluoroethyl)hydrazine for 1-benzylhydrazine dihydrochloride in Example 1.

MS (APCI) m/e 298 (M+H)$^+$; $^1$H NMR (300 MHz, CD$_3$OD) δ 4.17 (d, 1H), 3.48 (t, 2H), 3.68 (m, 1H), 1.84–0.90 (m, 13H).

EXAMPLE 19

(2RS,3R)-3-amino-4-cyclohexyl-2-hydroxybutanohydrazide

The desired product was prepared by substituting tert-butyl hydrazinecarboxylate for 1-benzylhydrazine dihydrochloride in Example 1.

MS (APCI) m/e 216 (M+H)$^+$; $^1$H NMR (300 MHz, CD$_3$OD) δ 4.39 (d, 1H), 3.68 (m, 1H), 1.84–0.92 (m, 13H).

EXAMPLE 20

(2RS,3R)-3-amino-4-cyclohexyl-2-hydroxy-N'-methyl-N'-(3-nitro-2-pyridinyl)butanohydrazide The desired product was prepared by substituting 2-(1-methylhydrazino)-3-nitropyridine for 1-benzylhydrazine dihydrochloride in Example 1.

MS (APCI) m/e 352 (M+H)$^+$; $^1$H NMR (300 MHz, CD$_3$OD) δ 8.39 (dd, 1H), 8.01 (d, 1H), 6.99 (dd, 1H), 4.14 (d, 1H), 3.66 (s, 3H), 3.53 (m, 1H), 1.84–0.92 (m, 13H).

EXAMPLE 21

(2RS,3R)-3-amino-4-cyclohexyl-2-hydroxy-N-((2S)-2-(methoxymethyl)pyrrolidinyl)butanamide The desired product was prepared by substituting (2S)-2-(methoxymethyl)-1-pyrrolidinamine for 1-benzylhydrazine dihydrochloride in Example 1.

MS (APCI) m/e 314 (M+H)$^+$; $^1$H NMR (300 MHz, CD$_3$OD) δ 4.33 (d, 1H), 4.21 (m, 1H), 3.68 (m, 2H), 3.60–3.42 (m, 2H), 3.34 (m, 5H), 1.98 (m, 2H), 1.88–1.65 (m, 7H), 1.52 (t, 2H), 1.37–1.20 (m, 4H), 1.60–0.89 (m, 2H).

EXAMPLE 22

(2RS,3R)-3-amino-4-cyclohexyl-2-hydroxy-N-(1-pyrrolidinyl)butanamide

The desired product was prepared by substituting 1-pyrrolidinamine for 1-benzylhydrazine dihydrochloride in Example 1.

MS (APCI) m/e 270 (M+H)$^+$; $^1$H NMR (300 MHz, CD$_3$OD) δ 4.43 (d, 1H), 3.78–3.63 (m, 5H), 2.19 (m, 4H), 1.84–0.92 (m, 13H).

EXAMPLE 23

(2RS,3R)-3-amino-4-cyclohexyl-N'-(2,4-difluorophenyl)-2-hydroxybutanohydrazide

The desired product was prepared by substituting 1-(2,4-difluorophenyl)hydrazine for 1-benzylhydrazine dihydrochloride in Example 1.

MS (APCI) m/e 328 (M+H)$^+$; $^1$H NMR (300 MHz, CD$_3$OD) δ 6.98–6.88 (m, 2H), 6.81 (m, 1H), 4.30 (d, 1H), 3.60 (m, 1H), 1.83–1.65 (m, 6H), 1.55–1.41 (m, 2H), 1.38–1.20 (m, 3H), 1.08–0.92 (m, 2H).

EXAMPLE 24

(2RS,3R)-3-amino-N',4-dicyclohexyl-2-hydroxybutanohydrazide

The desired product was prepared by substituting 1-cyclohexylhydrazine for 1-benzylhydrazine dihydrochloride in Example 1.

MS (APCI) m/e 298 (M+H)$^+$; $^1$H NMR (300 MHz, CD$_3$OD) δ 4.42 (d, 1H), 3.79 (m, 1H), 3.67 (m, 1H), 2.14–2.05 (m, 2H), 1.95–1.86 (m, 2H), 1.81–1.68 (m, 6H), 1.55–1.25 (m, 1H), 1.08–0.92 (m, 2H).

EXAMPLE 25

4-(2-((2RS,3R)-3-amino-4-cyclohexyl-2-hydroxybutanoyl)hydrazino)benzenesulfonamide The desired product was prepared by substituting 4-hydrazinobenzenesulfonamide for 1-benzylhydrazine dihydrochloride in Example 1.

MS (APCI) m/e 371 (M+H)$^+$; $^1$H NMR (300 MHz, CD$_3$OD) δ 7.72 (d, 2H), 6.90 (d, 2H), 4.34 (d, 1H), 3.67 (m, 1H), 1.88–1.65 (m, 6H), 1.60–1.47 (m, 2H), 1.37–1.21 (m, 3H), 1.02–0.92 (m, 2H).

EXAMPLE 26

(2RS,3R)-3-amino-4-cyclohexyl-2-hydroxy-N'-phenylbutanohydrazide

The desired product was prepared by substituting 1-phenylhydrazine for 1-benzylhydrazine dihydrochloride in Example 1.

MS (APCI) m/e 292 (M+H)$^+$; $^1$H NMR (300 MHz, CD$_3$OD) δ 7.19 (m, 2H), 6.83 (m, 3H), 4.29 (d, 1H), 3.61 (m, 1H), 1.84–1.64 (m, 6H), 1.56–1.42 (m, 2H), 1.38–1.17 (m, 3H), 1.18–0.90 (m, 2H).

EXAMPLE 27

(2RS,3R)-3-amino-4-cyclohexyl-2-hydroxy-N'-(2-pyridinyl)butanohydrazide

The desired product was prepared by substituting 2-hydrazinopyridine for 1-benzylhydrazine dihydrochloride in Example 1.

MS (APCI) m/e 293 (M+H)$^+$; $^1$H NMR (300 MHz, CD$_3$OD) δ 8.01 (m, 1H), 7.78 (m, 1H), 6.93 (m, 2H), 4.39 (d, 1H), 3.68 (m, 1H), 1.85–0.98 (m, 13H).

EXAMPLE 28

N'-((2RS,3R)-3-amino-4-cyclohexyl-2-hydroxybutanoyl)-4-ethoxybenzohydrazide

The desired product was prepared by substituting 4-ethoxybenzohydrazide for 1-benzylhydrazine dihydrochloride in Example 1.

MS (APCI) m/e 364 (M+H)+; 1H NMR (300 MHz, CD3OD) δ 7.86 (d, 2H), 7.00 (d, 2H), 4.35 (d, 1H), 4.11 (q, 2H), 3.69 (m, 1H), 1.88–1.70 (m, 6H), 1.66–1.52 (m, 2H), 1.41 (t, 3H), 1.37–1.20 (m, 3H), 1.10–0.96 (m, 2H).

EXAMPLE 29

(2RS,3R)-3-amino-4-cyclohexyl-2-hydroxy-N-(4-oxo-2-thioxo-1,3-thiazolidin-3-yl)butanamide The desired product was prepared by substituting 3-amino-2-thioxo-1,3-thiazolidin-4-one for 1-benzylhydrazine dihydrochloride in Example 1.

MS (APCI) m/e 332 (M+H)+; 1H NMR (300 MHz, CD3OD) δ 4.38 (d, 1H), 4.25 (br s, 1H), 3.74 (m, 1H), 1.86–0.96 (m, 13H).

EXAMPLE 30

(2RS,3R)-3-amino-N'-(6-chloro-3-pyridazinyl)-4-cyclohexyl-2-hydroxy-N'-methylbutanohydrazide The desired product was prepared by substituting 3-chloro-6-(1-methylhydrazino)pyridazine for 1-benzylhydrazine dihydrochloride in Example 1.

MS (APCI) m/e 342 (M+H)+; 1H NMR (300 MHz, CD3OD) δ 7.57 (d, 1H), 7.33 (d, 1H), 4.40 (d, 1H), 3.64 (m, 1H), 3.40 (s, 3H), 1.86–1.67 (m, 6H), 1.64–1.16 (m, 5H), 1.08–0.92 (m, 2H).

EXAMPLE 31

(2RS,3R)-3-amino-N'-(5-chloro-1-methyl-6-oxo-1,6-dihydro-4-pyridazinyl)-4-cyclohexyl-2-hydroxy-N'-methylbutanohydrazide The desired product was prepared by substituting 4-chloro-2-methyl-5-(1-methylhydrazino)-3(2H)-pyridazinone for 1-benzylhydrazine dihydrochloride in Example 1.

MS (APCI) m/e 372 (M+H)+.

EXAMPLE 32

(2RS,3R)-3-amino-4-cyclohexyl-2-hydroxy-N-(1-piperidinyl)butanamide

The desired product was prepared by substituting 1-aminopiperidine for 1-benzylhydrazine dihydrochloride in Example 1.

MS (APCI) m/e 284 (M+H)+; 1H NMR (300 MHz, CD3OD) δ 4.47 (d, 1H), 3.75–3.58 (m, 2H), 3.54–3.40 (m, 3H), 1.86–1.50 (m, 13H), 1.47–1.37 (m, 1H), 1.37–1.16 (m, 3H), 1.06–0.89 (m, 2H).

EXAMPLE 33

N'-((2RS,3R)-3-amino-4-cyclohexyl-2-hydroxybutanoyl)-3,5-dimethoxybenzohydrazide The desired product was prepared by substituting 3,5-dimethoxybenzohydrazide for 1-benzylhydrazine dihydrochloride in Example 1.

MS (APCI) m/e 380 (M+H)+; 1H NMR (300 MHz, CD3OD) δ 7.03 (m, 2H), 6.70 (m, 1H), 4.36 (d, 1H), 3.81 (m, 6H), 3.68 (m, 1H), 1.87–1.68 (m, 6H), 1.63–1.41 (m, 2H), 1.38–1.19 (m, 3H), 1.10–0.93 (m, 2H).

EXAMPLE 34

N'-((2RS,3R)-3-amino-4-cyclohexyl-2-hydroxybutanoyl)-1,3-benzodioxole-5-carbohydrazide The desired product was prepared by substituting 1,3-benzodioxole-5-carbohydrazide for 1-benzylhydrazine dihydrochloride in Example 1.

MS (APCI) m/e 364 (M+H)+; 1H NMR (300 MHz, CD3OD) δ 7.50 (dd, 1H), 7.35 (d, 1H), 6.92 (d, 1H), 4.35 (d, 1H), 4.27 (d, 1H), 3.80 (s, 2H), 3.61 (m, 1H), 1.86–1.18 (m, 11H), 1.10–0.92 (m, 2H).

EXAMPLE 35

(2RS,3R)-3-amino-N'-(4-bromophenyl)-4-cyclohexyl-2-hydroxybutanohydrazide

The desired product was prepared by substituting 1-(4-bromophenyl)hydrazine for 1-benzylhydrazine in Example 1.

MS (APCI) m/e 371(M+H)+; 1H NMR (300 MHz, CD3OD) δ 7.30 (d. 2H), 6.77 (d, 2H), 4.29 (d, 1H), 3.62 (m, 1H), 1.86–1.64 (m, 6H), 1.56–1.16 (m, 5H), 1.07–0.98 (m, 2H).

EXAMPLE 36

(2RS,3R)-3-amino-5-ethylsulfanyl-2-hydroxy-N'-(4-methylphenyl)pentanohydrazide

The desired product was prepared by substituting (2R)-2-((tert-butoxycarbonyl)amino)-4-(ethylsulfanyl)butanoic acid and 1-(4-methylphenyl)hydrazine for (2R)-2-((tert-butoxycarbonyl)amino)-3-cyclohexylpropanoic acid and 1-benzylhydrazine dihydrochloride, respectively, in Example 1.

MS (ESI) m/e 298 (M+H)+; 1H NMR (300 MHz, DMSO-d6) δ 10.04 (bs, 1H), 7.87 (bs, 1H), 6.95 (d, 2H), 6.68 (d, 2H), 4.13 (t, 1H), 3.43 (m, 1H), 2.73–2.60 (m, 2H), 2.56 (q, 2H), 2.18 (s, 3H), 1.98–1.78 (m, 2H), 1.21 (t, 3H).

EXAMPLE 37

(2RS,3R)-3-amino-5-ethyl sulfanyl-2-hydroxy-N'-(4-methoxyphenyl)p entanohydrazide The desired product was prepared by substituting 1-(4-methoxyphenyl)hydrazine for 1-(4-methylphenyl)hydrazine in Example 36.

MS (ESI) m/e 314 (M+H)+; 1H NMR (300 MHz, DMSO-d6) δ 10.03 (bs, 1H), 7.86 (bs, 1H), 6.74 (m, 4H), 4.13 (m, 1H), 3.37 (s, 3H), 3.40 (m, 1H), 2.73–2.60 (m, 2H), 2.56 (q, 2H), 1.98–1.78 (m, 2H), 1.21 (t, 3H).

EXAMPLE 38

(2RS,3R)-3-amino-5-ethylsulfanyl-2-hydroxy-N'-(1-naphthyl)pentanohydrazide

The desired product was prepared by substituting 1-(1-naphthyl)hydrazine for 1-(4-methylphenyl)hydrazine in Example 36.

MS (ESI) m/e 334 (M+H)+; 1H NMR (300 MHz, DMSO-d6) δ 10.27 (bs, 1H), 8.21 (m, 1H), 7.92 (bs, 1H), 7.83 (m, 1H), 7.48 (m, 2H), 7.32 (m, 1H), 6.80–6.72 (m, 2H), 4.25 (t, 1H), 3.48 (m, 1H), 2.73–2.60 (m, 2H), 2.56 (q, 2H), 1.98–1.78 (m, 2H), 1.21 (t, 3H).

EXAMPLE 39 methyl 2-(2-((2RS,3R)-3-amino-4-cyclohexyl-2-hydroxybutanoyl)hydrazino)-4-(trifluoromethyl)-5-pyrimidinecarboxylate The desired product was prepared by substituting methyl 2-hydrazino-4-(trifluoromethyl)-5-pyrimidinecarboxylate for 1-benzylhydrazine dihydrochloride in Example 1.

MS (APCI) m/e 420 (M+H)+.

EXAMPLE 40

(2RS,3R)-3-amino-4-cyclohexyl-2-hydroxy-N'-(2-methylphenyl)butanohydrazide

The desired product was prepared by substituting 1-(2-methylphenyl)hydrazine for 1-benzylhydrazine dihydrochloride in Example 1.

MS (APCI) m/e 306 (M+H)$^+$; $^1$H NMR (300 MHz, CD$_3$OD) δ 7.10–7.02 (m, 2H), 6.85–6.73 (m, 2H), 4.32 (d, 1H), 3.75 (m, 1H), 2.25 (s, 3H), 1.88–1.65 (m, 6H), 1.58–1.46 (m, 2H), 1.38–1.18 (m, 3H), 1.09–0.92 (m, 2H).

EXAMPLE 41

(2RS,3R)-3-amino-N'-(2-chlorophenyl)-4-cyclohexyl-2-hydroxybutanohydrazide

The desired product was prepared by substituting 1-(2-chlorophenyl)hydrazine for 1-benzylhydrazine dihydrochloride in Example 1.

MS (APCI) m/e 326 (M+H)$^+$; $^1$H NMR (300 MHz, CD$_3$OD) δ 7.28 (dd, 1H), 7.18 (m, 1H), 7.93 (dd, 1H), 6.82 (m, 1H), 4.34 (d, 1H), 3.66 (m, 1H), 1.86–1.66 (m, 6H), 1.58–1.18 (m, 5H), 1.06–0.89 (m, 2H).

EXAMPLE 42

(2RS,3R)-3-amino-4-cyclohexyl-2-hydroxy-N'-(3-(trifluoromethyl)phenyl)butanohydrazide The desired product was prepared by substituting 1-(2-(trifluoromethyl)phenyl)hydrazine for 1-benzylhydrazine dihydrochloride in Example 1.

MS (APCI) m/e 360 (M+H)$^+$; $^1$H NMR (300 MHz, CD$_3$OD) δ 7.36 (m, 1H), 7.08 (m, 3H), 4.32 (d, 1H), 3.62 (m, 1H), 1.88–1.62 (m, 6H), 1.58–1.16 (m, 5H), 1.08–0.87 (m, 2H).

EXAMPLE 43

(2RS,3R)-3-amino-4-cyclohexyl-2-hydroxy-N'-(2-hydroxy-3-(3-(trifluoromethyl)phenoxy)propyl)-N'-methylbutanohydrazide The desired product was prepared by substituting 1-(1-methylhydrazino)-3-(3-(trifluoromethyl)phenoxy)-2-propanol for 1-benzylhydrazine dihydrochloride in Example 1.

MS (APCI) m/e 448 (M+H)$^+$; $^1$H NMR (300 MHz, CD$_3$OD) δ 7.49 (m, 1H), 7.28–7.18 (m, 3H), 4.40 (dd, 1H), 4.33 (m, 1H), 4.10 (m, 2H), 3.58 (m, 1H), 3.34 (d, 3H), 3.12 (d, 2H), 1.84–1.62 (m, 6H), 1.58–1.20 (m, 5H), 1.06–0.87 (m, 2H).

EXAMPLE 44 methyl 3-(2-((2RS,3R)-3-amino-4-cyclohexyl-2-hydroxybutanoyl)hydrazino)-2-thiophenecarboxylate The desired product was prepared by substituting methyl 3-hydrazino-2-thiophenecarboxylate for 1-benzylhydrazine dihydrochloride in Example 1.

MS (APCI) m/e 356 (M+H)$^+$; $^1$H NMR (300 MHz, CD$_3$OD) δ 7.52 (d, 1H), 6.78 (d, 1H), 4.32 (d, 1H), 3.83 (s, 3H), 3.68 (m, 1H), 1.86–1.62 (m, 6H), 1.55–1.12 (m, 5H), 1.05–0.91 (m, 2H).

EXAMPLE 45

(2RS,3R)-3-amino-4-cyclohexyl-2-hydroxy-N'-(2-pyridinylcarbonyl)butanohydrazide

The desired product was prepared by substituting 2-pyridinecarbohydrazide for 1-benzylhydrazine dihydrochloride in Example 1.

MS (APCI) m/e 321 (M+H)$^+$; $^1$H NMR (300 MHz, CD$_3$OD) δ 8.81 (m, 1H), 8.33 (m, 2H), 7.88 (m, 1H), 4.40 (d, 1H), 3.71 (m, 1H), 1.88–1.64 (m, 6H), 1.64–1.42 (m, 2H), 1.42–1.22 (m, 3H), 1.10–0.94 (m, 2H).

EXAMPLE 46

N'-((2RS,3R)-3-amino-4-cyclohexyl-2-hydroxybutanoyl)-2-chlorobenzohydrazide

The desired product was prepared by substituting 2-chlorobenzohydrazide for 1-benzylhydrazine dihydrochloride in Example 1.

MS (APCI) m/e 354 (M+H)$^+$; $^1$H NMR (300 MHz, CD$_3$OD) δ 7.62 (m, 1H), 7.50 (m, 2H), 7.42 (m, 1H), 4.37 (d, 1H), 3.72 (m, 1H), 1.86–1.63 (m, 6H), 1.63–1.40 (m, 2H), 1.40–1.16 (m, 3H), 1.10–0.92 (m, 2H).

EXAMPLE 47

N'-((2RS,3R)-3-amino-4-cyclohexyl-2-hydroxybutanoyl)-3-bromobenzohydrazide

The desired product was prepared by substituting 3-bromobenzohydrazide for 1-benzylhydrazine dihydrochloride in Example 1.

MS (APCI) m/e 399 (M+H)$^+$; $^1$H NMR (300 MHz, CD$_3$OD) δ 8.06 (t, 1H), 7.87 (m, 1H), 7.78 (m, 1H), 7.45 (t, 1H), 4.38 (d, 1H), 3.69 (m, 1H), 1.88–1.66 (m, 6H), 1.62–1.42 (m, 2H), 1.38–1.18 (m, 3H), 1.10–0.95 (m, 2H).

EXAMPLE 48

N'-((2RS,3R)-3-amino-4-cyclohexyl-2-hydroxybutanoyl)-3-methoxybenzohydrazide

The desired product was prepared by substituting 3-methoxybenzohydrazide for 1-benzylhydrazine dihydrochloride in Example 1.

MS (APCI) m/e 350 (M+H)$^+$; $^1$H NMR (300 MHz, CD$_3$OD) δ 7.48 (d, 1H), 7.42 (q, 2H), 7.17 (d, 1H), 4.37 (d, 1H), 3.86 (s, 3H), 3.70 (m, 1H), 1.88–1.67 (m, 6H), 1.63–1.40 (m, 2H), 1.40–1.18 (m, 3H), 1.10–0.95 (m, 2H).

EXAMPLE 49

N'-((2RS,3R)-3-amino-4-cyclohexyl-2-hydroxybutanoyl)-2,5-dichlorobenzohydrazide

The desired product was prepared by substituting 2,5-dichlorobenzohydrazide for 1-benzylhydrazine dihydrochloride in Example 1.

MS (APCI) m/e 389 (M+H)$^+$; $^1$H NMR (300 MHz, CD$_3$OD) δ 7.67 (m, 1H), 7.52 (d, 2H), 4.36 (d, 1H), 3.68 (m, 1H), 1.87–1.67 (m, 6H), 1.62–1.50 (m, 1H), 1.50–1.40 (m, 1H), 1.40–1.20 (m, 3H), 1.10–0.95 (m, 2H).

EXAMPLE 50

N'-((2RS,3R)-3-amino-4-cyclohexyl-2-hydroxybutanoyl)-2-methoxybenzohydrazide

The desired product was prepared by substituting 2-methoxybenzohydrazide for 1-benzylhydrazine dihydrochloride in Example 1.

MS (APCI) m/e 350 (M+H)$^+$; $^1$H NMR (300 MHz, CD$_3$OD) δ 7.99 (dd, 1H), 7.57 (dt, 1H), 7.20 (d, 1H), 7.10 (t, 1H), 4.38 (d, 1H), 4.01 (s, 3H), 3.71 (m, 1H), 1.88–1.68 (m, 6H), 1.62–1.50 (m, 1H), 1.50–1.40 (m, 1H), 1.38–1.17 (m, 3H), 1.10–0.96 (m, 2H).

EXAMPLE 51

N'-((2RS,3R)-3-amino-4-cyclohexyl-2-hydroxybutanoyl)-3-chlorobenzohydrazide

The desired product was prepared by substituting 3-chlorobenzohydrazide for 1-benzylhydrazine dihydrochloride in Example 1.

MS (APCI) m/e 354 (M+H)$^+$; $^1$H NMR (300 MHz, CD$_3$OD) δ 7.91 (m, 1H), 7.82 (m, 1H), 7.62 (m, 1H), 7.51 (t, 1H), 4.38 (d, 1H), 3.69 (m, 1H), 1.88–1.68 (m, 6H), 1.62–1.52 (m, 1H), 1.52–1.40 (m, 1H), 1.38–1.20 (m, 3H), 1.10–0.94 (m, 2H).

EXAMPLE 52

N'-((2RS,3R)-3-amino-4-cyclohexyl-2-hydroxybutanoyl)-3-methylbenzohydrazide

The desired product was prepared by substituting 3-methylbenzohydrazide for 1-benzylhydrazide dihydrochloride in Example 1.

MS (APCI) m/e 334 (M+H)$^+$; $^1$H NMR (300 MHz, CD$_3$OD) δ 7.75–7.66 (m, 2H), 7.48–7.34 (m, 2H), 4.37 (d, 1H), 3.69 (m, 1H), 2.41 (s, 3H), 1.88–1.67 (m, 6H), 1.62–1.50 (m, 1H), 1.50–1.40 (m, 1H), 1.40–1.18 (m, 3H), 1.10–0.94 (m, 2H).

EXAMPLE 53

N'-((2RS,3R)-3-amino-4-cyclohexyl-2-hydroxybutanoyl)-2,4-dihydroxybenzohydrazide The desired product was prepared by substituting 2,4-dihydroxybenzohydrazide for 1-benzylhydrazine dihydrochloride in Example 1.

MS (APCI) m/e 352 (M+H)$^+$; $^1$H NMR (300 MHz, CD$_3$OD) δ 7.72 (d, 1H), 6.38 (dt, 2H), 4.37 (d, 1H), 3.67 (m, 1H), 1.87–1.65 (m, 6H), 1.62–1.52 (m, 1H), 1.52–1.49 (m, 1H), 1.39–1.18 (m, 3H), 1.10–0.97 (m, 2H).

EXAMPLE 54 ethyl 3-(2-((2RS,3R)-3-amino-4-cyclohexyl-2-hydroxybutanoyl)hydrazino)-6,6-dimethyl-4-oxo-4,5,6,7-tetrahydro-2-benzothiophene-1-carboxylate The desired product was prepared by substituting ethyl 3-hydrazino-6,6-dimethyl-4-oxo-4,5,6,7-tetrahydro-2-benzothiophene-1-carboxylate for 1-benzylhydrazine dihydrochloride in Example 1.

MS (APCI) m/e 466 (M+H)$^+$; $^1$H NMR (300 MHz, CD$_3$OD) δ 4.38 (d, 1H), 4.28 (q, 2H), 3.67 (m, 1H), 2.54 (d, 2H), 2.39 (s, 2H), 1.90–1.71 (m, 6H), 1.71–1.43 (m, 2H), 1.40–1.16 (m, 6H), 1.08 (s, 3H), (s, 3H), 1.10–0.94 (m, 2H).

EXAMPLE 55

(2RS,3R)-3-amino-4-cyclohexyl-2-hydroxy-N'-(4-iodophenyl)butanohydrazide

The desired product was prepared by substituting 1-(4-iodophenyl)hydrazine for 1-benzylhydrazine dihydrochloride in Example 1.

MS (APCI) m/e 418 (M+H)$^+$; $^1$H NMR (300 MHz, CD$_3$OD) δ 7.47 (d, 2H), 6.66 (d, 2H), 4.28 (d, 1H), 3.62 (m, 1H), 1.85–1.62 (m, 6H), 1.55–1.42 (m, 2H), 1.37–1.17 (m, 3H), 1.08–0.88 (m, 2H).

EXAMPLE 56

(2RS,3R)-3-amino-N'-(1,3-benzothiazol-2-yl)-4-cyclohexyl-2-hydroxybutanohydrazide The desired product was prepared by substituting 2-hydrazino-1,3-benzothiazole for 1-benzylhydrazine dihydrochloride in Example 1.

MS (APCI) m/e 349 (M+H)$^+$; $^1$H NMR (300 MHz, CD$_3$OD) δ 7.76 (dd, 1H), 7.51 (m, 2H), 7.33 (m, 1H), 3.87 (d, 1H), 3.78 (m, 1H), 1.82–1.60 (m, 6H), 1.48–1.16 (m, 5H), 1.16–0.91 (m, 2H).

EXAMPLE 57

N'-((2RS,3R)-3-amino-4-cyclohexyl-2-hydroxybutanoyl)-2,5-dimethoxybenzohydrazide The desired product was prepared by substituting 2,5-dimethoxybenzohydrazide for 1-benzylhydrazine dihydrochloride in Example 1.

MS (APCI) m/e 380 (M+H)$^+$; $^1$H NMR (300 MHz, CD$_3$OD) δ 7.54 (m, 1H), 7.14 (m, 2H), 4.38 (d, 1H), 3.96 (s, 3H), 3.79 (s, 3H), 3.71 (m, 1H), 1.88–1.67 (m, 6H), 1.62–1.50 (m, 1H), 1.50–1.40 (m, 1H), 1.38–1.18 (m, 3H), 1.10–0.93 (m, 2H).

EXAMPLE 58

(2RS,3R)-3-amino-N'-(3-chlorophenyl)-4-cyclohexyl-2-hydroxybutanohydrazide

The desired product was prepared by substituting 1-(3-chlorophenyl)hydrazine for 1-benzylhydrazine dihydrochloride in Example 1.

MS (APCI) m/e 326 (M+H)$^+$; $^1$H NMR (300 MHz, CD$_3$OD) δ 7.15 (t, 1H), 6.84–6.73 (m, 2H), 4.30 (d, 1H), 3.62 (m, 1H), 1.88–1.64 (m, 6H), 1.58–1.42 (m, 2H), 1.37–1.17 (m, 3H), 1.08–0.87 (m, 2H).

EXAMPLE 59

(2RS,3R)-3-amino-4-cyclohexyl-2-hydroxy-N'-(3-methoxyphenyl)butanohydrazide

The desired product was prepared by substituting 1-(3-methoxyphenyl)hydrazine for 1-benzylhydrazine dihydrochloride in Example 1.

MS (APCI) m/e 322 (M+H)$^+$; $^1$H NMR (300 MHz, CD$_3$OD) δ 7.12–7.05 (m, 1H), 6.46–6.39 (m, 2H), 4.27 (d, 1H), 3.73 (s, 3H), 3.61 (m, 1H), 1.84–1.63 (m, 6H), 1.56–1.40 (m, 2H), 1.40–1.25 (m, 3H), 1.08–0.96 (m, 2H).

EXAMPLE 60

(2RS,3R)-3-amino-4-cyclohexyl-N'-(3,5-dichlorophenyl)-2-hydroxybutanohydrazide

The desired product was prepared by substituting 1-(3,5-dichlorophenyl)hydrazine for 1-benzylhydrazine dihydrochloride in Example 1.

MS (APCI) m/e 361 (M+H)$^+$; $^1$H NMR (300 MHz, CD$_3$OD) δ 6.82 (m, 1H), 6.77 (m, 2H), 4.30 (d, 1H), 3.61 (m, 1H), 1.88–1.63 (m, 6H), 1.57–1.43 (m, 2H), 1.28–1.17 (m, 3H), 1.09–0.98 (m, 2H).

EXAMPLE 61

(2RS,3R)-3-amino-N'-(3-bromophenyl)-4-cyclohexyl-2-hydroxybutanohydrazide

The desired product was prepared by substituting 1-(3-bromophenyl)hydrazine for 1-benzylhydrazine dihydrochloride in Example 1.

MS (APCI) m/e 371 (M+H)$^+$; $^1$H NMR (300 MHz, CD$_3$OD) δ 7.09 (t, 1H), 7.00–6.91 (m, 2H), 6.81 (m, 1H), 4.29 (d, 1H), 3.62 (m, 1H), 1.87–1.63 (m, 6H), 1.56–1.43 (m, 2H), 1.37–1.18 (m, 3H), 1.09–0.90 (m, 2H),

EXAMPLE 62

(2RS,3R)-3-amino-4-cyclohexyl-2-hydroxy-N'-(trifluoroacetyl)butanohydrazide

The desired product was prepared by substituting 2,2,2-trifluoroacetohydrazide for 1-benzylhydrazine dihydrochloride in Example 1.

MS (APCI) m/e 312 (M+H)$^+$; $^1$H NMR (300 MHz, CD$_3$OD) δ 4.36 (d, 1H), 3.68 (m, 1H), 1.85–1.67 (m, 6H), 1.59–1.18 (m, 5H), 1.08–0.93 (m, 2H).

EXAMPLE 63

(2RS,3R)-3-amino-4-cyclohexyl-2-hydroxy-N'-(4-isopropylphenyl)butanohydrazide

The desired product was prepared by substituting 1-(4-isopropylphenyl)hydrazine for 1-benzylhydrazine dihydrochloride in Example 1.

MS (APCI) m/e 334 (M+H)$^+$; $^1$H NMR (300 MHz, CD$_3$OD) δ 7.12 (d, 2H), 6.78 (d, 2H), 4.29 (d, 1H), 3.61 (m, 1H), 2.83 (m, 1H), 1.82–0.95 (m, 19H).

EXAMPLE 64

(2RS,3R)-3-amino-N'-(3-chloro-4-methylphenyl)-4-cyclohexyl-2-hydroxybutanohydrazide The desired product was prepared by substituting 1-(3-chloro-4-methylphenyl)hydrazine for 1-benzylhydrazine dihydrochloride in Example 1.

MS (APCI) m/e 340 (M+H)$^+$; $^1$H NMR (300 MHz, CD$_3$OD) δ 7.91 (d, 1H), 7.85 (s, 1H), 6.73 (d, 1H), 4.28 (d, 1H), 3.62 (m, 1H), 2.25 (s, 3H), 1.83–1.00 (m, 13H).

EXAMPLE 65

(2RS,3R)-3-amino-4-cyclohexyl-2-hydroxy-N'-(4-(trifluoromethoxy)phenyl)butanohydrazide The desired product was prepared by substituting 1-(4-(trifluoromethoxy)phenyl)hydrazine for 1-benzylhydrazine dihydrochloride in Example 1.

MS (APCI) m/e 376 (M+H)$^+$; $^1$H NMR (300 MHz, CD$_3$OD) δ 7.11 (d, 2H), 6.93 (m, 2H), 4.28 (d, 1H), 3.62 (m, 1H), 1.80–1.02 (m, 13H).

EXAMPLE 66

(2RS,3R)-3-amino-4-cyclohexyl-N'-(4-fluorophenyl)-2-hydroxybutanohydrazide

The desired product was prepared by substituting 1-(4-fluorophenyl)hydrazine for 1-benzylhydrazine dihydrochloride in Example 1.

MS (APCI) m/e 310 (M+H)$^+$; $^1$H NMR (300 MHz, CD$_3$OD) δ 6.94 (m, 4H), 4.31 (d, 1H), 3.58 (m, 1H), 1.83–0.97 (m, 13H).

EXAMPLE 67

(2RS,3R)-3-amino-N'-(4-chlorophenyl)-4-cyclohexyl-2-hydroxybutanohydrazide

The desired product was prepared by substituting 1-(4-chlorophenyl)hydrazine for 1-benzylhydrazine dihydrochloride in Example 1.

MS (APCI) m/e 326 (M+H)$^+$; $^1$H NMR (300 MHz, CD$_3$OD) δ 7.20 (d, 2H), 6.83 (d, 2H), 4.29 (d, 1H), 3.61 (m, 1H), 1.80–1.00 (m, 13H).

EXAMPLE 68

(2RS,3R)-3-amino-4-cyclohexyl-N'-(2-ethylphenyl)-2-hydroxybutanohydrazide

The desired product was prepared by substituting 1-(2-ethylphenyl)hydrazine for 1-benzylhydrazine dihydrochloride in Example 1.

MS (APCI) m/e 320 (M+H)$^+$; $^1$H NMR (300 MHz, CD$_3$OD) δ 7.10 (m, 2H), 6.82 (m, 2H), 4.31 (d, 1H), 3.58 (m, 1H), 2.61 (q, 2H), 1.80–1.00 (m, 16H).

EXAMPLE 69

(2RS,3R)-3-amino-4-cyclohexyl-N'-(3-fluorophenyl)-2-hydroxybutanohydrazide

The desired product was prepared by substituting 1-(3-fluorophenyl)hydrazine for 1-benzylhydrazine dihydrochloride in Example 1.

MS (APCI) m/e 310 (M+H)$^+$; $^1$H NMR (300 MHz, CD$_3$OD) δ 7.17 (m, 1H), 6.62 (m, 3H), 4.30 (d, 1H), 3.61 (m, 1H), 2.63 (q, 2H), 1.80–1.00 (m, 13H).

EXAMPLE 70

N'-((2RS,3R)-3-amino-4-cyclohexyl-2-hydroxybutanoyl)-3-chloro-1-benzothiophene-2-carbohydrazide The desired product was prepared by substituting 3-chloro-1-benzothiophene-2-carbohydrazide for 1-benzylhydrazine dihydrochloride in Example 1.

MS (APCI) m/e 410 (M+H)$^+$; $^1$H NMR (300 MHz, CD$_3$OD) δ 8.01 (d, 2H), 7.60 (d, 2H), 4.38 (d, 1H), 3.71 (m, 1H), 1.80–1.00 (m, 13H).

EXAMPLE 71

N'-((2RS,3R)-3-amino-4-cyclohexyl-2-hydroxybutanoyl)-4-methylbenzohydrazide

The desired product was prepared by substituting 4-methylbenzohydrazide for 1-benzylhydrazine dihydrochloride in Example 1.

MS (APCI) m/e 334 (M+H)$^+$; $^1$H NMR (300 MHz, CD$_3$OD) δ 7.80 (d, 2H), 7.32 (d, 2H), 4.39 (d, 1H), 3.70 (m, 1H), 1.80–1.00 (m, 13H).

EXAMPLE 72

N'-((2RS,3R)-3-amino-4-cyclohexyl-2-hydroxybutanoyl)-4-nitrobenzohydrazide

The desired product was prepared by substituting 4-nitrobenzohydrazide for 1-benzylhydrazine dihydrochloride in Example 1.

MS (APCI) m/e 365 (M+H)$^+$; $^1$H NMR (300 MHz, CD$_3$OD) δ 8.42 (d, 2H), 8.08 (d, 2H), 4.42 (d, 1H), 3.73 (m, 1H), 1.80–1.00 (m, 13H).

EXAMPLE 73

N'-((2RS,3R)-3-amino-4-cyclohexyl-2-hydroxybutanoyl)-2-naphthohydrazide

The desired product was prepared by substituting 2-naphthohydrazide for 1-benzylhydrazine dihydrochloride in Example 1.

MS (APCI) m/e 370 (M+H)$^+$; $^1$H NMR (300 MHz, CD$_3$OD) δ 8.53 (s, 1H), 8.01 (m, 5H), 7.59 (m, 2H), 4.38 (d, 1H), 3.72 (m, 1H), 1.80–1.00 (m, 13H).

EXAMPLE 74

(2RS,3R)-3-amino-N'-(4-chloro-2-methylphenyl)-4-cyclohexyl-2-hydroxybutanohydrazide The desired product was prepared by substituting 1-(4-chloro-2-methylphenyl)hydrazine for 1-benzylhydrazine dihydrochloride in Example 1.

MS (APCI) m/e 340 (M+H)$^+$; $^1$H NMR (300 MHz, CD$_3$OD) δ 7.08–7.01 (m, 2H), 6.77 (d, 1H), 4.33 (d, 1H), 3.66 (m, 1H), 2.23 (s, 3H), 1.86–1.64 (m, 6H), 1.57–1.44 (m, 2H), 1.37–1.22 (m, 3H), 1.05–0.92 (m, 2H).

EXAMPLE 75

(2RS,3R)-3-amino-4-cyclohexyl-2-hydroxy-N'-mesitylbutanohydrazide

The desired product was prepared by substituting 1-mesitylhydrazine for 1-benzylhydrazine dihydrochloride in Example 1.

MS (APCI) m/e 334 (M+H)$^+$; $^1$H NMR (300 MHz, CD$_3$OD) δ 6.77 (bs, 1H), 6.74 (bs, 1H), 4.14 (d, 1H), 3.52 (m, 1H), 2.32 (d, 6H), 2.18 (d, 3H), 1.78–1.61 (m, 6H), 1.48–1.14 (m, 5H), 1.02–0.75 (m, 2H).

EXAMPLE 76

(2RS,3R)-3-amino-4-cyclohexyl-2-hydroxy-N'-(4-((E)-2-(2-pyridinyl)ethenyl)phenyl)butanohydrazide The desired product was prepared by substituting 2-((1E)-3-(4-hydrazinophenyl)-1-propenyl)pyridine for 1-benzylhydrazine dihydrochloride in Example 1.

MS (APCI) m/e 395 (M+H)$^+$.

EXAMPLE 77

(2RS,3R)-3-amino-4-cyclohexyl-N'-(2-fluorophenyl)-2-hydroxybutanohydrazide

The desired product was prepared by substituting 1-(2-fluorophenyl)hydrazine for 1-benzylhydrazine dihydrochloride in Example 1.

MS (APCI) m/e 310 (M+H)$^+$; $^1$H NMR (300 MHz, CD$_3$OD) δ 7.04 (dt, 1H), 7.00 (dd, 1H), 6.94 (dt, 1H), 6.82 (m, 1H), 4.31 (d, 1H), 3.64 (m, 1H), 1.86–1.64 (m, 6H), 1.57–1.42 (m, 2H), 1.42–1.17 (m, 3H), 1.08–0.92 (m, 2H).

EXAMPLE 78

(2RS,3R)-3-amino-4-cyclohexyl-2-hydroxy-N'-(2-quinoxalinyl)butanohydrazide

The desired product was prepared by substituting 2-hydrazinoquinoxaline for 1-benzylhydrazine dihydrochloride in Example 1.

MS (APCI) m/e 344 (M+H)$^+$; $^1$H NMR (300 MHz, CD$_3$OD) δ 8.71 (s, 1H), 8.03 (d, 1H), 7.93 (d, 1H), 7.78 (t, 1H), 7.66 (t, 1H), 4.55 (d, 1H), 3.77 (m, 1H), 1.87–1.65 (m, 6H), 1.65–1.44 (m, 2H), 1.44–1.16 (m, 3H), 1.10–0.94 (m, 2H).

EXAMPLE 79

(2RS,3R)-3-amino-4-cyclohexyl-2-hydroxy-N'-(4-(trifluoromethyl)phenyl)butanohydrazide The desired product was prepared by substituting 1-(4-(trifluoromethyl)phenyl)hydrazine for 1-benzylhydrazine dihydrochloride in Example 1.

MS (APCI) m/e 360 (M+H)$^+$; $^1$H NMR (300 MHz, CD$_3$OD) δ 8.07 (d, 2H), 7.84 (d, 2H), 4.39 (d, 1H), 3.70 (m, 1H), 1.87–1.67 (m, 6H), 1.62–1.52 (m, 1H), 1.52–1.42 (m, 1H), 1.42–1.16 (m, 3H), 1.10–0.94 (m, 2H).

EXAMPLE 80

(2RS,3R)-3-amino-N'-(2-chloro-6-fluorophenyl)-4-cyclohexyl-2-hydroxybutanohydrazide The desired product was prepared by substituting 1-(2-chloro-6-fluorophenyl)hydrazine for 1-benzylhydrazine dihydrochloride in Example 1.

MS (APCI) m/e 344 (M+H)$^+$; $^1$H NMR (300 MHz, CD$_3$OD) δ 7.16 (dt, 1H), 7.07–6.99 (m, 1H), 6.92 (dt, 1H), 4.20 (d, 1H), 3.55 (m, 1H), 1.80–1.66 (m, 6H), 1.50–1.35 (m, 2H), 1.35–1.18 (m, 3H), 1.03–0.87 (m, 2H).

EXAMPLE 81

(2RS,3R)-3-amino-4-cyclohexyl-2-hydroxy-N'-methyl-N'-(5-(trifluoromethyl)-2-pyridinyl)butanohydrazide The desired product was prepared by substituting 2-(1-methylhydrazino)-5-(trifluoromethyl)pyridine for 1-benzylhydrazine dihydrochloride in Example 1.

MS (APCI) m/e 375 (M+H)$^+$; $^1$H NMR (300 MHz, CD$_3$OD) δ 8.42 (bs, 1H), 8.11 (dd, 1H), 7.25 (d, 1H), 4.50 (d, 1H), 3.72 (m, 1H), 3.48 (s, 3H), 1.87–1.66 (m, 6H), 1.62–1.52 (m, 1H), 1.52–1.45 (m, 1H), 1.38–1.21 (m, 3H), 1.08–0.93 (m, 2H).

EXAMPLE 82

(2RS,3R)-3-amino-4-cyclohexyl-N'-(2,5-difluorophenyl)-2-hydroxybutanohydrazide

The desired product was prepared by substituting 1-(2,5-difluorophenyl)hydrazine for 1-benzylhydrazine dihydrochloride in Example 1.

MS (APCI) m/e 328 (M+H)$^+$; $^1$H NMR (300 MHz, CD$_3$OD) δ 7.01 (m, 1H), 6.67 (m, 1H), 6.50 (m, 1H), 4.33 (d, 1H), 3.65 (m, 1H), 1.86–1.65 (m, 6H), 1.58–1.44 (m, 2H), 1.38–1.18 (m, 3H), 1.06–0.92 (m, 2H).

EXAMPLE 83

(2RS,3R)-3-amino-4-cyclohexyl-N'-(1,3-dimethyl-4-nitro-1H-pyrazol-5-yl)-2-hydroxybutanohydrazide The desired product was prepared by substituting 5-hydrazino-1,3-dimethyl-4-nitro-1H-pyrazole for 1-benzylhydrazine dihydrochloride in Example 1.

MS (APCI) m/e 355 (M+H)$^+$; $^1$H NMR (300 MHz, CD$_3$OD) δ 4.39 (d, 1H), 3.74 (s, 3H), 3.67 (m, 1H), 2.40 (s, 3H), 1.83–1.64 (m, 6H), 1.55–1.17 (m, 5H), 1.08–0.90 (m, 2H).

EXAMPLE 84

2-((2RS,3R)-3-amino-4-cyclohexyl-2-hydroxybutanoyl)-N-phenylhydrazinecarboxamide The desired product was prepared by substituting N-phenylhydrazinecarboxamide for 1-benzylhydrazine dihydrochloride in Example 1.

MS (APCI) m/e 335 (M+H)$^+$; $^1$H NMR (300 MHz, CD$_3$OD) δ 7.41 (d, 2H), 7.28 (t, 2H), 7.03 (t, 1H), 4.33 (d,

1H), 3.68 (m, 1H), 1.87–1.67 (m, 6H), 1.60–1.50 (m, 1H), 1.50–1.38 (m, 1H), 1.37–1.18 (m, 3H), 1.08–0.97 (m, 2H).

EXAMPLE 85

2-((2RS,3R)-3-amino-4-cyclohexyl-2-hydroxybutanoyl)-N-(4-chloro-2-methoxyphenyl)hydrazinecarboxamide The desired product was prepared by substituting N-(4-chloro-2-methoxyphenyl)hydrazinecarboxamide for 1-benzylhydrazine dihydrochloride in Example 1.

MS (APCI) m/e 399 (M+H)$^+$; $^1$H NMR (300 MHz, CD$_3$OD) δ 8.10 (d, 1H), 6.96 (d, 2H), 4.34 (d, 1H), 3.90 (s, 3H), 3.68 (m, 1H), 1.86–1.66 (m, 6H), 1.62–1.50 (m, 1H), 1.50–1.38 (m, 1H), 1.38–1.17 (m, 3H), 1.11–0.93 (m, 2H).

EXAMPLE 86

2-((2RS,3R)-3-amino-4-cyclohexyl-2-hydroxybutanoyl)-N-(3-fluorophenyl)hydrazinecarboxamide The desired product was prepared by substituting N-(3-fluorophenyl)hydrazinecarboxamide for 1-benzylhydrazine dihydrochloride in Example 1.

MS (APCI) m/e 353 (M+H)$^+$; $^1$H NMR (300 MHz, CD$_3$OD) δ 7.41 (d, 1H), 7.26 (q, 1H), 7.09 (d, 1H), 6.75 (t, 1H), 4.34 (d, 1H), 3.68 (m, 1H), 1.87–1.66 (m, 6H), 1.62–1.50 (m, 1H), 1.50–1.48 (m, 1H), 1.48–1.118 (m, 3H), 1.00–0.93 (m, 2H).

EXAMPLE 87

N-((1R)-1-((2-((2RS,3R)-3-amino-4-cyclohexyl-2-hydroxybutanoyl)hydrazino)carbonyl)-3-(methylsulfanyl)propyl)-4-(trifluoromethyl)benzamide The desired product was prepared by substituting N-((1R)-1-(hydrazinocarbonyl)-3-(methylsulfanyl)propyl)-4-(trifluoromethyl)benzamide for 1-benzylhydrazine dihydrochloride in Example 1.

MS (APCI) m/e 519 (M+H)$^+$; $^1$H NMR (300 MHz, CD$_3$OD) δ 8.05 (d, 2H), 7.79 (d, 2H), 4.31 (d, 1H), 3.81 (q, 1H), 3.65 (m, 1H), 2.68 (m, 2H), 2.30–2.15 (m, 2H), 2.12 (s, 3H), 1.84–1.63 (m, 6H), 1.58–1.48 (m, 1H), 1.48–1.36 (m, 1H), 1.36–1.20 (m, 3H), 1.06–0.95 (m, 2H).

EXAMPLE 88

(2RS,3R)-3-amino-4-cyclohexyl-2-hydroxy-N'-(2-thienylcarbonyl)butanohydrazide

The desired product was prepared by substituting 2-thiophenecarbohydrazide for 1-benzylhydrazine dihydrochloride in Example 1.

MS (APCI) m/e 326 (M+H)$^+$; $^1$H NMR (300 MHz, CD$_3$OD) δ 7.81 (dd, 2H), 7.18 (d, 1H), 4.42 (d, 1H), 3.73 (m, 1H), 1.80–1.00 (m, 13H).

EXAMPLE 89

N'-((2RS,3R)-3-amino-4-cyclohexyl-2-hydroxybutanoyl)-4-chlorobenzohydrazide

The desired product was prepared by substituting 4-chlorobenzohydrazide for 1-benzylhydrazine dihydrochloride in Example 1.

MS (APCI) m/e 354 (M+H)$^+$; $^1$H NMR (300 MHz, CD$_3$OD) δ 7.91 (d, 2H), 7.55 (d, 2H), 4.43 (d, 1H), 3.68 (m, 1H), 1.80–1.00 (m, 13H).

EXAMPLE 90

(2RS,3R)-3-amino-N'-benzoyl-4-cyclohexyl-2-hydroxybutanohydrazide

The desired product was prepared by substituting benzohydrazide for 1-benzylhydrazine dihydrochloride in Example 1.

MS (APCI) m/e 320 (M+H)$^+$; $^1$H NMR (300 MHz, CD$_3$OD) δ 7.91 (d, 2H), 7.58 (m, 3H), 4.42 (d, 1H), 3.68 (m, 1H), 1.80–1.00 (m, 13H).

EXAMPLE 91

N'-((2RS,3R)-3-amino-4-cyclohexyl-2-hydroxybutanoyl)-4-bromobenzohydrazide

The desired product was prepared by substituting 3-bromobenzohydrazide for 1-benzylhydrazine dihydrochloride in Example 1.

MS (APCI) m/e 400 (M+H)$^+$; $^1$H NMR (300 MHz, CD$_3$OD) δ 7.81 (d, 2H), 7.72 (d, 2H), 4.37 (d, 1H), 3.69 (m, 1H), 1.80–1.00 (m, 13H).

EXAMPLE 92

N'-((2RS,3R)-3-amino-4-cyclohexyl-2-hydroxybutanoyl)-4-tert-butylbenzohydrazide

The desired product was prepared by substituting for 1-benzylhydrazine dihydrochloride in Example 1.

MS (APCI) m/e 376 (M+H)$^+$; $^1$H NMR (300 MHz, CD$_3$OD) δ 7.83 (d, 2H), 7.55 (d, 2H), 4.41 (d, 1H), 3.73 (m, 1H), 1.80–1.00 (m, 22H).

EXAMPLE 93

4-chlorobenzyl 2-(2-((2RS,3R)-3-amino-4-cyclohexyl-2-hydroxybutanoyl)hydrazino)-4-(trifluoromethyl)-5-pyrimidinecarboxylate The desired product was prepared by substituting 4-chlorobenzyl 2-hydrazino-4-(trifluoromethyl)-5-pyrimidinecarboxylate for 1-benzylhydrazine dihydrochloride in Example 1.

MS (APCI) m/e 530 (M+H)$^+$; $^1$H NMR (300 MHz, CD$_3$OD) δ 8.96 (bs, 1H)t, 7.41 (m, 4H), 4.34 (d, 1H), 3.62 (m, 1H), 1.85–1.67 (m, 6H), 1.62–1.40 (m, 2H), 1.40–1.17 (m, 3H), 1.08–0.93 (m, 2H).

EXAMPLE 94

(2RS,3R)-3-amino-N'-(3-chloro-4-fluorophenyl)-4-cyclohexyl-2-hydroxybutanohydrazide The desired product was prepared by substituting 3-chloro-4-fluorophenylhydrazine for 1-benzylhydrazine dihydrochloride in Example 1.

MS (APCI) m/e 344 (M+H)$^+$; $^1$H NMR (300 MHz, CD$_3$OD) δ 7.06 (t, 1H), 6.91 (q, 1H), 6.78 (m, 1H), 4.31 (d, 1H), 3.62 (m, 1H), 1.88–1.63 (m, 6H), 1.57–1.41 (m, 2H), 1.41–1.12 (m, 2H), 1.12 0.90 (m, 2H).

EXAMPLE 95

(2RS,3R)-3-amino-N'-(6-chloro-3-pyridazinyl)-4-cyclohexyl-2-hydroxybutanohydrazide The desired product was prepared by substituting 3-chloro-6-hydrazinopyridazine for 1-benzylhydrazine dihydrochloride in Example 1.

MS (APCI) m/e 328 (M+H)+; $^1$H NMR (300 MHz, CD$_3$OD) δ 7.55 (d, 1H), 7.17 (d, 1H), 4.38 (d, 1H), 3.64 (m, 1H), 1.87–1.68 (m, 6H), 1.56–1.49 (m, 1H), 1.49–1.37 (m, 1H), 1.37–1.17 (m, 3H), 1.07–0.95 (m, 2H).

EXAMPLE 96

(2RS,3R)-3-amino-N'-(2-chlorobenzyl)-4-cyclohexyl-2-hydroxybutanohydrazide

The desired product was prepared by substituting 1-(2-chlorobenzyl)hydrazine for 1-benzylhydrazine dihydrochloride in Example 1.

MS (APCI) m/e 340 (M+H)+; $^1$H NMR (300 MHz, CD$_3$OD) δ 7.54 (m, 1H), 7.49 (m, 1H), 7.28 (m, 2H), 4.13 (q, 2H), 4.11 (d, 1H), 3.52 (m, 1H), 1.80–1.66 (m, 6H), 1.60–1.50 (m, 1H), 1.45–1.16 (m, 4H), 1.00–0.96 (m, 2H).

EXAMPLE 97

(2RS,3R)-3-amino-4-cyclohexyl-2-hydroxy-N-((2R)-2-(methoxymethyl)pyrrolidinyl)butanamide The desired product was prepared by substituting (2R)-2-(methoxymethyl)-1-pyrrolidinamine for 1-benzylhydrazine dihydrochloride in Example 1.

MS (APCI) m/e 314 (M+H)+; $^1$H NMR (300 MHz, CD$_3$OD) δ 4.11 (d, 1H), 3.58 (m, 1H), 3.45 (q, 1H), 3.35 (t, 1H), 3.32 (s, 3H), 3.21 (m, 1H), 3.07 (m, 1H), 2.80 (q, 2H), 2.08–1.93 (m, 1H), 1.88–1.68 (m, 6H), 1.67–1.53 (ml 1H), 1.53–1.48 (m, 2H), 1.48–1.18 (m, 3H), 1.04–0.98 (m, 2H).

EXAMPLE 98

(2RS,3R)-3-amino-5-ethylsulfanyl-2-hydroxy-N-phenoxypentamide

EXAMPLE 98A 3-amino-3,4-dideoxy-5-S-ethyl-5-thio-D-glycero-pentonic acid

The desired product was prepared by substituting (2R)-2-((tert-butoxycarbonyl)amino)-4-(ethylsulfanyl)butanoic acid for (2R)-2-((tert-butoxycarbonyl)amino)-3-cyclohexylpropanoic acid in Examples 1A–C.

EXAMPLE 98B (2RS,3R)-3-amino-5-ethylsulfanyl-2-hydroxy-N-phenoxypentamide

A solution of Example 98A (0.39 g, 1.3 mmol), O-phenyl hydroxylamine hydrochloride (0.27 g, 1.9 mmol), 1-(3-dimethylaminopropyl)-3-ethylcarbodiimide hydrochloride (0.29 g, 1.5 mmol), 1-hydroxybenzotriazole hydrate (0.20 g, 1.5 mmol), and N-methylmorpholine (0.40 mL, 3.6 mmol) in 3:1 dichloromethane/DMF (8 mL) at room temperature was stirred for 16 hours, diluted with dichloromethane, washed sequentially with aqueous NaHCO$_3$, brine, 10% KHSO$_4$, and brine, dried (MgSO$_4$), filtered, and concentrated. The concentrate was purified by flash column chromatography on silica gel with 95:5/dichloromethane:methanol, and the purified concentrate was dissolved in saturated HCl/dioxane (2 mL), stirred for 1 hour, concentrated, treated with diethyl ether, then concentrated to provide the desired product.

MS (ESI) m/e 285 (M+H)+; $^1$H NMR (300 MHz, DMSO-d$_6$) δ 12.31 (bs, 1H), 8.08 (bs, 0.4H), 7.94 (bs, 0.6H), 7.34 (m, 2H), 7.03 (m, 3H), 6.73 (d, 0.6H), 6.62 (d, 0.4H), 4.41 (m, 0.4H), 4.28 (t, 0.6H), 3.48 (m, 1H), 2.73–2.60 (m, 2H), 2.56 (q, 2H), 1.98–1.78 (m, 2H), 1.21 (t, 3H).

EXAMPLE 99

(2RS,3R)-3-amino-4-cyclohexyl-2-hydroxy-N-phenoxybutanamide

The desired product was prepared by substituting Example 1C for Example 98A in Example 98B.

MS (ESI) m/e 293 (M+H)+; $^1$H NMR (300 MHz, DMSO-d$_6$) δ 7.92 (bs, 1H), 7.34 (m, 2H), 7.06 (m, 3H), 6.73 (d, 0.4H), 6.70 (d, 0.6H), 4.21 (m, 1H), 3.36 (m, 1H), ), 1.74–1.60 (m, 6H), 1.50–1.40 (m, 1H), 1.33–1.15 (m, 4H), 0.96–0.80 (m, 2H).

EXAMPLE 100

(2RS,3R)-3-amino-N-(benzyloxy)-4-cyclohexyl-2-hydroxybutanamide

A solution of Example 1C (0.20 g, 0.66 mmol), O-benzyl hydroxylamine hydrochloride (0.22 g, 1.4 mmol), 1-(3-dimethylaminopropyl)-3-ethylcarbodiimide hydrochloride (0.17 g, 0.89 mmol), 1-hydroxybenzotriazole (0.14 g, 1.0 mmol), and N-methylmorpholine (0.40 mL, 3.6 mmol) in 5:1 dichloromethane/DMF (6 mL) at room temperature was stirred for 16 hours, diluted with dichloromethane, washed sequentially with aqueous NaHCO$_3$, brine, 10% KHSO$_4$, and brine, dried (MgSO$_4$), filtered, and concentrated. The concentrate was purified by flash column chromatography on silica gel with 98:2/dichloromethane:methanol, and the purified concentrate was dissolved in saturated HCl/dioxane (8 mL), stirred for 1 hour, concentrated, treated with diethyl ether, then concentrated to provide the desired product.

MS (ESI) m/e 307 (M+H)+; $^1$H NMR (300 MHz, DMSO-d$_6$) δ 7.78 (br s, 1H), 7.40 (m, 5H), 6.42 (d, 1H), 4.84 (s, 2H), 3.95 (m, 1H), 1.74–1.60 (m, 6H), 1.50–1.40 (m, 1H), 1.33–1.15 (m, 4H), 0.90–0.80 (m, 2H).

EXAMPLE 101

(2RS,3R)-3-amino-N-(methoxy)-4-cyclohexyl-2-hydroxybutanamide

The desired product was prepared by substituting O-methyl hydroxylamine hydrochloride for O-benzyl hydroxylamine hydrochloride in Example 100.

MS (APCI) m/e 231 (M+H)+; $^1$H NMR (300 MHz, DMSO-d$_6$) δ 7.74 (br s, 1H), 6.42 (d, 1H) 3.95 (m, 1H), 3.63 (s, 3H), 1.74–1.60 (m, 6H), 1.50–1.40 (m, 1H), 1.33–1.15 (m, 4H), 0.96–0.80 (m, 2H).

EXAMPLE 102

(2RS,3R)-3-amino-N-(tert-butoxy)-4-cyclohexyl-2-hydroxybutanamide

The desired product was prepared by substituting O-tert-butyl hydroxylamine hydrochloride for O-benzyl hydroxylamine hydrochloride in Example 100.

MS (APCI) m/e 273 (M+H)+; $^1$H NMR (300 MHz, DMSO-d$_6$) δ 7.74 (br s, 1H), 6.44 (d, 1H) 3.92 (m, 1H), 1.74–1.60 (m, 6H), 1.50–1.40 (m, 1H), 1.33–1.15 (m, 4H), 1.19 (s, 9H), 0.96–0.80 (m, 2H).

EXAMPLE 103

(2RS,3R)-3-amino-4-cyclohexyl-N-ethoxy-2-hydroxybutanamide

The desired product was prepared by substituting O-ethyl hydroxylamine hydrochloride for O-benzyl hydroxylamine hydrochloride in Example 100.

MS (APCI) m/e 245 (M+H)+; 1H NMR (300 MHz, DMSO-d6) δ 7.73 (br s, 1H), 6.41 (d, 1H), 3.92 (m, 1H), 3.84 (q, 2H), 1.74–1.60 (m, 6H), 1.50–1.40 (m, 1H), 1.33–1.15 (m, 4H), 1.14 (t, 3H), 0.96–0.80 (m, 2H).

EXAMPLE 104

(2RS,3R)-N-(allyloxy)-3-amino-4-cyclohexyl-2-hydroxybutanamide

The desired product was prepared by substituting O-allyl hydroxylamine hydrochloride for O-benzyl hydroxylamine hydrochloride in Example 100.

MS (APCI) m/e 257 (M+H)+; 1H NMR (300 MHz, DMSO-d6) δ 7.74 (br s, 1H), 6.43 (d, 1H), 5.95 (m, 1H), 5.32 (dd, 1H), 5.27 (m, 1H), 4.32 (d, 2H), 3.92 (m, 1H), 1.74–1.60 (m, 6H), 1.50–1.40 (m, 1H), 1.33–1.15 (m, 4H), 0.96–0.80 (m, 2H).

EXAMPLE 105

(2RS,3R)-3-amino-4-cyclohexyl-2-hydroxy-N-isobutoxybutanamide

The desired product was prepared by substituting O-isobutyl hydroxylamine hydrochloride for O-benzyl hydroxylamine hydrochloride in Example 100.

MS (APCI) m/e 273 (M+H)+; 1H NMR (300 MHz, DMSO-d6) δ 7.73 (br s, 1H), 6.39 (d, 1H), 3.92 (m, 1H), 3.58 (d, 2H), 1.88 (sept, 1H), 1.74–1.60 (m, 6H), 1.50–1.40 (m, 1H), 1.33–1.15 (m, 4H), 0.91 (d, 6H), 0.90–0.75 (m, 2H).

EXAMPLE 106

(2RS,3R)-3-amino-4-cyclohexyl-N,2-dihydroxybutanamide

EXAMPLE 106A (2RS,3R)-3-(tert-butoxycarbonyl)amino-N-(benzyloxy)-4-cyclohexyl-2-hydroxybutanamide A solution of Example 1C (0.20 g, 0.66 mmol), O-benzyl hydroxylamine hydrochloride (0.22 g, 1.4 mmol), 1-(3-dimethylaminopropyl)-3-ethylcarbodiimide hydrochloride (0.17 g, 0.89 mmol), 1-hydroxybenzotriazole (0.14 g, 1.0 mmol), and N-methylmorpholine (0.40 mL, 3.6 mmol) in 5:1 dichloromethane/DMF (6 mL) at room temperature was stirred for 16 hours, diluted with dichloromethane, washed sequentially with aqueous NaHCO3, brine, 10% KHSO4, and brine, dried (MgSO4), filtered, and concentrated. The concentrate was purified by flash column chromatography on silica gel with 98:2/dichloromethane:methanol to provide the desired product.

MS (APCI) m/e 407 (M+H)+.

EXAMPLE 106B (2RS,3R)-3-amino-4-cyclohexyl-N,2-dihydroxybutanamide

A solution of Example 106A (0.33 g, 0.82 mmol), and 10% palladium on charcoal (0.13 g) in THF (8 mL) at room temperature was stirred for 16 hours under an atmosphere of hydrogen gas, filtered, and concentrated. The concentrate was dissolved in saturated HCl/dioxane (5 mL), stirred for 1 hour, concentrated, treated with diethyl ether, then concentrated to provide the desired product.

MS (APCI) m/e 217 (M+H)+; 1H NMR (300 MHz, DMSO-d6) δ 10.89 (br s, 1H), 8.89 (br s, 1H), 7.80 (br s, 2H), 6.31 (d, 1H), 3.92 (m, 1H), 1.74–1.60 (m, 6H), 1.50–1.40 (m, 1H), 1.33–1.15 (m, 4H), 0.90–0.75 (m, 2H).

EXAMPLE 107

(2RS,3S)-3-amino-4-(ethylsulfanyl)-2-hydroxy-N-phenoxybutanamide

The desired product was prepared by substituting O-phenylhydroxylamine for 4-methylphenylhydrazine in Example 193.

MS (ESI) m/e 271 (M+H)+; 1H NMR (500 MHz, CD3OD) δ 7.32 (t, 2H), 7.10 (d, 2H), 7.06 (m, 1H), 4.56 (d, 0.65H), 4.54 (d, 0.35H), 3.66 (m, 1H), 2.95 (dd, 1H), 2.78 (dd, 1H), 2.64 (dd, 1.3H), 2.59 (dd, 0.7H), 1.29 (t, 1.95H), 1.25 (t, 1.05H).

EXAMPLE 108

(2RS,3R)-3-amino-3-cyclohexyl-2-hydroxy-N-phenoxypropanamide

The desired product was prepared by substituting O-phenylhydroxylamine for 4-methylphenylhydrazine and Example 122A for Example 97A in Example 193.

MS (ESI) m/e 279 (M+H)+; 1H NMR (500 MHz, CD3OD) δ 7.33 (t, 2H), 7.08 (m, 3H), 4.51 (d, 0.65H), 4.48 (d, 0.35H), 3.37 (dd, 1H), 1.87–1.72 (m, 6H), 1.35–1.11 (m, 5H).

EXAMPLE 109

(2RS,3S)-3-amino-2-hydroxy-N-phenoxy-4-(propylsulfanyl)butanamide

The desired product was prepared by substituting O-phenylhydroxylamine for 4-methylphenylhydrazine and Example 195B for Example 97A in Example 193.

MS (ESI) m/e 285 (M+H)+; 1H NMR (500 MHz, CD3OD) δ 7.33 (t, 2H), 7.08 (m, 3H), 4.58 (d, 0.65H), 4.56 (d, 0.35H), 3.68 (m, 1H), 2.94 (dd, 0.65H), 2.87 (dd, 0.35H), 2.78 (m, 1H), 2.60 (dd, 1H), 2.54 (m, 1H), 1.65 (dd, 1H), 1.60 (dd, 1H), 1.02 (t, 1.95 H), 0.99 (t, 1.05H).

EXAMPLE 110

(2RS,3R)-3-amino-2-hydroxy-5-(isopropylsulfanyl)-N-phenoxypentanamide

The desired product was prepared by substituting O-phenylhydroxylamine for 4-methylphenylhydrazine and Example 124B for Example 97A in Example 193.

MS (ESI) m/e 299 (M+H)+; 1H NMR (500 MHz, CD3OD) δ 7.33 (dd, 2H), 7.08 (m, 3H), 4.48 (d, 0.35H), 4.31 (d, 0.65H), 3.75 (m, 1H), 2.97 (dd, 0.65H), 2.93 (dd, 0.35H), 2.71 (m, 1.65H), 2.67 (m, 0.35H), 2.10 (dd, 0.65H), 1.99 (dd, 0.35H), 1.92 (dd, 1H), 1.28 (d, 3H), 1.27 (d, 3H).

EXAMPLE 111

(2RS,3S)-3-amino-2-hydroxy-4-(isobutylsulfanyl)-N-phenoxybutanamide

The desired product was prepared by substituting O-phenylhydroxylamine for 4-methylphenylhydrazine and Example 124B for Example 97A in Example 193.

MS (ESI) m/e 299 (M+H)+; 1H NMR (500 MHz, CD3OD) δ 7.33 (t, 2H), 7.08 (m, 3H), 4.60 (d, 1H), 3.69 (ddd, 1H), 2.93 (dd, 1H), 2.78 (dd, 1H), 2.50 (m, 2H), 1.83 (ddd, 1H), 1.03 (d, 6H).

EXAMPLE 112

(2RS,3R)-3-amino-5-phenyl-2-hydroxy-N-phenoxypentanamide

The desired product was prepared by substituting O-phenylhydroxylamine for 4-methylphenylhydrazine and Example 125A for Example 97A in Example 193.

MS (ESI) m/e 301 (M+H)$^+$; $^1$H NMR (500 MHz, CD$_3$OD) δ 7.30 (m, 3H), 7.26–7.20 (m, 4H), 7.06 (m, 3H), 4.48 (d, 0.5H), 4.45 (d, 0.5H), 3.59 (m, 1H), 2.79 (m, 1.5H), 2.71 (m, 0.5H), 2.15 (m, 0.5H), 2.02 (m, 1H), 1.94 (m, 0.5H).

EXAMPLE 113

(2RS,3R)-3-amino-3-cyclooctyl-2-hydroxy-N-phenoxypropanamide

The desired product was prepared by substituting O-phenylhydroxylamine for 4-methylphenylhydrazine and Example 199A for Example 97A in Example 193.

MS (ESI) m/e 307 (M+H)$^+$; $^1$H NMR (500 MHz, CD$_3$OD) δ 7.33 (m, 2H), 7.10 (m, 3H), 3.86 (m, 1H), 3.79 (m, 1H), 1.80–1.52 (m, 15H).

EXAMPLE 114

(2RS,3R)-3-amino-5-cyclohexyl-2-hydroxy-N-phenoxypentanamide

The desired product was prepared by substituting O-phenylhydroxylamine for 4-methylphenylhydrazine and Example 238A for Example 97A in Example 193.

MS (ESI) m/e 307 (M+H)$^+$; $^1$H NMR (500 MHz, CD$_3$OD) δ 7.33 (m, 2H), 7.10 (m, 3H), 3.89 (m, 1H), 3.71 (d, 1H), 1.74 (m, 3H), 1.65 (m, 2H), 1.53 (m, 2H), 1.29 (m, 4H), 1.20 (m, 2H), 0.95 (m, 2H).

EXAMPLE 115

(2RS,3S)-3-amino-4-((cyclohexylmethyl)sulfanyl)-2-hydroxy-N-phenoxybutanamide

The desired product was prepared by substituting O-phenylhydroxylamine for 4-methylphenylhydrazine and Example 200B for Example 97A in Example 193.

MS (ESI) m/e 339 (M+H)$^+$; $^1$H NMR (500 MHz, CD$_3$OD) δ 7.32 (dd, 2H), 7.08 (dd, 3H), 4.60 (d, 0.65H), 4.56 (d, 0.35H), 3.70 (m, 1H), 2.91 (dd, 1H), 2.82 (dd, 0.35H), 2.77 (dd, 0.65H), 2.51 (m, 1.5H), 2.43 (m, 0.5H), 1.88 (m, 2H), 1.75–1.66 (m, 3H), 1.32–1.16 (m, 4H), 0.98 (m, 2H).

EXAMPLE 116 ethyl ((((2RS,3R)-3-amino-4-cyclohexyl-2-hydroxybutanoyl)amino)oxy)acetate

The desired product was prepared by substituting O-(carboethoxy)methyl hydroxylamine hydrochloride for O-benzyl hydroxylamine hydrochloride in Example 100.

MS (APCI) m/e 303 (M+H)$^+$; $^1$H NMR (300 MHz, DMSO-d$_6$) δ 7.95 (br s, 1H), 6.39 (d, 1H), 4.50 (d, 2H), 4.18 (m, 2H), 3.92 (m, 1H), 1.74–1.60 (m, 6H), 1.50–1.40 (m, 1H), 1.33–1.15 (m, 4H), 1.23 (t, 3H), 0.90–0.75 (m, 2H).

EXAMPLE 117 benzyl ((((2RS,3R)-3-amino-4-cyclohexyl-2-hydroxybutanoyl)amino)oxy)acetate

EXAMPLE 117A benzyl ((((2RS,3R)-3-(tert-butoxycarbonyl)amino-4-cyclohexyl-2-hydroxybutanoyl)amino)oxy)acetate The desired product was prepared by substituting O-(carbobenzyloxy)methyl hydroxylamine for O-(carboethoxy)methyl hydroxylamine hydrochloride in Example 106A.

MS (APCI) m/e 465 (M+H)$^+$.

EXAMPLE 117B benzyl ((((2RS,3R)-3-amino-4-cyclohexyl-2-hydroxybutanoyl)amino)oxy)acetate Example 117A was dissolved in saturated HCl/dioxane (3 mL), stirred for 1 hour, concentrated, treated with diethyl ether, then concentrated to provide the desired product.

MS (APCI) m/e 365 (M+H)$^+$; $^1$H NMR (300 MHz, DMSO-d$_6$) δ 7.96 (br s, 1H), 7.39 (m, 5H), 6.39 (d, 1H), 5.20 (s, 2H), 4.49 (s, 2H), 3.92 (m, 1H), 1.74–1.60 (m, 6H), 1.50–1.40 (m, 1H), 1.33–1.15 (m, 4H), 0.90–0.75 (m, 2H).

EXAMPLE 118

((((2RS,3R)-3-amino-4-cyclohexyl-2-hydroxybutanoyl)amino)oxy)acetic acid

EXAMPLE 118A ((((2RS,3R)-3-(tert-butoxycarbonyl)amino-4-cyclohexyl-2-hydroxybutanoyl)amino)oxy)acetic acid A solution of Example 117A (0.99 g, 2.1 mmol), and 10% Palladium on charcoal (0.21 g) in THF (10 mL) at room temperature was stirred for 4 hours under an atmosphere of hydrogen gas, filtered, and concentrated to provide the desired product.

MS (APCI) m/e 375 (M+H)$^+$;

EXAMPLE 118B ((((2RS,3R)-3-amino-4-cyclohexyl-2-hydroxybutanoyl)amino)oxy)acetic acid Example 118A (0.17 g, 0.45 mmol) was dissolved in saturated HCl/dioxane (4 mL), stirred for 1 hour, concentrated, treated with diethyl ether, then concentrated to provide the desired product.

MS (APCI) m/e 275 (M+H)$^+$; $^1$H NMR (300 MHz, DMSO-d$_6$) δ 7.96 (br s, 1H), 6.39 (d, 1H), 5.20 (s, 2H), 3.92 (m, 1H), 1.74–1.60 (m, 6H), 1.50–1.40 (m, 1H), 1.33–1.15 (m, 4H), 0.90–0.75 (m, 2H).

EXAMPLE 119 ethyl (2S)-2-((((((2RS,3R)-3-amino-4-cyclohexyl-2-hydroxybutanoyl)amino)oxy)acetyl)amino) propanoate A solution of Example 118A (0.17 g, 0.45 mmol), L-alanine ethyl ester hydrochloride (0.098 g, 0.64 mmol), 1-(3-dimethylaminopropyl)-3-ethylcarbodiimide hydrochloride (0.098 g, 0.51 mmol), 1-hydroxybenzotriazole (0.091 g, 0.67 mmol), and N-methylmorpholine (0.11 mL, 1.0 mmol) in dichloromethane (5 mL) at room temperature was stirred for 16 hours, diluted with dichloromethane, washed sequentially with 1 M HCl, aqueous NaHCO$_3$, dried (MgSO$_4$), filtered, and concentrated. The concentrate was dissolved in saturated HCl/dioxane (4 mL), stirred for 1 hour, concentrated, then purified by HPLC to provide the desired product.

MS (ESI) m/e 374 (M+H)$^+$; $^1$H NMR (300 MHz, DMSO-d$_6$) δ 11.71 (br s, 1H), 8.56 (br s, 1), 7.74 (br s, 2H), 6.55 (d,

1H), 4.35 (d, 2H), 4.29 (m, 1H), 4.09 (m, 2H), 4.03 (m, 1H), 1.74–1.60 (m, 6H), 1.40–1.35 (m, 1H), 1.31 (d, 3H), 1.33–1.15 (m, 4H), 1.19 (t, 3H), 0.96–0.80 (m, 2H).

EXAMPLE 120

(2RS,3R)-3-amino-4-cyclohexyl-2-hydroxy-N-(2-oxo-2-((2-phenylethyl)amino)ethoxy)butanamide The desired product was prepared by substituting 2-phenylethylamine for L-alanine ethyl ester hydrochloride in Example 119.

MS (APCI) m/e 378 (M+H)+; $^1$H NMR (300 MHz, DMSO-$d_6$) δ 11.69 (br s, 1H), 8.29 (br s, 1H), 7.75 (br s, 2H), 7.30 (m, 3H), 7.22 (m, 2H), 6.56 (d, 1H), 4.28 (d, 2H), 4.01 (m, 1H), 2.75 (m, 2H), 1.74–1.60 (m, 6H), 1.50–1.40 (m, 1H), 1.36 (m, 2H), 1.33–1.15 (m, 4H), 0.90–0.75 (m, 2H).

EXAMPLE 121

(2RS,3R)-3-amino-5-(ethylsulfanyl)-2-hydroxy-N-benzyloxypentanamide

The desired product was prepared by substituting O-benzyl hydroxylamine hydrochloride for O-phenyl hydroxylamine hydrochloride in Example 98B.

MS (ESI) m/e 299 (M+H)+; $^1$H NMR (300 MHz, DMSO-$d_6$) δ 11.51 (br s, 1H), 7.92 (br s, 0.3H), 7.84 (br s, 0.7H), 7.39 (m, 5H), 6.49 (d, 0.7H), 6.40 (d, 0.3H), 4.84 (s, 1.4H), 4.82 (s, 0.6H), 4.17 (m, 0.3H), 4.03 (m, 0.7H), 3.48 (m, 1H), 2.60 (m, 2H), 2.48 (q, 2H), 1.73 (m, 2H), 1.18 (t, 3H).

EXAMPLE 122

(2RS,3R)-3-amino-N-(benzyloxy)-3-cyclohexyl-2-hydroxypropanamide

EXAMPLE 122A (2RS,3R)-3-amino-3-cyclohexyl-2-hydroxypropanoic acid

The desired product was prepared by substituting (2R)-2-((tert-butoxycarbonyl)amino)-2-(cyclohexyl)ethanoic acid for (2R)-2-((tert-butoxycarbonyl)amino)-3-cyclohexylpropanoic acid in Examples 1A–C.

MS (ESI) m/e 288 (M+H)+.

EXAMPLE 122B (2RS,3R)-3-amino-N-(benzyloxy)-3-cyclohexyl-2-hydroxypropanamide The desired product was prepared by substituting O-benzyl hydroxylamine hydrochloride for O-phenyl hydroxylamine hydrochloride and Example 122A for Example 98A in Example 98B.

MS (ESI) m/e 293 (M+H)+; $^1$H NMR (300 MHz, DMSO-$d_6$) δ 11.52 (s, 1H), 7.73 (br s, 2H), 7.41 (m, 5H), 6.40 (m, 1H), 4.85 (s, 2H), 4.08 (m, 1H), 1.77–1.44 (m, 6H), 1.20–0.94 (m, 5H).

EXAMPLE 123

(2RS,3R)-3-amino-N-(benzyloxy)-2-hydroxy-5-(isopropylsulfanyl)pentanamide

EXAMPLE 123A (2R)-2-((tert-butoxycarbonyl)amino)-4-((isopropyl)sulfanyl)butanoic acid A solution of D-homocystine (20 g, 75 mmol) in liquid ammonia (600 mL) was treated sequentially with sodium (8.9 g, 390 mmol) and 2-bromopropane (20 mL, 210 mmol). The ammonia was allowed to evaporate under a stream of nitrogen, and the residues take up in 1:1 2-propanol/water (500 mL), then treated with di-tert-butyl dicarbonate (50 g, 230 mmol) at room temperature for 6 hours, then concentrated. The residues were taken up in water and the pH adjusted to 10 with NaOH. The solution was washed twice with ether, then adjusted to pH 2 with HCl, then extracted twice with ethyl acetate. The ethyl acetate extracts were dried (MgSO$_4$), filtered, then concentrated to provide the desired product.

MS (ESI) m/e 279 (M+H)+.

EXAMPLE 123B (2RS,3R)-3-amino-2-hydroxy-5-(isopropylsulfanyl)pentanoic acid The desired product was prepared by substituting Example 123A for (2R)-2-((tert-butoxycarbonyl)amino)-3-cyclohexylpropanoic acid in Examples 1A–C.

MS (ESI) m/e 308 (M+H)+.

EXAMPLE 123C (2RS,3R)-3-amino-N-(benzyloxy)-2-hydroxy-5-(isopropylsulfanyl)pentanamide The desired product was prepared by substituting O-benzyl hydroxylamine hydrochloride for O-phenyl hydroxylamine hydrochloride and Example 123B for Example 98A in Example 98B.

MS (ESI) m/e 313 (M+H)+; $^1$H NMR (300 MHz, DMSO-$d_6$) δ 11.50 (br s, 1H), 7.92 (br s, 0.6H), 7.84 (br s, 1.4H), 7.40 (m, 5H), 6.48 (d, 0.7H), 6.38 (d, 0.3H), 4.84 (s, 1.4H), 4.82 (s, 0.6H), 4.17 (m, 0.3H), 4.03 (m, 0.7H), 3.48 (m, 1H), 2.91 (m, 1H), 2.73 (m, 2H), 1.74 (m, 2H), 1.20 (d, 6H).

EXAMPLE 124

(2RS,3S)-3-amino-N-(benzyloxy)-2-hydroxy-4-(isobutylsulfanyl)butanamide

EXAMPLE 124A (2S)-2-((tert-butoxycarbonyl)amino)-3-(isobutylsulfanyl)propanoic acid The desired product was prepared by substituting D-cystine for D-homocystine and 1-bromo-2-methylpropane for 2-bromopropane in Example 123A.

MS (ESI) m/e 279 (M+H)+.

EXAMPLE 124B (2RS,3S)-3-((tert-butoxycarbonyl)amino)-2-hydroxy-4-(isobutylsulfanyl)butanoic acid The desired product was prepared by substituting Example 124A for (2R)-2-((tert-butoxycarbonyl)amino)-3-cyclohexylpropanoic acid in Examples 1A–C.

MS (ESI) m/e 308 (M+H)+.

EXAMPLE 124C (2RS,3S)-3-amino-N-(benzyloxy)-2-hydroxy-4-(isobutylsulfanyl)butanamide The desired product was prepared by substituting O-benzyl hydroxylamine hydrochloride for O-phenyl hydroxylamine hydrochloride and Example 124B for Example 98A in Example 98B.

MS (ESI) m/e 360 (M+H)$^+$; $^1$H NMR (300 MHz, DMSO-d$_6$) δ 11.55 (br s, 1H), 7.93 (br s, 2H), 7.40 (m, 5H), 6.56 (m, 1H), 4.86 (s, 2H), 4.21 (m, 1H), 2.63 (m, 2H), 2.42 (d, 2H), 1.75 (m, 1H), 0.95 (d, 6H).

EXAMPLE 125

(2RS,3R)-3-amino-N-(benzyloxy)-2-hydroxy-5-phenylpentanamide

EXAMPLE 125A (2RS,3R)-3-amino-2-hydroxy-5-phenylpentanoic acid

The desired product was prepared by substituting (2R)-2-((tert-butoxycarbonyl)amino)-4-phenylbutanoic acid for (2R)-2-((tert-butoxycarbonyl)amino)-3-cyclohexylpropanoic acid in Examples 1A–C.

MS (ESI) m/e 309 (M+H)$^+$.

EXAMPLE 125B (2RS,3R)-3-amino-N-(benzyloxy)-2-hydroxy-5-phenylpentanamide

The desired product was prepared by substituting O-benzyl hydroxylamine hydrochloride for O-phenyl hydroxylamine hydrochloride and Example 125A for Example 98A in Example 98B.

MS (ESI) m/e 315 (M+H)$^+$; $^1$H NMR (300 MHz, DMSO-d$_6$) δ 7.86 (br s, 2H), 7.35 (m, 5H), 7.20 (m, 5H), 6.48 (m, 1H), 4.82 (s, 2H), 4.05 (m, 1H), 2.65 (m, 2H), 1.78 (m, 2H).

EXAMPLE 126

(2S,3S)-3-amino-N-(cyclohexylmethoxy)-2-hydroxy-4-(isobutylsulfanyl)butanamide

EXAMPLE 126A

O-Cyclohexylmethylhydroxylamine

The title compound was prepared by substituting cyclohexylmethyl bromide for

EXAMPLE 128A in Example 128B–128C. $^1$H NMR (300 MHz, DMSO-d$_6$) δ 5.85 (s, 2H), 1.70–1.60 (m, 5H), 1.26–1.08 (m, 4H), 0.94–0.80 (m, 2H).

EXAMPLE 126B (2S,3S)-3-((tert-butoxycarbonyl)amino)-2-hydroxy-4-(isobutylsulfanyl)butanoic acid pentafluorophenyl ester A solution of Example 124B (0.921 g, 3.0 mmol), pentafluorophenol (0.61 g, 3.3 mmol), 1-hydroxybenzotriazole (0.61 g, 4.5 mmol) and 1,3-dicyclohexyl-carbodiimide (0.62 g, 3.0 mmol in dichloromethane (10 mL) was stirred at 0° C. for 1 h and room temperature for 18 h. Dicyclohexyl urea was removed by filtration, and the filtrate was diluted with ether, washed with NaHCO$_3$ and then brine, dried (MgSO$_4$), filtered, and concentrated. The crude material was purified by silica gel chromatography (10:90/ethylacetate:hexanes) to give the title compound.

MS (ESI) m/e 472 (M–H)$^+$. $^1$H NMR (300 MHz, DMSO-d$_6$) δ 6.64 (d, 1H), 6.10 (d, 1H), 4.85 (dd, 1H), 4.14 (m, 1H), 2.74 (m, 1H), 2.56 (m, 1H), 2.47 (d, 2H), 1.77 (m, 1H), 1.37 (s, 9H), 0.95 (d, 6H).

EXAMPLE 126C (2S,3S)-3-amino-N-(cyclohexylmethoxy)-2-hydroxy-4-(isobutylsulfanyl)butanamide A solution of Example 126B (0.24 g, 0.5 mmol) and Example 126A (0.065 g, 0.5 mmol) in DMF (5 mL) was stirred at room temperature for 18 h, diluted with ether, washed with brine, dried (Na$_2$SO$_4$) and concentrated, purified by silica gel chromatography (10:90/ethylacetate:hexanes),then treated with 4M HCl in dioxane to give the title compound.

MS (ESI) m/e 317 (M–H)$^+$. $^1$H NMR (300 MHz, DMSO-d$_6$) δ 11.38 (br s, 1H), 7.9 (br s, 2H), 6.5 (d, 1H), 4.18 (dd, 1H), 3.63 (d, 2H), 3.4 (m, 1H), 2.75–2.59 (m, 2H), 2.53 (d, 2H), 1.8–1.6 (m, 7H), 1.24–1.10 (m, 4H), 1.0–0.9 (m, 1H), 0.95 (d, 6H).

EXAMPLE 127

(2S,3S)-3-amino-2-hydroxy-4-(isobutylsulfanyl)-N-(mesitylmethoxy)butanamide

EXAMPLE 127A

O-2,4,6-trimethylbenzylhydroxylamine

The title compound was prepared by substituting 2,4,6-trimethylbenzyl bromide for EXAMPLE 128A in Example 128B–128C. $^1$H NMR (300 MHz, DMSO-d$_6$) δ 6.80 (s, 2H), 5.96 (s, 2H), 4.57 (s, 2H), 2.30 (s, 6H), 2.20 (s, 3H).

EXAMPLE 127B (2S,3S)-3-amino-2-hydroxy-4-(isobutylsulfanyl)-N-(mesitylmethoxy)butanamide The title compound was prepared by substituting Example 127A for Example 126B in Example 126C.

MS (ESI) m/e 353 (M–H)$^+$. $^1$H NMR (300 MHz, DMSO-d$_6$) δ 11.55 (br s, 1H), 7.78 (br s, 2H), 6.85 (s, 2H), 6.57 (d, 1H), 4.87 (s, 2H), 4.24 (dd, 1H), 3.44 (m, 1H), 2.75–2.59 (m, 2H), 2.44 (d, 2H), 2.38 (s, 6H), 2.21 (s, 3H), 1.8–1.7 (m, 1H), 0.95 (d, 6H).

EXAMPLE 128

(2RS,3R)-3-amino-2-hydroxy-5-(ethylsulfanyl)-N-((1RS)-1-phenylethoxy)pentanamide

EXAMPLE 128A 1-bromoethylbenzene

To a solution of DL-sec-phenethyl alcohol (1.81 ml, 15 mmol) in chloroform (20 ml) was added phosphorus tribromide (15.75 ml, 15.75 mmol) dropwise at room temperature. The mixture was stirred at room temperature for 18 hours, poured into wet ice, washed with brine (4×), dried (MgSO$_4$), then evaporated to dryness to yield 2.62 g of the title compound.

EXAMPLE 128B

N-(1-phenylethoxy)phthalimide

N-hydroxyphthalamide (2.31 g, 14.2 mmol), Example 128A (2.62 g, 14.2 mmol) and potassium carbonate (4.91 g, 35.5 mmol) in N,N-dimethylformamide (35 mL) were stirred at room temperature for 1 day, and stirred in 50° C. oil bath for 5 hours. The mixture was poured into ice-water, the precipitate was collected by filtration, washed with water and dried to yield 2.69 g of the title compound.

EXAMPLE 128C

O-(1-(phenyl)ethyl)hydroxylamine

Example 128B (2.18 g, 8.2 mmol) and hydrazine hydrate (0.306 ml, 9.84 mmol) in ethanol (35 mL) was stirred at room temperature for 1.5 hours. The solvent was removed, the residue triturated with 30 ml of ether, filtered, and the filtrate was concentrated in vacuo to yield the title compound (1.09 g) as an oil.

EXAMPLE 128D (2RS,3R)-3-amino-2-hydroxy-5-(ethylsulfanyl)-N-((1 RS)-1-phenylethoxy)pentanamide The desired product was prepared by substituting Example 128C for O-phenyl hydroxylamine hydrochloride in Example 98B.

MS (ESI) m/e 313(M+H)$^+$; $^1$H NMR (300 MHz, DMSO-$d_6$) δ 11.28 (d, 0.5H), 11.25 (d, 0.5H), 7.89–8.08 (br. 3H), 7.28–7.43 (m, 5H), 6.43 (d, 0.6H), 6.33 (d, 0.4H), 4.92–5.03 (m, 1H), 4.17 (br., 0.4H), 3.98 br., 0.6H), 2.42–2.67 (m, 4H), 1.60–1.73 (m, 2H), 1.42–1.46 (m, 3H), 1.13–1.21 (m, 3H).

EXAMPLE 129

(2S,3S)-3-amino-N-(benzyloxy)-2-hydroxy-4-(isobutylsulfanyl)-N-methylbutanamide

EXAMPLE 129A

N-methyl-O-benzylhydroxylamine hydrochloride

O-Benzylhydroxylamine hydrochloride (1.59 g, 0.01 mol), di-tert-butyl dicarbonate (2.18 g, 0.01 mol) and N-methyl morpholine (1.1 mL, 0.01 mol) in dichloromethane (40 mL) were stirred at room temperature for 16 hours. The reaction mixture was diluted with ether, washed with 10% NaHSO$_4$, then brine, dried over (Na$_2$SO$_4$), and concentrated. The residue was treated with methyl iodide (1.6 mL, 0.025 mmol) in the presence of NaH (0.4 g, 0.01 mol) in THF at 0° C., then stirred at room temperature for 16 hours. The reaction was quenched with 1N HCl, diluted with ether, washed with brine, dried (Na$_2$SO$_4$), concentrated, purified by silica gel chromatography (20:80/ethyl acetate:hexanes) and treated with 4M HCl in dioxane to give the title compound.

EXAMPLE 129B (2S,3S)-3-amino-N-(benzyloxy)-2-hydroxy-4-(isobutylsulfanyl)-N-methylbutanamide The title compound was prepared by substituting Example 129A for Example 126A in Example 126C.

MS (ESI) m/e 327 (M+H)$^+$. $^1$H NMR (300 MHz, DMSO-$d_6$) δ 7.9 (br s, 2H), 7.49 (m, 2H), 7.4 (m, 3H), 6.22 (br s, 1H), 4.98 (m, 2H), 4.79 (br s, 1H), 3.24(s, 3H), 2.55 (m, 2H), 2.3 (m, 2H),), 1.68 (m, 1H), 0.9 (d, 6H).

EXAMPLE 130

(2RS,3S)-3-amino-N-(benzyloxy)-2-hydroxy-5-(isopropylsulfanyl)-N-methylpentanamide The desired product was prepared by substituting Example 129A for O-phenyl hydroxylamine hydrochloride and Example 123B for Example 98A in Example 98B.

MS (ESI) m/e 327 (M+H)$^+$. $^1$H NMR (300 MHz, DMSO-$d_6$) δ 8.08 & 7.88 (br s, 2H), 7.55–7.38 (m, 5H), 6.25 & 5.97 (br s, 1H), 4.98 (br s, 2H), 4.77 & 4.55 (br s, 1H), 3.7 & 3.48 (m, 1H), 3.2 (br s, 3H), 2.85 (m, 1H), 1.8–1.6 (m, 2H), 1.15 (m,6H).

EXAMPLE 131

(2RS,3R)-3-amino-2-hydroxy-5-(isopropylsulfanyl)-N-((1RS)-1-phenylethoxy)pentanamide The desired product was prepared by substituting Example 128C for O-phenyl hydroxylamine hydrochloride and Example 123B for Example 98A in Example 98B.

MS (ESI) m/e 327(M+H)$^+$; $^1$H NMR (300 MHz, DMSO-$d_6$) δ 11.26 (d, 0.6H), 11.24 (d, 0.4H), 7.88–8.10 (br., 3H), 7.30–7.44 (m, 5H), 6.45 (d, 0.6H), 6.36 (d, 0.4H), 4.90–5.02 (m, 1H), 3.97 (br.m, 1H) 3.64–3.73 (m, 1H), 2.82–2.94 (m, 2H), 2.53–2.73 (m, 2H), 1.58–1.72 (m, 2H), 1.42–1.47 (m, 3H), 1.16–1.23 (m, 6H).

EXAMPLE 132

(2RS,3R)-3-amino-4-cyclohexyl-2-hydroxy-N'-((3RS)-3-(methylsulfanyl)butyl)-N'-phenylbutanohydrazide The desired product was prepared by substituting 1-(3-(methylsulfanyl)butyl)-1-phenylhydrazine for 1-benzylhydrazine dihydrochloride in Example 1.

MS (ESI) m/e 394 (M+H)$^+$; $^1$H NMR (300 MHz, CD$_3$OD) δ 7.20 (m, 2H), 6.88 (m, 2H), 6.80 (m, 1H), 4.27 (dd, 1H), 3.57 (m, 3H), 2.17 (m, 1H), 2.07 (s, 3H), 1.42–1.91 (m, 6H), 1.11–1.42 (m, 4H), 0.76–1.11 (m, 8H).

EXAMPLE 133

(2RS,3R)-3-amino-4-cyclohexyl-2-hydroxy-N'-phenyl-N'-(3-phenylpropyl)butanohydrazide The desired product was prepared by substituting 1-(3-phenylpropyl)-1-phenylhydrazine for 1-benzylhydrazine dihydrochloride in Example 1.

MS (ESI) m/e 410 (M+H)$^+$; $^1$H NMR (300 MHz, CD$_3$OD) δ 7.05–7.41 (m, 8H), 6.83 (m, 2H), 4.26 (d, 1H), 3.57 (m, 1H), 3.48 (m, 2H), 2.74 (t, 2H), 1.86–2.07 (m, 2H), 1.55–1.86 (m, 7H), 1.47 (m, 2H), 1.07–1.39 (m, 2H), 0.75–1.07 (m, 2H).

EXAMPLE 134

(2RS,3R)-3-amino-4-cyclohexyl-2-hydroxy-N'-isobutyl-N'-phenylbutanohydrazide

The desired product was prepared by substituting 1-(2-methylpropyl)-1-phenylhydrazine for 1-benzylhydrazine dihydrochloride in Example 1.

MS (ESI) m/e 348 (M+H)$^+$; $^1$H NMR (300 MHz, CD$_3$OD) δ 7.20 (m, 5H), 6.87 (m, 2H), 6.80 (m, 1H), 4.24 (d, 1H), 3.54 (m, 1H), 3.28 (d, 2H), 1.99 (m, 1H), 1.58–1.91 (m, 6H), 1.50 (m, 2H), 1.17–1.42 (m, 3H), 1.02 (s, 3H), 1.00 (s, 3H), 0.91 (m, 2H).

EXAMPLE 135

(2RS,3R)-3-amino-4-cyclohexyl-2-hydroxy-N'-pentyl-N'-phenylbutanohydrazide

The desired product was prepared by substituting 1-pentyl-1-phenylhydrazine for 1-benzylhydrazine dihydrochloride in Example 1.

MS (ESI) m/e 362 (M+H)+; $^1$H NMR (300 MHz, CD$_3$OD) δ 7.22 (m, 2H), 6.89 (m, 2H), 6.82 (m, 1H), 4.27 (d, 1H), 3.59 (m, 1H), 3.46 (dd, 2H), 1.58–1.92 (m, 6H), 1.11–1.58 (m, 12H), 0.83–1.11 (m, 4H).

EXAMPLE 136

(2RS,3R)-3-amino-4-cyclohexyl-2-hydroxy-N'-(2-methylbutyl)-N'-phenylbutanohydrazide The desired product was prepared by substituting 1-(2-methylbutyl)-1-phenylhydrazine for 1-benzylhydrazine dihydrochloride in Example 1.

MS (ESI) m/e 362 (M+H)+; $^1$H NMR (300 MHz, CD$_3$OD) δ 7.20 (m, 2H), 6.88 (m, 2H), 6.80 (m, 1H), 4.24 (dd, 1H), 3.53 (m, 1H), 3.40 (m, 1H), 3.24 (m, 1H), 1.42–1.91 (m, 9H), 1.11–1.42 (m, 4H), 0.76–1.11 (m, 8H).

EXAMPLE 137

(2RS,3R)-3-amino-4-cyclohexyl-2-hydroxy-N'-isopentyl-N'-phenylbutanohydrazide

The desired product was prepared by substituting 1-(3-methylbutyl)-1-phenylhydrazine for 1-benzylhydrazine dihydrochloride in Example 1.

MS (ESI) m/e 362 (M+H)+; $^1$H NMR (300 MHz, CD$_3$OD) δ 7.22 (m, 2H), 6.89 (m, 2H), 6.83 (m, 1H), 4.28 (d, 1H), 3.58 (m, 1H), 3.49 (m, 2H), 1.61–1.92 (m, 7H), 1.52 (m, 4H), 1.11–1.42 (m, 3H), 0.83–1.11 (m, 8H).

EXAMPLE 138

(2RS,3R)-3-amino-4-cyclohexyl-N'-hexyl-2-hydroxy-N'-phenylbutanohydrazide

The desired product was prepared by substituting 1-hexyl-1-phenylhydrazine for 1-benzylhydrazine dihydrochloride in Example 1.

MS (ESI) m/e 376 (M+H)+; $^1$H NMR (300 MHz, CD$_3$OD) δ 7.22 (m, 2H), 6.90 (m, 2H), 6.82 (m, 1H), 4.27 (d, 1H), 3.57 (m, 1H), 3.45 (m, 2H), 1.59–1.91 (m, 7H), 1.11–1.59 (m, 12H), 0.84–1.11 (m, 5H).

EXAMPLE 139

(2RS,3R)-3-amino-4-cyclohexyl-2-hydroxy-N'-(2-methylpentyl)-N'-phenylbutanohydrazide The desired product was prepared by substituting 1-(2-methylpentyl)-1-phenylhydrazine for 1-benzylhydrazine dihydrochloride in Example 1.

MS (ESI) m/e 376 (M+H)+; $^1$H NMR (300 MHz, CD$_3$OD) δ 7.20 (m, 2H), 6.87 (m, 2H), 6.80 (m, 1H), 4.19–4.28 (m, 1H), 3.53 (dt, 1H), 3.39 (m, 1H), 3.24 (m, 1H), 1.59–1.99 (m, 7H), 1.50 (m, 4H), 1.04–1.42 (m, 6H), 1.00 (d, 3H), 0.93 (t, 3H), 0.83–1.05 (m, 2H).

EXAMPLE 140

(2RS,3R)-3-amino-4-cyclohexyl-2-hydroxy-N'-(3-methylpentyl)-N'-phenylbutanohydrazide The desired product was prepared by substituting 1-(3-methylpentyl)-1-phenylhydrazine for 1-benzylhydrazine dihydrochloride in Example 1.

MS (ESI) m/e 376 (M+H)+; $^1$H NMR (300 MHz, CD$_3$OD) δ 7.22 (m, 2H), 6.88 (m, 2H), 6.83 (m, 1H), 4.27 (d, 1H), 3.39–3.65 (m, 3H), 1.59–1.93 (m, 7H), 1.37–1.59 (m, 5H), 1.10–1.37 (m, 4H), 0.83–1.10 (m, 8H).

EXAMPLE 141

(2RS,3R)-3-amino-4-cyclohexyl-N'-(3,3-dimethylbutyl)-2-hydroxy-N'-phenylbutanohydrazide The desired product was prepared by substituting 1-(3,3-dimethylbutyl)-1-phenylhydrazine for 1-benzylhydrazine dihydrochloride in Example 1.

MS (ESI) m/e 376 (M+H)+; $^1$H NMR (300 MHz, CD$_3$OD) δ 7.22 (m, 2H), 6.88 (m, 2H), 6.83 (m, 1H), 4.29 (d, 1H), 3.52 (m, 4H), 1.42–1.91 (m, 10H), 1.11–1.42 (m, 3H), 0.76–1.11 (m, 11H).

EXAMPLE 142

(2RS,3R)-3-amino-4-cyclohexyl-N'-(2-ethylbutyl)-2-hydroxy-N'-phenylbutanohydrazide The desired product was prepared by substituting 1-(2-ethylbutyl)-1-phenylhydrazine for 1-benzylhydrazine dihydrochloride in Example 1.

MS (ESI) m/e 376 (M+H)+; $^1$H NMR (300 MHz, CD$_3$OD) δ 7.20 (m, 2H), 6.88 (m, 2H), 6.81 (m, 1H), 4.23 (d, 1H), 3.52 (dt, 1H), 3.37 (d, 2H), 1.58–1.92 (m, 7H), 1.38–1.58 (m, 6H), 1.10–1.38 (m, 3H), 0.82–1.10 (m, 8H).

EXAMPLE 143

(2RS,3R)-3-amino-4-cyclohexyl-N'-(cyclopropylmethyl)-2-hydroxy-N'-phenylbutanohydrazide The desired product was prepared by substituting 1-(cyclopropylmethyl)-1-phenylhydrazine for 1-benzylhydrazine dihydrochloride in Example 1

MS (ESI) m/e 346 (M+H)+; $^1$H NMR (300 MHz, CD$_3$OD) δ 7.22 (m, 2H), 6.93 (m, 2H), 6.85 (m, 1H), 4.30 (d, 1H), 3.60 (ddd, 1H), 3.43 (m, 1H), 3.28 (m, 1H), 1.64–1.94 (m, 6H), 1.42–1.64 (m, 2H), 1.16–1.42 (m, 3H), 0.69–1.16 (m, 3H), 0.41–0.69 (m, 2H), 0.15–0.41 (m, 2H).

EXAMPLE 144

(2RS,3R)-3-amino-4-cyclohexyl-N'-dodecyl-2-hydroxy-N'-phenylbutanohydrazide

The desired product was prepared by substituting 1-dodecyl-1-phenylhydrazine for 1-benzylhydrazine dihydrochloride in Example 1.

MS (ESI) m/e 460 (M+H)+; $^1$H NMR (300 MHz, CD$_3$OD) δ 7.22 (m, 2H), 6.88 (m, 2H), 6.83 (m, 1H), 4.26 (d, 1H), 3.56 (dt, 1H), 3.46 (m, 2H), 1.57–1.93 (m, 8H), 1.51 (m, 2H), 1.10–1.45 (m, 21H), 0.82–1.10 (m, 5H).

EXAMPLE 145

(2RS,3R)-3-amino-4-cyclohexyl-2-hydroxy-N'-phenyl-N'-(3,5,5-trimethylhexyl)butanohydrazide The desired product was prepared by substituting 1-(3,5,5-trimethylhexyl)-1-phenylhydrazine for 1-benzylhydrazine dihydrochloride in Example 1.

MS (ESI) m/e 418 (M+H)+; $^1$H NMR (300 MHz, CD$_3$OD) δ 7.22 (m, 2H), 6.89 (m, 2H), 6.83 (m, 1H), 4.27 (d, 1H), 3.40–3.63 (m, 3H), 1.59–1.98 (m, 8H), 1.51 (m, 3H), 1.18–1.42 (m, 4H), 1.14 (m, 1H), 1.03 (m, 4H), 0.70–0.97 (m, 10H).

EXAMPLE 146

(2RS,3R)-3-amino-4-cyclohexyl-2-hydroxy-N'-octyl-N'-phenylbutanohydrazide

The desired product was prepared by substituting 1-octyl-1-phenylhydrazine for 1-benzylhydrazine dihydrochloride in Example 1.

MS (ESI) m/e 404 (M+H)$^+$; $^1$H NMR (300 MHz, CD$_3$OD) δ 7.22 (m, 2H), 6.88 (m, 2H), 6.82 (m, 1H), 4.27 (d, 1H), 3.56 (dt, 1H), 3.46 (m, 2H), 1.59–1.97 (m, 8H), 1.52 (m, 2H), 1.09–1.45 (m, 13H), 0.76–1.09 (m, 5H).

EXAMPLE 147

(2RS,3R)-3-amino-N'-(2-(benzyloxy)ethyl)-4-cyclohexyl-2-hydroxy-N'-phenylbutanohydrazide The desired product was prepared by substituting 1-(2-benzyloxymethyl)-1-phenylhydrazine for 1-benzylhydrazine dihydrochloride in Example 1.

MS (ESI) m/e 426 (M+H)$^+$; $^1$H NMR (300 MHz, CD$_3$OD) δ 7.35 (m, 10H), 6.92 (m, 2H), 6.83 (m, 1H), 4.53 (m, 4H), 4.32 (d, 1H), 3.60 (m, 3H), 1.58–1.91 (m, 6H), 1.50 (m, 2H), 1.17–1.42 (m, 3H), 0.91 (m, 2H).

EXAMPLE 148

(2RS,3R)-3-amino-4-cyclohexyl-2-hydroxy-N'-phenyl-N'-(2,2,5-trichloropentyl)butanohydrazide The desired product was prepared by substituting 1-(2,2,5-trichloropentyl)-1-phenylhydrazine for 1-benzylhydrazine dihydrochloride in Example 1.

MS (ESI) m/e 464 (M+H)$^+$; $^1$H NMR (300 MHz, CD$_3$OD) δ 7.20 (m, 2H), 6.85 (m, 3H), 4.38 (d, 1H), 3.79 (m, 1H), 3.68 (m, 2H), 2.46 (m, 2H), 2.17 (m, 2H), 1.58–1.91 (m, 8H), 1.50 (m, 2H), 1.17–1.42 (m, 3H), 0.91 (m, 2H).

EXAMPLE 149

(2RS,3R)-3-amino-4-cyclohexyl-2-hydroxy-N'-phenyl-N'-propylbutanohydrazide

The desired product was prepared by substituting 1-propyl-1-phenylhydrazine for 1-benzylhydrazine dihydrochloride in Example 1.

MS (ESI) m/e 334 (M+H)$^+$; $^1$H NMR (300 MHz, CD$_3$OD) δ 7.22 (m, 2H), 6.90 (m, 2H), 6.82 (m, 1H), 4.27 (d, 1H), 3.59 (m, 1H), 3.45 (m, 2H), 1.59–1.99 (m, 8H), 1.51 (m, 2H), 1.12–1.43 (m, 3H), 0.778–1.12 (m, 5H).

EXAMPLE 150

(2RS,3R)-3-amino-4-cyclohexyl-N'-heptyl-2-hydroxy-N'-phenylbutanohydrazide

The desired product was prepared by substituting 1-heptyl-1-phenylhydrazine for 1-benzylhydrazine dihydrochloride in Example 1.

MS (ESI) m/e 390 (M+H)$^+$; $^1$H NMR (300 MHz, CD$_3$OD) δ 7.22 (m, 2H), 6.88 (m, 2H), 6.82 (m, 1H), 4.27 (d, 1H), 3.56 (dt, 1H), 3.45 (m, 2H), 1.59–1.96 (m, 8H), 1.52 (m, 2H), 1.12–1.45 (m, 11H), 0.83–1.12 (m, 5H).

EXAMPLE 151

(2RS,3R)-3-amino-4-cyclohexyl-N'-ethyl-2-hydroxy-N'-phenylbutanohydrazide

The desired product was prepared by substituting 1-ethyl-1-phenylhydrazine for 1-benzylhydrazine dihydrochloride in Example 1.

MS (ESI) m/e 320 (M+H)$^+$; $^1$H NMR (300 MHz, CD$_3$OD) δ 7.23 (m, 2H), 6.91 (m, 2H), 6.83 (m, 1H), 4.30 (d, 1H), 3.61 (m, 1H), 3.54 (dd, 2H), 1.59–1.92 (m, 6H), 1.50 (m, 2H), 1.4–1.12 (m, 3H), 1.22 (t, 3H), 0.85–1.18 (m, 2H).

EXAMPLE 152

(2RS,3R)-3-amino-4-cyclohexyl-2-hydroxy-N'-(3-(methylsulfanyl)propyl)-N'-phenylbutanohydrazide The desired product was prepared by substituting 1-(3-(methylsulfanyl)propyl)-1-phenylhydrazine for 1-benzylhydrazine dihydrochloride in Example 1.

MS (ESI) m/e 380 (M+H)$^+$; $^1$H NMR (300 MHz, CD$_3$OD) δ 7.22 (m, 2H), 6.92 (m, 2H), 6.83 (m, 1H), 4.28 (d, 1H), 3.47–3.72 (m, 3H), 2.50–2.75 (m, 2H), 2.10 (s, 3H), 1.93 (m, 2H), 1.58–1.87 (m, 6H), 1.51 (m, 2H), 1.13–1.42 (m, 3H), 0.82–1.12 (m, 2H).

EXAMPLE 153

(2RS,3R)-3-amino-4-cyclohexyl-N'-(cyclopentylmethyl)-2-hydroxy-N'-phenylbutanohydrazide The desired product was prepared by substituting 1-(cyclopentylmethyl)-1-phenylhydrazine for 1-benzylhydrazine dihydrochloride in Example 1.

MS (ESI) m/e 374 (M+H)$^+$; $^1$H NMR (300 MHz, CD$_3$OD) δ 7.21 (m, 2H), 6.89 (m, 2H), 6.82 (m, 1H), 4.25 (d, 1H), 3.54 (dt, 1H), 3.41 (d, 2H), 2.26 (m, 1H), 1.42–2.00 (m, 15H), 1.10–1.43 (m, 5H), 0.80–1.10 (m, 2H).

EXAMPLE 154

(2RS,3R)-3-amino-4-cyclohexyl-2-hydroxy-N'-(5-hydroxypentyl)-N'-phenylbutanohydrazide The desired product was prepared by substituting 1-(5-hydroxypentyl)-1-phenylhydrazine for 1-benzylhydrazine dihydrochloride in Example 1.

MS (ESI) m/e 378 (M+H)$^+$; $^1$H NMR (300 MHz, CD$_3$OD) δ 7.22 (m, 2H), 6.90 (m, 2H), 6.82 (m, 1H), 4.28 (d, 1H), 3.68 (m, 1H), 3.57 (t, 2H), 3.48 (m, 2H), 1.41–2.11 (m, 14H), 1.12–1.41 (m, 4H), 0.80–1.12 (m, 2H).

EXAMPLE 155

(2RS,3R)-3-amino-4-cyclohexyl-N'-((2R)-2,3-dihydroxypropyl)-2-hydroxy-N'-phenylbutanohydrazide The desired product was prepared by substituting 1-((2R)-2,3-dihydroxypropyl)-1-phenylhydrazine for 1-benzylhydrazine dihydrochloride in Example 1.

MS (ESI) m/e 366 (M+H)$^+$; $^1$H NMR (300 MHz, CD$_3$OD) δ 7.20 (m, 2H), 6.86 (m, 3H), 4.27 (d, 1H), 3.62 (m, 3H), 3.28 (d, 4H), 1.58–1.91 (m, 6H), 1.50 (m, 2H), 1.17–1.42 (m, 3H), 0.91 (m, 2H).

EXAMPLE 156

(2RS,3R)-3-amino-4-cyclohexyl-N'-(2,2-dichlorohexyl)-2-hydroxy-N'-phenylbutanohydrazide The desired product was prepared by substituting 1-(2,2-dichlorohexyl)-1-phenylhydrazine for 1-benzylhydrazine dihydrochloride in Example 1.

MS (ESI) m/e 444 (M+H)$^+$; $^1$H NMR (300 MHz, CD$_3$OD) δ 7.20 (m, 2H), 6.87 (m, 3H), 4.29 (d, 1H), 3.57 (m, 3H), 2.27 (m, 2H), 1.58–1.91 (m, 6H), 1.50 (m, 4H), 1.17–1.42 (m, 5H), 1.05 (m, 2H), 0.92 (t, 3H).

EXAMPLE 157

(2RS,3R)-3-amino-4-cyclohexyl-2-hydroxy-N'-((3RS)-7-methoxy-3,7-dimethyloctyl)-N'-phenylbutanohydrazide The desired product was prepared by substituting 1-(7-methoxy-3,7-dimethyloctyl)-1-phenylhydrazine for 1-benzylhydrazine dihydrochloride in Example 1.

MS (ESI) m/e 462 (M+H)+; ¹H NMR (300 MHz, CD₃OD) δ 7.23 (m, 2H), 6.89 (m, 2H), 6.83 (m, 1H), 4.27 (s, 1H), 3.38–3.65 (m, 3H), 3.17 (s, 3H), 1.14 (s, 6H), 0.97 (d, 3H), 0.85–1.12 (m, 2H), 0.85–1.12 (m, 20H).

EXAMPLE 158

(2RS,3R)-3-amino-4-cyclohexyl-2-hydroxy-N'-(2-(4-methylphenyl)ethyl)-N'-phenylbutanohydrazide The desired product was prepared by substituting 1-(2-(4-methylphenyl)ethyl)-1-phenylhydrazine for 1-benzylhydrazine dihydrochloride in Example 1.

MS (ESI) m/e 410 (M+H)+; ¹H NMR (300 MHz, CD₃OD) δ 7.24 (m, 2H), 7.13 (m, 4H), 6.91 (m, 2H), 6.83 (m, 1H), 4.29 (d, 1H), 3.69 (m, 2H), 3.57 (m, 1H), 2.90 (t, 2H), 2.30 (s, 3H), 1.59–1.95 (m, 5H), 1.50 (m, 2H), 1.12–1.40 (m, 4H), 0.75–1.12 (m, 2H).

EXAMPLE 159

(2RS,3R)-3-amino-4-cyclohexyl-N'-((2RS)-2-ethylhexyl)-2-hydroxy-N'-phenylbutanohydrazide The desired product was prepared by substituting 1-(2-ethylhexyl)-1-phenylhydrazine for 1-benzylhydrazine dihydrochloride in Example 1.

MS (ESI) m/e 404 (M+H)+; ¹H NMR (300 MHz, CD₃OD) δ 7.21 (m, 2H), 6.88 (m, 2H), 6.81 (m, 1H), 4.23 (m, 1H), 3.52 (dt, 1H), 3.37 (m, 2H), 1.61–1.92 (m, 6H), 1.10–1.61 (m, 14H), 0.75–1.10 (m, 8H).

EXAMPLE 160

(2RS,3R)-3-amino-N'-((2RS)-2-(4-chlorophenyl)-2-cyanoethyl)-4-cyclohexyl-2-hydroxy-N'-phenylbutanohydrazide The desired product was prepared by substituting 1-(2-(4-chlorophenyl)-2-cyanoethyl)-1-phenylhydrazine for 1-benzylhydrazine dihydrochloride in Example 1.

MS (ESI) m/e 456 (M+H)+; ¹H NMR (300 MHz, CD₃OD) δ 7.50–7.10 (m, 9H), 6.84 (m, 1H), 4.57 (d, 1H), 3.82 (m, 1H), 3.41 (m, 2H), 1.58–1.91 (m, 6H), 1.50 (m, 2H), 1.17–1.42 (m, 3H), 0.91 (m, 2H).

EXAMPLE 161

(2RS,3R)-3-amino-4-cyclohexyl-2-hydroxy-N'-phenyl-N'-((2RS)-2-phenylpropyl)butanohydrazide The desired product was prepared by substituting 1-(2-phenylpropyl)-1-phenylhydrazine for 1-benzylhydrazine dihydrochloride in Example 1.

MS (ESI) m/e 410 (M+H)+; ¹H NMR (300 MHz, CD₃OD) δ 7.32 (m, 5H), 7.18 (m, 2H), 6.87 (m, 2H), 6.80 (m, 1H), 4.18 (d, 1H), 3.65 (m, 2H), 3.52 (m, 1H), 3.13 (m, 1H), 1.58–1.91 (m, 6H), 1.50 (m, 2H), 1.17–1.42 (m, 3H), 1.37 (d, 3H), 0.91 (m, 2H).

EXAMPLE 162

(2RS,3R)-3-amino-4-cyclohexyl-N'-(cyclooctylmethyl)-2-hydroxy-N'-phenylbutanohydrazide The desired product was prepared by substituting 1-(cyclooctylmethyl)-1-phenylhydrazine for 1-benzylhydrazine dihydrochloride in Example 1.

MS (ESI) m/e 416 (M+H)+; ¹H NMR (300 MHz, CD₃OD) δ 7.20 (m, 2H), 6.88 (m, 2H), 6.80 (m, 1H), 4.24 (d, 1H), 3.53 (dt, 1H), 3.27 (m, 2H), 1.11–2.08 (m, 26H), 0.82–1.11 (m, 2H).

EXAMPLE 163

(2RS,3R)-3-amino-4-cyclohexyl-N'-((11Z)-11-hexadecenyl)-2-hydroxy-N'-phenylbutanohydrazide The desired product was prepared by substituting 1-((11Z)-1-hexadecenyl)-1-phenylhydrazine for 1-benzylhydrazine dihydrochloride in Example 1.

MS (ESI) m/e 514 (M+H)+; ¹H NMR (300 MHz, CD₃OD) δ 7.22 (m, 2H), 6.88 (m, 2H), 6.82 (m, 1H), 5.34 (m, 2H), 4.27 (d, 1H), 3.56 (dt, 1H), 3.46 (m, 2H), 1.92–2.14 (m, 4H), 1.58–1.92 (m, 7H), 1.51 (m, 2H), 1.12–1.44 (m, 22H), 0.94–1.12 (m, 2H), 0.89 (m, 3H).

EXAMPLE 164

(2RS,3R)-3-amino-4-cyclohexyl-2-hydroxy-N'-phenyl-N'-tridecylbutanohydrazide

The desired product was prepared by substituting 1-tridecyl-1-phenylhydrazine for 1-benzylhydrazine dihydrochloride in Example 1.

MS (ESI) m/e 474 (M+H)+; ¹H NMR (300 MHz, CD₃OD) δ 7.22 (m, 2H), 6.90 (m, 2H), 6.83 (m, 1H), 4.27 (d, 1H), 3.56 (m, 1H), 3.46 (m, 2H), 1.57–1.91 (m, 7H), 1.51 (m, 2H), 1.12–1.44 (m, 21H), 1.01 (m, 2H), 0.90 (t, 3H).

EXAMPLE 165

4-(2-((2RS,3R)-3-amino-4-cyclohexyl-2-hydroxybutanoyl)-1-phenylhydrazino)butanoic acid The desired product was prepared by substituting 4-(1-phenylhydrazino)butanoic acid for 1-benzylhydrazine dihydrochloride in Example 1.

MS (ESI) m/e 378 (M+H)+; ¹H NMR (300 MHz, CD₃OD) δ 7.23 (m, 2H), 6.88 (m, 3H), 4.29 (m, 1H), 3.64 (m, 1H), 3.53 (m, 1H), 3.31 (m, 1H), 2.46 (t, 1H), 1.94 (m, 1H), 1.59–1.88 (m, 7H), 1.50 (m, 3H), 1.12–1.41 (m, 4H), 0.86–1.12 (m, 2H).

EXAMPLE 166

(2RS,3R)-3-amino-4-cyclohexyl-2-hydroxy-N'-((6Z)-6-nonenyl)-N'-phenylbutanohydrazide The desired product was prepared by substituting 1-((6Z)-6-nonenyl)-1-phenylhydrazine for 1-benzylhydrazine dihydrochloride in Example 1.

MS (ESI) m/e 416 (M+H)+; ¹H NMR (300 MHz, CD₃OD) δ 7.22 (m, 2H), 6.89 (m, 2H), 6.83 (m, 1H), 5.35 (m, 2H), 4.27 (d, 1H), 3.57 (dt, 1H), 3.46 (m, 2H), 2.06 (m, 4H), 1.58–1.90 (m, 7H), 1.52 (m, 2H), 1.42 (m, 4H), 1.12–1.38 (m, 4H), 0.95 (t, 3H), 0.86–1.09 (m, 2H).

EXAMPLE 167

(2RS,3R)-3-amino-4-cyclohexyl-N'-((4Z)-4-decenyl)-2-hydroxy-N'-phenylbutanohydrazide The desired product was prepared by substituting 1-((4Z)-4-decenyl)-1-phenylhydrazine for 1-benzylhydrazine dihydrochloride in Example 1.

MS (ESI) m/e 430 (M+H)+; ¹H NMR (300 MHz, CD₃OD) δ 7.22 (m, 2H), 6.89 (m, 2H), 6.83 (m, 1H), 5.41 (m, 2H), 4.26 (d, 1H), 3.57 (m, 1H), 3.47 (m, 2H), 2.05 (m,

4H), 1.59–1.90 (m, 7H), 1.51 (m, 2H), 1.12–1.42 (m, 10H), 0.82–1.08 (m, 5H).

EXAMPLE 168

(2RS,3R)-3-amino-4-cyclohexyl-2-hydroxy-N'-(4-pentenyl)-N'-phenylbutanohydrazide The desired product was prepared by substituting 1-(4-pentenyl)-1-phenylhydrazine for 1-benzylhydrazine dihydrochloride in Example 1.

MS (ESI) m/e 360 (M+H)$^+$; $^1$H NMR (300 MHz, CD$_3$OD) δ 7.20 (m, 2H), 6.87 (m, 2H), 6.78 (m, 1H), 5.87 (m, 1H), 5.05 (m, 2H), 4.27 (d, 1H), 3.58 (m, 1H), 3.48 (m, 2H), 2.20 (m, 2H), 1.58–1.91 (m, 8H), 1.50 (m, 2H), 1.17–1.42 (m, 3H), 0.97 (m, 2H).

EXAMPLE 169

(2RS,3R)-3-amino-4-cyclohexyl-N'-((3RS)-3,7-dimethyl-6-octenyl)-2-hydroxy-N'-phenylbutanohydrazide The desired product was prepared by substituting 1-(3,7-dimethyl-6-octenyl)-1-phenylhydrazine for 1-benzylhydrazine dihydrochloride in Example 1.

MS (ESI) m/e 430 (M+H)$^+$; $^1$H NMR (300 MHz, CD$_3$OD) δ 7.22 (m, 2H), 6.87 (m, 2H), 6.80 (m, 1H), 5.12 (m, 1H), 4.28 (d, 1H), 3.55 (m, 3H), 2.04 (m, 2H), 1.58–1.91 (m, 6H), 1.50 (m, 5H), 1.17–1.42 (m, 5H), 1.12 (s, 6H), 0.97 (d, 3H), 0.91 (m, 2H).

EXAMPLE 170

(2RS,3R)-3-amino-4-cyclohexyl-2-hydroxy-N'-phenyl-N'-(4,4,4-trifluorobutyl)butanohydrazide The desired product was prepared by substituting 1-(4,4,4-trifluorobutyl)-1-phenylhydrazine for 1-benzylhydrazine dihydrochloride in Example 1.

MS (ESI) m/e 402 (M+H)$^+$; $^1$H NMR (300 MHz, CD$_3$OD) δ 7.25 (m, 2H), 6.93 (m, 2H), 6.86 (m, 1H), 3.57 (m, 3H), 2.25–2.46 (m, 2H), 1.91 (m, 3H), 1.62–1.84 (m, 6H), 1.42–1.62 (m, 2H), 1.12–1.42 (m, 3H), 0.84–1.12 (m, 2H).

EXAMPLE 171

(2RS,3R)-3-amino-4-cyclohexyl-2-hydroxy-N'-((3RS)-3-hydroxybutyl)-N'-phenylbutanohydrazide The desired product was prepared by substituting 1-(3-hydroxybutyl)-1-phenylhydrazine for 1-benzylhydrazine dihydrochloride in Example 1.

MS (ESI) m/e 364 (M+H)$^+$; $^1$H NMR (300 MHz, CD$_3$OD) δ 7.23 (m, 2H), 6.92 (m, 2H), 6.84 (m, 1H), 4.30 (d, 1H), 3.44–3.71 (m, 4H), 1.63–1.91 (m, 7H), 1.54 (m, 3H); 1.35 (m, 3H), 1.19 (m, 4H), 0.84–1.12 (m, 2H).

EXAMPLE 172

(2RS,3R)-3-amino-4-cyclohexyl-N'-(2-(((3RS)-3,7-dimethyl-6-octenyl)oxy)ethyl)-2-hydroxy-N'-phenylbutanohydrazide The desired product was prepared by substituting 1-(2-((3,7-dimethyl-6-octenyl)oxy)ethyl)-1-phenylhydrazine for 1-benzylhydrazine dihydrochloride in Example 1.

MS (ESI) m/e 474 (M+H)$^+$; $^1$H NMR (300 MHz, CD$_3$OD) δ 7.24 (m, 2H), 6.93 (m, 2H), 6.85 (m, 1H), 5.09 (m, 1H), 4.33 (d, 1H), 3.72 (m, 2H), 3.67 (m, 2H), 3.50 (m, 3H), 2.04 (m, 2H), 1.58–1.91 (m, 6H), 1.50–1.20 (m, 10H), 1.17 (s, 3H), 1.12 (s, 3H), 0.91 (m, 2H), 0.87 (d, 3H).

EXAMPLE 173

(2RS,3R)-3-amino-4-cyclohexyl-N'-(2-((1 RS)-3,3-dimethylcyclohexyl)ethyl)-2-hydroxy-N'-phenylbutanohydrazide The desired product was prepared by substituting 1-(2-(3,3-dimethylcyclohexyl)ethyl)-1-phenylhydrazine for 1-benzylhydrazine dihydrochloride in Example 1.

MS (ESI) m/e 430 (M+H)$^+$; $^1$H NMR (300 MHz, CD$_3$OD) δ 7.22 (m, 2H), 6.89 (m, 2H), 6.82 (m, 1H), 4.26 (d, 1H), 3.53 (m, 3H), 1.65–1.94 (m, 7H), 1.18–1.65 (m, 11H), 0.94–1.18 (m, 4H), 0.92 (s, 3H), 0.91 (s, 3H), 0.65–0.87 (m, 2H).

EXAMPLE 174

(2RS,3R)-3-amino-N'-((4S)-6-bromo-4-methylhexyl)-4-cyclohexyl-2-hydroxy-N'-phenylbutanohydrazide The desired product was prepared by substituting 1-((4S)-6-bromo-4-methylhexyl)-1-phenylhydrazine for 1-benzylhydrazine dihydrochloride in Example 1.

MS (ESI) m/e 468, 470 (M+H)$^+$; $^1$H NMR (300 MHz, CD$_3$OD) δ 7.23 (m, 2H), 6.89 (m, 2H), 6.83 (m, 1H), 4.27 (d, 1H), 3.55 (m, 3H), 1.65–1.89 (m, 6H), 1.45–1.65 (m, 9H), 1.17–1.42 (m, 5H), 0.97 (d, 3H), 0.95 (m, 2H).

EXAMPLE 175

(2RS,3R)-3-amino-4-cyclohexyl-N'-(cyclohexylmethyl)-2-hydroxy-N'-phenylbutanohydrazide The desired product was prepared by substituting 1-cyclohexylmethyl-1-phenylhydrazine for 1-benzylhydrazine dihydrochloride in Example 1.

MS (ESI) m/e 388 (M+H)$^+$; $^1$H NMR (300 MHz, CD$_3$OD) δ 7.21 (m, 2H), 6.86 (m, 2H), 6.80 (m, 1H), 4.25 (d, 1H), 3.54 (dt, 1H), 3.31 (d, 2H), 1.92 (m, 2H), 1.59–1.84 (m, 10H), 1.51 (m, 2H), 1.13–1.42 (m, 6H), 0.81–1.13 (m, 4H).

EXAMPLE 176

N'-((2RS,3R)-3-amino-5-(ethylsulfanyl)-2-hydroxypentanoyl)-2-naphthohydrazide

The desired product was prepared by substituting 2-naphthoylhydrazine for O-phenyl hydroxylamine hydrochloride in Example 98B.

MS (ESI) m/e 362 (M+H)$^+$; $^1$H NMR (300 MHz, CD$_3$OD) δ 8.48 (m, 1H), 7.89–8.09 (m, 4H), 7.47–7.75 (m, 2H), 4.54 (d, 0.34H), 4.48 (d, 0.66H), 3.56–3.87 (m, 1H), 2.76 (m, 2H), 2.62 (q, 1.32H), 2.60 (q, 068H), 2.10–2.31 (m, 0.68H), 1.84–2.08 (m, 1.32H), 1.28 (t, 1.98H), 1.27 (t, 1.02H).

EXAMPLE 177

(2RS,3R)-3-amino-5-(ethylsulfanyl)-2-hydroxy-N-(1-piperidinyl)pentanamide

The desired product was prepared by substituting 1-aminopiperidine for O-phenyl hydroxylamine hydrochloride in Example 98B.

MS (ESI) m/e 276 (M+H)+; 1H NMR (300 MHz, CD3OD) δ 4.67 (m, 0.28H), 4.62 (m, 0.72H), 3.37–3.78 (m, 5H), 2.72–3.16 (m, 4H), 2.00–2.30 (m, 2H), 1.70 (m, 4H), 1.57 (m, 2H), 1.35 (t, 2.16H), 1.33 (m, 0.84H).

EXAMPLE 178

N'-((2RS,3R)-3-amino-5-(ethylsulfanyl)-2-hydroxypentanoyl)benzohydrazide

The desired product was prepared by substituting benzoylhydrazine for O-phenyl hydroxylamine hydrochloride in Example 98B.

MS (ESI) m/e 312 (M+H)+; 1H NMR (300 MHz, CD3OD) δ 7.89 (m, 2H), 7.61 (m, 1H), 7.50 (m, 2H), 4.49 (d, 0.24H), 4.44 (d, 0.76H), 3.79 (m, 1H), 2.71 (t, 2H), 2.60 (q, 2H), 2.17 (m, 1H), 1.99 (m, 1H), 1.27 (t, 3H.)

EXAMPLE 179

(2RS,3R)-3-amino-5-(ethylsulfanyl)-2-hydroxy-N'-(4-iodophenyl)pentanohydrazide

The desired product was prepared by substituting 1-(4-iodophenyl)hydrazine for 1-benzylhydrazine dihydrochloride and Example 98A for Example 1C in Example 1D.

MS (ESI) m/e 410 (M+H)+; 1H NMR (300 MHz, CD3OD) δ 7.48 (m, 2H), 6.67 (m, 2H), 4.43 (d, 0.38H), 4.36 (d, 0.62H), 3.74 (m, 1H), 2.72 (m, 2H), 2.57 (q, 0.76H), 2.51 (q, 1.24H), 2.11 (m, 0.76H), 1.93 (m, 1.24H), 1.26 (t, 1.86H), 1.22 (t, 1.14H).

EXAMPLE 180

(2RS,3R)-3-amino-5-(ethylsulfanyl)-2-hydroxy-N'-cyclopentylpentanohydrazide

The desired product was prepared by substituting 1-(cyclopentyl)hydrazine for 1-benzylhydrazine dihydrochloride and Example 98A for Example 1C in Example 1D.

MS (ESI) m/e 276 (M+H)+; 1H NMR (300 MHz, CD3OD) δ 4.36 (d, 0.23H), 4.27 (d, 0.77H), 3.67 (td, 1H), 3.53 (m, 1H), 2.68 (m, 2H), 2.57 (q, 1.54H), 2.54 (q, 0.46H), 2.07 (m, 0.46H), 1.91 (m, 1.54H), 1.76 (m, 4H), 1.44–1.67 (m, 4H), 1.26 (t, 2.31H), 1.24 (t, 0.69H).

EXAMPLE 181

(2RS,3R)-3-amino-5-(ethylsulfanyl)-2-hydroxy-N'-(3-chlorophenyl)pentanohydrazide The desired product was prepared by substituting 1-(3-chlorophenyl)hydrazine for 1-benzylhydrazine dihydrochloride and Example 98A for Example 1C in Example 1D.

MS (ESI) m/e 318 (M+H)+; 1H NMR (300 MHz, CD3OD) δ 7.15 (m, 1H), 6.85 (m, 1H), 6.77 (m, 2H), 5.98 (d, 0.32H), 5.85 (d, 0.68H), 3.71 (m, 1H), 3.43 (q, 1.36H), 3.36 (q, 0.64H), 2.70 (m, 2H), 2.11 (m, 0.64H), 1.95 (m, 1.36H), 1.67 (t, 2.04H), 1.63 (t, 0.96H).

EXAMPLE 182

(2RS,3R)-3-amino-5-(ethylsulfanyl)-2-hydroxy-N'-(3-methoxyphenyl)pentanohydrazide The desired product was prepared by substituting 1-(3-methoxyphenyl)hydrazine for 1-benzylhydrazine dihydrochloride and Example 98A for Example 1C in Example 1D.

MS (ESI) m/e 314 (M+H)+; 1H NMR (300 MHz, CD3OD) δ 7.09 (m, 1H), 6.44 (m, 3H), 4.43 (d, 0.37H), 4.36 (d, 0.63H), 3.75 (s, 3H), 3.69 (m, 1H), 2.71 (m, 2H), 2.57 (q, 1.26H), 2.50 (q, 0.74H), 2.12 (m, 0.74H), 1.82–2.04 (m, 1.26H), 1.25 (t, 1.89H), 1.21 (t, 1.11H).

EXAMPLE 183

(2RS,3R)-3-amino-5-(ethylsulfanyl)-2-hydroxy-N'-(2-chlorophenyl)pentanohydrazide The desired product was prepared by substituting 1-(2-chlorophenyl)hydrazine for 1-benzylhydrazine dihydrochloride and Example 98A for Example 1C in Example 1D.

MS (ESI) m/e 318 (M+H)+; 1H NMR (300 MHz, CD3OD) δ 7.29 (m, 1H), 7.17 (m, 1H), 6.93 (m, 1H), 6.83 (m, 1H), 4.47 (d, 0.23H), 4.41 (d, 0.77H), 3.76 (m, 1H), 2.71 (m, 2H), 2.58 (q, 1.54H), 2.52 (q, 0.46H), 2.13 (td, 0.46H), 1.95 (m, 1.54H), 1.26 (t, 2.31H), 1.22 (t, 0.69H).

EXAMPLE 184

(2RS,3R)-3-amino-5-(ethylsulfanyl)-2-hydroxy-N'-(3-trifluoromethylphenyl)pentanohydrazide The desired product was prepared by substituting 1-(3-(trifluoromethyl)phenyl)hydrazine for 1-benzylhydrazine dihydrochloride and Example 98A for Example 1C in Example 1D.

MS (ESI) m/e 352 (M+H)+; 1H NMR (300 MHz, CD3OD) δ 7.37 (m, 1H), 7.08 (m, 3H), 4.48 (d, 0.39H), 4.40 (d, 0.61H), 3.69 (m, 1H), 2.71 (m, 2H), 2.57 (q, 1.22H), 2.51 (q, 0.78H), 2.13 (m, 0.78H), 1.84–2.05 (m, 1.22H), 1.25 (t, 1.83H), 1.21 (t, 1.17H).

EXAMPLE 185

N'-((2RS,3R)-3-amino-5-(ethylsulfanyl)-2-hydroxypentanoyl)-3-chlorobenzohydrazide The desired product was prepared by substituting 3-chlorobenzoylhydrazine for O-phenyl hydroxylamine hydrochloride in Example 98B.

MS (ESI) m/e 346 (M+H)+; 1H NMR (300 MHz, CD3OD) δ 7.89 (m, 1H), 7.81 (m, 1H), 7.61 (m, 1H), 7.50 (m, 1H), 4.49 (d, 0.14H), 4.44 (d, 0.86H), 3.78 (m, 1H), 2.70 (t, 2H), 2.60 (dd, 2H), 2.16 (m, 1H), 1.98 (m, 1H), 1.27 (t, 3H).

EXAMPLE 186

N'-((2RS,3R)-3-amino-5-(ethylsulfanyl)-2-hydroxypentanoyl)-2-chlorobenzohydrazide The desired product was prepared by substituting 2-chlorobenzoylhydrazine for O-phenyl hydroxylamine hydrochloride in Example 98B.

MS (ESI) m/e 346 (M+H)+; 1H NMR (300 MHz, CD3OD) δ 7.62 (m, 1H), 7.46 (m, 3H), 4.49 (d, 0.26H), 4.43 (d, 0.74H), 3.80 (m, 1H), 2.71 (t, 2H), 2.60 (q, 0.52H), 2.57 (q, 1.48H), 2.16 (m, 0.52H), 1.99 (m, 1.48H), 1.27 (t, 2.22H), 1.24 (t, 0.78H).

EXAMPLE 187

(2RS,3R)-3-amino-5-(ethylsulfanyl)-2-hydroxy-N'-(4-isopropyl)pentanohydrazide

The desired product was prepared by substituting 1-(4-(2-methylethyl)phenyl)hydrazine for 1-benzylhydrazine dihydrochloride and Example 98A for Example 1C in Example 1D.

MS (ESI) m/e 326 (M+H)+; ¹H NMR (300 MHz, CD₃OD) δ 7.02 (d, 2H), 6.77 (d, 2H), 4.42 (d, 0.41H), 4.35 (d, 0.59H), 3.74 (m, 1H), 2.61–2.81 (m, 2H), 2.55 (m, 3H), 2.02–2.24 (m, 0.82H), 1.81–2.02 (m, 1.18H), 1.26 (t, 1.77H), 1.22 (t, 1.23H) 1.17 (d, 6H).

EXAMPLE 188

(2RS,3R)-3-amino-5-(ethylsulfanyl)-2-hydroxy-N'-(3-chloro-4-methylphenyl)pentanohydrazide The desired product was prepared by substituting 1-(3-chloro-4-methylphenyl)hydrazine for 1-benzylhydrazine dihydrochloride and Example 98A for Example 1C in Example 1D.

MS (ESI) m/e 332 (M+H)+; ¹H NMR (300 MHz, CD₃OD) δ 7.09 (m, 1H), 6.86 (m, 1H), 6.71 (m, 1H), 4.43 (d, 0.33H), 4.36 (d, 0.67H), 3.73 (m, 1H), 2.71 (m, 2H), 2.57 (q, 1.34H), 2.50 (q, 0.66H), 2.25 (m, 3H), 2.12 (m, 0.66H), 1.82–2.04 (m, 1.34H), 1.25 (t, 2.01H), 1.21 (t, 1H).

EXAMPLE 189

(2RS,3R)-3-amino-5-(ethylsulfanyl)-2-hydroxy-N'-(3-fluorophenyl)pentanohydrazide The desired product was prepared by substituting 1-(3-fluorophenyl)hydrazine for 1-benzylhydrazine dihydrochloride and Example 98A for Example 1C in Example 1D.

MS (ESI) m/e 302 (M+H)+; ¹H NMR (400 MHz, CD₃OD) δ 7.15 (m, 1H), 6.64 (m, 1H), 6.52 (m, 2H), 4.48 (d, 0.37H), 4.38 (d, 0.63H), 3.80 (m, 0.37H), 3.70 (m, 0.63H), 2.70 (m, 2H), 2.57 (q, 1.23H), 2.52 (q, 0.74H), 2.12 (m, 0.74H), 1.95 (m, 1.23H), 1.25 (t, 1.89H), 1.22 (t, 11H).

EXAMPLE 190

(2RS,3R)-3-amino-5-(ethylsulfanyl)-2-hydroxy-N'-(2-ethylphenyl)pentanohydrazide

The desired product was prepared by substituting 1-(2-ethylphenyl)hydrazine for 1-benzylhydrazine dihydrochloride and Example 98A for Example 1C in Example 1D.

MS (ESI) m/e 312 (M+H)+; ¹H NMR (300 MHz, CD₃OD) δ 7.07 (m, 1H), 6.90 (m, 1H), 6.86 (m, 1H), 6.73 (m, 1H), 4.44 (d, 0.26H), 4.37 (d, 0.74H), 3.80 (m, 1H), 2.45–2.71 (m, 6H), 2.02 (m, 2H), 1.15–1.27 (m, 6H).

EXAMPLE 191

(2RS,3R)-3-amino-5-(ethylsulfanyl)-2-hydroxy-N'-(4-fluorophenyl)pentanohydrazide The desired product was prepared by substituting 1-(4-fluorophenyl)hydrazine for 1-benzylhydrazine dihydrochloride and Example 98A for Example 1C in Example 1D.

MS (ESI) m/e 302 (M+H)+; ¹H NMR (300 MHz, CD₃OD) δ 6.96 (m, 2H), 6.84 (m, 2H), 4.42 (d, 0.41H), 4.35 (d, 0.59H), 3.74 (m, 1H), 2.61–2.81 (m, 2H), 2.57 (q, 1.18H), 2.51 (q, 0.82H), 2.02–2.24 (m, 0.82H), 1.81–2.02 (m, 1.18H), 1.26 (t, 1.77H), 1.22 (t, 1.23H).

EXAMPLE 192

(2RS,3R)-3-amino-5-(ethylsulfanyl)-2-hydroxy-N'-(4-trifluoromethoxyphenyl)pentanohydrazide The desired product was prepared by substituting 1-(4-(trifluoromethoxy)phenyl)hydrazine for 1-benzylhydrazine dihydrochloride and Example 98A for Example 1C in Example 1D.

MS (ESI) m/e 368 (M+H)+; ¹H NMR (300 MHz, CD₃OD) δ 7.00–7.20 (m, 2H), 6.87 (m, 2H), 4.44 (d, 0.42H), 4.37 (d, 0.58H), 3.63–3.83 (m, 1H), 2.71 (m, 2H), 2.57 (q, 1.16H), 2.51 (q, 0.84H), 2.11 (m, 0.84H), 1.82–2.03 (m, 1.16H), 1.25 (t, 1.74H), 1.22 (t, 1.26H).

EXAMPLE 193

(2RS,3 S)-3-amino-4-(ethylsulfanyl)-2-hydroxy-N'-(4-methylphenyl)butanohydrazide To DCC resin (148 mg, 0.225 mmol) in 1.0 mL of dichloromethane was added 0.5 mL of a 0.45 M solution of HOBt (0.225 mmol) in dimethylacetamide/dichloromethane (1:6), and 0.5 mL of a 0.3M solution of Example 97A (0.15 mmol) in dimethylacetamide. After 5 minutes, 1.0 mL of a 0.225 M solution of 4-methylphenylhydrazine (0.225 mmol) in dimethylacetamide/dichloromethane (1:1) was added. The mixture was agitated for 18 hours and quenched with 0.19 g of trisamine resin (0.75 mmol) followed by 0.13 g of isocyanate resin (0.225 mmol) and agitated for 4 hours. The mixture was filtered and the resins washed with 1×3 mL of dichloromethane, the solvent was removed in vacuo, and the crude material purified by reverse phase preparative HPLC. The resulting material was treated with 1 mL of 50% trifluoroacetic acid/dichloromethane and agitated at ambient temperature for 18 hours. The solvent was removed in vacuo to give the desired product.

MS (ESI) m/e 284 (M+H)+; ¹H NMR (500 MHz, CD₃OD) δ 7.02 (m, 2H), 6.77 (m, 2H), 4.51 (d, 0.65H), 4.39 (d, 0.35H), 3.77 (m, 1H), 2.96 (dd, 1H), 2.76 (dd, 1H), 2.63 (dd, 1.3H), 2.57 (dd, 0.7H), 2.23 (s, 3H), 1.28 (t, 1.95H), 1.23 (t, 1.05H).

EXAMPLE 194

(2RS,3R)-3-amino-3-cyclohexyl-2-hydroxy-N'-(4-methylphenyl)propanohydrazide

The desired product was prepared by substituting Example 122A for Example 97A in Example 193.

MS (ESI) m/e 292 (M+H)+; ¹H NMR (500 MHz, CD₃OD) δ 7.02 (m, 2H), 6.77 (m, 2H), 4.45 (d, 0.65H), 4.43 (d, 0.35H), 3.27 (m, 1H), 2.23 (s, 3H), 1.87–1.72 (m, 6H), 1.36–1.12 (m, 5H).

EXAMPLE 195

(2RS,3 S)-3-amino-2-hydroxy-N'-(4-methylphenyl)-4-(propylsulfanyl)butanohydrazide

EXAMPLE 195A (2S)-2-((tert-butoxycarbonyl)amino)-3-(propylsulfanyl)propanoic acid The desired product was prepared by substituting 1-bromopropane for 2-brompropane and D-cystine for D-homocystine in Example 123A.

EXAMPLE 195B (2RS,3S)-2-hydroxy-3-((tert-butoxycarbonyl)amino)-3-(propylsulfanyl)propanoic acid The desired product was prepared by substituting Example 195A for (2R)-2-((tert-butoxycarbonyl)amino)-3-cyclohexylpropanoic acid in Examples 1A–C.

MS (ESI) m/e 294 (M+H)+.

EXAMPLE 195C (2RS,3S)-3-amino-2-hydroxy-N'-(4-methylphenyl)-4-(propylsulfanyl)butanohydrazide The desired product was prepared by substituting Example 195B for Example 97A in Example 193.

MS (ESI) m/e 298 (M+H)+; $^1$H NMR (500 MHz, CD$_3$OD) δ 7.02 (dd, 2H), 6.77 (dd, 2H), 4.50 (d, 0.65H), 4.48 (d, 0.35H), 3.76 (m, 0.65H), 3.67–3.58 (m, 0.35H), 2.93 (dd, 0.65H), 2.84 (dd, 0.35H), 2.75 (m, 1H), 2.58 (dd, 1H), 2.51 (m, 1H), 2.23 (s, 3H), 1.65 (dd, 1H), 1.57 (dd, 1H), 1.02 (t, 1.95H), 0.98 (t, 1.05H).

EXAMPLE 196

(2RS,3R)-3-amino-2-hydroxy-5-(isopropylsulfanyl)-N'-(4-methylphenyl)pentanohydrazide The desired product was prepared by substituting Example 123B for Example 97A in Example193.

MS (ESI) m/e 312 (M+H)+; $^1$H NMR (500 MHz, CD$_3$OD) δ 7.01 (dd, 2H), 6.77 (d, 2H), 4.40 (d, 0.35H), 4.33 (d, 0.65H), 3.66 (m, 1H), 2.96 (dd, 0.65H), 2.89 (dd, 0.35H), 2.69 (m, 1.65H), 2.58 (m, 0.35H), 2.23 (s, 3H), 2.09 (dd, 0.65H), 1.96 (dd, 0.35H), 1.89 (dd, 1H), 1.27 (d, 3H), 1.26 (d, 3H).

EXAMPLE 197

(2RS,3S)-3-amino-2-hydroxy-4-(isobutylsulfanyl)-N'-(4-methylphenyl)butanohydrazide The desired product was prepared by substituting Example 124B for Example 97A in Example 193.

MS (ESI) m/e 312 (M+H)+; $^1$H NMR (500 MHz, CD$_3$OD) δ 7.02 (d, 2H), 6.77 (d, 2H), 4.52 (d, 1H), 3.65 (ddd, 1H), 2.94 (dd, 1H), 2.75 (dd, 1H), 2.51 (d, 2H), 2.23 (s, 3H), 1.82 (ddd, 1H), 1.02 (d, 6H).

EXAMPLE 198

(2RS,3R)-3-amino-2-hydroxy-5-phenyl-N'-(4-methylphenyl)pentanohydrazide

The desired product was prepared by substituting Example 125A for Example 97A in Example 193.

MS (ESI) m/e 314 (M+H)+; $^1$H NMR (500 MHz, CD$_3$OD) δ 7.30 (m, 2H), 7.25–7.18 (m, 3H), 6.97 (m, 2H), 6.74 (m, 2H), 4.43 (d, 0.5H), 4.40 (d, 0.5H), 3.57 (m, 1H), 2.78 (m, 1.5H), 2.67 (m, 0.5H), 2.27 (m, 0.5H), 2.23 (s, 1.5H), 2.21 (s, 1.5H), 2.14 (m, 0.5H), 2.00 (m, 0.5H), 1.93 (m, 0.5H).

EXAMPLE 199

(2S,3R)-3-amino-3-cyclooctyl-2-hydroxy-N'-(4-methylphenyl)propanohydrazide

EXAMPLE 199A (2S,3R)-3-(tertbutoxycarbonyl)amino-3-cyclooctyl-2-hydroxy-propanoic acid The desired product was prepared by substituting cyclooctyl aldehyde for 2-ethylhexanal in Examples 236A–236C.

EXAMPLE 199B (2S,3R)-3-amino-3-cyclooctyl-2-hydroxy-N'-(4-methylphenyl)propanohydrazide The desired product was prepared by substituting Example 199A for Example 97A in Example 193.

MS (ESI) m/e 320 (M+H)+; $^1$H NMR (500 MHz, CD$_3$OD) δ 7.02 (d, 2H), 6.77 (m, 2H), 4.46 (d, 0.35H), 4.38 (d, 0.65H), 3.85 (m, 1H), 3.78 (m, 1H), 2.25 (s, 1.05H), 2.23 (s, 2.95H), 1.80–1.50 (m, 14H).

EXAMPLE 200

(2RS,3S)-3-amino-4-((cyclohexylmethyl)sulfanyl)-2-hydroxy-N'-(4-methylphenyl)butanohydrazide

EXAMPLE 200A (2S)-2-((tert-butoxycarbonyl)amino)-3-(cyclohexylmethylsulfanyl)propanoic acid The desired product was prepared by substituting cyclohexylmethyl bromide for 2-brompropane and D-cystine for D-homocystine in Example 123A.

EXAMPLE 200B (2RS,3S)-2-((tert-butoxycarbonyl)amino)-3-(cyclohexylmethylsulfanyl)propanoic acid The desired product was prepared by substituting Example 200A for (2R)-2-((tert-butoxycarbonyl)amino)-3-cyclohexylpropanoic acid in Examples 1A–C.

EXAMPLE 200C (2RS,3S)-3-amino-4-((cyclohexylmethyl)sulfanyl)-2-hydroxy-N'-(4-methylphenyl)butanohydrazide The desired product was prepared by substituting Example 200B for Example 97A in Example 193.

MS (ESI) m/e 298 (M+H)+; $^1$H NMR (500 MHz, CD$_3$OD) δ 7.02 (dd, 2H), 6.77 (d, 2H), 4.52 (d, 0.65H), 4.50 (d, 0.35H), 3.76 (m, 0.35H), 3.67–3.58 (m, 0.65H), 2.93 (dd, 0.65H), 2.82 (dd, 0.35H), 2.75 (m, 1H), 2.48 (m, 1H), 2.41 (m, 1H), 2.23 (s, 3H), 1.86 (m, 2H), 1.75–1.66 (m, 3H), 1.47 (m, 1H), 1.32–1.15 (m, 3H), 1.00 (m, 2H).

EXAMPLE 201

(2RS,3S)-3-amino-4-(ethylsulfanyl)-2-hydroxy-N'-(1-naphthyl)butanohydrazide

The desired product was prepared by substituting 1-napthylhydrazine for 4-methylphenylhydrazine in Example 193.

MS (ESI) m/e 320 (M+H)+; $^1$H NMR (500 MHz, CD$_3$OD) δ 8.07 (m, 1H), 7.81 (ddd, 1H), 7.47 (ddd, 2H), 7.39 (dd, 1H), 7.33 (ddd, 1H), 6.91 (dd, 1H), 4.62 (d, 0.65H), 4.60 (d, 0.35H), 4.51 (m, 0.5H), 3.71 (m, 1H), 3.00 (dd, 0.5H), 2.81 (m, 1H), 2.65 (dd, 1.3H), 2.60 (dd, 0.7H), 1.30 (t, 1.95H), 1.25 (t, 1.05H).

EXAMPLE 202

(2RS,3R)-3-amino-3-cyclohexyl-2-hydroxy-N'-(1-naphthyl)propanohydrazide

The desired product was prepared by substituting 1-napthylhydrazine for 4-methylphenylhydrazine and Example 122A for Example 97A in Example 193.

MS (ESI) m/e 328 (M+H)+; $^1$H NMR (500 MHz, CD$_3$OD) δ 8.08 (m, 1H), 7.82 (ddd, 1H), 7.47 (ddd, 2H), 7.39 (d, 1H), 7.33 (m, 1H), 6.91 (dd, 1H), 4.56 (d, 0.65H), 4.53 (d, 0.35H), 3.37 (dd, 1H), 1.99–1.72 (m, 6H), 1.39–1.12 (m, 5H).

EXAMPLE 203

(2RS,3R)-3-amino-2-hydroxy-5-(isopropylsulfanyl)-N'-(1-naphthyl)pentanohydrazide The desired product was prepared by substituting 1-napthylhydrazine for 4-methylphenylhydrazine and Example 123B for Example 97A in Example 193.

MS (ESI) m/e 348 (M+H)$^+$; $^1$H NMR (500 MHz, CD$_3$OD) δ 8.07 (m, 1H), 7.81 (ddd, 1H), 7.47 (ddd, 2H), 7.39 (m, 1H), 7.34 (m, 1H), 6.90 (dd, 1H), 4.51 (d, 0.35H), 4.46 (d, 0.65H), 3.76 (m, 1H), 2.99 (dd, 0.65H), 2.93 (dd, 0.35H), 2.74 (m, 1.65H), 2.69 (m, 0.35H), 2.17 (dd, 0.65H), 2.05 (dd, 0.35H), 1.95 (dd, 1H), 1.29 (d, 3H), 1.27 (d, 3H).

EXAMPLE 204

(2RS,3S)-3-amino-2-hydroxy-4-(isobutylsulfanyl)-N'-(1-naphthyl)butanohydrazide

The desired product was prepared by substituting 1-napthylhydrazine for 4-methylphenylhydrazine and Example 124B for Example 97A in Example 193.

MS (ESI) m/e 347 (M+H)$^+$; $^1$H NMR (500 MHz, CD$_3$OD) δ 8.06 (m, 1H), 7.82 (ddd, 1H), 7.48 (ddd, 2H), 7.41 (m, 1H), 7.33 (t, 1H), 6.92 (d, 1H), 4.63 (d, 1H), 3.70 (ddd, 1H), 2.99 (dd, 1H), 2.80 (dd, 1H), 2.53 (d, 2H), 1.84 (ddd, 1H), 1.03 (d, 6H).

EXAMPLE 205

(2RS,3R)-3-amino-2-hydroxy-5-phenyl-N'-(1-naphthyl)pentanohydrazide

The desired product was prepared by substituting 1-napthylhydrazine for 4-methylphenylhydrazine and Example 125A for Example 97A in Example 193.

MS (ESI) m/e 350 (M+H)$^+$; $^1$H NMR (500 MHz, CD$_3$OD) δ 8.06 (m, 1H), 7.80 (m, 1H), 7.46 (m, 2H), 7.37 (m, 1H), 7.31 (dd, 1H), 7.25 (m, 5H), 6.86 (dd, 1H), 4.53 (d, 0.5H), 4.51 (d, 0.5H), 3.65 (m, 0.5H), 3.60 (m, 0.5H), 2.82 (m, 1.5H), 2.72 (m, 0.5H), 2.20 (m, 0.5H), 2.08 (m, 1H), 1.98 (m, 0.5H).

EXAMPLE 206

(2RS,3R)-3-amino-3-cyclooctyl-2-hydroxy-N'-(1-naphthyl)propanohydrazide

The desired product was prepared by substituting 1-napthylhydrazine for 4-methylphenylhydrazine and Example 199A for Example 97A in Example 193.

MS (ESI) m/e 356 (M+H)$^+$; $^1$H NMR (500 MHz, CD$_3$OD) δ 8.08 (m, 1H), 7.84 (m, 1H), 7.49 (m, 2H), 7.41 (m, 1H), 7.32 (t, 1H), 6.97 (ddd, 1H), 4.49 (d, 0.5H), 3.99 (d, 0.5H), 3.85 (m, 1H), 1.80–1.52 (m, 15H).

EXAMPLE 207

N'-((2RS,3S)-3-amino-4-(ethylsulfanyl)-2-hydroxybutanoyl)-3-chlorobenzohydrazide The desired product was prepared by substituting 3-chlorobenzoylhydrazide for 4-methylphenylhydrazine in Example 193.

MS (ESI) m/e 332 (M+H)$^+$; $^1$H NMR (500 MHz, CD$_3$OD) δ 7.91 (m, 1H), 7.81 (m, 1H), 7.62 (m, 1H), 7.51 (m, 1H), 4.63 (d, 0.65H), 4.58 (d, 0.35H), 3.70 (m, 1H), 3.00 (dd, 1H), 2.84 (m, 1H), 2.66 (dd, 1.3H), 2.62 (dd, 0.7H), 1.31 (t, 1.95H), 1.29 (t, 1.05H).

EXAMPLE 208

N'-((2RS,3R)-3-amino-3-cyclohexyl-2-hydroxypropanoyl)-3-chlorobenzohydrazide

The desired product was prepared by substituting 3-chlorobenzoylhydrazide for 4-methylphenylhydrazine and Example 122A for Example 97A in Example 193.

MS (ESI) m/e 340 (M+H)$^+$; $^1$H NMR (500 MHz, CD$_3$OD) δ 7.91 (m, 1H), 7.82 (m, 1H), 7.62 (m, 1H), 7.50 (m, 1H), 4.56 (d, 0.65H), 4.52 (d, 0.35H), 3.33 (m, 1H), 1.95 (m, 1H), 1.86 (m, 4H), 1.74 (m, 1H), 1.35 (m, 2H), 1.24 (m, 1H), 1.16 (m, 2H).

EXAMPLE 209

N'-((2RS,3S)-3-amino-2-hydroxy-4-(propylsulfanyl)butanoyl)-3-chlorobenzohydrazide The desired product was prepared by substituting 3-chlorobenzoylhydrazide for 4-methylphenylhydrazine and Example 195B for Example 97A in Example 193.

MS (ESI) m/e 346 (M+H)$^+$; $^1$H NMR (500 MHz, CD$_3$OD) δ 7.91 (ddd, 1H), 7.81 (ddd, 1H), 7.62 (ddd, 1H), 7.50 (m, 1H), 4.63 (d, 0.65H), 4.58 (d, 0.35H), 3.70 (m, 1H), 3.17 (dd, 0.35H), 2.98 (dd, 0.65H), 2.84 (dd, 0.65H), 2.80 (dd, 0.35H), 2.60 (m, 2H), 1.66 (m, 2H), 1.03 (t, 1.95H), 1.01 (t, 1.05H).

EXAMPLE 210

N'-((2RS,3R)-3-amino-2-hydroxy-5-(isopropylsulfanyl)pentanoyl)-3-chlorobenzohydrazide The desired product was prepared by substituting 3-chlorobenzoylhydrazide for 4-methylphenylhydrazine and Example 123B for Example 97A in Example 193.

MS (ESI) m/e 360 (M+H)$^+$; $^1$H NMR (500 MHz, CD$_3$OD) δ 7.90 (dt, 1H), 7.81 (m, 1H), 7.62 (m, 1H), 7.50 (m, 1H), 4.49 (d, 0.3H), 4.45 (d, 0.7H), 3.78 (m, 1H), 3.00 (m, 1H), 2.72 (t, 2H), 2.15 (m, 1H), 1.98 (m, 1H), 1.29–1.24 (m, 6H).

EXAMPLE 211

N'-((2RS,3S)-3-amino-2-hydroxy-4-(isobutylsulfanyl)butanoyl)-3-chlorobenzohydrazide The desired product was prepared by substituting 3-chlorobenzoylhydrazide for 4-methylphenylhydrazine and Example 124B for Example 97A in Example 193.

MS (ESI) m/e 360 (M+H)$^+$; $^1$H NMR (500 MHz, CD$_3$OD) δ 7.91 (dd, 1H), 7.82 (ddd, 1H), 7.63 (ddd, 1H), 7.51 (t, 1H), 4.64 (d, 1H), 3.70 (ddd, 1H), 2.97 (dd, 1H), 2.83 (dd, 1H), 2.53 (d, 2H), 1.85 (ddd, 1H), 1.04 (d, 6H).

EXAMPLE 212

N'-((2RS,3R)-3-amino-2-hydroxy-5-phenylpentanoyl)-3-chlorobenzohydrazide

The desired product was prepared by substituting 3-chlorobenzoylhydrazide for 4-methylphenylhydrazine and Example 125A for Example 97A in Example 193.

MS (ESI) m/e 362 (M+H)$^+$; $^1$H NMR (500 MHz, CD$_3$OD) δ 7.91 (m, 1H), 7.81 (ddd, 1H), 7.61 (ddd, 1H), 7.50 (m, 1H), 7.29 (m, 4H), 7.20 (m, 1H), 4.50 (m, 1H), 3.62 (m, 1H), 2.80 (m, 2H), 2.20 (m, 1H), 2.02 (m, 1H).

EXAMPLE 213

N'-((2RS,3R)-3-amino-3-cyclooctyl-2-hydroxypropanoyl)-3-chlorobenzohydrazide

The desired product was prepared by substituting 3-chlorobenzoylhydrazide for 4-methylphenylhydrazine and Example 199A for Example 97A in Example 193.

MS (ESI) m/e 368 (M+H)+; $^1$H NMR (500 MHz, CD$_3$OD) δ 7.90 (m, 1H), 7.82 (m, 1H), 7.62 (ddd, 1H), 7.50 (t, 1H), 3.95 (d, 1H), 3.82 (t, 1H), 1.81 (m, 4H), 1.68 (m, 4H), 1.55 (m, 7H).

EXAMPLE 214

N'-((2RS,3R)-3-amino-5-cyclohexyl-2-hydroxypentanoyl)-3-chlorobenzohydrazide

The desired product was prepared by substituting 3-chlorobenzoylhydrazide for 4-methylphenylhydrazine and Example 238A for Example 97A in Example 193.

MS (ESI) m/e 367 (M+H)+; $^1$H NMR (500 MHz, CD$_3$OD) δ 7.89 (dd, 1H), 7.80 (d, 1H), 7.62 (ddd, 1H), 7.50 (t, 1H), 3.90 (m, 1H), 3.78 (d, 1H), 1.81–1.72 (m, 5H), 1.68 (m, 1H), 1.54 (m, 2H), 1.29 (m, 4H), 1.21 (m, 1H), 0.96 (m, 2H).

EXAMPLE 215

(2RS,3R)-3-amino-5-cyclohexyl-2-hydroxy-N'-(4-methylphenyl)pentanohydrazide

The desired product was prepared by substituting Example 238A for Example 97A in Example 193.

MS (ESI) m/e 320 (M+H)+; $^1$H NMR (500 MHz, CD$_3$OD) δ 7.07 (d, 0.5H), 7.00 (d, 1.5H), 6.77 (m, 2H), 3.81 (m, 1H), 3.62 (d, 1H), 2.22 (s, 3H), 1.77–1.60 (m, 6H), 1.50 (m, 2H), 1.29–1.17 (m, 6H), 0.97–0.91 (m, 1H).

EXAMPLE 216

(2RS,3S)-3-amino-2-hydroxy-N'-(1-naphthyl)-4-(propylsulfanyl)butanohydrazide

The desired product was prepared by substituting 1-naphthylhydrazine for 4-methylphenylhydrazine and Example 195B for Example 97A in Example 193.

MS (ESI) m/e 334 (M+H)+; $^1$H NMR (500 MHz, CD$_3$OD) δ 8.06 (m, 1H), 7.81 (ddd, 1H), 7.47 (ddd, 2H), 7.39 (d, 1H), 7.34 (m, 1H), 6.90 (dd, 1H), 4.62 (d, 0.65H), 4.59 (d, 0.35H), 3.71 (m, 1H), 2.99 (dd, 0.56H), 2.92 (dd, 0.35H), 2.81 (m, 1H), 2.60 (dd, 1H), 2.54 (m, 1H), 1.66 (dd, 1H), 1.59 (dd, 1H), 1.02 (t, 1.95H), 0.98 (t, 1.05H).

EXAMPLE 217

(2RS,3R)-3-amino-5-cyclohexyl-2-hydroxy-N'-(1-naphthyl)pentanohydrazide

The desired product was prepared by substituting 1-naphthylhydrazine for 4-methylphenylhydrazine and Example 238A for Example 97A in Example 193.

MS (ESI) m/e 356 (M+H)+; $^1$H NMR (500 MHz, CD$_3$OD) δ 8.06 (m, 1H), 7.81 (m, 1H), 7.47 (m, 2H), 7.41 (m, 1H), 7.31 (t, 1H), 6.95 (dd, 1H), 3.91 (m, 1H), 3.78 (d, 1H), 1.74 (m, 5H), 1.55 (m, 2H), 1.28 (m, 4H), 1.20 (m, 2H), 0.97 (m, 2H).

EXAMPLE 218

(2RS,3S)-3-amino-4-((cyclohexylmethyl)sulfanyl)-2-hydroxy-N'-(1-naphthyl)butanohydrazide The desired product was prepared by substituting 1-naphthylhydrazine for 4-methylphenylhydrazine and Example 200B for Example 97A in Example 193.

MS (ESI) m/e 388 (M+H)+; $^1$H NMR (500 MHz, CD$_3$OD) δ 8.06 (m, 1H), 7.81 (ddd, 1H), 7.47 (ddd, 2H), 7.39 (dd, 1H), 7.32 (m, 1H), 6.90 (dd, 1H), 4.62 (d, 0.65H), 4.58 (d, 0.35H), 3.68 (m, 1H), 2.96 (dd, 1H), 2.83 (dd, 0.35H), 2.77 (dd, 0.65H), 2.51 (d, 1.5H), 2.44 (d, 0.5H), 1.88 (m, 2H), 1.75–1.66 (m, 3H), 1.50 (m, 1H), 1.22, (m, 3H), 0.98 (m, 2H).

EXAMPLE 219

N'-((2RS,3S)-3-amino-4-((cyclohexylmethyl)sulfanyl)-2-hydroxybutanoyl)-3-chlorobenzohydrazide The desired product was prepared by substituting 3-chlorobenzoylhydrazide for 4-methylphenylhydrazine and Example 200B for Example 97A in Example 193.

MS (ESI) m/e 401 (M+H)+; $^1$H NMR (500 MHz, CD$_3$OD) δ 7.91 (m, 1H), 7.81 (dd, 1H), 7.61 (ddd, 1H), 7.50 (t, 1H), 4.63 (d, 0.65H), 4.56 (d, 0.35H), 3.68 (m, 1H), 2.95 (dd, 1H), 2.81 (dd, 1H), 2.78 (dd, 0.35H), 2.52 (d, 1H), 2.46 (m, 0.65H), 1.88 (m, 2H), 1.76–1.64 (m, 3H), 1.51 (m, 1H), 1.32–1.16 (m, 3H), 0.99 (m, 2H).

Example 220

(2RS,3R)-3-amino-2-hydroxy-5-phenyl-N'-(1-naphthyl)pentanohydrazide

The desired product was prepared by substituting 2-naphthoylhydrazine for O-phenyl hydroxylamine hydrochloride and Example 125A for Example 98A in Example 98B.

MS (ESI) m/e 378 (M+H)+; $^1$H NMR (300 MHz, DMSO-d$_6$) δ 10.73 (br s, 1H), 10.32 (br s, 1H), 8.52 (s, 1H), 8.04 (m, 6H), 7.65 (m, 2H), 7.30 (m, 5H), 6.69 (m, 1H), 4.32 (m, 1H), 2.74 (m, 2H), 2.06 (m, 1H), 1.89 (m, 1H).

EXAMPLE 221

N'-((2RS,3R)-3-amino-3-cyclohexyl-2-hydroxypropanoyl)-2-naphthohydrazide

The desired product was prepared by substituting 2-naphthoylhydrazine for O-phenyl hydroxylamine hydrochloride and Example 122A for Example 98A in Example 98B.

MS (ESI) m/e 356 (M+H)+; $^1$NMR (300 MHz, DMSO-d$_6$) δ 10.60 (s, 1H), 10.29 (s, 1H), 8.51 (s, 1H), 8.07 (m, 4H), 7.80 (br s, 2H), 7.64 (m, 2H), 6.54 (m, 1H), 4.41 (m, 1H), 1.77–1.44 (m, 6H), 1.20–0.94 (m, 5H).

EXAMPLE 222

N'-((2RS,3R)-3-amino-2-hydroxy-5-isopropylsulfanylpentanoyl)-2-naphthohydrazide

The desired product was prepared by substituting 2-naphthoylhydrazine for O-phenyl hydroxylamine hydrochloride and Example 123B for Example 98A in Example 98B.

MS (ESI) m/e 376 (M+H)+; $^1$H NMR (300 MHz, DMSO-d$_6$) δ 10.56 (br s, 0.7H), 10.47 (br s, 0.3H), 9.90 (br s, 0.3H), 9.83 (br s, 0.7H), 8.75 (s, 0.3H), 8.51 (s, 0.7H), 8.00 (m, 3H), 7.63 (m, 2H), 7.38 (m, 1H), 7.22 (m, 1H), 6.89 (m, 1H), 6.18 (m, 1H), 4.21 (m, 0.7H), 4.13 (m, 0.3H), 2.96 (m, 1H), 2.70 (m, 1H), 2.62 (m, 1H), 1.91 (m, 1H), 1.73 (m, 1H), 1.21 (d, 6H).

EXAMPLE 223

N'-((2RS,3S)-3-amino-2-hydroxy-4-(isobutylsulfanyl)butanoyl)-2-naphthohydrazide

The desired product was prepared by substituting 2-naphthoylhydrazine for O-phenyl hydroxylamine hydrochloride and Example 124B for Example 98A in Example 98B.

MS (ESI) m/e 376 (M+H)+; 1H NMR (300 MHz, DMSO-d6) δ 8.52 (s, 1H), 8.04 (m, 6H), 7.65 (m, 2H), 6.74 (m, 1H), 4.40 (m, 1H), 2.94 (dd. 1H), 2.72 (dd, 1H), 2.48 (d, 2H), 1.80 (m, 1H), 0.98 (d, 6H).

EXAMPLE 224

N'-((2S,3R)-3-amino-2-hydroxy-5-(isopropylsulfanyl)pentanoyl)-3-chlorobenzohydrazide

EXAMPLE 224A

N'-((2S,3R)-3-(tert-butoxycarbonyl)amino-2-hydroxy-5-(isopropylsulfanyl)pentanoyl)-3-chlorobenzohydrazide A solution of Example 123B (0.20 g, 0.65 mmol), 3-chlorobenzoyl hydrazine (0.17 g, 1.0 mmol), 1-(3-dimethylaminopropyl)-3-ethylcarbodiimide hydrochloride (0.13 g, 0.68 mmol), 1-hydroxybenzotriazole (0.11 g, 0.81 mmol), and N-methylmorpholine (0.070 mL, 0.64 mmol) in dichloromethane (6 mL) at room temperature was stirred for 16 hours, diluted with dichloromethane, washed sequentially with aqueous NaHCO3, brine, 10% KHSO4, and brine, dried (MgSO4), filtered, and concentrated. The concentrate was purified by HPLC on silica gel with 4:1/hexanes:acetone to provide the desired product.

MS (ESI) m/e 460 (M+H)+;

EXAMPLE 224B

N'-((2S,3R)-3-amino-2-hydroxy-5-(isopropylsulfanyl)pentanoyl)-3-chlorobenzohydrazide The desired product was prepared by substituting Example 224A for Example 118A in Example 118B.

MS (ESI) m/e 360 (M+H)+; 1H NMR (300 MHz, DMSO-d6) δ 11.60 (br s, 1H), 10.30 (br s, 1H), 8.01 (br s, 2H), 7.92 (m, 1H), 7.85 (d, 1H), 7.69 (m, 1H), 7.57 (t, 1H), 6.67 (d, 1H), 4.26 (m, 1H), 2.97 (m, 1H), 2.70 (m, 1H), 2.62 (m, 1H), 1.97 (m, 1H), 1.85 (m, 1H), 1.21 (d, 6H).

EXAMPLE 225

N'-((2S,3R)-3-amino-2-hydroxy-5-(ethylsulfanyl)pentanoyl)-3-chlorobenzohydrazide

EXAMPLE 225A

N'-((2S,3R)-3-(tert-butoxycarbonyl)amino-2-hydroxy-5-(isopropylsulfanyl)pentanoyl)-3-chlorobenzohydrazide The desired product was prepared by substituting Example 98A for Example 123B in Example 224A.

MS (ESI) m/e 446 (M+H)+.

EXAMPLE 225B

N'-((2S,3R)-3-amino-2-hydroxy-5-(ethylsulfanyl)pentanoyl)-3-chlorobenzohydrazide The desired product was prepared by substituting Example 225A for Example 118A in Example 118B.

MS (ESI) m/e 346 (M+H)+; 1H NMR (300 MHz, DMSO-d6) δ 10.68 (br s, 1H), 10.29 (br s, 1H), 7.99 (br s, 2H), 7.91 (m, 1H), 7.84 (m, 1H), 7.69 (m, 1H), 7.57 (t, 1H), 6.67 (d, 1H), 4.25 (m, 1H), 3.40 (m, 1H), 2.67 (m, 2H), 2.50 (m, 2H), 1.99 (m, 1H), 1.85 (m, 1H), 1.19 (t, 3H).

EXAMPLE 226

N'-((2RS,3R)-3-amino-4-cyclohexyl-2-hydroxybutanoyl)-1-naphthohydrazide

The desired product was prepared by substituting 1-naphthoylhydrazine for O-phenyl hydroxylamine hydrochloride and Example 1C for Example 98A in Example 98B.

MS (ESI) m/e 370 (M+H)+; 1H NMR (300 MHz, DMSO-d6) δ 10.53 (br s, 1H), 10.34 (br s, 1H), 8.34 (dd, 1H), 8.08 (d, 1H), 8.01 (m, 1H), 7.85 (br s, 2H), 7.66 (m, 1H), 7.59 (m, 3H), 6.61 (d, 1H), 4.20 (m, 1H), 1.74–1.60 (m, 6H), 1.50–1.40 (m, 1H), 1.33–1.15 (m, 4H), 0.96–0.80 (m, 2H).

EXAMPLE 227

N'-((2RS,3R)-3-amino-4-cyclohexyl-2-hydroxybutanoyl)-3-hydroxy-2-naphthohydrazide The desired product was prepared by substituting 3-hydroxy-2-naphthoylhydrazine for O-phenyl hydroxylamine hydrochloride and Example 1 C for Example 98A in Example 98B.

MS (ESI) m/e 386 (M+H)+; 1H NMR (300 MHz, DMSO-d6) δ 11.44 (br s, 1H), 10.70 (br s, 1H), 10.58 (br s, 1H), 8.52 (s, 1H), 7.93 (d, 1H), 7.79 (m, 3H), 7.53 (t, 1H), 7.38 (d, 1H), 7.43 (s, 1H), 6.61 (d, 1H), 4.22 (m, 1H), 1.74–1.60 (m, 6H), 1.50–1.40 (m, 1H), 1.33–1.15 (m, 4H), 0.96–0.80 (m, 2H).

EXAMPLE 228

N'-((2RS,3R)-3-amino-5-(ethylsulfanyl)-2-hydroxypentanoyl)-1-naphthohydrazide

The desired product was prepared by substituting 1-naphthoylhydrazine for O-phenyl hydroxylamine hydrochloride in Example 98B.

MS (ESI) m/e 362 (M+H)+; 1H NMR (300 MHz, DMSO-d6) δ 10.54 (br s, 1H), 10.37 (br s, 1H), 8.34 (br s, 1H), 8.01 (m, 3H), 7.59 (m, 4H), 6.68 (d, 0.7H), 6.60 (d, 0.3H), 4.40 (m, 0.3H), 4.26 (m, 0.7H), 3.39 (m, 1H), 2.70 (m, 2H), 2.54 (m, 2H), 2.06 (m, 1H), 1.87 (m, 1H), 1.19 (t, 3H).

EXAMPLE 229

N'-((2RS,3R)-3-amino-5-(ethylsulfanyl)-2-hydroxypentanoyl)-3-hydroxy-2-naphthohydrazide The desired product was prepared by substituting 3-hydroxy-2-naphthoylhydrazine for O-phenyl hydroxylamine hydrochloride in Example 98B.

MS (ESI) m/e 378 (M+H)+; 1H NMR (300 MHz, DMSO-d6) δ 11.45 (br s, 1H), 10.69 (br s, 1H), 10.58 (br s, 1H), 8.52 (br s, 1H), 8.03 (br s, 2H), 7.90 (m, 2H), 7.77 (m, 1H), 7.53 (t, 1H), 7.38 (d, 1H), 7.33 (m, 1H), 6.68 (d, 0.6H), 6.62 (d, 0.4H), 4.40 (m, 0.4H), 4.29 (m, 0.6H), 3.39 (m, 1H), 2.6 (m, 2H), 2.54 (m, 2H), 1.97 (m, 1H), 1.87 (m, 1H), 1.20 (t, 3H).

EXAMPLE 230

N'-((2S,3R)-3-amino-2-hydroxy-5-phenylpentanoyl)-1-naphthohydrazide

The desired product was prepared by substituting 1-naphthoylhydrazine for O-phenyl hydroxylamine hydrochloride and Example 125A for Example 98A in Example 98B.

MS (ESI) m/e 378 (M+H)$^+$; $^1$H NMR (300 MHz, DMSO-d$_6$) δ 10.54 (br s, 1H), 10.38 (br s, 1H), 8.35 (m, 1H), 8.08 (m, 1H), 8.00 (br s, 2H), 7.59 (m, 4H), 7.29 (m, 5H), 7.18 (m, 1H), 6.68 (m, 1H), 4.31 (m, 1H), 2.74 (m, 2H), 2.06 (m, 1H), 1.89 (m, 1H).

EXAMPLE 231

N'-((2S,3R)-3-amino-2-hydroxy-5-phenylpentanoyl)-3-hydroxy-2-naphthohydrazide

The desired product was prepared by substituting 3-hydroxy-2-naphthoylhydrazine for O-phenyl hydroxylamine hydrochloride and Example 125A for Example 98A in Example 98B.

MS (ESI) m/e 394 (M+H)$^+$; $^1$H NMR (300 MHz, DMSO-d$_6$) δ 11.43 (br s, 1H), 10.70 (br s, 1H), 10.58 (br s, 1H), 8.52 (s, 1H), 7.94 (m, 3H), 7.77 (d, 1H), 7.53 (t, 1H), 7.30 (m, 7H), 6.69 (d, 1H), 4.35 (m, 1H), 2.72 (m, 2H), 1.99 (m, 1H), 1.91 (m, 1H).

EXAMPLE 232

(2S,3R)-3-amino-4-cyclohexyl-2-hydroxybutanohydrazide

EXAMPLE 232A (2S,3R)-3-((tert-butoxycarbonyl)amino)-4-cyclohexyl-2-hydroxybutanoic acid pentafluorophenyl ester The title compound was prepared by substituting Example 1C for Example 124A in Example 126B.

MS (ESI) m/e 466 (M−H)$^+$.

EXAMPLE 232B (2S,3R)-3-amino-4-cyclohexyl-2-hydroxybutanohydrazide

The title compound was prepared by substituting Example 232A for Example 126B and anhydrous hydrazine for Example 126A in Example 126C.

MS (ESI) m/e 216 (M+H)$^+$. $^1$H NMR (300 MHz, DMSO-d$_6$) δ 11.05 (br s, 1H), 7.97 (br s, 2H), 6.75 (br s, 1H), 4.22 (d, 2H), 1.74–1.60 (m 6H), 1.42 (d, 2H), 1.28–1.10 (m, 3H), 0.92–0.74 (m, 2H).

EXAMPLE 233

N'-((2R,3R)-3-amino-2-hydroxy-5-(ethylsulfanyl)pentanoyl)-3-chlorobenzoyl hydrazide

EXAMPLE 233A

N'-((2R,3R)-3-(tert-butoxycarbonyl)amino-2-hydroxy-5-(ethylsulfanyl)pentanoyl)-3-chlorobenzoyl hydrazide The desired product was prepared by substituting Example 98A for Example 123B in Example 224A.

MS (ESI) m/e 446 (M+H)$^+$.

EXAMPLE 233B

N'-((2R,3R)-3-amino-2-hydroxy-5-(ethylsulfanyl)pentanoyl)-3-chlorobenzoyl hydrazide The desired product was prepared by substituting Example 233A for Example 118A in Example 118B.

MS (ESI) m/e 346 (M+H)$^+$; $^1$H NMR (300 MHz, DMSO-d$_6$) δ 10.52 (br s, 1H), 10.20 (br s, 1H), 8.07 (br s, 2H), 7.90 (m, 1H), 7.83 (m, 1H), 7.67 (m, 1H), 7.56 (t, 1H), 6.60 (d, 1H), 4.39 (m, 1H), 3.57 (m, 1H), 2.69 (m, 2H), 2.53 (m, 2H), 1.95 (m, 1H), 1.86 (m, 1H), 1.18 (t, 3H).

EXAMPLE 234

N'-((2R,3R)-3-amino-2-hydroxy-5-(isopropylsulfanyl)pentanoyl)-3-chlorobenzoyl hydrazide

EXAMPLE 234A

N'-((2R,3R)-3-amino-2-hydroxy-5-(isopropylsulfanyl)pentanoyl)-3-chlorobenzoyl hydrazide The desired product was prepared as described in Example 224A.

MS (ESI) m/e 460 (M+H)$^+$.

EXAMPLE 234B

N'-((2R,3R)-3-amino-2-hydroxy-5-(isopropylsulfanyl)pentanoyl)-3-chlorobenzoyl hydrazide The desired product was prepared by substituting Example 234A for Example 118A in Example 118B.

MS (ESI) m/e 360 (M+H)$^+$; $^1$H NMR (300 MHz, DMSO-d$_6$) δ 10.52 (br s, 1H), 10.18 (br s, 1H), 8.11 (br s, 2H), 7.90 (m, 1H), 7.84 (d, 1H), 7.64 (m, 1H), 7.56 (t, 1H), 6.59 (d, 1H), 4.42 (m, 1H), 2.97 (m, 1H), 2.69 (m, 1H), 2.62 (m, 1H), 1.89 (m, 2H), 1.20 (d, 6H).

EXAMPLE 235

3-(2-aminoethyl)-N'-((2S,3S)-3-amino-2-hydroxy-4-(isobutylsulfanyl)butanoyl)benzohydrazide

EXAMPLE 235A methyl 3-(cyanomethyl)benzoate

A solution of methyl 3-(bromomethyl)benzoate (2.29 g, 0.01 mol) and potassium cyanide (3.26 g, 0.05 mol) in DMSO (20 mL) was heated to 100° C. for 1 h. The reaction mixture was cooled, partitioned between ether and water, washed with brine, dried (Na$_2$SO$_4$) and concentrated to give the title compound.

MS (ESI) m/e 193 (M+NH4)$^+$.

EXAMPLE 235B 3-(2-(tertbutoxycarbonylamino)ethyl)benzoyl hydrazide

A solution of Example 235A (1.23 g, 7 mmol) in methanol (15 mL) was hydrogenated in the presence of RaNi (2.5 g) for 18 h. After filtration and evaporation of the solvent, the resulting oil (0.1 g, 0.6 mmol) was dissolved in dichloromethane (5 mL), treated with di-tert-butyl dicarbonate (0.13 g, 0.6 mmol) for 16 h at room temperature. The solvent was evaporated and the residue treated with hydrazine hydrate (0.2 mL, 6.0 mmol) in ethanol at reflux for 48 h. After the solvent was evaporated, and the residue purified by silica gel chromatography (10:90/methanol:dichloromethane) to give the title compound.

MS (ESI) m/e 280 (M+H)$^+$.

EXAMPLE 235C 3-(2-aminoethyl)-N'-((2S,3S)-3-amino-2-hydroxy-4-(isobutylsulfanyl)butanoyl)benzohydrazide The title compound was prepared by substituting Example 235B for Example 126A in Example 126C.

MS (ESI) m/e 367 (M−H)+. $^1$H NMR (300 MHz, DMSO-d$_6$) δ 10.62 (s, 1H), 10.27 (s, 1H), 8.12 (br s, 2H), 8.0 (br s, 2H), 7.78 (m, 2H), 7.5 (m, 2H), 6.74 (d, 1H), 4.4 (t, 1H), 3.7 (m, 2H), 2.92 (m, 3H), 2.75 (m, 1H), 2.48 (d, 2H), 1.84–1.7 (m, 1H), 0.97 (d, 6H).

EXAMPLE 236

N'-((2S,3R,4RS)-3-amino-4-ethyl-2-hydroxyoctanoyl)-3-chlorobenzohydrazide

EXAMPLE 236A

Ethyl 4-ethyl-oct-2-enoate

A solution of 2-ethyl-hexanal (5.0 g, 39 mmol), triethyl phosphonoacetate (8.0 mL, 40 mmol), lithium bromide (3.65 g, 42 mmol), and triethylamine (5.6 mL, 40 mmol) in tetrahydrofuran (160 mL) at room temperature was stirred for 16 hours, quenched with water, stirred for 15 minutes, diluted with ethyl acetate, washed sequentially with pH 7 buffer and brine, dried (MgSO$_4$), filtered, and concentrated. The concentrate was purified by flash column chromatography on silica gel with 1:1/dichloromethane:hexanes to provide the desired product.

MS (ESI) m/e 199 (M+H)+.

EXAMPLE 236B ethyl (2S,3R,4RS)-3-(tert-butoxycarbonyl)amino-4-ethyl-2-hydroxyoctanoate A solution of tert-butylcarbamate (2.85 g, 24 mmol), tert-butylhypochlorite (2.7 mL, 24 mmol), and 0.5 M NaOH (50 mL, 25 mmol) in 1-propanol (75 mL) at room temperature was stirred for 15 minutes. Example 236A (1.70 g, 8.6 mmol), potassium osmate dihydrate (0.27 g, 0.73 mmol) and hydroquinidine 1,4-phthalazinediyl diether (0.62 g, 0.80 mmol) were added, and the mixture stirred in an ice bath for 2 hours, diluted with ethyl acetate, washed sequentially with water, 1 M HCl, aqueous NaHCO$_3$, and brine, dried (MgSO$_4$), filtered, and concentrated. The concentrate was purified by flash column chromatography on silica gel with 1:4/ethyl acetate:hexanes to provide the desired product.

MS (ESI) m/e 331 (M+H)+.

EXAMPLE 236C (2S,3R,4RS)-3-(tert-butoxycarbonyl)amino-4-ethyl-2-hydroxyoctanoic acid A solution of Example 236B (0.168 g, 0.51 mmol), 30% hydrogen peroxide (0.25 mL, 2.2 mmol), and lithium hydroxide monohydrate (0.042 g, 1.0 mmol) in 3:1 tetrahydrofuran/water (7 mL) was stirred in an ice bath for 3 hours, then concentrated. The residues were taken up in water and the pH adjusted to 10 with NaOH. The solution was washed twice with ether, adjusted to pH 2 with HCl, then extracted twice with ethyl acetate. The ethyl acetate extracts were dried (MgSO$_4$), filtered, then concentrated to provide the desired product.

MS (ESI) m/e 304 (M+H)+.

EXAMPLE 236D

N'-((2S,3R,4RS)-3-amino-4-ethyl-2-hydroxyoctanoyl)-3-chlorobenzohydrazide

The desired product was prepared by substituting 3-chlorobenzoylhydrazine for O-phenyl hydroxylamine hydrochloride and Example 236C for Example 98A in Example 98B.

MS (ESI) m/e 356 (M+H)+; $^1$H NMR (300 MHz, DMSO-d$_6$) δ 8.17 (br s, 2H), 7.96 (m, 1H), 7.87 (d, 1H), 7.58 (m, 1H), 7.52 (t, 1H), 5.79 (m, 1H), 3.70 (m, 1H), 1.58 (m, 2H), 1.40–0.80 (m, 5H), 0.70 (t, 3H), 0.64 (m, 2H), 0.42 (t, 3H).

EXAMPLE 237

N'-((2S,3S)-3-amino-2-hydroxy-4-(isobutylsulfanyl)butanoyl)-3-propoxybenzohydrazide

EXAMPLE 237A methyl 3-propoxybenzoate

The title compound was prepared by substituting 1-bromopropane for Example 364A in Example 364B. $^1$H NMR (300 MHz, DMSO-d$_6$) δ 7.54 (m, 1H), 7.43 (m, 2H), 7.23 (m, 1H), 3.98 (t, 2H), 3.84 (s, 3H), 1.8–1.66 (m, 2H), 0.99 (t, 3H).

EXAMPLE 237B

N'-((2S,3S)-3-amino-2-hydroxy-4-(isobutylsulfanyl)butanoyl)-3-propoxybenzohydrazide The title compound was prepared by substituting Example 237B for Example 126A in Example 126C.

MS (ESI) m/e 382 (M−H)+. $^1$H NMR (300 MHz, DMSO-d$_6$) δ 10.58 (s, 1H), 10.24 (s, 1H), 8.07 (br s, 2H), 7.44 (m, 3H), 7.16 (m, 1H), 6.24 (d, 1H), 4.4 (t, 1H), 3.98 (t, 2H), 3.4 (m, 1H), 2.92 (dd, 1H), 2.46 (d, 2H), 1.84–1.7 (m, 3H), 1.0 (t, 3H), 0.97 (d, 6H).

EXAMPLE 238

N'-((2S,3R)-3-amino-5-cyclohexyl-2-hydroxypentanoyl)-3-chlorobenzohydrazide

EXAMPLE 238A (2S,3R)-3-(tert-butoxycarbonyl)amino-5-cyclohexyl-2-hydroxypentanoic acid The desired product was prepared by substituting 3-cyclohexylpropanal for 2-ethylhexanal in Examples 236A–236C.

MS (ESI) m/e 316 (M+H)+.

EXAMPLE 238B

N'-((2S,3R)-3-amino-5-cyclohexyl-2-hydroxypentanoyl)-3-chlorobenzohydrazide

The desired product was prepared by substituting 3-chlorobenzoylhydrazine for O-phenyl hydroxylamine hydrochloride and Example 238A for Example 98A in Example 98B.

MS (ESI) m/e 368 (M+H)+; $^1$H NMR (300 MHz, DMSO-d$_6$) δ 10.67 (br s, 1H), 10.27 (br s, 1H), 7.91 (m, 1H), 7.85 (m, 3H), 7.69 (d, 1H), 7.57 (t, 1H), 6.58 (m, 1H), 4.18 (m, 1H), 1.80–1.50 (m, 7H), 1.35–1.10 (m, 6H), 0.89 (m, 2H).

EXAMPLE 239

N'-((2RS,3R)-3-amino-5-(ethylsulfanyl)-2-hydroxypentanoyl)-3-trifluoromethylsulfanylbenzohydrazide

EXAMPLE 239A

N'-((2RS,3R)-3-(tert-butoxycarbonyl)amino-5-(ethylsulfanyl)-2-hydroxypentanoyl)hydrazide To a solution of Example 97A (2.00 g, 6.5 mmol) in acetonitrile (120 mL) was added HOAt (0.443 g, 3.3 mmol) and the mixture stirred for 5 min until homogeneous. To this solution was added DCC (2.00 g, 9.75 mmol) in acetonitrile (20 mL) and the mixture was stirred for 2 minutes. Hydrazine monohydrate (0.306 mL, 9.76 mmol) was added and the reaction stirred to 16 hours. The solvent was removed in vacuo and the crude material filtered, the solid washed With dichloromethane, and the resulting oil was purified by column chromatography using ethyl acetate to give the desired product 1.2 g (60%).

EXAMPLE 239B

N'-((2RS,3R)-3-amino-5-(ethylsulfanyl)-2-hydroxypentanoyl)-3-trifluoromethylsulfanylbenzohydrazide To DCC resin (148 mg, 0.225 mmol) in 1.0 mL of dichloromethane was added 0.5 mL of a 0.45 M solution of HOBt (0.225 mmol) in dimethylacetamide/dichloromethane (1:6), and 0.5 mL of a 0.3M solution of 3-(ethylsulfanyl)benzoic acid (0.15 mmol) in dimethylacetamide. After 5 minutes, 1.0 mL of a 0.225 M solution of Example 239A (0.225 mmol) in dimethylacetamide/dichloromethane (1:1) was added. The mixture was agitated for 18 hours and quenched with 0.19 g of trisamine resin (0.75 mmol) followed by 0.13 g of isocyanate resin (0.225 mmol) and agitated for 4 hours. The mixture was filtered and the resins washed with 1×3 mL of dichloromethane, the solvent was removed in vacuo, and the crude material purified by reverse phase preparative HPLC. The resulting material was treated with 1 mL of 50% trifluoroacetic acid/dichloromethane and agitated at ambient temperature for 18 hours. The solvent was removed in vacuo to give the desired product.

MS (ESI) m/e 412 (M+H)$^+$; $^1$H NMR (500 MHz, CD$_3$OD) δ 8.22 (d, 1H), 8.07 (dd, 1H), 7.93 (t, 1H), 7.65 (m, 1H), 4.49 (d, 0.35), 4.45 (d, 0.65), 3.78 (m, 1H), 2.71 (t, 2H), 2.61 (dd, 2H), 2.17 (dd, 1H), 1.99 (dt, 1H), 1.28 (t, 1.95H), 1.25 (t, 1.05H).

EXAMPLE 240

N'-((2RS,3R)-3-amino-5-(ethylsulfanyl)-2-hydroxypentanoyl)-2-methylbenzohydrazide The desired product was prepared by substituting 2-methylbenzoic acid for 3-(ethylsulfanyl)benzoic acid in Example 239B.

MS (ESI) m/e 326 (M+H)$^+$; $^1$H NMR (500 MHz, CD$_3$OD) δ 7.49 (m, 1H), 7.40 (dd, 1H), 7.28 (m, 2H), 4.48 (d, 0.35), 4.44 (d, 0.65), 3.80 (m, 1H), 2.71 (t, 2H), 2.61 (dd, 2H), 2.47 (s, 1.95H), 2.46 (s, 1.05H), 2.17 (dd, 1H), 1.99 (dt, 1H), 1.27 (t, 1.95H), 1.245 (t, 1.05H).

EXAMPLE 241

N'-((2RS,3R)-3-amino-5-(ethylsulfanyl)-2-hydroxypentanoyl)-3-methylbenzohydrazide The desired product was prepared by substituting 3-methylbenzoic acid for 3-(ethylsulfanyl)benzoic acid in Example 239B.

MS (ESI) m/e 326 (M+H)$^+$; $^1$H NMR (500 MHz, CD$_3$OD) δ 7.72 (d, 1H), 7.67 (dd, 1H), 7.42 (t, 1H), 7.38 (m, 1H), 4.48 (d, 0.35), 4.43 (d, 0.65), 3.77 (m, 1H), 2.71 (t, 2H), 2.61 (dd, 2H), 2.41 (s, 3H), 2.16 (dd, 1H), 1.99 (dt, 1H), 1.28 (t, 1.95H), 1.25 (t, 1.05H).

EXAMPLE 242

N'-((2RS,3R)-3-amino-5-(ethylsulfanyl)-2-hydroxypentanoyl)-4-methylbenzohydrazide The desired product was prepared by substituting 4-methylbenzoic acid for 3-(ethylsulfanyl)benzoic acid in Example 239B.

MS (ESI) m/e 326 (M+H)$^+$; $^1$H NMR (500 MHz, CD$_3$OD) δ 7.79 (m, 2H), 7.32 (m, 2H), 4.48 (d, 0.35), 4.44 (d, 0.65), 3.78 (m, 1H), 2.71 (t, 2H), 2.61 (dd, 2H), 2.41 (s, 3H), 2.16 (dd, 1H), 2.00 (dt, 1H), 1.27 (t, 1.95H), 1.26 (t, 1.05H).

EXAMPLE 243

N'-((2RS,3R)-3-amino-5-(ethylsulfanyl)-2-hydroxypentanoyl)-2-aminobenzohydrazide The desired product was prepared by substituting 2-aminobenzoic acid for 3-(ethylsulfanyl)benzoic acid in Example 239B.

MS (ESI) m/e 327 (M+H)$^+$; $^1$H NMR (500 MHz, CD$_3$OD) δ 7.56 (dd, 1H), 7.24 (m, 1H), 6.78 (d, 1H), 6.65 (ddd, 1H), 4.48 (d, 0.35), 4.44 (d, 0.65), 3.78 (m, 1H), 2.71 (t, 2H), 2.61 (dd, 2H), 2.17 (dd, 1H), 2.00 (dt, 1H), 1.28 (t, 1.95H), 1.25 (t, 1.05H).

EXAMPLE 244

N'-((2RS,3R)-3-amino-5-(ethylsulfanyl)-2-hydroxypentanoyl)-3-aminobenzohydrazide The desired product was prepared by substituting 3-aminobenzoic acid for 3-(ethylsulfanyl)benzoic acid in Example 239B.

MS (ESI) m/e 327 (M+H)$^+$; $^1$H NMR (500 MHz, CD$_3$OD) δ 7.26 (m, 3H), 6.99 (m, 1H), 4.48 (d, 0.35), 4.43 (d, 0.65), 3.78 (m, 1H), 2.71 (t, 2H), 2.61 (dd, 2H), 2.16 (dd, 1H), 1.99 (dt, 1H), 1.27 (t, 1.95H), 1.25 (t, 1.05H).

EXAMPLE 245

N'-((2RS,3R)-3-amino-5-(ethylsulfanyl)-2-hydroxypentanoyl)-4-aminobenzohydrazide The desired product was prepared by substituting 4-aminobenzoic acid for 3-(ethylsulfanyl)benzoic acid in Example 239B.

MS (ESI) m/e 327 (M+H)$^+$; $^1$H NMR (500 MHz, CD$_3$OD) δ 7.66 (dd, 2H), 6.67 (dd, 2H), 4.46 (d, 0.35), 4.42 (d, 0.65), 3.76 (m, 1H), 2.70 (t, 2H), 2.61 (dd, 2H), 2.15 (dd, 1H), 1.99 (dt, 1H), 1.27 (t, 1.05H).

EXAMPLE 246

N'-((2RS,3R)-3-amino-5-(ethylsulfanyl)-2-hydroxypentanoyl)-2-hydroxybenzohydrazide The desired product was prepared by substituting 2-hydroxybenzoic acid for 3-(ethylsulfanyl)benzoic acid in Example 239B.

MS (ESI) m/e 328 (M+H)$^+$; $^1$H NMR (500 MHz, CD$_3$OD) δ 7.86 (ddd, 1H), 7.44 (m, 1H), 6.96 (m, 2H), 4.49

(d, 0.3), 4.44 (d, 0.65), 3.78 (m, 1H), 2.71 (t, 2H), 2.61 (dd, 2H), 2.17 (dd, 1H), 1.99 (dt, 1H), 1.27 (t, 1.95H), 1.25 (t, 1.05H).

EXAMPLE 247

N'-((2RS,3R)-3-amino-5-(ethylsulfanyl)-2-hydroxypentanoyl)-3-hydroxybenzohydrazide The desired product was prepared by substituting 3-hydroxybenzoic acid for 3-(ethylsulfanyl)benzoic acid in Example 239B.

MS (ESI) m/e 328 (M+H)$^+$; $^1$H NMR (500 MHz, CD$_3$OD) δ 7.30 (m, 3H), 7.00 (ddd, 1H), 4.46 (d, 0.35), 4.42 (d, 0.65), 3.75 (m, 1H), 2.71 (t, 2H), 2.61 (dd, 2H), 2.15 (dd, 1H), 1.98 (dt, 1H), 1.27 (t, 1.95H), 1.25 (t, 1.05H).

EXAMPLE 248

N'-((2RS,3R)-3-amino-5-(ethylsulfanyl)-2-hydroxypentanoyl)-4-hydroxybenzohydrazide The desired product was prepared by substituting 4-hydroxybenzoic acid for 3-(ethylsulfanyl)benzoic acid in Example 239B.

MS (ESI) m/e 328 (M+H)$^+$; $^1$H NMR (500 MHz, CD$_3$OD) δ 7.77 (m, 2H), 6.85 (m, 2H), 4.47 (d, 0.35), 4.43 (d, 0.65), 3.77 (m, 1H), 2.71 (t, 2H), 2.61 (dd, 2H), 2.16 (dd, 1H), 1.99 (dt, 1H), 1.27 (t, 1.95H), 1.25 (t, 1.05H).

EXAMPLE 249

N'-((2RS,3R)-3-amino-5-(ethylsulfanyl)-2-hydroxypentanoyl)-3-methoxybenzohydrazide The desired product was prepared by substituting 3-methoxybenzoic acid for 3-(ethylsulfanyl)benzoic acid in Example 239B.

MS (ESI) m/e 342 (M+H)$^+$; $^1$H NMR (500 MHz, CD$_3$OD) δ 7.44 (m, 3H), 7.16 (ddd, 1H), 4.49 (d, 0.35), 4.44 (d, 0.65), 3.85 (s, 3H), 3.78 (m, 1H), 2.71 (t, 2H), 2.61 (dd, 2H), 2.17 (dd, 1H), 2.00 (dt, 1H), 1.28 (t, 1.95H), 1.25 (t, 1.05H).

EXAMPLE 250

N'-((2RS,3R)-3-amino-5-(ethylsulfanyl)-2-hydroxypentanoyl)-4-methoxybenzohydrazide The desired product was prepared by substituting 4-hydroxybenzoic acid for 3-(ethylsulfanyl)benzoic acid in Example 239B.

MS (ESI) m/e 342 (M+H)$^+$; $^1$H NMR (500 MHz, CD$_3$OD) δ 7.87 (m, 2H), 7.02 (m, 2H), 4.47 (d, 0.35), 4.43 (d, 0.65), 3.87 (s, 3H), 3.76 (m, 1H), 2.71 (t, 2H), 2.61 (dd, 2H), 2.15 (dd, 1H), 1.99 (dt, 1H), 1.27 (t, 1.95H), 1.25 (t, 1.05H).

EXAMPLE 251

N'-((2RS,3R)-3-amino-5-(ethylsulfanyl)-2-hydroxypentanoyl)-2-fluorobenzohydrazide The desired product was prepared by substituting 2-fluorobenzoic acid for 3-(ethylsulfanyl)benzoic acid in Example 239B.

MS (ESI) m/e 330 (M+H)$^+$; $^1$H NMR (500 MHz, CD$_3$OD) δ 7.82 (m, 1H), 7.60 (m, 1H), 7.73 (t, 1H), 7.26 (m, 1H), 4.48 (d, 0.35), 4.44 (d, 0.65), 3.79 (m, 1H), 2.71 (t, 2H), 2.61 (dd, 2H), 2.16 (dd, 1H), 1.99 (dt, 1H), 1.27 (t, 1.95H), 1.25 (t, 1.05H).

EXAMPLE 252

N'-((2RS,3R)-3-amino-5-(ethylsulfanyl)-2-hydroxypentanoyl)-3-fluorobenzohydrazide The desired product was prepared by substituting 3-fluorobenzoic acid for 3-(ethylsulfanyl)benzoic acid in Example 239B.

MS (ESI) m/e 330 (M+H)$^+$; $^1$H NMR (500 MHz, CD$_3$OD) δ 7.71 (dd, 1H), 7.62 (m, 1H), 7.53 (t, 1H), 7.36 (m, 1H), 4.49 (d, 0.35), 4.45 (d, 0.65), 3.78 (m, 1H), 2.71 (t, 2H), 2.61 (dd, 2H), 2.17 (dd, 1H), 2.00 (dt, 1H), 1.28 (t, 1.95H), 1.25 (t, 1.05H).

EXAMPLE 253

N'-((2RS,3R)-3-amino-5-(ethylsulfanyl)-2-hydroxypentanoyl)-4-fluorobenzohydrazide The desired product was prepared by substituting 4-fluorobenzoic acid for 3-(ethylsulfanyl)benzoic acid in Example 239B.

MS (ESI) m/e 330 (M+H)$^+$; $^1$H NMR (500 MHz, CD$_3$OD) δ 7.95 (m, 2H), 7.24 (m, 2H), 4.49 (d, 0.35), 4.44 (d, 0.65), 3.78 (m, 1H), 2.71 (t, 2H), 2.61 (dd, 2H), 2.17 (dd, 1H), 2.00 (dt, 1H), 1.27 (t, 1.95H), 1.26 (t, 1.05H).

EXAMPLE 254

(2RS,3R)-N'-acetyl-3-amino-5-(ethylsulfanyl)-2-hydroxypentanohydrazide

The desired product was prepared by substituting acetic acid for 3-(ethylsulfanyl)benzoic acid in Example 239B.

MS (ESI) m/e 250 (M+H)$^+$; $^1$H NMR (500 MHz, CD$_3$OD) δ 4.41 (d, 0.35), 4.37 (d, 0.65), 3.72 (m, 1H), 2.68 (ddd, 2H), 2.58 (dd, 1.3H), 2.55 (dd, 0.7H), 2.10 (m, 1H), 2.03 (s, 1.95H), 2.01 (s, 1.05H), 1.95 (m, 1H), 1.23–1.28 (m, 3H).

EXAMPLE 255

(2RS,3R)-3-amino-5-(ethylsulfanyl)-2-hydroxy-N'-isobutyrylpentanohydrazide

The desired product was prepared by substituting 2-methylpropionic acid for 3-(ethylsulfanyl)benzoic acid in Example 239B.

MS (ESI) m/e 278 (M+H)$^+$; $^1$H NMR (500 MHz, CD$_3$OD) δ 4.41 (d, 0.35), 4.37 (d, 0.65), 3.73 (m, 1H), 2.73–2.51 (m, 5H), 2.10 (m, 1H), 1.95 (dt, 1H), 1.26 (t, 1.95H), 1.24 (t, 1.05H), 1.17 (m, 6H).

EXAMPLE 256

(2RS,3R)-3-amino-5-(ethylsulfanyl)-2-hydroxy-N'-(3-methylbutanoyl)pentanohydrazide The desired product was prepared by substituting 3-methylbutyric acid for 3-(ethylsulfanyl)benzoic acid in Example 239B.

MS (ESI) m/e 292 (M+H)$^+$; $^1$H NMR (500 MHz, CD$_3$OD) δ 4.41 (d, 0.35), 4.37 (d, 0.65), 3.73 (m, 1H), 2.67 (dd, 2H), 2.59 (dd, 1.3H), 2.55 (dd, 0.7H), 2.07–2.16 (m, 4H), 1.95 (dt, 1H), 1.26 (t, 1.95H), 1.24 (t, 1.05H), 1.10 (t, 6H).

EXAMPLE 257

(2RS,3R)-3-amino-5-(ethylsulfanyl)-N'-heptanoyl-2-hydroxypentanohydrazide

The desired product was prepared by substituting heptanoic acid for 3-(ethylsulfanyl)benzoic acid in Example 239B.

MS (ESI) m/e 320 (M+H)+; $^1$H NMR (500 MHz, CD$_3$OD) δ 4.41 (d, 0.35), 4.37 (d, 0.65), 3.73 (m, 1H), 2.67 (dd, 2H), 2.59 (dd, 1.3H), 2.55 (dd, 0.7H), 2.28 (dd, 2H), 2.12 (ddd, 1H), (1.95 (dt, 1H), 1.64 (dd, 2H), 1.31–1.40 (m, 6H), 1.26 (t, 1.95H), 1.24 (t, 1.05H), 0.91 (t, 3H).

EXAMPLE 258

(2RS,3R)-3-amino-5-(ethylsulfanyl)-2-hydroxy-N'-(tetrahydro-2-furanylcarbonyl)pentanohydrazide The desired product was prepared by substituting 2-tetrahydrofuroic acid for 3-(ethylsulfanyl)benzoic acid in Example 239B.

MS (ESI) m/e 306 (M+H)+; $^1$H NMR (500 MHz, CD$_3$OD) δ 4.48–4.41 (m, 1.35), 4.37 (d, 0.65), 4.01 (m, 1H), 3.88 (m, 1H), 3.73 (m, 1H), 2.67 (dd, 2H), 2.59 (dd, 1.3H), 2.55 (dd, 0.7H), 2.29 (m, 1H), 2.08 (m, 2H), 1.96 (m, 3H), 1.26 (t, 1.95H), 1.24 (t, 1.05H).

EXAMPLE 259

(2RS,3R)-3-amino-N'-(cyclohexylacetyl)-5-(ethylsulfanyl)-2-hydroxyheptanohydrazide The desired product was prepared by substituting cyclohexylacetic acid for 3-(ethylsulfanyl)benzoic acid in Example 239B.

MS (ESI) m/e 332 (M+H)+; $^1$H NMR (500 MHz, CD$_3$OD) δ 4.41 (d, 0.35), 4.36 (d, 0.65), 3.73 (m, 1H), 2.67 (dd, 2H), 2.59 (dd, 1.3H), 2.55 (dd, 0.7H), 2.16–2.07 (m, 3H), 1.95 (dt, 1H), 1.65–1.81 (m, 9H), 1.26 (t, 1.95H), 1.24 (t, 1.05H) 1.02 (dd, 2H).

EXAMPLE 261

N'-((2RS,3R)-3-amino-5-(ethylsulfanyl)-2-hydroxypentanoyl)-4-bromobenzohydrazide The desired product was prepared by substituting 4-bromobenzoic acid for 3-(ethylsulfanyl)benzoic acid in Example 239B.

MS (ESI) m/e 391 (M+H)+; $^1$H NMR (500 MHz, CD$_3$OD) δ 7.80 (m, 2H), 7.68 (m, 2H), 4.49 (d, 0.35), 4.44 (d, 0.65), 3.78 (m, 1H), 2.71 (t, 2H), 2.61 (dd, 2H), 2.16 (dd, 1H), 1.99 (dt, 1H), 1.27 (t, 1.95H), 1.25 (t, 1.05H).

EXAMPLE 262

(2RS,3R)-3-amino-5-(ethylsulfanyl)-2-hydroxy-N'-(phenylacetyl)pentanohydrazide

The desired product was prepared by substituting phenylacetic acid for 3-(ethylsulfanyl)benzoic acid in Example 239B.

MS (ESI) m/e 326 (M+H)+; $^1$H NMR (500 MHz, CD$_3$OD) δ 7.35–7.23 (m, 5H), 4.41 (d, 0.35), 4.37 (d, 0.65), 3.72 (m, 1H), 3.61 (d, 2H), 2.67 (t, 2H), 2.58 (dd, 1.3H), 2.53 (dd, 0.7H), 2.11 (dd, 1H), 1.94 (dt, 1H), 1.25 (t, 1.95H), 1.21 (t, 1.05H).

EXAMPLE 263

(2RS,3R)-3-amino-5-(ethylsulfanyl)-2-hydroxy-N'-((2-methoxyphenyl)acetyl)pentanohydrazide The desired product was prepared by substituting 2-methoxyphenylacetic acid for 3-(ethylsulfanyl)benzoic acid in Example 239B.

MS (ESI) m/e 356 (M+H)+; $^1$H NMR (500 MHz, CD$_3$OD) δ 7.21 (dt, 1H), 6.94 (d, 1H), 6.90 (d, 1H), 6.81 (m, 1H), 4.41 (d, 0.35), 4.37 (d, 0.65), 3.78 (s, 3H), 3.72 (m, 1H), 3.58 (d, 2H), 2.67 (t, 2H), 2.58 (dd, 1.3H), 2.53 (dd, 0.7H), 2.11 (dd, 1H), 1.94 (dt, 1H), 1.25 (t, 1.95H), 1.21 (t, 1.05H).

EXAMPLE 264

(2RS,3R)-3-amino-5-(ethylsulfanyl)-2-hydroxy-N'-((3-methoxyphenyl)acetyl)pentanohydrazide The desired product was prepared by substituting 3-methoxyphenylacetic acid for 3-(ethylsulfanyl)benzoic acid in Example 239B.

MS (ESI) m/e 356 (M+H)+; $^1$H NMR (500 MHz, CD$_3$OD) δ 7.25 (m, 2H), 6.95 (d, 1H), 6.90 (d, 1H), 4.41 (d, 0.35), 4.37 (d, 0.65), 3.83 (s, 3H), 3.72 (m, 1H), 3.61 (dd, 2H), 2.67 (t, 2H), 2.58 (dd, 1.3H), 2.53 (dd, 0.7H), 2.11 (dd, 1H), 1.94 (dt, 1H), 1.25 (t, 1.95H), 1.21 (t, 1.05H).

EXAMPLE 265

(2RS,3R)-3-amino-5-(ethylsulfanyl)-2-hydroxy-N'-((4-methoxyphenyl)acetyl)pentanohydrazide The desired product was prepared by substituting 4-methoxyphenylacetic acid for 3-(ethylsulfanyl)benzoic acid in Example 239B.

MS (ESI) m/e 356 (M+H)+; $^1$H NMR (500 MHz, CD$_3$OD) δ 7.25 (d, 2H), 6.87 (dd, 2H), 4.41 (d, 0.35), 4.37 (d, 0.65), 3.77 (s, 3H), 3.72 (m, 1H), 3.53 (d, 2H), 2.67 (t, 2H), 2.58 (dd, 1.3H), 2.53 (dd, 0.7H), 2.11 (dd, 1H), 1.94 (dt, 1H), 1.25 (t, 1.95H), 1.21 (t, 1.05H).

EXAMPLE 266

(2RS,3R)-3-amino-5-(ethylsulfanyl)-2-hydroxy-N'-((2-chlorophenyl)acetyl)pentanohydrazide The desired product was prepared by substituting 2-chlorophenylacetic acid for 3-(ethylsulfanyl)benzoic acid in Example 239B.

MS (ESI) m/e 360 (M+H)+; $^1$H NMR (500 MHz, CD$_3$OD) δ 7.43 (m,-2H), 7.27 (m, 2H), 4.42 (d, 0.35), 4.38 (d, 0.6), 3.80 (d, 1H), 3.78 (s, 1H), 3.73 (m, 1H), 2.67 (t, 2H), 2.58 (dd, 1.3H), 2.53 (dd, 0.7H), 2.11 (dd, 1H), 1.94 (dt, 1H), 1.25 (t, 1.95H), 1.21 (t, 1.05H).

EXAMPLE 267

(2RS,3R)-3-amino-5-(ethylsulfanyl)-2-hydroxy-N'-((3-chlorophenyl)acetyl)pentanohydrazide The desired product was prepared by substituting 3-chlorophenylacetic acid for 3-(ethylsulfanyl)benzoic acid in Example 239B.

MS (ESI) m/e 360 (M+H)+; $^1$H NMR (500 MHz, CD$_3$OD) δ 7.39 (m, 1H), 7.25–7.31 (m, 3H), 4.42 (d, 0.35), 4.38 (d, 0.65), 3.72 (m, 1H), 3.61 (d, 2H), 2.67 (t, 2H), 2.58 (dd, 1.3H), 2.53 (dd, 0.7H), 2.11 (dd, 1H), 1.94 (dt, 1H), 1.25 (t, 1.95H), 1.21 (t, 1.05H).

EXAMPLE 268

(2RS,3R)-3-amino-5-(ethylsulfanyl)-2-hydroxy-N'-((4-chlorophenyl)acetyl)pentanohydrazide The desired product was prepared by substituting 4-chlorophenylacetic acid for 3-(ethylsulfanyl)benzoic acid in Example 239B.

MS (ESI) m/e 360 (M+H)+; 1H NMR (500 MHz, CD3OD) δ 7.32 (m, 4H), 4.42 (d, 0.35), 4.37 (d, 0.65), 3.72 (m, 1H), 3.61 (d, 2H), 2.67 (t, 2H), 2.58 (dd, 1.3H), 2.53 (dd, 0.7H), 2.11 (dd, 1H), 1.94 (dt, 1H), 1.25 (t, 1.95H), 1.21 (t, 1.05H).

EXAMPLE 269

N'-((2RS,3R)-3-amino-5-(ethylsulfanyl)-2-hydroxypentanoyl)-2-(1,1'-biphenyl)-4-ylacetohydrazide The desired product was prepared by substituting 4-phenylphenylacetic acid for 3-(ethylsulfanyl)benzoic acid in Example 239B.

MS (ESI) m/e 402 (M+H)+; 1H NMR (500 MHz, CD3OD) δ 7.58 (m, 4H), 7.42 (m, 4H), 7.32 (m, 1H), 4.42 (d, 0.35), 4.38 (d, 0.65), 3.72 (m, 1H), 3.65 (d, 2H), 2.67 (t, 2H), 2.58 (dd, 1.3H), 2.53 (dd, 0.7H), 2.11 (dd, 1H), 1.94 (dt, 1H), 1.25 (t, 1.95H), 1.21 (t, 1.05H).

EXAMPLE 270

N'-((2RS,3R)-3-amino-5-(ethylsulfanyl)-2-hydroxypentanoyl)-2-(4-dimethylaminophenyl)acetohydrazide The desired product was prepared by substituting 4-dimethylaminophenylacetic acid for 3-(ethylsulfanyl)benzoic acid in Example 239B.

MS (ESI) m/e 369 (M+H)+; 1H NMR (500 MHz, CD3OD) δ 7.36 (m, 2H), 7.13 (m, 2H), 4.42 (d, 0.35), 4.37 (d, 0.65), 3.72 (m, 1H), 3.59 (d, 2H), 3.09 (s, 3H), 3.07 (s, 3H), 2.67 (t, 2H), 2.58 (dd, 1.3H), 2.53 (dd, 0.7H), 2.11 (dd, 1H), 1.94 (dt, 1H), 1.25 (t, 1.95H), 1.21 (t, 1.05H).

EXAMPLE 271

N'-((2RS,3R)-3-amino-5-(ethylsulfanyl)-2-hydroxypentanoyl)-2-(1-naphthyl)acetohydrazide The desired product was prepared by substituting 1-naphthylacetic acid for 3-(ethylsulfanyl)benzoic acid in Example 239B.

MS (ESI) m/e 369 (M+H)+; 1H NMR (500 MHz, CD3OD) δ 8.10 (d, 1H), 7.88 (d, 1H), 7.81 (d, 1H), 7.51 (m, 3H), 7.45 (t, 1H), 4.42 (d, 0.35), 4.37 (d, 0.65), 4.10 (d, 2H), 3.70 (m, 1H), 2.65 (t, 2H), 2.56 (dd, 1.3H), 2.47 (dd, 0.7H), 2.09 (dd, 1H), 1.92 (dt, 1H), 1.24 (t, 1.95H), 1.15 (t, 1.05H).

EXAMPLE 272

N'-((2RS,3R)-3-amino-5-(ethylsulfanyl)-2-hydroxypentanoyl)-2-(2-naphthyl)acetohydrazide The desired product was prepared by substituting 2-naphthylacetic acid for 3-(ethylsulfanyl)benzoic acid in Example 239B.

MS (ESI) m/e 376 (M+H)+; 1H NMR (500 MHz, CD3OD) δ 7.82 (m, 4H), 7.46 (m, 3H), 4.42 (d, 0.35), 4.38 (d, 0.65), 3.78 (d, 2H), 3.73 (m, 1H), 2.66 (t, 2H), 2.57 (dd, 1.3H), 2.52 (dd, 0.7H), 2.09 (dd, 1H), 1.94 (dt, 1H), 1.25 (t, 1.95H), 1.19 (t, 1.05H).

EXAMPLE 273

N'-((2RS,3R)-3-amino-5-(ethylsulfanyl)-2-hydroxypentanoyl)-2-furohydrazide

The desired product was prepared by substituting 2-furoic acid for 3-(ethylsulfanyl)benzoic acid in Example 239B.

MS (ESI) m/e 302 (M+H)+; 1H NMR (500 MHz, CD3OD) δ 7.73 (dd, 0.65H), 7.72 (dd, 0.35H), 7.24 (dd, 0.65H), 7.22 (dd, 0.35H), 6.64 (dd, 0.65H), 6.63 (dd, 0.35H), 4.47 (d, 0.35), 4.43 (d, 0.65), 3.77 (m, 1H), 2.70 (t, 2H), 2.60 (dd, 1.3H), 2.58 (dd, 0.7H), 2.15 (dd, 1H), 1.98 (dt, 1H), 1.27 (t, 1.95H), 1.25 (t, 1.05H).

EXAMPLE 274

N'-((2RS,3R)-3-amino-5-(ethylsulfanyl)-2-hydroxypentanoyl)-3-furohydrazide

The desired product was prepared by substituting 3-furoic acid for 3-(ethylsulfanyl)benzoic acid in Example 239B.

MS (ESI) m/e 302 (M+H)+; 1H NMR (500 MHz, CD3OD) δ 8.16 (m, 0.65H), 8.14 (m, 0.35H), 7.62 (dd, 0.65H), 7.61 (dd, 0.35H), 6.83 (m, 1H), 4.47 (d, 0.35), 4.42 (d, 0.65), 3.76 (m, 1H), 2.70 (t, 2H), 2.60 (dd, 1.3H), 2.58 (dd, 0.7H), 2.15 (dd, 1H), 1.98 (dt, 1H), 1.27 (t, 1.95H), 1.25 (t, 1.05H).

EXAMPLE 275

N'-((2RS,3R)-3-amino-5-(ethylsulfanyl)-2-hydroxypentanoyl)-2-thiophenecarbohydrazide The desired product was prepared by substituting 2-thiophene carboxylic acid for 3-(ethylsulfanyl)benzoic acid in Example 239B.

MS (ESI) m/e 318 (M+H)+; 1H NMR (500 MHz, CD3OD) δ 7.79 (dd, 0.65H), 7.78 (dd, 0.35H), 7.77 (dd, 0.65H), 7.75 (dd, 0.35H), 7.17 (m, 1H), 4.47 (d, 0.35), 4.43 (d, 0.65), 3.76 (m, 1H), 2.70 (t, 2H), 2.60 (dd, 1.3H), 2.58 (dd, 0.7H), 2.16 (dd, 1H), 1.98 (dt, 1H), 1.27 (t, 1.95H), 1.25 (t, 1.05H).

EXAMPLE 276

N'-((2RS,3R)-3-amino-5-(ethylsulfanyl)-2-hydroxypentanoyl)-3-thiophenecarbohydrazide The desired product was prepared by substituting 3-thiophene carboxylic acid for 3-(ethylsulfanyl)benzoic acid in Example 239B.

MS (ESI) m/e 318 (M+H)+; 1H NMR (500 MHz, CD3OD) δ 8.18 (dd, 0.65H), 8.16 (dd, 0.35H), 7.53 (m, 2H), 4.48 (d, 0.35), 4.43 (d, 0.65), 3.77 (m, 1H), 2.71 (t, 2H), 2.60 (dd, 1.3H), 2.58 (dd, 0.7H), 2.16 (dd, 1H), 1.99 (dt, 1H), 1.27 (t, 1.95H), 1.25 (t, 1.05H).

EXAMPLE 277

N'-((2RS,3R)-3-amino-5-(ethylsulfanyl)-2-hydroxypentanoyl)-1 H-pyrrole-2-carbohydrazide The desired product was prepared by substituting 2-pyrrole carboxylic acid for 3-(ethylsulfanyl)benzoic acid in Example 239B.

MS (ESI) m/e 301 (M+H)+; 1H NMR (500 MHz, CD3OD) δ 6.99 (dd, 0.65H), 6.98 (dd, 0.35H), 6.91 (dd, 0.65H, 6.89 (dd, 0.35H), 6.21 (m, 1H), 4.46 (d, 0.35), 4.42 (d, 0.65), 3.77 (m, 1H), 2.71 (m, 2H), 2.60 (dd, 1.3H), 2.58 (dd, 0.7H), 2.15 (dd, 1H), 1.99 (dt, 1H), 1.27 (t, 1.95H), 1.25 (t, 1.05H).

EXAMPLE 278

N'-((2RS,3R)-3-amino-5-(ethylsulfanyl)-2-hydroxypentanoyl)-1,3-thiazole-2-carbohydrazide The desired product was prepared by substituting 2-thiazole carboxylic acid for 3-(ethylsulfanyl)benzoic acid in Example 239B.

MS (ESI) m/e 319 (M+H)⁺; ¹H NMR (500 MHz, CD₃OD) δ 8.02 (d, 0.65H), 8.00 (d, 0.35H), 7.94 (d, 0.65H), 7.91 (d, 0.35H), 4.49 (d, 0.35), 4.44 (d, 0.65), 3.79 (m, 1H), 2.71 (m, 2H), 2.60 (dd, 1.3H), 2.58 (dd, 0.7H), 2.16 (dd, 1H), 1.98 (dt, 1H), 1.27 (t, 1.95H), 1.25 (t, 1.05H).

EXAMPLE 279

N'-((2RS,3R)-3-amino-5-(ethylsulfanyl)-2-hydroxypentanoyl)-1,3-thiazole-4-carbohydrazide The desired product was prepared by substituting 4-thiazole carboxylic acid for 3-(ethylsulfanyl)benzoic acid in Example 239B.

MS (ESI) m/e 319 (M+H)⁺; ¹H NMR (500 MHz, CD₃OD) δ 9.06 (d, 0.65H), 9.04 (d, 0.35H), 8.40 (d, 0.65H), 8.37 (d, 0.35H), 4.48 (d, 0.35), 4.45 (d, 0.65), 3.79 (m, 1H), 2.71 (t, 2H), 2.60 (dd, 1.3H), 2.58 (dd, 0.7H), 2.16 (dd, 1H), 1.98 (dt, 1H), 1.27 (t, 1.95H), 1.25 (t, 1.05H).

EXAMPLE 280

N'-((2RS,3R)-3-amino-5-(ethylsulfanyl)-2-hydroxypentanoyl)-1,3-thiazole-5-carbohydrazide The desired product was prepared by substituting 5-thiazole carboxyl acid for 3-(ethylsulfanyl)benzoic acid in Example 239B.

MS (ESI) m/e 319 (M+H)⁺; ¹H NMR (500 MHz, CD₃OD) δ 9.21 (s, 0.65H), 9.19 (s, 0.35H), 8.49 (s, 0.65H), 8.47 (s, 0.35H), 4.49 (d, 0.35), 4.44 (d, 0.65), 3.78 (m, 1H), 2.70 (t, 2H), 2.60 (dd, 1.3H), 2.58 (dd, 0.7H), 2.16 (dd, 1H), 1.98 (dt, 1H), 1.27 (t, 1.95H), 1.25 (t, 1.05H).

EXAMPLE 281

N'-((2RS,3R)-3-amino-5-(ethylsulfanyl)-2-hydroxypentanoyl)-1H-pyrazole-5-carbohydrazide The desired product was prepared by substituting 1H-pyrazole-5-carboxylic acid for 3-(ethylsulfanyl)benzoic acid in Example 239B.

MS (ESI) m/e 302 (M+H)⁺; ¹H NMR (500 MHz, CD₃OD) δ 7.74 (d, 0.65H), 7.73 (d, 0.35H), 8.83 (m, 1H), 4.47 (d, 0.35), 4.43 (d, 0.65), 3.78 (m, 1H), 2.70 (t, 2H), 2.60 (dd, 1.3H), 2.58 (dd, 0.7H), 2.15 (dd, 1H), 1.98 (dt, 1H), 1.27 (t, 1.95H), 1.25 (t, 1.05H).

EXAMPLE 282

N'-((2RS,3R)-3-amino-5-(ethylsulfanyl)-2-hydroxypentanoyl)-1 H-pyrazole-4-carbohydrazide The desired product was prepared by substituting 1-H-pyrazole-4-carboxylic acid for 3-(ethylsulfanyl)benzoic acid in Example 239B.

MS (ESI) m/e 302 (M+H)⁺; ¹H NMR (500 MHz, CD₃OD) δ 8.11 (s, 1H), 8.10 (s, 1H), 4.47 (d, 0.35), 4.43 (d, 0.65), 3.76 (m, 1H), 2.70 (t, 2H), 2.60 (dd, 1.3H), 2.58 (dd, 0.7H), 2.15 (dd, 1H), 1.99 (dt, 1H), 1.27 (t, 1.95H), 1.25 (t, 1.05H).

EXAMPLE 283

N'-((2RS,3R)-3-amino-5-(ethylsulfanyl)-2-hydroxypentanoyl)-5-isoxazolecarbohydrazide The desired product was prepared by substituting 5-isoxazole caboxylic acid for 3-(ethylsulfanyl)benzoic acid in Example 239B.

MS (ESI) m/e 303 (M+H)⁺; ¹H NMR (500 MHz, CD₃OD) δ 8.58 (d, 0.65H), 8.56 (d, 0.35H), 7.09 (d, 0.65H), 7.06 (d, 0.35H), 4.49 (d, 0.35), 4.44 (d, 0.65), 3.78 (m, 1H), 2.70 (t, 2H), 2.60 (dd, 1.3H), 2.58 (dd, 0.7H), 2.16 (dd, 1H), 1.97 (dt, 1H), 1.27 (t, 1.95H), 1.25 (t, 1.05H).

EXAMPLE 284

N'-((2RS,3R)-3-amino-5-(ethylsulfanyl)-2-hydroxypentanoyl)-2-pyridinecarbohydrazide The desired product was prepared by substituting 2-pyridine caboxylic acid for 3-(ethylsulfanyl)benzoic acid in Example 239B.

MS (ESI) m/e 313 (M+H)⁺; ¹H NMR (500 MHz, CD₃OD) δ 8.67 (t, 1H), 8.11 (t, 1H), 7.99 (m, 1H), 7.60 (m, 1H), 4.49 (d, 0.35), 4.45 (d, 0.65), 3.78 (m, 1H), 2.71 (t, 2H), 2.61 (dd, 1.3H), 2.58 (dd, 0.7H), 2.16 (dd, 1H), 1.99 (dt, 1H), 1.28 (t, 1.95H), 1.26 (t, 1.05H).

EXAMPLE 285

N'-((2RS,3R)-3-amino-5-(ethylsulfanyl)-2-hydroxypentanoyl)-2-(2-pyridinyl)acetohydrazide The desired product was prepared by substituting 2-pyridylacetic acid for 3-(ethylsulfanyl)benzoic acid in Example 239B.

MS (ESI) m/e 327 (M+H)⁺; ¹H NMR (500 MHz, CD₃OD) δ 8.63 (d, 0.35H), 8.59 (d, 0.65H), 8.11 (dt, 0.35H), 8.04 (dt, 0.65H), 7.71 (d, 0.35H), 7.66 (d, 0.65H), 7.59 (ddd, 0.35H), 7.53 (ddd, 0.65H), 4.44 (d, 0.35), 4.38 (d, 0.65), 3.73 (m, 1H), 2.67 (t, 2H), 2.58 (dd, 1.3H), 2.52 (dd, 0.7H), 2.10 (dd, 1H), 1.93 (dt, 1H), 1.25 (t, 1.95H), 1.20 (t, 1.05H).

EXAMPLE 286

N'-((2RS,3R)-3-amino-5-(ethylsulfanyl)-2-hydroxypentanoyl)-3-pyridinecarbohydrazide The desired product was prepared by substituting 3-pyridylacetic acid for 3-(ethylsulfanyl)benzoic acid in Example 239B.

MS (ESI) m/e 313 (M+H)⁺; ¹H NMR (500 MHz, CD₃OD) δ 9.04 (m, 1H), 8.77 (d, 1H), 8.32 (dd, 0.35H), 8.30 (dd, 0.65H), 7.61 (d, 0.35H), 7.60 (d, 0.65H), 4.51 (d, 0.35), 4.46 (d, 0.65), 3.79 (m, 1H), 2.71 (t, 2H), 2.61 (dd, 1.3H), 2.58 (dd, 0.7H), 2.17 (dd, 1H), 2.00 (dt, 1H), 1.28 (t, 1.95H), 1.25 (t, 1.05H).

EXAMPLE 287

N'-((2RS,3R)-3-amino-5-(ethylsulfanyl)-2-hydroxypentanoyl)-2-(3-pyridinyl)acetohydrazide The desired product was prepared by substituting 3-pyridylacetic acid for 3-(ethylsulfanyl)benzoic acid in Example 239B.

MS (ESI) m/e 327 (M+H)⁺; ¹H NMR (500 MHz, CD₃OD) δ 8.69 (d, 1H), 8.61 (m, 1H), 8.24 (d, 0.35H), 8.19 (dd, 0.65H), 7.75 (dd, 0.35H), 7.71 (dd, 0.65H), 4.44 (d, 0.35), 4.38 (d, 0.65), 3.81 (m, 2H), 3.73 (m, 1H), 2.67 (t, 2H), 2.57 (dd, 1.3H), 2.52 (dd, 0.7H), 2.10 (dd, 1H), 1.93 (dt, 1H), 1.25 (t, 1.95H), 1.20 (t, 1.05H).

EXAMPLE 288

N'-((2RS,3R)-3-amino-5-(ethylsulfanyl)-2-hydroxypentanoyl)-4-pyridinecarbohydrazide The desired product was prepared by substituting 4-pyridine caboxylic acid for 3-(ethylsulfanyl)benzoic acid in Example 239B.

MS (ESI) m/e 313 (M+H)⁺; ¹H NMR (500 MHz, CD₃OD) δ 8.76 (m, 2H), 7.86 (m, 2H), 4.51 (d, 0.35), 4.45 (d, 0.6), 3.79 (m, 1H), 2.71 (t, 2H), 2.60 (dd, 1.3H), 2.58 (dd, 0.7H), 2.17 (dd, 1H), 2.00 (dt, 1H), 1.27 (t, 1.95H), 1.25 (t, 1.05H).

EXAMPLE 289

N'-((2RS,3R)-3-amino-5-(ethylsulfanyl)-2-hydroxypentanoyl)-2-(4-pyridinyl)acetohydrazide The desired product was prepared by substituting 4-pyridylacetic acid for 3-(ethylsulfanyl)benzoic acid in Example 239B.

MS (ESI) m/e 327 (M+H)⁺; ¹H NMR (500 MHz, CD₃OD) δ 8.68 (t, 2H), 7.87 (d, 0.7H), 7.83 (d, 1.3H), 4.45 (d, 0.35), 4.38 (d, 0.65), 3.73 (m, 1H), 2.67 (t, 2H), 2.58 (dd, 1.3H), 2.52 (dd, 0.7H), 2.10 (dd, 1H), 1.93 (dt, 1H), 1.25 (t, 1.95H), 1.20 (t, 1.05H).

EXAMPLE 290

N'-((2RS,3R)-3-amino-5-(ethylsulfanyl)-2-hydroxypentanoyl)-3-pyridazinecarbohydrazide The desired product was prepared by substituting 3-pyridazine carboxylic acid for 3-(ethylsulfanyl)benzoic acid in Example 239B.

MS (ESI) m/e 314 (M+H)⁺; ¹H NMR (500 MHz, CD₃OD) δ 9.37 (ddd, 1H), 8.31 (ddd, 1H), 7.92 (dd, 1H), 4.51 (d, 0.35), 4.47 (d, 0.65), 3.81 (m, 1H), 2.72 (t, 2H), 2.61 (dd, 2H), 2.18 (dd, 1H), 2.00 (dt, 1H), 1.28 (t, 1.95H), 1.26 (t, 1.05H).

EXAMPLE 291

N'-((2RS,3R)-3-amino-5-(ethylsulfanyl)-2-hydroxypentanoyl)-4-pyrimidinecarbohydrazide The desired product was prepared by substituting 4-pyrimidine carboxylic acid for 3-(ethylsulfanyl)benzoic acid in Example 239B.

MS (ESI) m/e 314 (M+H)⁺; ¹H NMR (500 MHz, CD₃OD) δ 9.31 (d, 0.65H), 9.30 (d, 0.35H), 9.07 (d, 0.65H), 9.06 (0.35H), 8.11 (dd, 0.65H), 8.09 (dd, 0.35H), 4.50 (d, 0.35), 4.45 (d, 0.65), 3.79 (m, 1H), 2.71 (t, 2H), 2.61 (dd, 2H), 2.17 (dd, 1H), 1.99 (dt, 1H), 1.27 (t, 1.95H), 1.26 (t, 1.05).

EXAMPLE 292

N'-((2RS,3R)-3-amino-5-(ethylsulfanyl)-2-hydroxypentanoyl)-2-pyrazinecarbohydrazide The desired product was prepared by substituting 2-pyrazine carboxylic acid for 3-(ethylsulfanyl)benzoic acid in Example 239B.

MS (ESI) m/e 314 (M+H)⁺; ¹H NMR (500 MHz, CD₃OD) δ 9.25 (d, 0.65H), 9.24 (d, 0.35H), 8.85 (d, 0.65H), 8.83 (0.35H), 8.72 (dd, 0.65H), 8.71 (dd, 0.35H), 4.50 (d, 0.35), 4.46 (d, 0.65), 3.80 (m, 1H), 2.71 (t, 2H), 2.60 (t, 2H), 2.18 (dd, 1H), 1.99 (dt, 1H), 1.28 (t, 1.95H), 1.26 (t, 1.05H).

EXAMPLE 293

N'-((2RS,3R)-3-amino-5-(ethylsulfanyl)-2-hydroxypentanoyl)-4-isopropylbenzohydrazide The desired product was prepared by substituting 4-(2-methylethyl)phenylbenzoic acid for 3-(ethylsulfanyl)benzoic acid in Example 239B.

MS (ESI) m/e 355 (M+H)⁺; ¹H NMR (500 MHz, CD₃OD) δ 7.82 (m, 2H), 7.37 (m, 2H), 4.48 (d, 0.35), 4.44 (d, 0.65), 3.78 (m, 1H), 2.71 (t, 2H), 2.60 (dd, 2H), 2.16 (dd, 1H), 1.99 (dt, 1H), 1.24–1.29 (m, 10H)

EXAMPLE 294

N'-((2RS,3R)-3-amino-5-(ethylsulfanyl)-2-hydroxypentanoyl)-4-propoxybenzohydrazide The desired product was prepared by substituting 4-propoxybenzoic acid for 3-(ethylsulfanyl)benzoic acid in Example 239B.

MS (ESI) m/e 370 (M+H)⁺; ¹H NMR (500 MHz, CD₃OD) δ 7.86 (m, 2H), 7.01 (m, 2H), 4.48 (d, 0.35), 4.44 (d, 0.65), 4.01 (dt, 2H), 3.77 (m, 1H), 2.71 (t, 2H), 2.60 (dd, 2H), 2.16 (dd, 1H), 1.99 (dt, 1H), 1.82 (ddd, 2H), 1.28 (t, 1.95H), 1.25 (t, 1.05H) 1.05 (t, 3H).

EXAMPLE 295

N'-((2RS,3R)-3-amino-5-(ethylsulfanyl)-2-hydroxypentanoyl)-4-(methylsulfanyl)benzohydrazide The desired product was prepared by substituting 4-methylsulfanylbenzoic acid for 3-(ethylsulfanyl)benzoic acid in Example 239B.

MS (ESI) m/e 358 (M+H)⁺; ¹H NMR (500 MHz, CD₃OD) δ 7.81 (m, 2H), 7.35 (m, 2H), 4.48 (d, 0.35), 4.44 (d, 0.65), 3.78 (m, 1H), 2.71 (t, 2H), 2.61 (dd, 2H), 2.53 (s, 3H), 2.16 (dd, 1H), 1.99 (dt, 1H), 1.28 (t, 1.95H), 1.25 (t, 1.05H).

EXAMPLE 296

N'-((2RS,3R)-3-amino-5-(ethylsulfanyl)-2-hydroxypentanoyl)-4-isopropoxybenzohydrazide The desired product was prepared by substituting 4-(2-methylethoxy)benzoic acid for 3-(ethylsulfanyl)benzoic acid in Example 239B.

MS (ESI) m/e 370 (M+H)⁺; ¹H NMR (500 MHz, CD₃OD) δ 7.84 (m, 2H), 6.99 (m, 2H), 4.71 (ddd, 1H), 4.48 (d, 0.35), 4.44 (d, 0.65), 3.78 (m, 1H), 2.71 (t, 2H), 2.61 (dd, 2H), 2.16 (dd, 1H), 2.00 (dt, 1H), 1.34 (d, 6H), 1.28 (t, 1.95H), 1.25 (t, 1.05H).

EXAMPLE 297

N'-((2RS,3R)-3-amino-5-(ethylsulfanyl)-2-hydroxypentanoyl)-4-(diethylamino)benzohydrazide The desired product was prepared by substituting 4-(diethylamino)benzoic acid for 3-(ethylsulfanyl)benzoic acid in Example 239B.

MS (ESI) m/e 383 (M+H)⁺; ¹H NMR (500 MHz, CD₃OD) δ 7.76 (dd, 2H), 6.73 (m, 2H), 4.47 (d, 0.35), 4.43 (d, 0.65), 3.77 (m, 1H), 3.46 (q, 4H), 2.70 (t, 2H), 2.61 (dd, 2H), 2.16 (dd, 1H), 2.00 (dt, 1H), 1.28 (t, 1.95H), 1.26 (t, 1.05H), 1.19 (t, 6H).

EXAMPLE 298

N'-((2RS,3R)-3-amino-5-(ethylsulfanyl)-2-hydroxypentanoyl)-4-butoxybenzohydrazide The desired product was prepared by substituting 4-butoxybenzoic acid for 3-(ethylsulfanyl)benzoic acid in Example 239B.

MS (ESI) m/e 384 (M+H)⁺; ¹H NMR (500 MHz, CD₃OD) δ 7.85 (m, 2H), 6.99 (m, 2H), 4.48 (d, 0.35), 4.44 (d, 0.65), 4.06 (dt, 2H), 3.77 (m, 1H), 2.71 (t, 2H), 2.61 (dd, 2H), 2.16 (dd, 1H), 2.00 (dt, 1H), 1.78 (ddd, 2H), 1.53 (ddd, 2H), 1.28 (t, 1.95H), 1.26 (t, 1.05H), 0.99 (t, 3H).

EXAMPLE 299

N'-((2RS,3R)-3-amino-5-(ethylsulfanyl)-2-hydroxypentanoyl)-3,4-diethoxybenzohydrazide The desired product was prepared by substituting 2,3-diethoxybenzoic acid for 3-(ethylsulfanyl)benzoic acid in Example 239B.

MS (ESI) m/e 400 (M+H)⁺; ¹H NMR (500 MHz, CD₃OD) δ 7.52 (dd, 1H), 7.48 (d, 1H), 7.03 (m, 1H), 4.48 (d, 0.35), 4.44 (d, 0.65), 4.13 (m, 4H), 3.77 (m, 1H), 2.71 (t, 2H), 2.61 (dd, 2H), 2.16 (dd, 1H), 2.00 (dt, 1H), 1.43 (m, 6H), 1.28 (t, 1.95H), 1.25 (t, 1.05H).

EXAMPLE 300

N'-((2RS,3R)-3-amino-5-(ethylsulfanyl)-2-hydroxypentanoyl)-4-chlorobenzohydrazide The desired product was prepared by substituting 4-chlorobenzoic acid for 3-(ethylsulfanyl)benzoic acid in Example 239B.

MS (ESI) m/e 346 (M+H)⁺; ¹H NMR (500 MHz, CD₃OD) δ 7.87 (dd, 2H), 7.52 (dd, 2H), 4.49 (d, 0.35), 4.44 (d, 0.65), 3.78 (m, 1H), 2.71 (t, 2H), 2.61 (dd, 2H), 2.17 (dd, 1H), 1.99 (dt, 1H), 1.27 (t, 1.95H), 1.25 (t, 1.05H).

EXAMPLE 301

N'-((2RS,3R)-3-amino-5-(ethylsulfanyl)-2-hydroxypentanoyl)-2-bromobenzohydrazide The desired product was prepared by substituting 2-bromobenzoic acid for 3-(ethylsulfanyl)benzoic acid in Example 239B.

MS (ESI) m/e 391 (M+H)⁺; ¹H NMR (500 MHz, CD₃OD) δ 7.69 (dd, 1H), 7.59 (ddd, 1H), 7.47 (m, 1H), 7.41 (m, 1H), 4.48 (d, 0.35), 4.43 (d, 0.65), 3.79 (m, 1H), 2.71 (t, 2H), 2.61 (dd, 2H), 2.16 (dd, 1H), 1.99 (dt, 1H), 1.27 (t, 1.95H), 1.24 (t, 1.05H).

EXAMPLE 302

(2RS,3R)-3-amino-N'-((2RS,3S)-3-amino-2-hydroxy-5-(isopropylsulfanyl)pentanoyl)-2-hydroxy-5-(isopropylsulfanyl)pentanohydrazide The title compound is obtained by substituting hydrazine hydrate for O-phenylhydroxylamine hydrochloride and Example 123B for Example 98A in Example 98B.

MS (ESI) m/e 409 (M–H)⁺. ¹H NMR (300 MHz, DMSO-d₆) δ 10.94 (br s, 1H), 10.11 & 9.93 (s, 1H), 8.2 & 8.02 (m, 4H), 6.8 & 6.65(br s, 2H), 4.44 & 4.28 (m, 1H), 4.2 (m, 1H), 3.0–2.9 (m, 2H), 2.75–2.55 (m, 4H), 1.95–1.75 (m, 4H), 1.2 (d, 12H).

EXAMPLE 304

N'-((2RS,3R)-3-amino-5-(ethylsulfanyl)-2-hydroxypentanoyl)-3-(dimethylamino)benzohydrazide The desired product was prepared by substituting 3-dimethylaminobenzoic acid for 3-(ethylsulfanyl)benzoic acid in Example 239B.

MS (ESI) m/e 355 (M+H)⁺; ¹H NMR (500 MHz, CD₃OD) δ 7.32 (dd, 1H), 7.28 (m, 1H), 7.21 (d, 1H), 7.01 (dd, 1H), 4.48 (d, 0.35), 4.44 (d, 0.65), 3.79 (m, 1H), 3.00 (s, 6H), 2.71 (t, 2H), 2.61 (dd, 2H), 2.17 (dd, 1H), 2.00 (dt, 1H), 1.28 (t, 1.95H), 1.26 (t, 1.05H).

EXAMPLE 305

N'-((2RS,3R)-3-amino-5-(ethylsulfanyl)-2-hydroxypentanoyl)-4-(dimethylamino)benzohydrazide The desired product was prepared by substituting 4-dimethylaminobenzoic acid for 3-(ethylsulfanyl)benzoic acid in Example 239B.

MS (ESI) m/e 355 (M+H)⁺; ¹H NMR (500 MHz, CD₃OD) δ 7.78 (dd, 2H), 6.75 (d, 2H), 4.46 (d, 0.35), 4.43 (d, 0.65), 3.77 (m, 1H), 3.04 (s, 6H), 2.70 (t, 2H), 2.61 (dd, 2H), 2.16 (dd, 1H), 2.00 (dt, 1H), 1.28 (t, 1.95H), 1.26 (t, 1.05H).

EXAMPLE 306

N'-((2RS,3R)-3-amino-5-(ethylsulfanyl)-2-hydroxypentanoyl)-3-(ethylsulfanyl)benzoic (trifluoromethyl)benzohydrazide The desired product was prepared by substituting 3-(trifluoromethyl)benzoic acid for 3-(ethylsulfanyl)benzoic acid in Example 239B.

MS (ESI) m/e 380 (M+H)⁺; ¹H NMR (500 MHz, CD₃OD) δ 8.21 (d, 1H), 8.14 (t, 1H), 7.92 (t, 1H), 7.73 (dd, 1H), 4.50 (d, 0.35), 4.46 (d, 0.65), 3.79 (m, 1H), 2.72 (t, 2H), 2.61 (dd, 2H), 2.18 (dd, 1H), 2.00 (dt, 1H), 1.28 (t, 1.95H), 1.26 (t, 1.05H).

EXAMPLE 307

N'-((2RS,3R)-3-amino-5-(ethylsulfanyl)-2-hydroxypentanoyl)-4-(trifluoromethyl)benzohydrazide The desired product -was prepared by substituting 4-(trifluoromethyl)benzoic acid for 3-(ethylsulfanyl)benzoic acid in Example 239B.

MS (ESI) m/e 380 (M+H)⁺; ¹H NMR (500 MHz, CD₃OD) δ 8.05 (dd, 2H), 7.82 (dd, 2H), 4.50 (d, 0.35), 4.45 (d, 0.65), 3.79 (m, 1H), 2.71 (t, 2H), 2.61 (dd, 2H), 2.17 (dd, 1H), 2.00 (dt, 1H), 1.28 (t, 1.95H), 1.25 (t, 1.05H).

EXAMPLE 308

N'-((2RS,3R)-3-amino-5-(ethylsulfanyl)-2-hydroxypentanoyl)-3-(trifluoromethoxy)benzohydrazide The desired product was prepared by substituting 3-(trifluoromethoxy)benzoic acid for 3-(ethylsulfanyl) benzoic acid in Example 239B.

MS (ESI) m/e 396 (M+H)⁺; ¹H NMR (500 MHz, CD₃OD) δ 7.89 (dd, 1H), 7.80 (d, 1H), 7.62 (dd, 1H), 7.53 (dd, 1H), 4.50 (d, 0.35), 4.45 (d, 0.65), 3.78 (m, 1H), 2.71 (t, 2H), 2.61 (dd, 2H), 2.17 (dd, 1H), 200 (dt, 1H), 1.28 (t, 1.95H), 1.25 (t, 1.05H).

EXAMPLE 309

N'-((2RS,3R)-3-amino-5-(ethylsulfanyl)-2-hydroxypentanoyl)-4-phenoxybenzohydrazide The desired product was prepared by substituting 4-phenoxybenzoic acid for 3-(ethylsulfanyl)benzoic acid in Example 239B.

MS (ESI) m/e 404 (M+H)⁺; ¹H NMR (500 MHz, CD₃OD) δ 7.89 (m, 2H), 7.42 (m, 2H), 7.22 (m, 1H), 7.08 (m, 2H), 7.04 (m, 2H), 4.48 (d, 0.35), 4.44 (d, 0.65), 3.78 (m, 1H), 2.71 (t, 2H), 2.61 (dd, 2H), 2.16 (dd, 1H), 2.00 (dt, 1H), 1.27 (t, 1.95H), 1.26 (t, 1.05H).

EXAMPLE 310

N'-((2RS,3R)-3-amino-5-(ethylsulfanyl)-2-hydroxypentanoyl)-4-(phenoxymethyl)benzohydrazide The desired product was prepared by substituting 4-(phenoxymethyl)benzoic acid for 3-(ethylsulfanyl)benzoic acid in Example 239B.

MS (ESI) m/e 418 (M+H)⁺; ¹H NMR (500 MHz, CD₃OD) δ 7.87 (m, 2H), 7.44 (d, 2H), 7.38 (t, 2H), 7.32 (t, 1H), 7.11 (m, 2H), 5.17 (s, 2H), 4.48 (d, 0.35), 4.44 (d, 0.65), 3.77 (m, 1H), 2.71 (t, 2H), 2.61 (dd, 2H), 2.16 (dd, 1H), 2.00 (dt, 1H), 1.27 (t, 1.95H), 1.25 (t, 1.05H).

EXAMPLE 311

N'-((2RS,3R)-3-amino-5-(ethylsulfanyl)-2-hydroxypentanoyl)-2,3-dimethylbenzohydrazide The desired product was prepared by substituting 2,3-dimethylbenzoic acid for 3-(ethylsulfanyl)benzoic acid in Example 239B.

MS (ESI) m/e 340 (M+H)⁺; ¹H NMR (500 MHz, CD₃OD) δ 7.29 (m, 2H), 7.16 (m, 1H), 4.48 (d, 0.35), 4.43 (d, 0.6), 3.80 (m, 1H), 2.71 (t, 2H), 2.61 (dd, 2H), 2.36 (s, 3H), 2.32 (s, 3H), 2.17 (dd, 1H), 1.99 (dt, 1H), 1.28 (t, 1.95H), 1.24 (t, 1.05H).

EXAMPLE 312

N'-((2RS,3R)-3-amino-5-(ethylsulfanyl)-2-hydroxypentanoyl)-2,4-dimethylbenzohydrazide The desired product was prepared by substituting 2,4-dimethylbenzoic acid for 3-(ethylsulfanyl)benzoic acid in Example 239B.

MS (ESI) m/e 340 (M+H)⁺; ¹H NMR (500 MHz, CD₃OD) δ 7.40 (m, 1H), 7.12 (d, 1H), 7.08 (dd, 1H), 4.48 (d, 0.35), 4.43 (d, 0.65), 3.79 (m, 1H), 2.71 (t, 2H), 2.61 (dd, 2H), 2.43 (s, 3H), 2.34 (s, 3H), 2.16 (dd, 1H), 1.99 (dt, 1H), 1.27 (t, 1.95H), 1.24 (t, 1.05H).

EXAMPLE 313

N'-((2RS,3R)-3-amino-5-(ethylsulfanyl)-2-hydroxypentanoyl)-2,5-dimethylbenzohydrazide The desired product was prepared by substituting 2,5-dimethylbenzoic acid for 3-(ethylsulfanyl)benzoic acid in Example 239B.

MS (ESI) m/e 340 (M+H)⁺; ¹H NMR (500 MHz, CD₃OD) δ 7.33 (m, 1H), 7.21 (dd, 1H), 7.17 (m, 1H), 4.48 (d, 0.35), 4.43 (d, 0.65), 3.79 (m, 1H), 2.71 (t, 2H), 2.61 (dd, 2H), 2.41 (s, 3H), 2.34 (s, 3H), 2.16 (dd, 1H), 1.99 (dt, 1H), 1.27 (t, 1.95H), 1.24 (t, 1.05H).

EXAMPLE 314

N'-((2RS,3R)-3-amino-5-(ethylsulfanyl)-2-hydroxypentanoyl)-4,5-dimethylbenzohydrazide The desired product was prepared by substituting 3,4-dimethylbenzoic acid for 3-(ethylsulfanyl)benzoic acid in Example 239B.

MS (ESI) m/e 340 (M+H)⁺; ¹H NMR (500 MHz, CD₃OD) δ 7.68 (d, 1H), 7.61 (dd, 1H), 7.25 (m, 1H), 4.48 (d, 0.35), 4.44 (d, 0.65), 3.78 (m, 1H), 2.71 (t, 2H), 2.61 (dd, 2H), 2.33 (s, 6H), 2.16 (dd, 1H), 2.00 (dt, 1H), 1.28 (t, 1.95H), 1.25 (t, 1.05H).

EXAMPLE 315

N'-((2RS,3R)-3-amino-5-(ethylsulfanyl)-2-hydroxypentanoyl)-3,5-dimethylbenzohydrazide The desired product was prepared by substituting 3,5-dimethylbenzoic acid for 3-(ethylsulfanyl)benzoic acid in Example 239B.

MS (ESI) m/e 340 (M+H)⁺; ¹H NMR (500 MHz, CD₃OD) δ 7.50 (d, 2H), 7.25 (d, 1H), 4.48 (d, 0.35), 4.44 (d, 0.65), 3.78 (m, 1H), 2.71 (t, 2H), 2.61 (dd, 2H), 2.37 (s, 6H), 2.16 (dd, 1H), 2.00 (dt, 1H), 1.28 (t, 1.95H), 1.26 (t, 1.05H).

EXAMPLE 316

N'-((2RS,3R)-3-amino-5-(ethylsulfanyl)-2-hydroxypentanoyl)-2,3-dimethoxybenzohydrazide The desired product was prepared by substituting 2,3-dimethoxybenzoic acid for 3-(ethylsulfanyl)benzoic acid in Example 239B.

MS (ESI) m/e 372 (M+H)⁺; ¹H NMR (500 MHz, CD₃OD) δ 7.42 (dd, 0.65H), 7.40 (dd, 0.35H), 7.24 (ddd, 1H), 7.19 (m, 1H), 4.48 (d, 0.35), 4.44 (d, 0.65), 3.95 (s, 1.95H), 3.94 (s, 1.05H), 3.91 (s, 1.95H), 3.90 (s, 1.05H), 3.79 (m, 1H), 2.71 (t, 2H), 2.61 (dd, 2H), 2.16 (dd, 1H), 1.99 (dt, 1H), 1.27 (t, 1.95H), 1.25 (t, 1.05H).

EXAMPLE 317

N'-((2RS,3R)-3-amino-5-(ethylsulfanyl)-2-hydroxypentanoyl)-2,4-dimethoxybenzohydrazide The desired product was prepared by substituting 2,4-dimethoxybenzoic acid for 3-(ethylsulfanyl)benzoic acid in Example 239B.

MS (ESI) m/e 372 (M+H)⁺; ¹H NMR (500 MHz, CD₃OD) δ 7.98 (m, 1H), 6.68 (m, 2H), 4.47 (d, 0.35), 4.44 (d, 0.65), 4.00 (s, 1.95H), 3.99 (s, 1.05H), 3.88 (s, 3H), 3.78 (m, 1H), 2.70 (t, 2H), 2.61 (dd, 1H), 1.99 (dt, 1H), 1.28 (t, 1.95H), 1.25 (t, 1.05H).

EXAMPLE 318

N'-((2RS,3R)-3-amino-5-(ethylsulfanyl)-2-hydroxypentanoyl)-2,5-dimethoxybenzohydrazide The desired product was prepared by substituting 2,5-dimethoxybenzoic acid for 3-(ethylsulfanyl)benzoic acid in Example 239B.

MS (ESI) m/e 372 (M+H)⁺; ¹H NMR (500 MHz, CD₃OD) δ 7.54 (dd, 0.65H), 7.53 (dd, 0.35H), 7.14 (m, 2H), 4.48 (d, 0.35), 4.45 (d, 0.65), 3.96 (s, 1.95H), 3.95 (s, 1.05H), 3.79 (s, 3H), 3.78 (m, 1H), 2.71 (t, 2H), 2.61 (dd, 2H), 2.16 (dd, 1H), 1.99 (dt, 1H), 1.28 (t, 1.95H), 1.25 (t, 1.05H).

EXAMPLE 319

N'-((2RS,3R)-3-amino-5-(ethylsulfanyl)-2-hydroxypentanoyl)-3,4-dimethoxybenzohydrazide The desired product was prepared by substituting 3,4-dimethoxybenzoic acid for 3-(ethylsulfanyl)benzoic acid in Example 239B.

MS (ESI) m/e 372 (M+H)+; ¹H NMR (500 MHz, CD₃OD) δ 7.55 (ddd, 1H), 7.49 (dd, 1H), 7.05 (m, 1H), 4.48 (d, 0.35), 4.44 (d, 0.65), 3.90 (s, 1.95H), 3.89 (s, 1.05H), 3.88 (s, 3H), 3.78 (m, 1H), 2.71 (t, 2H), 2.61 (dd, 2H), 2.17 (dd, 1H), 2.00 (dt, 1H), 1.28 (t, 1.95H), 1.26 (t, 1.05H).

EXAMPLE 320

N'-((2RS,3R)-3-amino-5-(ethylsulfanyl)-2-hydroxypentanoyl)-3,5-dimethoxybenzohydrazide The desired product was prepared by substituting 3,5-dimethoxybenzoic acid for 3-(ethylsulfanyl)benzoic acid in Example 239B.

MS (ESI) m/e 372 (M+H)+; ¹H NMR (500 MHz, CD₃OD) δ 7.04 (m, 2H), 6.71 (dd, 0.65H), 6.99 (dd, 0.35H), 4.48 (d, 0.35), 4.44 (d, 0.65), 3.83 (s, 6H), 3.78 (m, 1H), 2.71 (t, 2H), 2.61 (dd, 2H), 2.17 (dd, 1H), 1.99 (dt, 1H), 1.28 (t, 1.95H), 1.25 (t, 1.05H).

EXAMPLE 321

N'-((2RS,3R)-3-amino-5-(ethylsulfanyl)-2-hydroxypentanoyl)-1,3-benzodioxole-5-carbohydrazide The desired product was prepared by substituting 1,3-benzodioxole carboxylic acid for 3-(ethylsulfanyl)benzoic acid in Example 239B.

MS (ESI) m/e 356 (M+H)+; ¹H NMR (500 MHz, CD₃OD) δ 7.49 (m, 1H), 7.35 (d, 0.65H), 7.34 (d, 0.35H), 6.92 (m, 1H), 6.06 (s, 1.3H), 6.05 (s, 0.7H), 4.47 (d, 0.35), 4.43 (d, 0.65), 3.77 (m, 1H), 2.70 (t, 2H), 2.60 (dd, 2H), 2.16 (dd, 1H), 1.99 (dt, 1H), 1.27 (t, 1.95H), 1.25 (t, 1.05H).

EXAMPLE 322

N'-((2RS,3R)-3-amino-5-(ethylsulfanyl)-2-hydroxypentanoyl)-3,4,5-trimethoxybenzohydrazide The desired product was prepared by substituting 3,4,5-trimethoxybenzoic acid for 3-(ethylsulfanyl)benzoic acid in Example 239B.

MS (ESI) m/e 402 (M+H)+; ¹H NMR (500 MHz, CD₃OD) δ 7.25 (s, 1.3H), 7.24 (s, 0.7H), 4.50 (d, 0.35), 4.45 (d, 0.65), 3.89 (s, 6H), 3.83 (s, 1.95H), 3.82 (s, 1.05H), 3.78 (m, 1H), 2.71 (t, 2H), 2.61 (dd, 2H), 2.17 (dd, 1H), 2.00 (dt, 1H), 1.28 (t, 1.95H), 1.26 (t, 1.05H).

EXAMPLE 323

N'-((2RS,3R)-3-amino-5-(ethylsulfanyl)-2-hydroxypentanoyl)-2,3-dichlorobenzohydrazide The desired product was prepared by substituting 2,3-dichlorobenzoic acid for 3-(ethylsulfanyl)benzoic acid in Example 239B.

MS (ESI) m/e 381 (M+H)+; ¹H NMR (500 MHz, CD₃OD) δ 7.68 (ddd, 1H), 7.54 (m, 1H), 7.41 m, 1H), 4.48 (d, 0.35), 4.43 (d, 0.65), 3.80 (m, 1H), 2.71 (t, 2H), 2.61 (dd, 2H), 2.17 (dd, 1H), 1.99 (dt, 1H), 1.27 (t, 1.95H), 1.24 (t, 1.05H).

EXAMPLE 324

N'-((2RS,3R)-3-amino-5-(ethylsulfanyl)-2-hydroxypentanoyl)-2,4-dichlorobenzohydrazide The desired product was prepared by substituting 2,4-dichlorobenzoic acid for 3-(ethylsulfanyl)benzoic acid in Example 239B.

MS (ESI) m/e 381 (M+H)+; ¹H NMR (500 MHz, CD₃OD) δ 7.60 (m, 2H), 7.46 (m, 1H), 4.48 (d, 0.35), 4.43 (d, 0.65), 3.79 (m, 1H), 2.71 (t, 2H), 2.60 (dd, 2H), 2.16 (dd, 1H), 1.99 (dt, 1H), 1.27 (d, 1.95H), 1.24 (t, 1.05H).

EXAMPLE 325

N'-((2RS,3R)-3-amino-5-(ethylsulfanyl)-2-hydroxypentanoyl)-2,5-dichlorobenzohydrazide The desired product was prepared by substituting 2,5-dichlorobenzoic acid for 3-(ethylsulfanyl)benzoic acid in Example 239B.

MS (ESI) m/e 381 (M+H)+; ¹H NMR (500 MHz, CD₃OD) δ 7.65 (m, 1H), 7.52 (m, 2H), 4.48 (d, 0.35), 4.43 (d, 0.65), 3.79 (m, 1H), 2.71 (t, 2H), 2.60 (dd, 2H), 2.16 (dd, 1H), 1.99 (dt, 1H), 1.27 (d, 1.95H), 1.24 (t, 1.05H).

EXAMPLE 326

N'-((2RS,3R)-3-amino-5-(ethylsulfanyl)-2-hydroxypentanoyl)-3,4-dichlorobenzohydrazide The desired product was prepared by substituting 3,4-dichlorobenzoic acid for 3-(ethylsulfanyl)benzoic acid in Example 239B.

MS (ESI) m/e 381 (M+H)+; ¹H NMR (500 MHz, CD₃OD) δ 8.05 (d, 0.65H), 8.04 (d, 0.35H), 7.80 (m, 1H), 7.68 (m, 1H), 4.49 (d, 0.35), 4.44 (d, 0.65), 3.79 (m, 1H), 2.71 (t, 2H), 2.61 (dd, 2H), 2.16 (dd, 1H), 2.00 (dt, 1H), 1.27 (t, 1.95H), 1.25 (t, 1.05H).

EXAMPLE 327

N'-((2RS,3R)-3-amino-5-(ethylsulfanyl)-2-hydroxypentanoyl)-3,5-dichlorobenzohydrazide The desired product was prepared by substituting 3,5-dichlorobenzoic acid for 3-(ethylsulfanyl)benzoic acid in Example 239B.

MS (ESI) m/e 381 (M+H)+; ¹H NMR (500 MHz, CD₃OD) δ 7.85 (d, 1.3H), 7.83 (d, 0.7H), 7.72 (t, 0.65H), 7.70 (t, 0.35H), 4.49 (d, 0.35), 4.44 (d, 0.65), 3.79 (m, 1H), 2.71 (t, 2H), 2.61 (dd, 2H), 2.16 (dd, 1H), 1.99 (dt, 1H), 1.27 (t, 1.95H), 1.25 (t, 1.05H).

EXAMPLE 328

N'-((2RS,3R)-3-amino-4-cyclohexyl-2-hydroxybutanoyl)-2-hydroxybenzohydrazide

The desired compound was prepared by substituting salicylic acid for o-toluic acid in Example 329B.

MS (ESI) m/e 336 (M+H)+; ¹H NMR (500 MHz, CD₃OD) δ 7.87 (m, 1H), 7.44 (m, 1H), 6.95 (m, 2H), 4.45 (d, 0.3H), 4.38 (d, 0.7H), 3.69 (m, 1H), 1.76 (m, 6H), 1.58 (m, 1H), 1.47 (m, 1H), 1.32 (m, 1H), 1.24 (m, 1H), 1.03 (m, 1.4H), 0.93 (m, 0.6H).

EXAMPLE 329

N'-((2RS,3R)-3-amino-4-cyclohexyl-2-hydroxybutanoyl)-2-methylbenzohydrazide

Example 329A

N'-((2RS,3R)-3-(tert-butoxycarbonyl)amino-4-cyclohexyl-2-hydroxybutanoyl)hydrazide The desired compound was prepared by substituting Example 1C for Example 97A acid in Example 239A.

EXAMPLE 329B

N'-((2RS,3R)-3-amino-4-cyclohexyl-2-hydroxybutanoyl)-2-methylbenzohydrazide

To DCC resin (148 mg, 0.225 mmol) in 1.0 mL of dichloromethane was added 0.5 mL of a 0.45 M solution of HOBt (0.225 mmol) in dimethylacetamide/dichloromethane (1:6), and 0.5 mL of a 0.3M solution of o-toluic acid (0.15 mmol) in dimethylacetamide. After 5 minutes, 1.0 mL of a 0.225 M solution of Example 329A (0.225 mmol) in dimethylacetamide/dichloromethane (1:1) was added. The mixture was agitated for 18 hours and quenched with 0.19 g of trisamine resin (0.75 mmol) followed by 0.13 g of isocyanate resin (0.225 mmol) and agitated for 4 hours. The mixture was filtered and the resins washed with 1×3 mL of dichloromethane, the solvent was removed in vacuo, and the crude material purified by reverse phase preparative HPLC. The resulting material was treated with 1 mL of 50% trifluoroacetic acid/dichloromethane and agitated at ambient temperature for 18 hours. The solvent was removed in vacuo to give the desired product.

MS (ESI) m/e 334 (M+H)$^+$; $^1$H NMR (500 MHz, CD$_3$OD) δ 7.50 (m, 1H), 7.39 (ddd, 1H), 7.28 (m, 2H), 4.44 (d, 0.3H), 4.36 (d, 0.7H), 3.71 (m, 0.7H), 3.67 (m 0.3H), 2.46 (s, 3H), 1.73 (m, 6H), 1.56 (m, 1H), 1.47 (m, 1H), 1.28 (m, 3H), 1.02 (m, 1.4H), 0.93 (m, 0.6H).

EXAMPLE 330

2-amino-N'-((2RS,3R)-3-amino-4-cyclohexyl-2-hydroxybutanoyl)benzohydrazide

The desired compound was prepared by substituting o-aminobenzoic acid for o-toluic acid in Example 329B.

MS (ESI) m/e 335 (M+H)$^+$; $^1$H NMR (500 MHz, CD$_3$OD) δ 7.57 (m, 1H), 7.25 (m, 1H), 6.80 (m, 1H), 6.67 (m, 1H), 4.44 (d, 0.3H), 4.36 (d, 0.7H), 3.69 (m, 0.7H), 3.65 (m 0.3H), 1.76 (m, 6H), 1.57 (m, 1H), 1.47 (m, 1H), 1.37–1.20 (m, 3H), 1.03 (m, 1.4H), 0.93 (m, 0.6H).

EXAMPLE 331

4-amino-N'-((2RS,3R)-3-amino-4-cyclohexyl-2-hydroxybutanoyl)benzohydrazide

The desired compound was prepared by substituting p-aminobenzoic acid for o-toluic acid in Example 329B.

MS (ESI) m/e 335 (M+H)$^+$; $^1$H NMR (500 MHz, CD$_3$OD) δ 7.67 (m, 2H), 6.69 (m, 2H), 4.42 (d, 0.4H), 4.35 (d, 0.6H), 3.69–3.62 (m, 1H), 1.85–1.61 (m, 6H), 1.56 (m, 1H), 1.46 (m, 1H), 1.37–1.20 (m, 3H), 1.03 (m, 1.2H), 0.91 (m, 0.8H).

EXAMPLE 332

3-amino-N'-((2RS,3R)-3-amino-4-cyclohexyl-2-hydroxybutanoyl)benzohydrazide

The desired compound was prepared by substituting m-aminobenzoic acid for o-toluic acid in Example 329B.

MS (ESI) m/e 335 (M+H)$^+$; $^1$H NMR (500 MHz, CD$_3$OD) δ 7.36 (m, 3H), 7.09 (m, 1H), 4.45 (d, 0.25H), 4.36 (d, 0.75H), 3.69 (m, 1H), 1.85–1.64 (m, 6H), 1.56 (m, 1H), 1.47 (m, 1H), 1.33 (m, 2H), 1.22 (m, 1H), 1.02 (m, 1.5 H), 0.92 (m, 0.5H).

EXAMPLE 333

N'-((2RS,3R)-3-amino-4-cyclohexyl-2-hydroxybutanoyl)-3-hydroxybenzohydrazide

The desired compound was prepared by substituting 3-hydroxybenzoic acid for o-toluic acid in Example 329B.

MS (ESI) m/e 336 (M+H)$^+$; $^1$H NMR (500 MHz, CD$_3$OD) δ 7.31 (m, 3H), 7.01 (m, 1H), 6.80 (m, 1H), 4.44 (d, 0.3H), 4.36 (d, 0.7H), 3.69 (m, 0.7H), 3.65 (m 0.3H), 1.85–1.64 (m, 6H), 1.57 (m, 1H), 1.47 (m, 1H), 1.33 (m, 2H), 1.24 (m, 1H), 1.03 (m, 1.4H), 0.93 (m, 0.6H).

EXAMPLE 334

N'-((2RS,3R)-3-amino-4-cyclohexyl-2-hydroxybutanoyl)-4-hydroxybenzohydrazide

The desired compound was prepared by substituting 4-hydroxybenzoic acid for o-toluic acid in Example 329B.

MS (ESI) m/e 336 (M+H)$^+$; $^1$H NMR (500 MHz, CD$_3$OD) δ 7.78 (m, 2H), 6.85 (m, 2H), 4.43 (d, 0.3H), 4.36 (d, 0.7H), 3.71–3.62 (m, 1H), 1.75 (m, 6H), 1.57 (m, 1H), 1.47 (m, 1H), 1.38–1.20 (m, 3H), 1.03 (m, 1.4H), 0.92 (m, 0.6H).

EXAMPLE 335

N'-((2RS,3R)-3-amino-4-cyclohexyl-2-hydroxybutanoyl)-4-methoxybenzohydrazide

The desired compound was prepared by substituting p-anisic acid for o-toluic acid in Example 329B.

MS (ESI) m/e 350 (M+H)$^+$; $^1$H NMR (500 MHz, CD$_3$OD) δ 7.87 (m, 2H), 7.02 (m, 2H), 6.80 (m, 1H), 6.67 (m, 1H), 4.44 (d, 0.3H), 4.36 (d, 0.7H), 3.70–3.64 (m, 1H), 1.84–1.62 (m, 6H), 1.57 (m, 1H), 1.47 (m, 1H), 1.39–1.20 (m, 3H), 1.03 (m, 1.4H), 0.93 (m, 0.6H).

EXAMPLE 336

N'-((2RS,3R)-3-amino-4-cyclohexyl-2-hydroxybutanoyl)-2-fluorobenzohydrazide

The desired compound was prepared by substituting 2-fluorobenzoic acid for o-toluic acid in Example 329B.

MS (ESI) m/e 338 (M+H)$^+$; $^1$H NMR (500 MHz, CD$_3$OD) δ 7.81 (m, 1H), 7.61 (m, 1H), 7.34–7.23 (m, 2H), 4.44 (d, 0.3H), 4.37 (d, 0.7H), 3.69 (m, 1H), 1.75 (m, 6H), 1.56 (m, 1H), 1.47 (m, 1H), 1.38–1.20 (m, 3H), 1.03 (m, 1.4H), 0.93 (m, 0.6H).

EXAMPLE 337

N'-((2RS,3R)-3-amino-4-cyclohexyl-2-hydroxybutanoyl)-3-fluorobenzohydrazide

The desired compound was prepared by substituting 3-fluorobenzoic acid for o-toluic acid in Example 329B.

MS (ESI) m/e 338 (M+H)$^+$; $^1$H NMR (500 MHz, CD$_3$OD) δ 7.72 (m, 1H), 7.63 (m, 1H), 6.53 (m, 1H), 7.35 (m, 1H), 4.45 (d, 0.25H), 4.37 (d, 0.75H), 3.68 (m, 1H), 1.83–1.64 (m, 6H), 1.57 (m, 1H), 1.47 (m, 1H), 1.33 (m, 2H), 1.24 (m, 1H), 1.02 (m, 1.5H), 0.92 (m, 0.5H).

EXAMPLE 338

N'-((2RS,3R)-3-amino-4-cyclohexyl-2-hydroxybutanoyl)-4-fluorobenzohydrazide

The desired compound was prepared by substituting 4-fluorobenzoic acid for o-toluic acid in Example 329B.

MS (ESI) m/e 338 (M+H)$^+$; $^1$H NMR (500 MHz, CD$_3$OD) δ 7.95 (m, 2H), 7.24 (m, 2H), 6.53 (m, 1H), 7.35 (m, 1H), 4.45 (d, 0.3H), 4.37 (d, 0.7H), 3.68 (m, 1H), 1.85–1.64 (m, 6H), 1.57 (m, 1H), 1.47 (m, 1H), 1.33 (m, 2H), 1.24 (m, 1H), 1.02 (m, 1.4H), 0.92 (m, 0.6H).

EXAMPLE 339

N'-((2RS,3R)-3-amino-4-cyclohexyl-2-hydroxybutanoyl)-2-bromobenzohydrazide

The desired compound was prepared by substituting 2-bromobenzoic acid for o-toluic acid in Example 329B.

MS (ESI) m/e 399 (M+H)$^+$; $^1$H NMR (500 MHz, CD$_3$OD) δ 7.72 (m, 1H), 7.69 (m, 1H), 7.46 (m, 1H), 7.41 (m, 1H), 4.44 (d, 0.3H), 4.36 (d, 0.7H), 3.68 (m, 1H), 1.85–1.65 (m, 6H), 1.56 (m, 1H), 1.47 (m, 1H), 1.38–1.18 (m, 3H), 1.03 (m, 1.4H), 0.92 (m, 0.6H).

EXAMPLE 340

N'-((2RS,3R)-3-amino-4-cyclohexyl-2-hydroxybutanoyl)-3-cyanobenzohydrazide

The desired compound was prepared by substituting 3-cyanobenzoic acid for o-toluic acid in Example 329B.

MS (ESI) m/e 345 (M+H)$^+$; $^1$H NMR (500 MHz, CD$_3$OD) δ 8.23 (m, 1H), 8.17 (m, 1H), 7.96 (m, 1H), 7.71 (m, 1H), 4.46 (d, 0.3H), 4.38 (d, 0.7H), 3.69 (m, 1H), 1.85–1.65 (m, 6H), 1.58 (m, 1H), 1.47 (m, 1H), 1.33 (m, 2H), 1.24 (m, 1H), 1.02 (m, 1.5H), 0.92 (m, 0.5H).

EXAMPLE 341

N'-((2RS,3R)-3-amino-4-cyclohexyl-2-hydroxybutanoyl)-4-cyanobenzohydrazide

The desired compound was prepared by substituting 4-cyanobenzoic acid for o-toluic acid in Example 329B.

MS (ESI) m/e 345 (M+H)$^+$; $^1$H NMR (500 MHz, CD$_3$OD) δ 8.02 (m, 2H), 7.88 (m, 2H), 4.46 (d, 0.3H), 4.37 (d, 0.7H), 3.69 (m, 1H), 1.85–1.65 (m, 6H), 1.56 (m, 1H), 1.46 (m, 1H), 1.33 (m, 2H), 1.24 (m, 1H), 1.03 (m, 1.4H), 0.92 (m, 0.6H).

EXAMPLE 342

N'-((2RS,3R)-3-amino-4-cyclohexyl-2-hydroxybutanoyl)-3-(dimethylamino)benzohydrazide The desired compound was prepared by substituting 3-dimethylaminobenzoic acid for o-toluic acid in Example 329B.

MS (ESI) m/e 363 (M+H)$^+$; $^1$H NMR (500 MHz, CD$_3$OD) δ 7.32 (t, 1H), 7.28 (m, 1H), 7.21 (m, 1H), 7.01 (dd, 1H), 4.44 (d, 0.3H), 4.37 (d, 0.7H), 3.68 (m, 1H), 3.01–3.00 (2S, 6H), 1.85–1.65 (m, 6H), 1.57 (m, 1H), 1.47 (m, 1H), 1.32 (m, 2H), 1.24 (m, 1H), 1.03 (m, 1.4H), 0.92 (m, 0.6H).

EXAMPLE 343

N'-((2RS,3R)-3-amino-4-cyclohexyl-2-hydroxybutanoyl)-4-(dimethylamino)benzohydrazide The desired compound was prepared by substituting 4-dimethylaminobenzoic acid for o-toluic acid in Example 329B.

MS (ESI) m/e 363 (M+H)$^+$; $^1$H NMR (500 MHz, CD$_3$OD) δ 7.78 (d, 2H), 7.65 (d, 2H), 6.53 (m, 1H), 4.42 (d, 0.3H), 4.35 (d, 0.7H), 3.68 (m, 1H), 3.04 (2S, 6H), 1.85–1.63 (m, 6H), 1.57 (m, 1H), 1.46 (m, 1H), 1.33 (m, 2H), 1.24 (m, 1H), 1.02 (m, 1.4H), 0.92 (m, 0.6H).

EXAMPLE 344

N'-((2RS,3R)-3-amino-4-cyclohexyl-2-hydroxybutanoyl)-3-(trifluoromethyl)benzohydrazide The desired compound was prepared by substituting 3-(trifluoromethyl)benzoic acid for o-toluic acid in Example 329B.

MS (ESI) m/e 388 (M+H)$^+$; $^1$H NMR (500 MHz, CD$_3$OD) δ 8.21 (s, 1H), 8.14 (m, 1H), 7.93 (m, 1H), 7.73 (m, 1H), 4.45 (d, 0.3H), 4.38 (d, 0.7H), 3.69 (m, 1H), 1.85–1.65 (m, 6H), 1.57 (m, 1H), 1.47 (m, 1H), 1.33 (m, 2H), 1.24 (m, 1H), 1.03 (m, 1.4H), 0.92 (m, 0.6H).

EXAMPLE 345

N'-((2RS,3R)-3-amino-4-cyclohexyl-2-hydroxybutanoyl)-4-(trifluoromethyl)benzohydrazide The desired compound was prepared by substituting 4-(trifluoromethyl)benzoic acid for o-toluic acid in Example 329B.

MS (ESI) m/e 388 (M+H)$^+$; $^1$H NMR (500 MHz, CD$_3$OD) δ 8.06 (m, 2H), 7.82 (m, 2H), 4.46 (d, 0.3H), 4.38 (d, 0.7H), 3.69 (m, 1H), 1.85–1.65 (m, 6H), 1.57 (m, 1H), 1.47 (m, 1H), 1.33 (m, 2H), 1.24 (m, 1H), 1.02 (m, 1.4H), 0.92 (m, 0.6H).

EXAMPLE 346

N'-((2RS,3R)-3-amino-4-cyclohexyl-2-hydroxybutanoyl)-3-(trifluoromethoxy)benzohydrazide The desired compound was prepared by substituting 3-(trifluoromethoxy)benzoic acid for o-toluic acid in Example 329B.

MS (ESI) m/e 404 (M+H)$^+$; $^1$H NMR (500 MHz, CD$_3$OD) δ 7.89 (m, 1H), 7.80 (s, 1H), 7,62 (m, 1H), 7.53 (m, 1H), 4.46 (d, 0.3H), 4.38 (d, 0.7H), 3.69 (m, 1H), 1.85–1.65 (m, 6H), 1.57 (m, 1H), 1.47 (m, 1H), 1.33 (m, 2H), 1.24 (m, 1H), 1.02 (m, 1.4H), 0.92 (m, 0.6H).

EXAMPLE 347

N'-((2RS,3R)-3-amino-4-cyclohexyl-2-hydroxybutanoyl)-4-phenoxybenzohydrazide

The desired compound was prepared by substituting 4-phenoxybenzoic acid for o-toluic acid in Example 329B.

MS (ESI) m/e 412 (M+H)$^+$; $^1$H NMR (500 MHz, CD$_3$OD) δ 7.89 (m, 2H), 7.42 (m, 2H), 7.21 (m, 1H), 7.07 (m, 2H), 7.03 (m, 2H), 4.44 (d, 0.3H), 4.37 (d, 0.7H), 3.69 (m, 1H), 1.85–1.64 (m, 6H), 1.56 (m, 1H), 1.46 (m, 1H), 1.33 (m, 2H), 1.24 (m, 1H), 1.02 (m, 1.4H), 0.92 (m, 0.6H).

EXAMPLE 348

N'-((2RS,3R)-3-amino-4-cyclohexyl-2-hydroxybutanoyl)-2,4-dimethylbenzohydrazide

The desired compound was prepared by substituting 2,4-dimethylbenzoic acid for o-toluic acid in Example 329B.

MS (ESI) m/e 348 (M+H)$^+$; $^1$H NMR (500 MHz, CD$_3$OD) δ 7.41 (dd, 1H), 7.12 (s, 1H), 7.09 (m, 1H), 4.43 (d, 0.25H), 4.36 (d, 0.75H), 3.70 (m, 0.75H), 3.66 (m, 0.25H), 2.43 (s, 3H), 2.34 (s, 3H), 1.85–1.65 (m, 6H), 1.57

(m, 1H), 1.46 (m, 1H), 1.32 (m, 2H), 1.24 (m, 1H), 1.02 (m, 1.5H), 0.92 (m, 0.5H).

EXAMPLE 349

N'-((2RS,3R)-3-amino-4-cyclohexyl-2-hydroxybutanoyl)-2,5-dimethylbenzohydrazide

The desired compound was prepared by substituting 2,5-dimethylbenzoic acid for o-toluic acid in Example 329B.

MS (ESI) m/e 348 (M+H)$^+$; $^1$H NMR (500 MHz, CD$_3$OD) δ 7.33 (s, 1H), 7.21 (m, 1H), 7.17 (m, 1H), 4.44 (d, 0.3H), 4.36 (d, 0.7H), 3.70 (m, 0.7H), 3.66 (m, 0.3H), 2.41 (s, 3H), 2.34 (s, 3H), 1.85–1.65 (m, 6H), 1.57 (m, 1H), 1.47 (m, 1H), 1.33 (m, 2H), 1.24 (m, 1H), 1.02 (m, 1.4H), 0.92 (m, 0.6H).

EXAMPLE 350

N'-((2RS,3R)-3-amino-4-cyclohexyl-2-hydroxybutanoyl)-3,4-dimethylbenzohydrazide

The desired compound was prepared by substituting 3,4-dimethylbenzoic acid for o-toluic acid in Example 329B.

MS (ESI) m/e 348 (M+H)$^+$; $^1$H NMR (500 MHz, CD$_3$OD) δ 7.66 (s, 1H), 7.62 (dd, 1H), 7.26 (dd, 1H), 4.44 (d, 0.3H). 4.36 (d, 0.7H), 3.68 (m, 1H), 2.07 (s, 6H), 1.85–1.65 (m, 6H), 1.56 (m, 1H), 1.47 (m, 1H), 1.33 (m, 2H), 1.24 (m, 1H), 1.02 (m, 1.4H), 0.92 (m, 0.6H).

EXAMPLE 351

N'-((2RS,3R)-3-amino-4-cyclohexyl-2-hydroxybutanoyl)-3,5-dimethylbenzohydrazide

The desired compound was prepared by substituting 3,5-dimethylbenzoic acid for o-toluic acid in Example 329B.

MS (ESI) m/e 348 (M+H)$^+$; $^1$H NMR (500 MHz, CD$_3$OD) δ 7.50 (s, 2H), 7.26 (s, 0.75H), 7.24 (s, 0.25H), 4.44 (d, 0.25H), 4.36 (d, 0.75H), 3.68 (m, 1H), 2.37 (s, 6H), 1.85–1.65 (m, 6H), 1.55 (m, 1H), 1.47 (m, 1H), 1.33 (m, 2H), 1.24 (m, 1H), 1.03 (m, 1.5H), 0.92 (m, 0.5H).

EXAMPLE 352

N'-((2RS,3R)-3-amino-4-cyclohexyl-2-hydroxybutanoyl)-2,3-dimethoxybenzohydrazide The desired compound was prepared by substituting 2,3-dimethoxybenzoic acid for o-toluic acid in Example 329B.

MS (ESI) m/e 380 (M+H)$^+$; $^1$H NMR (500 MHz, CD$_3$OD) δ 7.41 (m, 1H), 7.24 (td, 2H), 7.19 (td, 1H), 4.43 (d, 0.3H), 4.37 (d, 0.7H), 3.95 (s, 2.1H), 3.95 (s, 0.9H), 3.91 (s, 2.1H), 3.90 (s, 0.9H), 3.69 (m, 1H), 1.85–1.65 (m, 6H), 1.57 (m, 1H), 1.46 (m, 1H), 1.33 (m, 2H), 1.24 (m, 1H), 1.02 (m, 1.4H), 0.92 (m, 0.6H).

EXAMPLE 353

N'-((2RS,3R)-3-amino-4-cyclohexyl-2-hydroxybutanoyl)-3,4-dimethoxybenzohydrazide The desired compound was prepared by substituting 3,4-dimethoxybenzoic acid for o-toluic acid in Example 329B.

MS (ESI) m/e 380 (M+H)$^+$; $^1$H NMR (500 MHz, CD$_3$OD) δ 7.55 (m, 1H), 7.50 (d, 1H), 7.05 (dd, 1H), 4.44 (d, 0.3H), 4.37 (d, 0.7H), 3.90 (s, 3H), 3.88 (s, 3H), 3.69 (m, 1H), 1.85–1.65 (m, 6H), 1.57 (m, 1H), 1.47 (m, 1H), 1.33 (m, 2H), 1.24 (m, 1H), 1.02 (m, 1.4H), 0.92 (m, 0.6H).

EXAMPLE 354

N'-((2RS,3R)-3-amino-4-cyclohexyl-2-hydroxybutanoyl)-3,4,5-trimethoxybenzohydrazide The desired compound was prepared by substituting 3,4,5-trimethoxybenzoic acid for o-toluic acid in Example 329B.

MS (ESI) m/e 410 (M+H)$^+$; $^1$H NMR (500 MHz, CD$_3$OD) δ 7.25 (s, 2H), 4.46 (d, 0.3H), 4.37 (d, 0.7H), 3.89 (s, 6H), 3.83 (s, 3H), 3.69 (m, 1H), 1.85–1.65 (m, 6H), 1.57 (m, 1H), 1.47 (m, 1H), 1.33 (m, 2H), 1.24 (m, 1H), 1.02 (m, 1.4H), 0.92 (m, 0.6H).

EXAMPLE 355

N'-((2RS,3R)-3-amino-4-cyclohexyl-2-hydroxybutanoyl)-2,3-dichlorobenzohydrazide

The desired compound was prepared by substituting 2,3-dichlorobenzoic acid for o-toluic acid in Example 329B.

MS (ESI) m/e 389 (M+H)$^+$; $^1$H NMR (500 MHz, CD$_3$OD) δ 7.68 (td, 1H), 7.54 (dt, 1H), 6.42 (td, 1H), 4.44 (d, 0.3H), 4.36 (d, 0.7H), 3.69 (m, 1H), 1.85–1.65 (m, 6H), 1.55 (m, 1H), 1.47 (m, 1H), 1.33 (m, 2H), 1.24 (m, 1H), 1.02 (m, 1.4H), 0.92 (m, 0.6H).

EXAMPLE 356

N'-((2RS,3R)-3-amino-4-cyclohexyl-2-hydroxybutanoyl)-2,4-dichlorobenzohydrazide

The desired compound was prepared by substituting 2,4-dichlorobenzoic acid for o-toluic acid in Example 329B.

MS (ESI) m/e 389 (M+H)$^+$; $^1$H NMR (500 MHz, CD$_3$OD) δ 7.60 (m, 2H), 7.46 (m, 1H), 4.44 (d, 0.3H), 4.35 (d, 0.7H), 3.68 (m, 1H), 1.85–1.65 (m, 6H), 1.55 (m, 1H), 1.46 (m, 1H), 1.33 (m, 2H), 1.23 (m, 1H), 1.02 (m, 1.4H), 0.92 (m, 0.6H).

EXAMPLE 357

N'-((2RS,3R)-3-amino-4-cyclohexyl-2-hydroxybutanoyl)-3,4-dichlorobenzohydrazide

The desired compound was prepared by substituting 3,4-dichlorobenzoic acid for o-toluic acid in Example 329B.

MS (ESI) m/e 389 (M+H)$^+$; $^1$H NMR (500 MHz, CD$_3$OD) δ 8.05 (m, 1H), 7.80 (m, 1H), 7.68 (m, 1H), 4.45 (d, 0.3H), 4.37 (d, 0.7H), 3.67 (m, 1H), 1.85–1.65 (m, 6H), 1.56 (m, 1H), 1.47 (m, 1H), 1.33 (m, 2H), 1.24 (m, 1H), 1.02 (m, 1.4H), 0.92 (m, 0.6H).

EXAMPLE 358

N'-((2RS,3R)-3-amino-4-cyclohexyl-2-hydroxybutanoyl)-3,5-dichlorobenzohydrazide

The desired compound was prepared by substituting 3,5-dichlorobenzoic acid for o-toluic acid in Example 329B.

MS (ESI) m/e 389 (M+H)$^+$; $^1$H NMR (500 MHz, CD$_3$OD) δ 7.97–7.69 (m, 3H), 4.45 (d, 0.3H), 4.37 (d, 0.7H), 3.68 (m, 1H), 1.85–1.65 (m, 6H), 1.56 (m, 1H), 1.47 (m, 1H), 1.33 (m, 2H), 1.24 (m, 1H), 1.02 (m, 1.4H), 0.92 (m, 0.6H).

EXAMPLE 359

N'-((2RS,3R)-3-amino-4-cyclohexyl-2-hydroxybutanoyl)-2,3-dimethylbenzohydrazide

The desired compound was prepared by substituting 2,3-dimethylbenzoic acid for o-toluic acid in Example 329B.

MS (ESI) m/e 348 (M+H)+; 1H NMR (500 MHz, CD3OD) δ 7.29 (m, 2H), 7.16 (m, 1H), 4.44 (d, 0.3H), 4.36 (d, 0.7H), 3.68 (m, 1H), 1.85–1.64 (m, 6H), 1.57 (m, 1H), 1.47 (m, 1H), 1.33 (m, 2H), 1.24 (m, 1H), 1.02 (m, 1.4H), 0.92 (m, 0.6H).

EXAMPLE 360

N'-((2RS,3R)-3-amino-5-(ethylsulfanyl)-2-hydroxypentanoyl)benzenesulfonohydrazide The desired product was prepared by substituting benzenesulfonylhydrazine for O-phenyl hydroxylamine hydrochloride in Example 98B.

MS (ESI) m/e 348 (M+H)+; 1H NMR (300 MHz, DMSO-d6) δ 7.38 (m, 5H), 6.68 (d, 0.6H), 6.62 (d, 0.4H), 4.30 (m, 0.4H), 4.14 (m, 0.6H), 3.87 (m, 1H), 2.60 (m, 2H), 2.45 (m, 2H), 1.64 (m, 1H), 1.36 (m, 1H), 1.16 (t, 3H).

EXAMPLE 361

N'-((2RS,3R)-3-amino-5-(ethylsulfanyl)-2-hydroxypentanoyl)-3-chlorobenzenesulfonohydrazide The desired product was prepared by substituting 3-chlorophenylsulfonylhydrazine for O-phenyl hydroxylamine hydrochloride in Example 98B.

MS (ESI) m/e 383 (M+H)+; 1H NMR (300 MHz, DMSO-d6) δ 10.25 (m, 1H), 10.14 (m, 1H), 8.55 (br s, 2H), 7.85 (m, 1H), 7.78 (m, 2H), 7.65 (m, 1H), 6.68 (d, 0.6H), 6.62 (d, 0.4H), 4.30 (m, 0.4H), 4.14 (m, 0.6H), 3.87 (m, 1H), 2.60 (m, 2H), 2.45 (m, 2H), 1.64 (m, 1H), 1.36 (m, 1H), 1.16 (t, 3H).

EXAMPLE 362

N'-((2RS,3R)-3-amino-5-(ethylsulfanyl)-2-hydroxypentanoyl)-1-naphthalenesulfonohydrazide The desired product was prepared by substituting 1-naphthylsulfonylhydrazine for O-phenyl hydroxylamine hydrochloride in Example 98B.

MS (ESI) m/e 398 (M+H)+; 1H NMR (300 MHz, DMSO-d6) δ 10.25 (m, 1H), 10.14 (m, 1H), 8.70 (br s, 2H), 8.27 (m, 1H), 8.17 (m, 1H), 8.13 (m, 1H), 7.68 (m, 4H), 6.68 (d, 0.6H), 6.62 (d, 0.4H), 4.30 (m, 0.4H), 4.14 (m, 0.6H), 3.87 (m, 1H), 2.60 (m, 2H), 2.45 (m, 2H), 1.64 (m, 1H), 1.36 (m, 1H), 1.6 (t, 3H).

EXAMPLE 363

N'-((2RS,3R)-3-amino-5-(ethylsulfanyl)-2-hydroxypentanoyl)-4-methylbenzenesulfonohydrazide The desired product was prepared by substituting 4-methylphenylsulfonylhydrazine for O-phenyl hydroxylamine hydrochloride in Example 98B.

MS (ESI) m/e 362 (M+H)+; 1H NMR (300 MHz, DMSO-d6) δ 7.72 (m, 2H), 7.38 (m, 2H), 6.68 (d, 0.6H), 6.62 (d, 0.4H), 4.30 (m, 0.4H), 4.14 (m, 0.6H), 3.87 (m, 1H), 2.60 (m, 2H), 2.45 (m, 2H), 2.40 (s, 3H), 1.64 (m, 1H), 1.36 (m, 1H), 1.16 (t, 3H).

EXAMPLE 364

(2RS,3R)-3-amino-N'-(3-(2-aminoethoxy)phenyl)-2-hydroxy-5-(isopropylsulfanyl)pentanohydrazide

Example 364A

N-(tert-butoxycarbonyl)-2-bromoethylamine

A solution of 2-bromoethylamine hydrobromide (1.0 g, 4.9 mmol), di-tert-butyl dicarbonate (1.06 g, 4.9 mmol) and triethylamine (0.7 mL, 4.9 mmol) in dichloromethane (40 mL) was stirred at room temperature for 18 h. The reaction mixture was diluted with ether, washed with brine, dried (Na2SO4), and concentrated to give the title compound.

EXAMPLE 364B 3-(2-(tertbutoxycarbonylamino)ethoxy)benzoyl hydrazide

Example 364A, methyl-3-hydroxy-benzoate (1.09 g, 4.9 mmol) and potassium tert-butoxide (6.5 g, 5.8 mmol) in DMSO were stirred at room temperature for 16 hours. The reaction was poured into ice water and extracted with ether, washed with brine, dried over Na2SO4, evaporated, and treated with hydrazine hydrate in ethanol at reflux for 48 h. The reaction mixture was evaporated to dryness to give the title compound.

EXAMPLE 364C (2RS,3R)-3-amino-N'-(3-(2-aminoethoxy)phenyl)-2-hydroxy-5-(isopropylsulfanyl)pentanohydrazide The desired product was prepared by substituting Example 364A for O-phenyl hydroxylamine hydrochloride and Example 123B for Example 98A in Example 98B.

MS (ESI) m/e 383 (M−H)+. 1H NMR (300 MHz, DMSO-d6) δ 10.6 & 10.42 (s, 1H), 10.25 & 10.12 (s, 1H), 8.15 & 8.04 (br s, 2H), 7.56–7.33 (m, 3H), 7.2 (m, 1H), 6.67 & 6.59 (br s, 1H), 4.45 & 4.24 (m, 3H), 3.25 (m, 2H), 3.0–2.9 (m, 1H), 2.75–2.55 (m, 2H), 2.0–1.80 (m, 2H), 1.2 (m,6H).

EXAMPLE 365

N'-((2RS,3R)-3-amino-5-(ethylsulfanyl)-2-hydroxypentanoyl)-3-bromobenzohydrazide The desired product was prepared by substituting 3-bromobenzoic acid for 3-(ethylsulfanyl)benzoic acid in Example 239B.

MS (ESI) m/e 391 (M+H)+; 1H NMR (500 MHz, CD3OD) δ 8.06 (ddd, 1H), 7.85 (ddd, 1H), 7.77 (ddd, 1H), 7.44 (m, 1H), 4.49 (d, 0.35), 4.44 (d, 0.65), 3.78 (m, 1H), 2.71 (t, 2H), 2.61 (dd, 2H), 2.17 (dd, 1H), 1.99 (dt, 1H), 1.28 (t, 1.95H), 1.25 (t, 1.05H).

EXAMPLE 366

N'-((2RS,3R)-3-amino-5-(ethylsulfanyl)-2-hydroxypentanoyl)-3-cyanobenzohydrazide The desired product was prepared by substituting 2-cyanobenzoic acid for 3-(ethylsulfanyl)benzoic acid in Example 239B.

MS (ESI) m/e 337 (M+H)+; 1H NMR (500 MHz, CD3OD) δ 8.23 (ddd, 1H), 8.16 (ddd, 1H), 7.96 (ddd, 1H), 7.71 (m, 1H), 4.50 (d, 0.35), 4.45 (d, 0.65), 3.79 (m, 1H), 2.71 (t, 2H), 2.61 (dd, 2H), 2.17 (dd, 1H), 2.00 (dt, 1H), 1.28 (t, 1.95H), 1.25 (t, 1.05H).

EXAMPLE 367

N'-((2RS,3R)-3-amino-5-(ethylsulfanyl)-2-hydroxypentanoyl)-4-cyanobenzohydrazide The desired product was prepared by substituting 4-cyanobenzoic acid for 3-(ethylsulfanyl)benzoic acid in Example 239B.

MS (ESI) m/e 337 (M+H)+; 1H NMR (500 MHz, CD3OD) δ 8.02 (m, 2H), 7.88 (m, 2H), 4.50 (d, 0.35), 4.45

(d, 0.6), 3.79 (m, 1H), 2.71 (t, 2H), 2.61 (dd, 2H), 2.17 (dd, 1H), 2.00 (dt, 1H), 1.27 (t, 1.95H) 1.25 (t, 1.05H).

EXAMPLE 368

N'-((2RS,3R)-3-amino-2-hydroxy-5-(isopropylsulfanyl)pentanoyl)-3-hydroxybenzohydrazide The title compound is obtained by substituting 3-hydroxybenzoyl hydrazide for O-phenylhydroxylamine hydrochloride and Example 123B for Example 98A in Example 98B.

MS (ESI) m/e 340 (M−H)+. $^1$H NMR (300 MHz, DMSO-d$_6$) δ 10.44 & 10.26 (s, 1H), 10.17 & 10.06 (s, 1H), 9.78 & 9.74 (s, 1H), 8.05 & 8.7.97 (br s, 2H), 7.26 (m, 3H), 6.97 (m, 1H), 6.63 & 6.595(bd, 1H), 4.38 & 4.22 (m, 1H), 3.7 & 3.6 (m, 1H), 3.0–2.9 (m, 1H), 2.75–2.55 (m, 2H), 2.05–1.77 (m, 2H), 1.2 (m, 6H).

EXAMPLE 369

N'-((2RS,3R)-3-amino-2-hydroxy-5-(isopropylsulfanyl)pentanoyl)-2-methylbenzohydrazide

Example 369A

N'-((2RS,3R)-3-(tert-butoxycarbonyl)amino-5-(isopropylsulfanyl)-2-hydroxypentanoyl)hydrazide The desired compound was prepared by substituting Example 123B for Example 97A acid in Example 239A.

EXAMPLE 369B

N'-((2RS,3R)-3-amino-2-hydroxy-5-(isopropylsulfanyl)pentanoyl)-2-methylbenzohydrazide To DCC resin (148 mg, 0.225 mmol) in 1.0 mL of dichloromethane was added 0.5 mL of a 0.45 M solution of HOBt (0.225 mmol) in dimethylacetamide/dichloromethane (1:6), and 0.5 mL of a 0.3M solution of o-toluic acid (0.15 mmol) in dimethylacetamide. After 5 minutes, 1.0 mL of a 0.225 M solution of Example 369A (0.225 mmol) in dimethylacetamide/dichloromethane (1:1) was added. The mixture was agitated for 18 hours and quenched with 0.19 g of trisamine resin (0.75 mmol) followed by 0.13 g of isocyanate resin (0.225 mmol) and agitated for 4 hours. The mixture was filtered and the resins washed with 1×3 mL of dichloromethane, the solvent was removed in vacuo, and the crude material purified by reverse phase preparative HPLC. The resulting material was treated with 1 mL of 50% trifluoroacetic acid/dichloromethane and agitated at ambient temperature for 18 hours. The solvent was removed in vacuo to give the desired product.

MS (ESI) m/e 340 (M+H)+; $^1$H NMR (500 MHz, CD$_3$OD) δ 7.50 (m, 1H), 7.40 (ddd, 1H), 7.28 (m, 2H), 4.49 (d, 0.3H), 4.44 (d, 0.7H), 3.79 (m, 1H), 3.00 (m, 1H), 2.72 (t, 2H), 2.47 (2s, 3H), 2.16 (m, 1H), 1.98 (m, 1H), 1.29–1.25 (m, 6H).

EXAMPLE 370

N'-((2RS,3R)-3-amino-2-hydroxy-5-(isopropylsulfanyl)pentanoyl)-3-methylbenzohydrazide The desired compound was prepared by substituting m-toluic acid for o-toluic acid in Example 369.

MS (ESI) m/e 340 (M+H)+; $^1$H NMR (500 MHz, CD$_3$OD) δ 7.69 (m, 2H), 7.40 (m, 2H), 4.49 (d, 0.3H), 4.44 (d, 0.7H), 3.78 (m, 1H), 3.00 (m, 1H), 2.72 (t, 2H), 2.41 (s, 3H), 2.16 (m, 1H), 1.98 (m, 1H), 1.29–1.25 (m, 6H).

EXAMPLE 371

N'-((2RS,3R)-3-amino-2-hydroxy-5-(isopropylsulfanyl)pentanoyl)-4-methylbenzohydrazide The desired compound was prepared by substituting p-toluic acid for o-toluic acid in Example 369.

MS (ESI) m/e 340 (M+H)+; $^1$H NMR (500 MHz, CD$_3$OD) δ 7.78 (m, 2H), 7.31 (m, 2H), 4.49 (d, 0.3H), 4.44 (d, 0.7H), 3.77 (m, 1H), 3.00 (m, 1H), 2.72 (t, 2H), 2.41 (s, 3H), 2.15 (m, 1H), 1.99 (m, 1H), 1.29–1.24 (m, 6H).

EXAMPLE 372

N'-((2RS,3R)-3-amino-2-hydroxy-5-(isopropylsulfanyl)pentanoyl)-2-methoxybenzohydrazide The desired compound was prepared by substituting o-anisic acid for o-toluic acid in Example 369.

MS (ESI) m/e 356 (M+H)+; $^1$H NMR (500 MHz, CD$_3$OD) δ 7.99 (dd, 1H), 7.57 (m, 1H), 7.19 (m, 1H), 7.09 (m, 1), 4.48 (d, 0.3H), 4.45 (d, 0.7H), 4.00 (s, 2.1H), 3.99 (s, 0.9H), 3.78 (m, 1H), 3.00 (m, 1H), 2.72 (t, 2H), 2.14 (m, 1H), 1.98 (m, 1H), 1.29–1.24 (m, 6H).

EXAMPLE 373

N'-((2RS,3R)-3-amino-2-hydroxy-5-(isopropylsulfanyl)pentanoyl)-3-methoxybenzohydrazide The desired compound was prepared by substituting m-anisic acid for o-toluic acid in Example 369.

MS (ESI) m/e 356 (M+H)+; $^1$H NMR (500 MHz, CD$_3$OD) δ 7.43 (m, 3H), 7.16 (m, 1H), 4.49 (d, 0.3H), 4.44 (d, 0.7H), 3.85 (s, 3H), 3.78 (m, 1H), 3.00 (m, 1H), 2.72 (t, 2H), 2.16 (m, 1H), 1.98 (m, 1H), 1.29–1.24 (m, 6H).

EXAMPLE 374

N'-((2RS,3R)-3-amino-2-hydroxy-5-(isopropylsulfanyl)pentanoyl)-4-methoxybenzohydrazide The desired compound was prepared by substituting p-anisic acid for o-toluic acid in Example 369.

MS (ESI) m/e 356 (M+H)+; $^1$H NMR (500 MHz, CD$_3$OD) δ 7.87 (m, 2H), 7.02 (m, 2H), 4.48 (d, 0.3H), 4.44 (d, 0.7H), 3.87 (s, 2,1H), 3.86 (s, 0.9H), 3.77 (m, 1H), 3.00 (m, 1H), 2.71 (t, 2H), 2.14 (m, 1H), 1.98 (m, 1H), 1.29–1.25 (m, 6H).

EXAMPLE 375

N'-((2RS,3R)-3-amino-2-hydroxy-5-(isopropylsulfanyl)pentanoyl)-2-fluorobenzohydrazide The desired compound was prepared by substituting o-fluorobenzoic acid for o-toluic acid in Example 369.

MS (ESI) m/e 344 (M+H)+; $^1$H NMR (500 MHz, CD$_3$OD) δ 7.81 (m, 1H), 7.60 (m, 1H), 7.33 (m, 1H), 7.27

(m, 1H), 4.48 (d, 0.3H), 4.44 (d, 0.7H), 3.78 (m, 1H), 3.00 (m, 1H), 2.72 (t, 2H), 2.15 (m, 1H), 1.98 (m, 1H), 1.29–1.24 (m, 6H).

EXAMPLE 376

N'-((2RS,3R)-3-amino-2-hydroxy-5-(isopropylsulfanyl)pentanoyl)-3-fluorobenzohydrazide The desired compound was prepared by substituting m-fluorobenzoic acid for o-toluic acid in Example 369.

MS (ESI) m/e 344 (M+H)$^+$; $^1$H NMR (500 MHz, CD$_3$OD) δ 7.72 (t, 1H), 7.62 (m, 1H), 7.53 (ddd, 1H), 7.36 (ddd, 1H), 4.49 (d, 0.3H), 4.44 (d, 0.7H), 3.78 (m, 1H), 3.00 (m, 1H), 2.72 (t, 2H), 2.16 (m, 1H), 1.98 (m, 1H), 1.29–1.24 (m, 6H).

EXAMPLE 377

N'-((2RS,3R)-3-amino-2-hydroxy-5-(isopropylsulfanyl)pentanoyl)-4-fluorobenzohydrazide The desired compound was prepared by substituting p-fluorobenzoic acid for o-toluic acid in Example 369.

MS (ESI) m/e 344 (M+H)$^+$; $^1$H NMR (500 MHz, CD$_3$OD) δ 7.95 (m, 2H), 7.24 (m, 2H), 4.48 (d, 0.3H), 4.44 (d, 0.7H), 3.77 (m, 1H), 3.00 (m, 1H), 2.72 (t, 2H), 2.15 (m, 1H), 1.98 (m, 1H), 1.29–1.25 (m, 6H).

EXAMPLE 378

N'-((2RS,3R)-3-amino-2-hydroxy-5-(isopropylsulfanyl)pentanoyl)-2-chlorobenzohydrazide The desired compound was prepared by substituting o-chlorobenzoic acid for o-toluic acid in Example 369.

MS (ESI) m/e 360 (M+H)$^+$; $^1$H NMR (500 MHz, CD$_3$OD) δ 7.61 (m, 1H), 7.50 (m, 2H), 7.42 (m, 1H), 4.48 (d, 0.3H), 4.43 (d, 0.7H), 3.78 (m, 1H), 3.00 (m, 1H), 2.72 (t, 2H), 2.15 (m, 1H), 1.98 (m, 1H), 1.29–1.24 (m, 6H).

(399005) EXAMPLE 379

N'-((2RS,3R)-3-amino-2-hydroxy-5-(isopropylsulfanyl)pentanoyl)-4-chlorobenzohydrazide The desired compound was prepared by substituting p-chlorobenzoic acid for o-toluic acid in Example 369.

MS (ESI) m/e 360 (M+H)$^+$; $^1$H NMR (500 MHz, CD$_3$OD) δ 7.87 (m, 2H), 7.52 (m, 2H), 4.49 (d, 0.3H), 4.44 (d, 0.7H), 3.77 (m, 1H), 3.00 (m, 1H), 2.72 (t, 2H), 2.15 (m, 1H), 1.98 (m, 1H), 1.29–1.24 (m, 6H).

EXAMPLE 380

N'-((2RS,3R)-3-amino-2-hydroxy-5-(isopropylsulfanyl)pentanoyl)-2-bromobenzohydrazide The desired compound was prepared by substituting o-bromobenzoic acid for o-toluic acid in Example 369.

MS (ESI) m/e 405 (M+H)$^+$; $^1$H NMR (500 MHz, CD$_3$OD) δ 7.69 (m, 1H), 7.59 (m, 1H), 7.46 (m, 1H), 7.42 (m, 1H), 4.48 (d, 0.3H), 4.43 (d, 0.7H), 3.78 (m, 1H), 3.00 (m, 1H), 2.72 (t, 2H), 2.15 (m, 1H), 1.98 (m, 1H), 1.29–1.24 (m, 6H).

EXAMPLE 381

N'-((2RS,3R)-3-amino-2-hydroxy-5-(isopropylsulfanyl)pentanoyl)-3-bromobenzohydrazide The desired compound was prepared by substituting 3-bromobenzoic acid for o-toluic acid in Example 369.

MS (ESI) m/e 405 (M+H)$^+$; $^1$H NMR (500 MHz, CD$_3$OD) δ 8.06 (dt, 1H), 7.85 (m, 1H), 7.77 (m, 1H), 7.44 (m, 1H), 4.49 (d, 0.3H), 4.44 (d, 0.7H), 3.78 (m, 1H), 3.00 (m, 1H), 2.72 (t, 2H), 2.15 (m, 1H), 1.98 (m, 1H), 1.29–1.24 (m, 6H).

EXAMPLE 382

N'-((2RS,3R)-3-amino-2-hydroxy-5-(isopropylsulfanyl)pentanoyl)-4-bromobenzohydrazide The desired compound was prepared by substituting 4-bromobenzoic acid for o-toluic acid in Example 369.

MS (ESI) m/e 405 (M+H)$^+$; $^1$H NMR (500 MHz, CD$_3$OD) δ 7.80 (m, 2H), 7.68 (m, 2H), 4.49 (d, 0.3H), 4.44 (d, 0.7H), 3.77 (m, 1H), 3.00 (m, 1H), 2.72 (t, 2H), 2.15 (m, 1H), 1.98 (m, 1H), 1.29–1.24 (m, 6H).

EXAMPLE 383

N'-((2RS,3R)-3-amino-2-hydroxy-5-(isopropylsulfanyl)pentanoyl)-2,3-dichlorobenzohydrazide The desired compound was prepared by substituting 2,3-dichlorobenzoic acid for o-toluic acid in Example 369.

MS (ESI) m/e 395 (M+H)$^+$; $^1$H NMR (500 MHz, CD$_3$OD) δ 7.69 (td, 1H), 7.53 (m, 1H), 7.42 (m, 1H), 4.49 (d, 0.3H), 4.43 (d, 0.7H), 3.78 (m, 1H), 3.00 (m, 1H), 2.72 (t, 2H), 2.15 (m, 1H), 1.98 (m, 1H), 1.29–1.24 (m, 6H).

EXAMPLE 384

(2RS,3R)-3-amino-2-hydroxy-5-(isopropylsulfanyl)-N'-(tetrahydro-2-furanylcarbonyl)pentanohydrazide The desired compound was prepared by substituting tetrahydrofuran-2-carboxylic acid for o-toluic acid in Example 369.

MS (ESI) m/e 320 (M+H)$^+$; $^1$H NMR (500 MHz, CD$_3$OD) δ 4.45 (m, 1.3H), 4.38 (d, 0.7H), 4.02 (m, 1H), 3.87 (m, 1H), 3.73 (m, 1H), 2.98 (m, 1H), 2.69 (t, 2H), 2.29 (m, 1H), 2.10 (m, 2H), 1.94 (m, 3H), 1.28–1.23 (m, 6H).

EXAMPLE 385

(2RS,3R)-3-amino-2-hydroxy-5-(isopropylsulfanyl)-N'-(tetrahydro-3-furanylcarbonyl)pentanohydrazide The desired compound was prepared by substituting tetrahydro-3-furic acid for o-toluic acid in Example 369.

MS (ESI) m/e 320 (M+H)$^+$; $^1$H NMR (500 MHz, CD$_3$OD) δ 4.42 (d, 0.3H), 4.38 (d, 0.7H), 3.96 (m, 1H), 3.88 (m, 2H), 3.79 (m, 1H), 3.72 (m, 1H), 3.10 (m, 1H), 2.98 (m, 1H), 2.69 (t, 2H), 2.13 (m, 3H), 1.94 (m, 1H), 1.28–1.23 (m, 6H).

EXAMPLE 386

(2RS,3R)-3-amino-2-hydroxy-5-(isopropylsulfanyl)-N'-cyclopentylpentanohydrazide

The desired compound was prepared by substituting cyclopentanecarboxylic acid for o-toluic acid in Example 369.

MS (ESI) m/e 318 (M+H)+; ¹H NMR (500 MHz, CD₃OD) δ 4.41 (d, 0.3H), 4.37 (d, 0.7H), 3.72 (m, 1H), 2.98 (m, 1H), 2.70 (m, 2H), 2.11 (m, 1H), 2.10 (m, 1H), 1.91 (m, 3H), 1.77 (m, 5H), 1.62 (m, 1H), 1.28–1.23 (m, 6H).

EXAMPLE 387

N'-((2RS,3R)-3-amino-2-hydroxy-5-(isopropylsulfanyl)pentanoyl)-2-cyclopentylacetohydrazide The desired compound was prepared by substituting cyclopentylacetic acid for o-toluic acid in Example 369.

MS (ESI) m/e 332 (M+H)+; ¹H NMR (500 MHz, CD₃OD) δ 4.41 (d, 0.3H), 4.37 (d, 0.7H), 3.72 (m, 1H), 2.98 (m, 1H), 2.69 (t, 2H), 2.27 (m, 3H), 2.10 (m, 1H), 1.94 (m, 1H), 1.85 (m, 2H), 1.67 (m, 2H), 1.58 (m, 2H), 1.28–1.23 (m, 8H).

EXAMPLE 388

(2RS,3R)-3-amino-2-hydroxy-5-(isopropylsulfanyl)-N'-cyclohexylpentanohydrazide

The desired compound was prepared by substituting cyclohexanecarboxylic acid for o-toluic acid in Example 369.

MS (ESI) m/e 332 (M+H)+; ¹H NMR (500 MHz, CD₃OD) δ 4.41 (d, 0.3H), 4.37 (d, 0.7H), 3.72 (m, 1H), 2.98 (m, 1H) 2.69 (t, 2H), 2.30 (m, 1H), 2.10 (m, 1H), 1.94 (m, 1H), 1.82 (m, 4H), 1.71 (m, 1H), 1.48 (m, 2H), 1.37–1.23 (m, 9H).

EXAMPLE 389

N'-((2RS,3R)-3-amino-2-hydroxy-5-(isopropylsulfanyl)pentanoyl)-2-cyclohexylacetohydrazide The desired compound was prepared by substituting cyclohexylacetic acid for o-toluic acid in Example 369.

MS (ESI) m/e 346 (M+H)+; ¹H NMR (500 MHz, CD₃OD) δ 4.41 (d, 0.3H), 4.36 (d, 0.7H), 3.72 (m, 1H), 2.98 (m, 1H), 2.69 (t, 2H), 2.12 (m, 3H), 1.94 (m, 1H), 1.74 (m, 6H), 1.26 (m, 9H), 1.02 (m, 2H).

EXAMPLE 390

N'-((2RS,3R)-3-amino-2-hydroxy-5-(isopropylsulfanyl)pentanoyl)-2-furohydrazide

The desired compound was prepared by substituting furan-2-carboxylic acid for o-toluic acid in Example 369.

MS (ESI) m/e 316(M+H)+; ¹H NMR (500 MHz, CD₃OD) δ 7.74 (d, 0.7H), 7.72 (d, 0.3H), 7.24 (d, 0.7H), 7.21 (d, 0.3H), 6.64 (m, 1H), 4.47 (d, 0.3H), 4.43 (d, 0.7H), 3.77 (m, 1H), 3.00 (m, 1H), 2.71 (t, 2H), 2.14 (m, 1H), 1.97 (m, 1H), 1.28–1.23 (m, 6H).

EXAMPLE 391

N'-((2RS,3R)-3-amino-2-hydroxy-5-(isopropylsulfanyl)pentanoyl)-3-furohydrazide

The desired compound was prepared by substituting furan-3-carboxylic acid for o-toluic acid in Example 369.

MS (ESI) m/e 316 (M+H)+; ¹H NMR (500 MHz, CD₃OD) δ 8.17 (d, 0.7H), 8.14 (d, 0.3H), 7.62 (m, 1H), 6.83 (m, 1H), 4.47 (d, 0.3H), 4.43 (d, 0.7H), 3.75 (m, 1H), 3.00 (m, 1H), 2.71 (t, 2H), 2.14 (m, 1H), 1.97 (m, 1H), 1.28–1.23 (m, 6H).

EXAMPLE 392

N'-((2RS,3R)-3-amino-2-hydroxy-5-(isopropylsulfanyl)pentanoyl)-2,5-dimethyl-3-furohydrazide The desired compound was prepared by substituting 2,5-dimethyl-3-furoic acid for o-toluic acid in Example 369.

MS (ESI) m/e 344 (M+H)+; ¹H NMR (500 MHz, CD₃OD) δ 6.32 (s, 0.7H), 6.31 (d, 0.3H), 4.46 (d, 0.3H), 4.41 (d, 0.7H), 3.75 (m, 1H), 3.00 (m, 1H), 2.70 (t, 2H), 2.50 (s, 3H), 2.25 (s, 3H), 2.14 (m, 1H), 1.97 (m, 1H), 1.28–1.23 (m, 6H).

EXAMPLE 393

N'-((2RS,3R)-3-amino-2-hydroxy-5-(isopropylsulfanyl)pentanoyl)-2-thiophenecarbohydrazide The desired compound was prepared by substituting thiophene-2-carboxylic acid for o-toluic acid in Example 369.

MS (ESI) m/e 332 (M+H)+; ¹H NMR (500 MHz, CD₃OD) δ 7.77 (m, 2H), 7.17 (m, 1H), 4.48 (d, 0.3H), 4.43 (d, 0.7H), 3.78 (m, 1H), 3.00 (m, 1H), 2.71 (t, 2H), 2.14 (m, 1H), 1.97 (m, 1H), 1.29–1.25 (m, 6H).

EXAMPLE 394

N'-((2RS,3R)-3-amino-2-hydroxy-5-(isopropylsulfanyl)pentanoyl)-3-thiophenecarbohydrazide The desired compound was prepared by substituting thiophene-3-carboxylic acid for o-toluic acid in Example 369.

MS (ESI) m/e 332 (M+H)+; ¹H NMR (500 MHz, CD₃OD) δ 8.19 (m, 0.7H), 8.16 (m, 0.3H), 7.54 (m, 2H), 4.48 (d, 0.3H), 4.44 (d, 0.7H), 3.77 (m, 1H), 3.00 (m, 1H), 2.71 (t, 2H), 2.14 (m, 1H), 1.98 (m, 1H), 1.29–1.24 (m, 6H).

EXAMPLE 395

N'-((2RS,3R)-3-amino-2-hydroxy-5-(isopropylsulfanyl)pentanoyl)-3-methyl-2-thiophenecarbohydraz The desired compound was prepared by substituting 3-methylthiophene-2-carboxylic acid for o-toluic acid in Example 369.

MS (ESI) m/e 346 (M+H)+; ¹H NMR (500 MHz, CD₃OD) δ 7.56 (d, 0.7H), 7.53 (d, 0.3H), 6.99 (m, 1H), 4.47 (d, 0.3H), 4.43 (d, 0.7H), 3.77 (m, 1H), 3.00 (m, 1H), 2.71 (t, 2H), 2.51 (s, 2.1H), 2.50 (s, 0.9H), 2.14 (m, 1H), 1.97 (m, 1H), 1.29–1.24 (m, 6H).

EXAMPLE 396

N'-((2RS,3R)-3-amino-2-hydroxy-5-(isopropylsulfanyl)pentanoyl)-5-methyl-2-thiophenecarbohydrazide The desired compound was prepared by substituting 5-methylthiophene-2-carboxylic acid for o-toluic acid in Example 369.

MS (ESI) m/e 346 (M+H)+; ¹H NMR (500 MHz, CD₃OD) δ 7.61 (d, 0.7H), 7.58 (d, 0.3H), 6.86 (m, 1H), 4.46 (d, 0.3H), 4.42 (d, 0.7H), 3.76 (m, 1H), 3.00 (m, 1H), 2.71 (t, 2H), 2.53(s, 3H), 2.14 (m, 1H), 1.97 (m, 1H), 1.28–1.24 (m, 6H).

EXAMPLE 397

N'-((2RS,3R)-3-amino-2-hydroxy-5-(isopropylsulfanyl)pentanoyl)-1H-pyrrole-2-carbohydrazide The desired compound was prepared by substituting pyrrole-2-carboxylic acid for o-toluic acid in Example 369.

MS (ESI) m/e 315 (M+H)$^+$; $^1$H NMR (500 MHz, CD$_3$OD) δ 6.99 (m, 1H), 6.90 (m, 1H), 6.21 (m, 1H), 4.45 (d, 0.3H), 4.42 (d, 0.7H), 3.76 (m, 1H), 3.00 (m, 1H), 2.71 (t, 2H), 2.13 (m, 1H), 1.97 (m, 1H), 1.29–1.25 (m, 6H).

EXAMPLE 398

N'-((2RS,3R)-3-amino-2-hydroxy-5-(isopropylsulfanyl)pentanoyl)-1-methyl-1H-pyrrole-2-carbohydrazide The desired compound was prepared by substituting 1-methylpyrrole-2-carboxylic acid for o-toluic acid in Example 369.

MS (ESI) m/e 329 (M+H)$^+$; $^1$H NMR (500 MHz, CD$_3$OD) δ 6.90 (m, 2H), 6.10 (m, 1H), 4.45 (d, 0.3H), 4.42 (d, 0.7H), 3.89 (s, 3H), 3.76 (m, 1H), 3.00 (m, 1H), 2.71 (t, 2H), 2.14 (m, 1H), 1.98 (m, 1H), 1.29–1.24 (m, 6H).

EXAMPLE 399

N'-((2RS,3R)-3-amino-2-hydroxy-5-(isopropylsulfanyl)pentanoyl)-1,3-thiazole-2-carbohydrazide The desired compound was prepared by substituting thiazole-2-carboxylic acid for o-toluic acid in Example 369.

MS (ESI) m/e 333 (M+H)$^+$; $^1$H NMR (500 MHz, CD$_3$OD) δ 8.02 (d, 0.6H), 8.00 (d, 0.4H), 7.94 (d, 0.6H), 7.92 (d, 0.4H), 4.49 (d, 0.4H), 4.44 (d, 0.6H), 3.78 (m, 1H), 3.00 (m, 1H), 2.71 (t, 2H), 2.15 (m, 1H), 1.97 (m, 1H), 1.29–1.26 (m, 6H).

EXAMPLE 400

N'-((2RS,3R)-3-amino-2-hydroxy-5-(isopropylsulfanyl)pentanoyl)-1,3-thiazole-4-carbohydrazide The desired compound was prepared by substituting thiazole-4-carboxylic acid for o-toluic acid in Example 369.

MS (ESI) m/e 333 (M+H)$^+$; $^1$H NMR (500 MHz, CD$_3$OD) δ 90.6 (d, 0.7H), 9.04 (d, 0.3H), 8.41 (d, 0.7H), 8.37 (d, 0.3H), 4.48 (d, 0.3H), 4.45 (d, 0.7H), 3.78 (m, 1H), 3.00 (m, 1H), 2.71 (t, 2H), 2.15 (m, 1H), 1.98 (m, 1H), 1.29–1.24 (m, 6H).

EXAMPLE 401

N'-((2RS,3R)-3-amino-2-hydroxy-5-isopropylpentanoyl)-2-pyridinecarbohydrazide

The desired compound was prepared by substituting pyridine-2-carboxylic acid for o-toluic acid in Example 369.

MS (ESI) m/e 327 (M+H)$^+$; $^1$H NMR (500 MHz, CD$_3$OD) δ 8.67 (t, 1H), 8.11 (t, 1H), 7.99 (m, 1H), 7.61 (m, 1H), 4.49 (d, 0.3H), 4.45 (d, 0.7H), 3.79 (m, 1H), 3.00 (m, 1H), 2.72 (t, 2H), 2.15 (m, 1H), 1.98 (m, 1H), 1.29–1.24 (m, 6H).

EXAMPLE 402

N'-((2RS,3R)-3-amino-2-hydroxy-5-(isopropylsulfanyl)pentanoyl)-6-chloro-2H-chromene-3-carbohydrazide The desired compound was prepared by substituting 6-chloro(2H)-1-benzopyran-3-carboxylic acid for o-toluic acid in Example 369.

MS (ESI) m/e 414 (M+H)$^+$; $^1$H NMR (500 MHz, CD$_3$OD) δ 7.28 (s, 1H), 7.23 (m, 2H), 6.84 (m, 1H), 4.97 (s, 2H), 4.47 (d, 0.3H), 4.42 (d, 0.7H), 3.75 (m, 1H), 3.00 (m, 1H), 2.71 (t, 2H), 2.13 (m, 1H), 1.96 (m, 1H), 1.28–1.24 (m, 6H).

EXAMPLE 403

N'-((2RS,3R)-3-amino-2-hydroxy-7-(isopropylsulfanyl)pentanoyl)-2-(4-morpholinyl)acetohydrazide The desired compound was prepared by substituting 1-morpholineacetic acid for o-toluic acid in Example 369.

MS (ESI) m/e 349 (M+H)$^+$; $^1$H NMR (500 MHz, CD$_3$OD) δ 4.48 (d, 0.3H), 4.39 (d, 0.7H), 3.91 (m, 6H), 3.73 (m, 1H), 3.27 (m, 4H), 2.98 (m, 1H), 2.70 (t, 2H), 2.11 (m, 1H), 1.94 (m, 1H), 1.27–1.23 (m, 6H).

EXAMPLE 404

N'-((2RS,3R)-3-amino-2-hydroxy-7-(isopropylsulfanyl)pentanoyl)-2-(4-methyl-1-piperazinyl)acetohydrazide The desired compound was prepared by substituting 4-N-methylpiperazine-1-acetic acid for o-toluic acid in Example 369.

MS (ESI) m/e 362 (M+H)$^+$; $^1$H NMR (500 MHz, CD$_3$OD) δ 4.47–4.30 (m, 1H), 3.73 (m, 2H), 3.48 (m, 2H), 3.31 (m, 3H), 3.16 (m, 2H), 3.00 (m, 1H), 2.90 (s, 2H), 2.69 (m, 4H), 2.09 (m, 1H), 1.93 (m, 2H), 1.28–1.22 (m, 6H).

EXAMPLE 405

1-acetyl-N'-((2RS,3R)-3-amino-2-hydroxy-7-(isopropylsulfanyl)pentanoyl)-4-piperidinecarbohydrazide The desired compound was prepared by substituting 1-acetylpiperidine-4-carboxylic acid for o-toluic acid in Example 369.

MS (ESI) m/e 375 (M+H)$^+$; $^1$H NMR (500 MHz, CD$_3$OD) δ 4.49 (m, 1H), 4.42 (d, 0.3H), 4.37 (d, 0.7H), 3.96 (m, 1H), 3.72 (m, 1H), 3.19 (m, 1H), 2.98 (m, 1H), 2.70 (m, 2H), 2.59 (m, 1H), 2.10 (m, 4H), 1.91 (m, 3H), 1.66 (m, 2H), 1.28–1.23 (m, 6H).

EXAMPLE 406

N'-((2RS,3R)-3-amino-2-hydroxy-5-(isopropylsulfanyl)pentanoyl)-4-ethylbenzohydrazide The desired compound was prepared by substituting 4-ethylbenzoic acid for o-toluic acid in Example 369.

MS (ESI) m/e 354 (M+H)$^+$; $^1$H NMR (500 MHz, CD$_3$OD) δ 7.82 (m, 2H), 7.34 (m, 2H), 4.48 (d, 0.3H), 4.44 (d, 0.7H), 3.77 (m, 1H), 3.00 (m, 1H), 2.72 (t, 4H), 2.15 (m, 1H), 1.98 (m, 1H), 1.29–1.24 (m, 9H).

EXAMPLE 407

N'-((2RS,3R)-3-amino-2-hydroxy-5-(isopropylsulfanyl)pentanoyl)-3-fluoro-2-methylbenzohydrazide The desired compound was prepared by substituting 3-fluoro-2-methyl-benzoic acid for o-toluic acid in Example 369.

MS (ESI) m/e 358 (M+H)$^+$; $^1$H NMR (500 MHz, CD$_3$OD) δ 7.32 (m, 2H), 7.21 (m, 1H), 4.48 (d, 0.3H), 4.44 (d, 0.7H), 3.79 (m, 1H), 3.00 (m, 1H), 2.72 (t, 2H), 2.36 (m, 3H), 2.16 (m, 1H), 1.98 (m, 1H), 1.29–1.24 (m, 6H).

EXAMPLE 408

N'-((2RS,3R)-3-amino-2-hydroxy-5-(isopropylsulfanyl)pentanoyl)-2,3-difluorobenzohydrazide The desired compound was prepared by substituting 2,3-difluorobenzoic acid for o-toluic acid in Example 369.

MS (ESI) m/e 362 (M+H)$^+$; $^1$H NMR (500 MHz, CD$_3$OD) δ 7.55 (m, 1H), 7.49 (m, 1H), 7.31 (m, 1H), 4.48 (d, 0.3H), 4.44 (d, 0.7H), 3.78 (m, 1H), 3.00 (m, 1H), 2.71 (t, 2H), 2.15 (m, 1H), 1.97 (m, 1H), 1.29–1.24 (m, 6H).

EXAMPLE 409

N'-((2RS,3R)-3-amino-2-hydroxy-5-(isopropylsulfanyl)pentanoyl)-4-propylbenzohydrazide The desired compound was prepared by substituting 4-N-propylbenzoic acid for o-toluic acid in Example 369.

MS (ESI) m/e 368 (M+H)$^+$; $^1$H NMR (500 MHz, CD$_3$OD) δ 7.81 (m, 1H), 7.32 (m, 1H), 4.48 (d, 0.3H), 4.44 (d, 0.7H), 3.78 (m, 1H), 3.00 (m, 4H), 2.70 (t, 4H), 2.15 (m, 1H), 1.98 (m, 1H), 1.68 (m, 2H), 1.29–1.24 (m, 6H), 0.95 (t, 1H).

EXAMPLE 410

N'-((2RS,3R)-3-amino-2-hydroxy-5-(isopropylsulfanyl)pentanoyl)-4-isopropylbenzohydrazide The desired compound was prepared by substituting 4-isopropylbenzoic acid for o-toluic acid in Example 369.

MS (ESI) m/e 368 (M+H)$^+$; $^1$H NMR (500 MHz, CD$_3$OD) δ 7.82 (m, 2H), 7.38 (m, 2H), 4.48 (d, 0.3H), 4.44 (d, 0.7H), 3.78 (m, 1H), 3.00 (m, 2H), 2.72 (t, 2H), 2.15 (m, 1H), 1.98 (m, 1H), 1.29–1.24 (m, 12H).

EXAMPLE 411

N'-((2RS,3R)-3-amino-2-hydroxy-5-(isopropylsulfanyl)pentanoyl)-2-ethoxybenzohydrazide The desired compound was prepared by substituting 2-ethoxybenzoic acid for o-toluic acid in Example 369.

MS (ESI) m/e 370 (M+H)$^+$; $^1$H NMR (500 MHz, CD$_3$OD) δ 7.97 (m, 1H), 7.54 (m, 1H), 7.18 (m, 1H), 7.09 (t, 1H), 4.49 (d, 0.3H), 4.44 (d, 0.7H), 4.29 (q, 2H), 3.78 (m, 1H), 3.00 (m, 1H), 2.71 (t, 2H), 2.15 (m, 1H), 1.97 (m, 1H), 1.51 (t, 3H), 1.29–1.24 (m, 6H).

EXAMPLE 412

N'-((2RS,3R)-3-amino-2-hydroxy-5-(isopropylsulfanyl)pentanoyl)-4-ethoxybenzohydrazide The desired compound was prepared by substituting 4-ethoxybenzoic acid for o-toluic acid in Example 369.

MS (ESI) m/e 370 (M+H)$^+$; $^1$H NMR (500 MHz, CD$_3$OD) δ 7.85 (m, 1H), 6.99 (m, 1H), 7.31 (m, 1H), 4.48 (d, 0.3H), 4.44 (d, 0.7H), 4.12 (q, 2H), 3.77 (m, 1H), 3.00 (m, 1H), 2.71 (t, 2H), 2.15 (m, 1H), 1.98 (m, 1H), 1.41 (t, 3H), 1.29–1.24 (m, 6H).

EXAMPLE 413

N'-((2RS,3R)-3-amino-2-hydroxy-5-(isopropylsulfanyl)pentanoyl)-1-naphthohydrazide The desired compound was prepared by substituting 1-naphthoic acid for o-toluic acid in Example 369.

MS (ESI) m/e 376 (M+H)$^+$; $^1$H NMR (500 MHz, CD$_3$OD) δ 7.38 (m, 1H), 8.04 (t, 1H), 7.95 (m, 1H), 7.77 (t, 1H), 7.56 (m, 3H), 4.53 (d, 0.3H), 4.49 (d, 0.7H), 3.84 (m, 1H), 3.02 (m, 1H), 2.74 (t, 2H), 2.19 (m, 1H), 2.01 (m, 1H), 1.31–1.24 (m, 6H).

EXAMPLE 414

N'-((2RS,3R)-3-amino-2-hydroxy-5-(isopropylsulfanyl)pentanoyl)-4-tert-butylbenzohydrazide The desired compound was prepared by substituting 4-tert-butylbenzoic acid for o-toluic acid in Example 369.

MS (ESI) m/e 382 (M+H)$^+$; $^1$H NMR (500 MHz, CD$_3$OD) δ 7.83 (m, 2H), 7.55 (m, 2H), 4.48 (d, 0.3H), 4.44 (d, 0.7H), 3.78 (m, 1H), 3.00 (m, 1H), 2.72 (t, 2H), 2.15 (m, 1H), 1.99 (m, 1H), 1.35 (s, 9H), 1.29–1.24 (m, 6H).

EXAMPLE 415

N-(4-((2-((2RS,3R)-3-amino-2-hydroxy-5-(isopropylsulfanyl)pentanoyl)hydrazino)carbonyl)phenyl)acetamide The desired compound was prepared by substituting 4-acetamidobenzoic acid for o-toluic acid in Example 369.

MS (ESI) m/e 383 (M+H)$^+$; $^1$H NMR (500 MHz, CD$_3$OD) δ 7.86 (m, 2H), 7.71 (m, 2H), 4.48 (d, 0.3H), 4.44 (d, 0.7H), 3.78 (m, 1H), 3.00 (m, 1H), 2.72 (t, 2H), 2.15 (m, 4H), 1.97 (m, 1H), 1.29–1.24 (m, 6H).

EXAMPLE 416

N'-((2RS,3R)-3-amino-2-hydroxy-5-(isopropylsulfanyl)pentanoyl)-4-propoxybenzohydrazide The desired compound was prepared by substituting p-propoxybenzoic acid for o-toluic acid in Example 369.

MS (ESI) m/e 384 (M+H)$^+$; $^1$H NMR (500 MHz, CD$_3$OD) δ 7.85 (m, 2H), 7.00 (m, 2H), 7.31 (m, 1H), 4.48 (d, 0.3H), 4.44 (d, 0.7H), 4.01 (m,2H), 3.78 (m, 1H), 3.00 (m, 1H), 2.71 (t, 2H), 2.15 (m, 1H), 1.97 (m, 1H), 1.82 (m, 2H), 1.29–1.24 (m, 6H), 1.05 (t, 3H).

EXAMPLE 417

N'-((2RS,3R)-3-amino-2-hydroxy-5-(isopropylsulfanyl)pentanoyl)-4-isopropoxybenzohydrazide The desired compound was prepared by substituting 4-isopropoxybenzoic acid for o-toluic acid in Example 369.

MS (ESI) m/e 384 (M+H)$^+$; $^1$H NMR (500 MHz, CD$_3$OD) δ 7.84 (m, 2H), 6.98 (m, 2H), 4.71 (m, 1H), 4.48 (d, 0.3H), 4.44 (d, 0.7H), 3.78 (m, 1H), 3.00 (m, 1H), 2.71 (t, 2H), 2.14 (m, 1H), 1.98 (m, 1H), 1.34 (d, 6H), 1.29–1.24 (m, 6H).

EXAMPLE 418

N'-((2RS,3R)-3-amino-2-hydroxy-5-(isopropylsulfanyl)pentanoyl)-5-chloro-2-methoxybenzohydrazide The desired compound was prepared by substituting 5-chloro-2-methoxybenzoic acid for o-toluic acid in Example 369.

MS (ESI) m/e 390 (M+H)$^+$; $^1$H NMR (500 MHz, CD$_3$OD) δ 7.92 (d, 0.7H), 7.89 (d, 0.3H), 7.55 (td, 1H), 7.20 (m, 1H), 4.47 (d, 0.3H), 4.44 (d, 0.7H), 4.00 (s, 2.1H), 3.98 (s, 0.9H), 3.78 (m, 1H), 3.00 (m, 1H), 2.72 (t, 2H), 2.14 (m, 1H), 1.98 (m, 1H), 1.29–1.25 (m, 6H).

EXAMPLE 419

N'-((2RS,3R)-3-amino-2-hydroxy-5-(isopropylsulfanyl)pentanoyl)-4-(methylsulfonyl)benzohydrazide The desired compound was prepared by substituting 4-(methylsulfonyl)benzoic acid for o-toluic acid in Example 369.

MS (ESI) m/e 404 (M+H)$^+$; $^1$H NMR (500 MHz, CD$_3$OD) δ 8.10 (s, 2.8H), 8.09 (s, 1.2H), 4.51 (d, 0.3H), 4.46 (d, 0.7H), 3.78 (m, 1H), 3.17 (s, 2.8H), 3.17 (s, 1.2H), 3.01 (m, 1H), 2.72 (t, 2H), 2.16 (m, 1H), 1.98 (m, 1H), 1.29–1.24 (m, 6H).

EXAMPLE 420

N'-((2RS,3R)-3-amino-2-hydroxy-5-(isopropylsulfanyl)pentanoyl)-2-chloro-5-(methylsulfanyl)benzohydrazide The desired compound was prepared by substituting 2-chloro-5-(methylthio)benzoic acid for o-toluic acid in Example 369.

MS (ESI) m/e 406 (M+H)$^+$; $^1$H NMR (500 MHz, CD$_3$OD) δ 7.49 (d, 1H), 7.43–7.35 (m, 2H), 4.48 (d, 0.3H), 4.43 (d, 0.7H), 3.78 (m, 1H), 3.00 (m, 1H), 2.72 (t, 2H), 2.52 (s, 1H), 2.15 (m, 1H), 1.97 (m, 1H), 1.29–1.24 (m, 6H).

EXAMPLE 421

N'-((2RS,3R)-3-amino-2-hydroxy-5-(isopropylsulfanyl)pentanoyl)-3,4-diethoxybenzohydrazide The desired compound was prepared by substituting 3,4-diethoxybenzoic acid for o-toluic acid in Example 369.

MS (ESI) m/e 414 (M+H)$^+$; $^1$H NMR (500 MHz, CD$_3$OD) δ 7.51 (m, 1H), 7.48 (m, 1H), 7.02 (m, 1H), 4.47 (d, 0.3H), 4.44 (d, 0.7H), 4.12 (m, 4H), 3.77 (m, 1H), 3.00 (m, 1H), 2.72 (t, 2H), 2.15 (m, 1H), 1.98 (m, 1H), 1.43 (m, 6H), 1.29–1.24 (m, 6H).

EXAMPLE 422

N'-((2RS,3R)-3-amino-2-hydroxy-5-(isopropylsulfanyl)pentanoyl)-2-benzylbenzohydrazide The desired compound was prepared by substituting alpha-phenyl-o-toluic acid for o-toluic acid in Example 369.

MS (ESI) m/e 416 (M+H)$^+$; $^1$H NMR (500 MHz, CD$_3$OD) δ 7.54 (t, 1H), 7.40 (m, 1H), 7.29 (t, 1H), 7.23 (m, 5H), 7.16 (m, 1H), 4.49 (d, 0.3H), 4.43 (d, 0.7H), 4.19 (m, 1H), 3.78 (m, 1H), 3.00 (m, 1H), 2.71 (t, 2H), 2.15 (m, 1H), 1.97 (m, 1H), 1.29–1.19 (m, 6H).

EXAMPLE 423

N'-((2RS,3R)-3-amino-2-hydroxy-5-(isopropylsulfanyl)pentanoyl)-2-anilinobenzohydrazide The desired compound was prepared by substituting N-phenylanthranilic acid for o-toluic acid in Example 369.

MS (ESI) m/e 417 (M+H)$^+$; $^1$H NMR (500 MHz, CD$_3$OD) δ 7.68 (m, 1H), 7.32 (m, 4H), 7.16 (d, 2H), 7.02 (m, 1H), 6.83 (m, 1H), 4.49 (d, 0.3H), 4.44 (d, 0.7H), 3.78 (m, 1H), 3.00 (m, 1H), 2.71 (t, 2H), 2.16 (m, 1H), 1.98 (m, 1H), 1.28–1.19 (m, 6H).

EXAMPLE 424

N'-((2RS,3R)-3-amino-2-hydroxy-5-(isopropylsulfanyl)pentanoyl)-2-(2-phenylethyl)benzohydrazide The desired compound was prepared by substituting 2-bibenzylcarboxylic acid for o-toluic acid in Example 369.

MS (ESI) m/e 430 (M+H)$^+$; $^1$H NMR (500 MHz, CD$_3$OD) δ 7.53 (m, 1H), 7.40 (m, 1H), 7.28 (m, 2H), 7.23 (d, 4H), 7.15 (m, 1H), 4.50 (d, 0.3H), 4.45 (d, 0.7H), 3.81 (m, 1H), 3.10 (m, 2H), 3.01 (m, 1H), 2.93 (m, 2H), 2.72 (t, 2H), 2.17 (m, 1H), 1.99 (m, 1H), 1.29–1.20 (m, 6H).

EXAMPLE 425

N'-((2RS,3R)-3-amino-2-hydroxy-5-(isopropylsulfanyl)pentanoyl)-3-(methylsulfanyl)benzohydrazide The desired compound was prepared by substituting 3-(methylthio)benzoic acid for o-toluic acid in Example 369.

MS (ESI) m/e 372 (M+H)$^+$; $^1$H NMR (500 MHz, CD$_3$OD) δ 7.77 (m, 1H), 7.63 (m, 1H), 7.48 (m, 1H), 7.42 (m, 1H), 4.49 (d, 0.3H), 4.45 (d, 0.7H), 3.78 (m, 1H), 3.00 (m, 1H), 2.72 (t, 2H), 2.53 (s, 3H), 2.15 (m, 1H), 1.98 (m, 1H), 1.29–1.24 (m, 6H).

EXAMPLE 426

N'-((2RS,3R)-3-amino-2-hydroxy-5-(isopropylsulfanyl)pentanoyl)-3-(ethylsulfanyl)benzohydrazide The desired compound was prepared by substituting 3-(ethylthio)benzoic acid for o-toluic acid in Example 369.

MS (ESI) m/e 386 (M+H)$^+$; $^1$H NMR (500 MHz, CD$_3$OD) δ 7.83 (m, 1H), 7.67 (m, 1H), 7.54 (m, 1H), 7.43 (m, 1H), 4.49 (d, 0.3H), 4.45 (d, 0.7H), 3.78 (m, 1H), 3.00 (m, 3H), 2.72 (t, 2H), 2.15 (m, 1H), 1.98 (m, 1H), 1.33–1.25 (m, 9H).

EXAMPLE 427

N'-((2RS,3R)-3-amino-2-hydroxy-5-(isopropylsulfanyl)pentanoyl)-3-(propylsulfanyl)benzohydrazide The desired compound was prepared by substituting 3-(propylthio)benzoic acid for o-toluic acid in Example 369.

MS (ESI) m/e 400 (M+H)$^+$; $^1$H NMR (500 MHz, CD$_3$OD) δ 7.83 (m, 1H), 7.66 (t, 1H), 7.54 (m, 1H), 7.42 (m,

1H), 4.49 (d, 0.3H), 4.45 (d, 0.7H), 3.78 (m, 1H), 3.00 (m, 3H), 2.72 (t, 2H), 2.15 (m, 1H), 1.98 (m, 1H), 1.68 (m, 2H), 1.29–1.24 (m, 6H), 1.04 (t, 3H).

EXAMPLE 428

N'-((2RS,3R)-3-amino-2-hydroxy-5-(isopropylsulfanyl)pentanoyl)-3-(butylsulfanyl)benzohydrazide The desired compound was prepared by substituting 3-(butylthio)benzoic acid for o-toluic acid in Example 369.

MS (ESI) m/e 414 (M+H)$^+$; $^1$H NMR (500 MHz, CD$_3$OD) δ 7.83 (m, 1H), 7.66 (t, 1H), 7.54 (t, 1H), 7.42 (m, 1H), 4.49 (d, 0.3H), 4.45 (d, 0.7H), 3.78 (m, 1H), 3.00 (m, 3H), 2.72 (t, 2H), 2.15 (m, 1H), 1.98 (m, 1H), 1.64 (m, 2H), 1.49 (m, 2H), 1.29–1.24 (m, 6H), 0.94 (t, 3H).

EXAMPLE 429

N'-((2RS,3R)-3-amino-2-hydroxy-5-(isopropylsulfanyl)pentanoyl)-3-(hexylsulfanyl)benzohydrazide The desired compound was prepared by substituting 3-(hexylthio)benzoic acid for o-toluic acid in Example 369.

MS (ESI) m/e 442 (M+H)$^+$; $^1$H NMR (500 MHz, CD$_3$OD) δ 7.83 (m, 1H), 7.66 (t, 1H), 7.54 (m, 1H), 7.42 (m, 1H), 4.48 (d, 0.3H), 4.44 (d, 0.7H), 3.78 (m, 1H), 3.00 (m, 3H), 2.72 (t, 2H), 2.15 (m, 1H), 1.98 (m, 1H), 1.65 (m, 2H), 1.46 (m, 2H), 1.32–1.24 (m, 10H), 0.90 (t, 3H).

EXAMPLE 430

N'-((2RS,3R)-3-amino-2-hydroxy-5-(isopropylsulfanyl)pentanoyl)-3-(isopropylsulfanyl)benzohydrazide The desired compound was prepared by substituting 3-(isopropylthio)benzoic acid for o-toluic acid in Example 369.

MS (ESI) m/e 400 (M+H)$^+$; $^1$H NMR (500 MHz, CD$_3$OD) δ 7.90 (m, 1H), 7.73 (m, 1H), 7.61 (m, 1H), 7.45 (m, 1H), 4.49 (d, 0.3H), 4.45 (d, 0.7H), 3.78 (m, 1H), 3.51 (m, 1H), 3.00 (m, 1H), 2.72 (t, 2H), 2.15 (m, 1H), 1.98 (m, 1H), 1.30–1.24 (m, 12H).

EXAMPLE 431

N'-((2RS,3R)-3-amino-2-hydroxy-5-(isopropylsulfanyl)pentanoyl)-3-(isobutylsulfanyl)benzohydrazide The desired compound was prepared by substituting 3-(2-methylpropylthio)benzoic acid for o-toluic acid in Example 369.

MS (ESI) m/e 414 (M+H)$^+$; $^1$H NMR (500 MHz, CD$_3$OD) δ 7.84 (m, 1H), 7.65 (m, 1H), 7.54 (m, 1H), 7.42 (m, 1H), 4.49 (d, 0.3H), 4.45 (d, 0.7H), 3.78 (m, 1H), 3.00 (m, 1H), 2.90 (d, 2H), 2.72 (t, 2H), 2.15 (m, 1H), 1.98 (m, 1H), 1.86 (m, 1H), 1.29–1.24 (m, 6H), 1.05 (d, 6H).

EXAMPLE 432

N'-((2RS,3R)-3-amino-2-hydroxy-5-(isopropylsulfanyl)pentnoyl)-3-((4-methylpentyl)sulfanyl)benzohydrazide The desired compound was prepared by substituting 3-(4-methylpentylthio)benzoic acid for o-toluic acid in Example 369.

MS (ESI) m/e 442 (M+H)$^+$; $^1$H NMR (500 MHz, CD$_3$OD) δ 7.83 (m, 1H), 7.66 (m, 1H), 7.54 (m, 1H), 7.42 (m, 1H), 4.49 (d, 0.3H), 4.44 (d, 0.7H), 3.78 (m, 1H), 3.00 (m, 3H), 2.72 (t, 2H), 2.15 (m, 1H), 1.98 (m, 1H), 1.66 (m, 2H), 1.56 (m, 1H), 1.34 (m, 2H), 1.29–1.24 (m, 6H), 0.89 (d, 6).

EXAMPLE 433

N'-((2RS,3R)-3-amino-2-hydroxy-5-(isopropylsulfanyl)pentanoyl)-3-(sec-butylsulfanyl)benzohydrazide The desired compound was prepared by substituting 3-(1-methylpropylthio)benzoic acid for o-toluic acid in Example 369.

MS (ESI) m/e 414 (M+H)$^+$; $^1$H NMR (500 MHz, CD$_3$OD) δ 7.90 (m, 1H), 7.72 (m, 1H), 7.61 (m, 1H), 7.44 (m, 1H), 4.49 (d, 0.3H), 4.45 (d, 0.7H), 3.78 (m, 1H), 3.31 (m, 1H), 3.00 (m, 1H), 2.72 (t, 2H), 2.15 (m, 1H), 1.98 (m, 1H), 1.62 (m, 2H), 1.29–1.24 (m, 9H), 1.03 (t, 3H).

EXAMPLE 434

N'-((2RS,3R)-3-amino-2-hydroxy-5-(isopropylsulfanyl)pentanoyl)-3-(neopentylsulfanyl)benzohydrazide The desired compound was prepared by substituting 3-(2,2-dimethylpropylthio)benzoic acid for o-toluic acid in Example 369.

MS (ESI) m/e 428 (M+H)$^+$; $^1$H NMR (500 MHz, CD$_3$OD) δ 7.86 (m, 1H), 7.65 (m, 1H), 7.57 (m, 1H), 7.40 (m, 1H), 4.49 (d, 0.3H), 4.45 (d, 0.7H), 3.78 (m, 1H), 3.00 (m, 3H), 2.72 (t, 2H), 2.15 (m, 1H), 1.98 (m, 1H), 1.29–1.24 (m, 6H), 1.05 (s, 9H).

EXAMPLE 435

N'-((2RS,3R)-3-amino-2-hydroxy-5-(isopropylsulfanyl)pentanoyl)-3-(cyclohexylsulfanyl)benzohydrazide The desired compound was prepared by substituting 3-(cyclohexylthio)benzoic acid for o-toluic acid in Example 369.

MS (ESI) m/e 440 (M+H)$^+$; $^1$H NMR (500 MHz, CD$_3$OD) δ 7.90 (m, 1H), 7.72 (m, 1H), 7.60 (m, 1H), 7.43 (m, 1H), 4.49 (d, 0.3H), 4.45 (d, 0.7H), 3.78 (m, 1H), 3.25 (m, 1H), 3.00 (m, 1H), 2.72 (t, 2H), 2.15 (m, 1H), 1.98 (m, 3H), 1.78 (m, 2H), 1.65 (m, 2H), 1.38 (m, 4H), 1.29–1.24 (m, 6H).

EXAMPLE 436

N'-((2RS,3R)-3-amino-2-hydroxy-5-(isopropylsulfanyl)pentanoyl)-3-((cyclohexylmethyl)sulfanyl)benzohydrazide The desired compound was prepared by substituting 3-(2-cyclohexylethylthio)benzoic acid for o-toluic acid in Example 369.

MS (ESI) m/e 454 (M+H)$^+$; $^1$H NMR (500 MHz, CD$_3$OD) δ 7.82 (m, 1H), 7.65 (t, 1H), 7.53 (t, 1H), 7.41 (m, 1H), 4.48 (d, 0.3H), 4.44 (d, 0.7H), 3.78 (m, 1H), 3.00 (m, 1H), 2.90 (d, 2H), 2.72 (t, 2H), 2.15 (m, 1H), 1.98 (m, 1H), 1.91 (m, 2H), 1.74 (m, 2H), 1.66 (m, 2H), 1.53 (m, 1H), 1.29–1.18 (m, 8H), 1.05 (m, 2H).

EXAMPLE 437

N'-((2RS,3R)-3-amino-2-hydroxy-5-(isopropylsulfanyl)pentanoyl)-3-(benzylsulfanyl)benzohydrazide The desired compound was prepared by substituting 3-(benzylthio)benzoic acid for o-toluic acid in Example 369.

MS (ESI) m/e 448 (M+H)+; ¹H NMR (500 MHz, CD₃OD) δ 7.86 (m, 1H), 7.67 (m, 1H), 7.52 (m, 1H), 7.39 (m, 1H), 7.31 (d, 2H), 7.26 (t, 2H), 7.20 (m, 1H), 4.49 (d, 0.3H), 4.45 (d, 0.7H), 4.22 (s, 2H), 3.77 (m, 1H), 3.00 (m, 1H), 2.72 (t, 2H), 2.15 (m, 1H), 1.98 (m, 1H), 1.29–1.25 (m, 6H).

EXAMPLE 438

N'-((2RS,3R)-3-amino-2-hydroxy-5-(isopropylsulfanyl)pentanoyl)-3-((2-phenylethyl)sulfanyl)benzohydrazide The desired compound was prepared by substituting 3-(2-phenylethylthio)benzoic acid for o-toluic acid in Example 369.

MS (ESI) m/e 462 (M+H)+; ¹H NMR (500 MHz, CD₃OD) δ 7.87 (m, 1H), 7.68 (m, 1H), 7.57 (m, 1H), 7.44 (m, 1H), 7.27 (t, 2H), 7.23–7.17 (m, 3H), 4.49 (d, 0.3H), 4.45 (d, 0.7H), 3.77 (m, 1H), 3.26 (t, 2H), 3.00 (m, 1H), 2.93 (t, 2H), 2.72 (t, 2H), 2.15 (m, 1H), 1.98 (m, 1H), 1.29–1.24 (m, 6H).

EXAMPLE 439

N'-((2RS,3R)-3-amino-2-hydroxy-5-(isopropylsulfanyl)pentanoyl)-3-((3-phenylpropyl)sulfanyl)benzohydrazide The desired compound was prepared by substituting 3-(3-phenylpropylthio)benzoic acid for o-toluic acid in Example 369.

MS (ESI) m/e 476 (M+H)+; ¹H NMR (500 MHz, CD₃OD) δ 7.84 (m, 1H), 7.67 (m, 1H), 7.51 (m, 1H), 7.41 (m, 1H), 7.25 (t, 2H), 7.15 (m, 3H), 4.49 (d, 0.3H), 4.44 (d, 0.7H), 3.78 (m, 1H), 3.00 (m, 3H), 2.76 (t, 2H), 2.72 (t, 2H), 2.15 (m, 1H), 1.96 (m, 3H), 1.29–1.24 (m, 6H).

EXAMPLE 440

N'-((2RS,3R)-3-amino-2-hydroxy-5-(isopropylsulfanyl)pentanoyl)-3-(((1,1'-biphenyl)-4-ylmethyl)sulfanyl)benzohydrazide The desired compound was prepared by substituting 3-(biphenylmethylthio)benzoic acid for o-toluic acid in Example 369.

MS (ESI) m/e 524 (M+H)+; ¹H NMR (500 MHz, CD₃OD) δ 7.89 (s, 1H), 7.68 (m, 1H), 7.55 (m, 5H), 7.40 (m, 5H), 7.31 (m, 1H), 4.48 (d, 0.3H), 4.44 (d, 0.7H), 4.27 (m, 2H), 3.77 (m, 1H), 3.00 (m, 1H), 2.71 (t, 2H), 2.15 (m, 1H), 1.98 (m, 1H), 1.29–1.24 (m, 6H).

EXAMPLE 441

N'-((2RS,3R)-3-amino-2-hydroxy-5-(isopropylsulfanyl)pentanoyl)-4-(methylsulfanyl)benzohydrazide The desired compound was prepared by substituting 4-(methylthio)benzoic acid for o-toluic acid in Example 369.

MS (ESI) m/e 372 (M+H)+; ¹H NMR (500 MHz, CD₃OD) δ 7.81 (m, 2H), 7.34 (m, 2H), 4.49 (d, 0.3H), 4.44 (d, 0.7H), 3.77 (m, 1H), 3.00 (m, 1H), 2.72 (t, 2H), 2.53 (s, 3H), 2.15 (m, 1H), 1.98 (m, 1H), 1.29–1.25 (m, 6H).

EXAMPLE 442

N'-((2RS,3R)-3-amino-2-hydroxy-5-(isopropylsulfanyl)pentanoyl)-4-(ethylsulfanyl)benzohydrazide The desired compound was prepared by substituting 4-(ethylthio)benzoic acid for o-toluic acid in Example 369.

MS (ESI) m/e 386 (M+H)+; ¹H NMR (500 MHz, CD₃OD) δ 7.81 (m, 2H), 7.38 (m, 2H), 4.48 (d, 0.3H), 4.44 (d, 0.7H), 3.77 (m, 1H), 3.03 (m, 3H), 2.72 (t, 2H), 2.15 (m, 1H), 1.98 (m, 1H), 1.35 (t, 3H), 1.29–1.25 (m, 6H).

EXAMPLE 443

N'-((2RS,3R)-3-amino-2-hydroxy-5-(isopropylsulfanyl)pentanoyl)-4-(propylsulfanyl)benzohydrazide The desired compound was prepared by substituting 4-(propylthio)benzoic acid for o-toluic acid in Example 369.

MS (ESI) m/e 400 (M+H)+; ¹H NMR (500 MHz, CD₃OD) δ 7.80 (m, 2H), 7.38 (m, 2H), 4.48 (d, 0.3H), 4.44 (d, 0.7H), 3.77 (m, 1H), 3.01 (m, 3H), 2.71 (t, 2H), 2.15 (m, 1H), 1.98 (m, 1H), 1.72 (m, 2H), 1.29–1.24 (m, 6H), 1.06 (t, 3H).

EXAMPLE 444

N'-((2RS,3R)-3-amino-2-hydroxy-5-(isopropylsulfanyl)pentanoyl)-4-(butylsulfanyl)benzohydrazide The desired compound was prepared by substituting 4-(butylthio)benzoic acid for o-toluic acid in Example 369.

MS (ESI) m/e 414 (M+H)+; ¹H NMR (500 MHz, CD₃OD) δ 7.80 (m, 2H), 7.37 (m, 2H), 4.48 (d, 0.3H), 4.44 (d, 0.7H), 3.77 (m, 1H), 3.02 (m, 3H), 2.71 (t, 2H), 2.15 (m, 1H), 1.98 (m, 1H), 1.67 (m, 2H), 1.50 (m, 2H), 1.29–1.24 (m, 6H), 0.95 (t, 3H).

EXAMPLE 445

N'-((2RS,3R)-3-amino-2-hydroxy-5-(isopropylsulfanyl)pentanoyl)-4-(hexylsulfanyl)benzohydrazide The desired compound was prepared by substituting 4-(hexylthio)benzoic acid for o-toluic acid in Example 369.

MS (ESI) m/e 442 (M+H)+; ¹H NMR (500 MHz, CD₃OD) δ 7.80 (m, 2H), 7.37 (t, 2H), 4.48 (d, 0.3H), 4.44 (d, 0.7H), 3.77 (m, 1H), 3.02 (m, 3H), 2.72 (t, 2H), 2.15 (m, 1H), 1.98 (m, 1H), 1.68 (m, 2H), 1.47 (m, 2H), 1.33 (m, 4H), 1.29–1.24 (m, 6H), 0.91 (t, 3H).

EXAMPLE 446

N'-((2RS,3R)-3-amino-2-hydroxy-5-(isopropylsulfanyl)pentanoyl)-4-(isopropylsulfanyl)benzohydrazide The desired compound was prepared by substituting 4-(isopropylthio)benzoic acid for o-toluic acid in Example 369.

MS (ESI) m/e 400 (M+H)+; ¹H NMR (500 MHz, CD₃OD) δ 7.81 (m, 2H), 7.43 (dd, 2H), 4.48 (d, 0.3H), 4.44 (d, 0.7H), 3.77 (m, 1H), 3.62 (m, 1H), 3.00 (m, 1H), 2.72 (t, 2H), 2.15 (m, 1H), 1.98 (m, 1H), 1.34 (d, 6H), 1.29–1.24 (m, 6H).

EXAMPLE 447

N'-((2RS,3R)-3-amino-2-hydroxy-5-(isopropylsulfanyl)pentanoyl)-4-(isobutylsulfanyl)benzohydrazide The desired compound was prepared by substituting 4-(2-methylpropylthio)benzoic acid for o-toluic acid in Example 369.

MS (ESI) m/e 414 (M+H)+; 1H NMR (500 MHz, CD3OD) δ 7.80 (m, 2H), 7.38 (m, 2H), 4.48 (d, 0.3H), 4.44 (d, 0.7H), 3.78 (m, 1H), 3.00 (m, 1H), 2.92 (d, 2H), 2.71 (t, 2H), 2.15 (m, 1H), 1.98 (m, 1H), 1.90 (m, 1H), 1.29–1.24 (m, 6H), 1.06 (d, 6H).

EXAMPLE 448

N'-((2RS,3R)-3-amino-2-hydroxy-5-(isopropylsulfanyl)pentnoyl)-4-((4-methylpentyl)sulfanyl)benzohydrazide The desired compound was prepared by substituting 4-(4-methylpentylthio)benzoic acid for o-toluic acid in Example 369.

MS (ESI) m/e 442 (M+H)+; 1H NMR (500 MHz, CD3OD) δ 7.80 (m, 2H), 7.38 (m, 2H), 4.45 (d, 0.3H), 4.41 (d, 0.7H), 3.71 (m, 1H), 3.01 (m, 3H), 2.71 (t, 2H), 2.13 (m, 1H), 1.96 (m, 1H), 1.69 (m, 2H), 1.57 (m, 1H), 1.36 (m, 2H), 1.29–1.24 (m, 6H), 0.89 (d, 6H).

EXAMPLE 449

N'-((2RS,3R)-3-amino-2-hydroxy-5-(isopropylsulfanyl)pentanoyl)-4-(sec-butylsulfanyl)benzohydrazide The desired compound was prepared by substituting 4-(1-methylpropylthio)benzoic acid for o-toluic acid in Example 369.

MS (ESI) m/e 414 (M+H)+; 1H NMR (500 MHz, CD3OD) δ 7.80 (m, 2H), 7.43 (dd, 2H), 4.49 (d, 0.3H), 4.44 (d, 0.3H), 4.44 (d, 0.7H), 3.77 (m, 1H), 3.00 (m, 1H), 2.72 (t, 2H), 2.15 (m, 1H), 1.98 (m, 1H), 1.65 (m, 2H), 1.33 (d, 3H), 1.29–1.24 (m, 6H), 1.04 (t, 3H).

EXAMPLE 450

N'-((2RS,3R)-3-amino-2-hydroxy-5-(isopropylsulfanyl)pentanoyl)-4-(neopentylsulfanyl)benzohydrazide The desired compound was prepared by substituting 4-(2,2-dimethylpropylthio)benzoic acid for o-toluic acid in Example 369.

MS (ESI) m/e 428 (M+H)+; 1H NMR (500 MHz, CD3OD) δ 7.79 (m, 2H), 7.42 (m, 2H), 4.48 (d, 0.3H), 4.44 (d, 0.7H), 3.77 (m, 1H), 3.00 (m, 3H), 2.72 (t, 2H), 2.14 (m, 1H), 1.98 (m, 1H), 1.29–1.24 (m, 6H), 1.06 (s, 9H).

EXAMPLE 451

N'-((2RS,3R)-3-amino-2-hydroxy-5-(isopropylsulfanyl)pentanoyl)-4-(cyclohexylsulfanyl)benzohydrazide The desired compound was prepared by substituting 4-(cyclohexylthio)benzoic acid for o-toluic acid in Example 369.

MS (ESI) m/e 440 (M+H)+; 1H NMR (500 MHz, CD3OD) δ 7.80 (m, 2H), 7.41 (m, 2H), 4.49 (d, 0.3H), 4.44 (d, 0.7H), 3.78 (m, 1H), 3.37 (m, 1H), 3.00 (m, 1H), 2.72 (t, 2H), 2.15 (m, 1H), 1.98 (m, 3H), 1.79 (m, 2H), 1.65 (m, 2H), 1.39 (m, 4H), 1.29–1.24 (m, 6H).

EXAMPLE 452

N'-((2RS,3R)-3-amino-2-hydroxy-5-(isopropylsulfanyl)pentanoyl)-4-((cyclohexylmethyl)sulfanyl)benzohydrazide The desired compound was prepared by substituting 4-(2-cyclohexylethylthio)benzoic acid for o-toluic acid in Example 369.

MS (ESI) m/e 454 (M+H)+; 1H NMR (500 MHz, CD3OD) δ 7.79 (m, 2H), 7.37 (m, 1H), 4.48 (d, 0.3H), 4.44 (d, 0.7H), 3.77 (m, 1H), 3.00 (m, 1H), 2.91 (d, 2H), 2.72 (t, 2H), 2.15 (m, 1H), 1.98 (m, 1H), 1.92 (m, 2H), 1.75 (m, 2H), 1.67 (m, 2H), 1.56 (m, 1H), 1.29–1.21 (m, 8H), 1.06 (m, 2H).

EXAMPLE 453

N'-((2RS,3R)-3-amino-2-hydroxy-5-(isopropylsulfanyl)pentanoyl)-4-(benzylsulfanyl)benzohydrazide The desired compound was prepared by substituting 4-(benzylthio)benzoic acid for o-toluic acid in Example 369.

MS (ESI) m/e 448 (M+H)+; 1H NMR (500 MHz, CD3OD) δ 7.77 (m, 2H), 7.39 (m, 4H), 7.28 (t, 2H), 7.22 (m, 1H), 4.48 (d, 0.3H), 4.43 (d, 0.7H), 4.27 (s, 0.7H), 4.26 (s, 0.3H), 3.77 (m, 1H), 3.00 (m, 1H), 2.72 (t, 2H), 2.15 (m, 1H), 1.98 (m, 1H), 1.29–1.23 (m, 6H).

EXAMPLE 454

N'-((2RS,3R)-3-amino-2-hydroxy-5-(isopropylsulfanyl)pentanoyl)-4-((2-phenylethyl)sulfanyl)benzohydrazide The desired compound was prepared by substituting 4-(2-phenylethylthio)benzoic acid for o-toluic acid in Example 369.

MS (ESI) m/e 462 (M+H)+; 1H NMR (500 MHz, CD3OD) δ 7.82 (m, 2H), 7.41 (m, 2H), 7.28 (m, 2H), 7.21 (m, 3H), 7.27 (t, 2H), 7.23–7.17 (m, 3H), 4.48 (d, 0.3H), 4.44 (d, 0.7H), 3.77 (m, 1H), 3.28 (m, 2H), 3.00 (m, 1H), 2.96 (t, 2H), 2.72 (t, 2H), 2.15 (m, 1H), 1.98 (m, 1H), 1.29–1.24 (m, 6H).

EXAMPLE 456

N'-((2RS,3R)-3-amino-2-hydroxy-5-(isopropylsulfanyl)pentanoyl)-4-((3-phenylpropyl)sulfanyl)benzohydrazide The desired compound was prepared by substituting 4-(3-phenylpropylthio)benzoic acid for o-toluic acid in Example 369.

MS (ESI) m/e 476 (M+H)+; 1H NMR (500 MHz, CD3OD) δ 7.78 (m, 2H), 7.33 (m, 2H), 7.27 (m, 2H), 7.18 (m, 3H), 4.48 (d, 0.3H), 4.44 (d, 0.7H), 3.77 (m, 1H), 3.01 (m, 3H), 2.77 (t, 2H), 2.71 (t, 2H), 2.15 (m, 1H), 1.98 (m, 3H), 1.29–1.24 (m, 6H).

EXAMPLE 457

N'-((2RS,3R)-3-amino-2-hydroxy-5-(isopropylsulfanyl)pentanoyl)-4-(((1,1'-biphenyl)-4-ylmethyl)sulfanyl)benzohydrazide The desired compound was prepared by substituting 4-(biphenylmethylthio)benzoic acid for o-toluic acid in Example 369.

MS (ESI) m/e 524 (M+H)+; 1H NMR (500 MHz, CD3OD) δ 5 7.78 (m, 2H), 7.58 (d, 2H), 7.55 (d, 2H), 7.43 (m, 6H), 7.31 (m, 1H), 4.48 (d, 0.3H), 4.43 (d, 0.7H), 4.32 (s, 1.4H), 4.31 (s, 0.6H), 3.76 (m, 1H), 3.00 (m, 1H), 2.71 (t, 2H), 2.15 (m, 1H), 1.98 (m, 1H), 1.29–1.25 (m, 6H).

EXAMPLE 458

(2S,3R)-3-amino-N'-(3-chlorobenzoyl)-2-hydroxy-5-phenylpentanohydrazide

Example 458A 4-phenylbutanal

A solution of 4-phenylbutyric acid (1.64 g, 10.0 mmol), N,O-dimethyl hydroxylamine hydrochloride (1.58 g, 16 mmol), 1-(3-dimethylaminopropyl)-3-ethylcarbodiimide hydrochloride (2.06 g, 10.7 mmol), 1-hydroxybenzotriazole (1.56 g, 11.6 mmol), and N-methylmorpholine (2.8 mL, 26 mmol) in dichloromethane (40 mL) at room temperature was stirred for 16 hours, diluted with dichloromethane, washed sequentially with aqueous $NaHCO_3$, brine, 10% $KHSO_4$, and brine, dried ($MgSO_4$), filtered, and concentrated. The concentrate and lithium aluminum hydride (9.0 mmol, 1 equivalent) in diethyl ether (49 mL) at room temperature was stirred 90 minutes, treated with 1M $NaHSO_4$, diluted with ether, washed sequentially with 10% $KHSO_4$, and brine, dried ($MgSO_4$), filtered then concentrated to provide the desired product.

MS (ESI) m/e 148 (M+H)$^+$.

EXAMPLE 458B (2S,3R)-3-(tert-butoxycarbonyl)amino-2-hydroxy-6-phenylhexanoic acid The desired product was prepared by substituting Example 458A for 2-ethylhexanal in Examples 236A–236C.

MS (ESI) m/e 324 (M+H)$^+$.

EXAMPLE 458C (2S,3R)-3-amino-N'-(3-chlorobenzoyl)-2-hydroxy-5-phenylpentanohydrazide The desired product was prepared by substituting 3-chlorobenzoylhydrazine for O-phenyl hydroxylamine hydrochloride and Example 458B for Example 98A in Example 98B.

MS (ESI) m/e 376 (M+H)$^+$; $^1$H NMR (300 MHz, DMSO-d$_6$) δ 10.69 (br s, 1H), 10.30 (br s, 1H), 8.24 (br s, 2H), 7.92 (m, 1H), 7.86 (d, 1H), 7.69 (d, 1H), 7.57 (t, 1H), 7.24 (m, 5H), 6.62 (m, 1H), 4.21 (m, 1H), 2.60 (m, 2H) 1.90–1.55 (m, 4H).

EXAMPLE 459

(2S,3R)-3-amino-N'-(3-chlorobenzoyl)-2-hydroxy-5-(1H-indol-3-yl)pentanohydrazide

EXAMPLE 459A 3-(3-indolyl)propanal

The desired product was prepared by substituting 3-indolylpropionic acid for 4-phenylbutyric acid in Example 458A.

MS (ESI) m/e 174 (M+H)$^+$.

EXAMPLE 459B (2S,3R)-3-(tert-butoxycarbonyl)amino-2-hydroxy-5-(3-indolyl)pentanoic acid The desired product was prepared by substituting Example 459A for 2-ethylhexanal in Examples 236A–236C.

MS (ESI) m/e 349 (M+H)$^+$.

EXAMPLE 459

(2S,3R)-3-amino-N'-(3-chlorobenzoyl)-2-hydroxy-5-(1H-indol-3-yl)pentanohydrazide The desired product was prepared by substituting 3-chlorobenzoylhydrazine for O-phenyl hydroxylamine hydrochloride and Example 459B for Example 98A in Example 98B.

MS (ESI) m/e 400 (M+H)$^+$; 1H NMR (300 MHz, DMSO-d$_6$) δ 10.69 (br s, 1H), 10.33 (br s, 1H), 7.98 (br s, 2H), 7.90 (m, 1H), 7.85 (d, 1H), 7.68 (d, 1H), 7.56 (t, 1H), 7.34 (m, 2H), 7.17 (m, 1H), 7.08 (m, 1H), 6.98 (m, 1H), 6.67 (m, 1H), 4.23 (m, 1H), 2.80 (m, 2H), 2.27 (m, 1H), 1.91 (m, 1H).

EXAMPLE 460

(2RS,3R)-3-amino-N'-(3-(2,3-dihydroxypropoxy)benzoyl)-2-hydroxy-5-(isopropylsulfanyl)pentanohydrazide

EXAMPLE 460A methyl 3-(prop-2-enyloxy)benzoate

Methyl-3-hydroxy-benzoate (1.09 g, 4.9 mmol), allyl bromide (0.73 g, 6.0 mmol) and potassium tert-butoxide (6.5 g, 5.8 mmol) in DMSO (15 mL) was stirred at room temperature for 16 hours. The mixture was poured into ice water, extracted with ether, washed with brine, dried ($Na_2SO_4$), and evaporated to give the title compound. $^1$H NMR (300 MHz, DMSO-d$_6$) δ 7.55 (m, 1H), 7.45 (m, 2H), 7.24 (m, 1H), 6.12–5.98 (m, 1H), 5.44–5.26 (m, 2H), 4.64 (m, 2H), 3.84 (s, 3H).

EXAMPLE 460B methyl 3-(2,3-dihydoxypropyloxy)benzoate

A solution of Example 460A (0.3 g, 1.5 mmol), 4-methylmorpholine N-oxide (0.55 g, 4.5 mmol) and osmium tetroxide (4 wt % solution in water 0.1 mL, 0.015 mmol) in 9:1/acetone:water was stirred at room temperature for 48 h. The reaction was quenched with 10% $Na_2S_2O_3$ and stirred for 15 minutes, extracted with ethyl acetate, washed with brine, dried ($Na_2SO_4$), and concentrated to give the title compound.

MS (ESI) m/e 249 (M+Na)$^+$. $^1$H NMR (300 MHz, DMSO-d$_6$) δ 7.54 (m, 1H), 7.44 (m, 2H), 7.23 (m, 1H), 4.98 (d, 1H), 4.68 (t, 1H), 4.05 (dd, 1H), 3.51 (dd, 1H), 3.85 (s, 3H), 3.8 (m, 1H), 3.55 & 3.45 (t, 2H).

EXAMPLE 460C

Methyl 3-(2,3-di(tertbutyldimethylsilyloxy)propoxy)benzoate

A solution of Example 460B (0.26 g, 1.15 mmol), tert-butyldimethylsilyl chloride (0.44 g, 2.87 mmol) and imidazole (0.31 g, 4.6 mmol) in DMF (10 mL) was stirred at room temperature for 18 hours. The mixture was diluted with ether, washed with brine, dried ($Na_2SO_4$), and concentrated to give the title compound.

MS (ESI) m/e 455 (M+H)$^+$. $^1$H NMR (300 MHz, DMSO-d$_6$) δ 7.58 (m, 1H), 7.47 (m, 2H), 7.26 (m, 1H), 4.09 (dd, 1H), 3.98 (dd, 1H), 3.89 (s, 3H), 3.85 (m, 1H), 3.67 (d, 2H), 0.91 (s, 9H), 0.89 (s, 9H), 0.08 (s, 6H), 0.05 (s, 6H).

EXAMPLE 460D (2RS,3R)-3-amino-N'-(3-(2,3-dihydroxypropoxy)benzoyl)-2-hydroxy-5-(isopropylsulfanyl)pentanohydrazide Example 460C was treated with hydrazine hydrate in ethanol at reflux for 48 h. After evaporation of the reaction mixture to dryness, the resulting hydrazide was reacted with Example 123B as in Example 98B.

MS (ESI) m/e 414 (M–H)$^+$. $^1$H NMR (300 MHz, DMSO-d$_6$) δ 10.57 & 10.38 (s, 11H), 10.23 & 10.12 (s, 1H), 8.05

& 7.97 (br s, 2H), 7.48–7.38(m, 3H), 7.16 (m, 1H), 6.65 & 6.56 (d, 1H), 4.98 & 4.7 (br s, 1H), 4.39 & 4.25 (t, 1H), 4.05 (dd, 1H), 3.92 (m, 1H), 3.81 (m, 1H), 3.46 (d, 2H), 3.02–2.92(m, 1H), 2.75–2.55 (m, 2H), 2.05–1.75 (m, 2H), 1.2 (m,6H).

It will be evident to one skilled in the art that the present invention is not limited to the forgoing illustrative examples, and that it can be embodied in other specific forms without departing from the essential attributes thereof. It is therefore desired that the examples be considered in all respects as illustrative and not restrictive, reference being made to the appended claims, and all changes which come within the meaning and range of equivalency of the claims and therefore intended to be embraced therein.

What is claimed is:

1. A compound of formula (I),

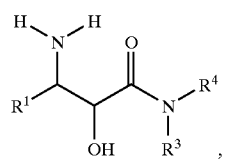

or a therapeutically acceptable salt or prodrug thereof, wherein $R^1$ is selected from the group consisting of alkyl, aryl, arylalkyl, cycloalkyl, (cycloalkyl)alkyl, (heterocycle)alkyl, and $R^5$S-(alkylene)-;

wherein each group is drawn with its right-hand end being the end that is attached to the parent molecular moiety;

$R^3$ is selected from the group consisting of hydrogen, alkyl, and arylalkyl;

$R^4$ is selected from the group consisting of —$NR^6R^7$, and —$OR^8$;

wherein each group is drawn with its left-hand end being the end that is attached to the parent molecular moiety;

$R^5$ is selected from the group consisting of alkyl, aryl, arylalkyl, cycloalkyl, and (cycloalkyl)alkyl;

$R^6$ and $R^7$ are independently selected from the group consisting of hydrogen, alkanoyl, alkenyl, alkenyloxyalkyl, alkoxyalkyl, alkoxycarbonylalkyl, alkyl, alkylsulfanylalkyl, aryl, arylalkanoyl, arylalkoxyalkyl, arylalkoxycarbonyl, arylalkyl, aryloxyalkyl, (aryl)oyl, arylsulfonyl, carboxyalkyl, cycloalkyl, (cycloalkyl)alkyl, (cycloalkyl)alkanoyl, (cycloalkyl)oyl, haloalkanoyl, haloalkyl, heterocycle, (heterocycle)alkanoyl, (heterocycle)oyl, hydroxyalkyl, a nitrogen protecting group, and —C(O)$NR^9R^{10}$; or $R^6$ and $R^7$ together are arylalkylidene; or $R^6$ and $R^7$, together with the nitrogen atom to which they are attached, form a heterocycle;

$R^8$ is selected from the group consisting of hydrogen, alkanoylalkyl, alkenyl, alkoxycarbonylalkyl, alkyl, amidoalkyl, aryl, arylalkyl, arylalkoxycarbonylalkyl, (aryl)oylalkyl, carboxyalkyl, and (cycloalkyl)alkyl; and $R^9$ and $R^{10}$ are independently selected from the group consisting of hydrogen, alkyl and aryl.

2. A compound according to claim 1, wherein $R^1$ is selected from the group consisting of alkyl, cycloalkyl, (cycloalkyl)alkyl, arylalkyl, and (heterocycle)alkyl.

3. A compound according to claim 2, wherein $R^4$ is —$OR^8$.

4. A compound according to claim 3 selected from the group consisting of
(2RS,3R)-3-amino-4-cyclohexyl-2-hydroxy-N-phenoxybutanamide;
(2RS,3R)-3-amino-N-(benzyloxy)-4-cyclohexyl-2-hydroxybutanamide;
(2RS,3R)-3-amino-N-(methoxy)-4-cyclohexyl-2-hydroxybutanamide;
(2RS,3R)-3-amino-N-(tert-butoxy)-4-cyclohexyl-2-hydroxybutanamide;
(2RS,3R)-3-amino-4-cyclohexyl-N-ethoxy-2-hydroxybutanamide;
(2RS,3R)-N-(allyloxy)-3-amino-4-cyclohexyl-2-hydroxybutanamide;
(2RS,3R)-3-amino-4-cyclohexyl-2-hydroxy-N-isobutoxybutanamide;
(2RS,3R)-3-amino-4-cyclohexyl-N,2-dihydroxybutanamide;
(2RS,3R)-3-amino-3-cyclohexyl-2-hydroxy-N-phenoxypropanamide;
(2RS,3R)-3-amino-5-phenyl-2-hydroxy-N-phenoxypentanamide;
(2RS,3R)-3-amino-3-cyclooctyl-2-hydroxy-N-phenoxypropanamide;
(2RS,3R)-3-amino-5-cyclohexyl-2-hydroxy-N-phenoxypentanamide;
ethyl ((((2RS,3R)-3-amino-4-cyclohexyl-2-hydroxybutanoyl)amino)oxy)acetate;
benzyl ((((2RS,3R)-3-amino-4-cyclohexyl-2-hydroxybutanoyl)amino)oxy)acetate;
((((2RS,3R)-3-amino-4-cyclohexyl-2-hydroxybutanoyl)amino)oxy)acetic acid;
ethyl (2S)-2-((((((2RS,3R)-3-amino-4-cyclohexyl-2-hydroxybutanoyl)amino)oxy)acetyl)amino)propanoate;
(2RS,3R)-3-amino-4-cyclohexyl-2-hydroxy-N-(2-oxo-2-((2-phenylethyl)amino)ethoxy)butanamide;
(2RS,3R)-3-amino-N-(benzyloxy)-3-cyclohexyl-2-hydroxypropanamide; and
(2RS,3R)-3-amino-N-(benzyloxy)-2-hydroxy-5-phenylpentanamide.

5. A compound according to claim 2 wherein $R^4$ is —$NR^6R^7$.

6. A compound according to claim 5 wherein one of $R^6$ and $R^7$ is hydrogen and the other is (aryl)oyl.

7. A compound according to claim 6 selected from the group consisting of
N'-((2RS,3R)-3-amino-4-cyclohexyl-2-hydroxybutanoyl)-1-naphthohydrazide;
N'-((2RS,3R)-3-amino-4-cyclohexyl-2-hydroxybutanoyl)-4-ethoxybenzohydrazide;
N'-((2RS,3R)-3-amino-4-cyclohexyl-2-hydroxybutanoyl)-3,5-dimethoxybenzohydrazide;
N'-((2RS,3R)-3-amino-4-cyclohexyl-2-hydroxybutanoyl)-2-chlorobenzohydrazide;
N'-((2RS,3R)-3-amino-4-cyclohexyl-2-hydroxybutanoyl)-3-bromobenzohydrazide;
N'-((2RS,3R)-3-amino-4-cyclohexyl-2-hydroxybutanoyl)-3-methoxybenzohydrazide;
N'-((2RS,3R)-3-amino-4-cyclohexyl-2-hydroxybutanoyl)-2,5-dichlorobenzohydrazide;
N'-((2RS,3R)-3-amino-4-cyclohexyl-2-hydroxybutanoyl)-2-methoxybenzohydrazide;

N'-((2RS,3R)-3-amino-4-cyclohexyl-2-hydroxybutanoyl)-3-chlorobenzohydrazide;
N'-((2RS,3R)-3-amino-4-cyclohexyl-2-hydroxybutanoyl)-3-methylbenzohydrazide;
N'-((2RS,3R)-3-amino-4-cyclohexyl-2-hydroxybutanoyl)-2,4-dihydroxybenzohydrazide;
N'-((2RS,3R)-3-amino-4-cyclohexyl-2-hydroxybutanoyl)-2,5-dimethoxybenzohydrazide;
N'-((2RS,3R)-3-amino-4-cyclohexyl-2-hydroxybutanoyl)-4-methylbenzohydrazide;
N'-((2RS,3R)-3-amino-4-cyclohexyl-2-hydroxybutanoyl)-4-nitrobenzohydrazide;
N'-((2RS,3R)-3-amino-4-cyclohexyl-2-hydroxybutanoyl)-2-naphthohydrazide;
N'-((2RS,3R)-3-amino-4-cyclohexyl-2-hydroxybutanoyl)-4-chlorobenzohydrazide;
(2RS,3R)-3-amino-N'-benzoyl-4-cyclohexyl-2-hydroxybutanohydrazide;
N'-((2RS,3R)-3-amino-4-cyclohexyl-2-hydroxybutanoyl)-4-bromobenzohydrazide;
N'-((2RS,3R)-3-amino-4-cyclohexyl-2-hydroxybutanoyl)-4-tert-butylbenzohydrazide;
N'-((2RS,3R)-3-amino-3-cyclohexyl-2-hydroxypropanoyl)-3-chlorobenzohydrazide;
N'-((2RS,3R)-3-amino-2-hydroxy-5-phenylpentanoyl)-3-chlorobenzohydrazide;
N'-((2RS,3R)-3-amino-3-cyclooctyl-2-hydroxypropanoyl)-3-chlorobenzohydrazide;
N'-((2RS,3R)-3-amino-5-cyclohexyl-2-hydroxypentanoyl)-3-chlorobenzohydrazide;
(2RS,3R)-3-amino-2-hydroxy-5-phenyl-N'-(1-naphthyl)pentanohydrazide;
N'-((2RS,3R)-3-amino-3-cyclohexyl-2-hydroxypropanoyl)-2-naphthohydrazide;
N'-((2RS,3R)-3-amino-4-cyclohexyl-2-hydroxybutanoyl)-1-naphthohydrazide;
N'-((2RS,3R)-3-amino-4-cyclohexyl-2-hydroxybutanoyl)-3-hydroxy-2-naphthohydrazide;
N'-((2S,3R)-3-amino-2-hydroxy-5-phenylpentanoyl)-1-naphthohydrazide;
N'-((2S,3R)-3-amino-2-hydroxy-5-phenylpentanoyl)-3-hydroxy-2-naphthohydrazide;
N'-((2S,3R,4RS)-3-amino-4-ethyl-2-hydroxyoctanoyl)-3-chlorobenzohydrazide;
N'-((2S,3R)-3-amino-5-cyclohexyl-2-hydroxypentanoyl)-3-chlorobenzohydrazide;
N'-((2RS,3R)-3-amino-4-cyclohexyl-2-hydroxybutanoyl)-2-hydroxybenzohydrazide;
N'-((2RS,3R)-3-amino-4-cyclohexyl-2-hydroxybutanoyl)-2-methylbenzohydrazide;
2-amino-N'-((2RS,3R)-3-amino-4-cyclohexyl-2-hydroxybutanoyl)benzohydrazide;
4-amino-N'-((2RS,3R)-3-amino-4-cyclohexyl-2-hydroxybutanoyl)benzohydrazide;
3-amino-N'-((2RS,3R)-3-amino-4-cyclohexyl-2-hydroxybutanoyl)benzohydrazide;
N'-((2RS,3R)-3-amino-4-cyclohexyl-2-hydroxybutanoyl)-3-hydroxybenzohydrazide;
N'-((2RS,3R)-3-amino-4-cyclohexyl-2-hydroxybutanoyl)-4-hydroxybenzohydrazide;
N'-((2RS,3R)-3-amino-4-cyclohexyl-2-hydroxybutanoyl)-4-methoxybenzohydrazide;
N'-((2RS,3R)-3-amino-4-cyclohexyl-2-hydroxybutanoyl)-2-fluorobenzohydrazide;
N'-((2RS,3R)-3-amino-4-cyclohexyl-2-hydroxybutanoyl)-3-fluorobenzohydrazide;
N'-((2RS,3R)-3-amino-4-cyclohexyl-2-hydroxybutanoyl)-4-fluorobenzohydrazide;
N'-((2RS,3R)-3-amino-4-cyclohexyl-2-hydroxybutanoyl)-2-bromobenzohydrazide;
N'-((2RS,3R)-3-amino-4-cyclohexyl-2-hydroxybutanoyl)-3-cyanobenzohydrazide;
N'-((2RS,3R)-3-amino-4-cyclohexyl-2-hydroxybutanoyl)-4-cyanobenzohydrazide;
N'-((2RS,3R)-3-amino-4-cyclohexyl-2-hydroxybutanoyl)-3-(dimethylamino)benzohydrazide;
N'-((2RS,3R)-3-amino-4-cyclohexyl-2-hydroxybutanoyl)-4-(dimethylamino)benzohydrazide;
N'-((2RS,3R)-3-amino-4-cyclohexyl-2-hydroxybutanoyl)-3-(trifluoromethyl)benzohydrazide;
N'-((2RS,3R)-3-amino-4-cyclohexyl-2-hydroxybutanoyl)-4-(trifluoromethyl)benzohydrazide;
N'-((2RS,3R)-3-amino-4-cyclohexyl-2-hydroxybutanoyl)-3-(trifluoromethoxy)benzohydrazide;
N'-((2RS,3R)-3-amino-4-cyclohexyl-2-hydroxybutanoyl)-4-phenoxybenzohydrazide;
N'-((2RS,3R)-3-amino-4-cyclohexyl-2-hydroxybutanoyl)-2,4-dimethylbenzohydrazide;
N'-((2RS,3R)-3-amino-4-cyclohexyl-2-hydroxybutanoyl)-2,5-dimethylbenzohydrazide;
N'-((2RS,3R)-3-amino-4-cyclohexyl-2-hydroxybutanoyl)-3,4-dimethylbenzohydrazide;
N'-((2RS,3R)-3-amino-4-cyclohexyl-2-hydroxybutanoyl)-3,5-dimethylbenzohydrazide;
N'-((2RS,3R)-3-amino-4-cyclohexyl-2-hydroxybutanoyl)-2,3-dimethoxybenzohydrazide;
N'-((2RS,3R)-3-amino-4-cyclohexyl-2-hydroxybutanoyl)-3,4-dimethoxybenzohydrazide;
N'-((2RS,3R)-3-amino-4-cyclohexyl-2-hydroxybutanoyl)-3,4,5-trimethoxybenzohydrazide;
N'-((2RS,3R)-3-amino-4-cyclohexyl-2-hydroxybutanoyl)-2,3-dichlorobenzohydrazide;
N'-((2RS,3R)-3-amino-4-cyclohexyl-2-hydroxybutanoyl)-2,4-dichlorobenzohydrazide;
N'-((2RS,3R)-3-amino-4-cyclohexyl-2-hydroxybutanoyl)-3,4-dichlorobenzohydrazide;
N'-((2RS,3R)-3-amino-4-cyclohexyl-2-hydroxybutanoyl)-3,5-dichlorobenzohydrazide;
N'-((2RS,3R)-3-amino-4-cyclohexyl-2-hydroxybutanoyl)-2,3-dimethylbenzohydrazide;
(2S,3R)-3-amino-N'-(3-chlorobenzoyl)-2-hydroxy-5-phenylpentanohydrazide; and
(2S,3R)-3-amino-N'-(3-chlorobenzoyl)-2-hydroxy-5-(1H-indol-3-yl)pentanohydrazide.

8. A compound according to claim 5 wherein one of $R^6$ and $R^7$ is selected from the group consisting of hydrogen, alkyl, and aryl; and the other is selected from the group consisting of hydrogen, aryl, and arylalkyl.

9. A compound according to claim 8 selected from the group consisting of
(2RS,3R)-3-amino-N'-benzyl-4-cyclohexyl-2-hydroxybutanohydrazide;
(2RS,3R)-3-amino-N'-benzyl-4-cyclohexyl-2-hydroxybutanohydrazide;

(2RS,3R)-3-amino-4-cyclohexyl-2-hydroxy-N'-(2-phenylethyl)butanohydrazide;
(2RS,3R)-3-amino-4-cyclohexyl-2-hydroxy-N'-methyl-N'-phenylbutanohydrazide;
(2RS,3R)-3-amino-4-cyclohexyl-2-hydroxy-N'-(4-methylphenyl)butanohydrazide;
(2RS,3R)-3-amino-4-cyclohexyl-2-hydroxy-N'-(4-methoxyphenyl)butanohydrazide;
(2RS,3R)-3-amino-4-cyclohexyl-2-hydroxy-N'-(1-naphthyl)butanohydrazide;
(2RS,3R)-3-amino-4-cyclohexyl-2-hydroxybutanohydrazide;
(2RS,3R)-3-amino-4-cyclohexyl-N'-(2,4-difluorophenyl)-2-hydroxybutanohydrazide;
4-(2-((2RS,3R)-3-amino-4-cyclohexyl-2-hydroxybutanoyl)hydrazino)benzenesulfonamide;
(2RS,3R)-3-amino-4-cyclohexyl-2-hydroxy-N'-phenylbutanohydrazide;
(2RS,3R)-3-amino-N'-(4-bromophenyl)-4-cyclohexyl-2-hydroxybutanohydrazide;
(2RS,3R)-3-amino-4-cyclohexyl-2-hydroxy-N'-(2-methylphenyl)butanohydrazide;
(2RS,3R)-3-amino-N'-(2-chlorophenyl)-4-cyclohexyl-2-hydroxybutanohydrazide;
(2RS,3R)-3-amino-4-cyclohexyl-2-hydroxy-N'-(3-(trifluoromethyl)phenyl)butanohydrazide;
(2RS,3R)-3-amino-4-cyclohexyl-2-hydroxy-N'-(4-iodophenyl)butanohydrazide;
(2RS,3R)-3-amino-N'-(3-chlorophenyl)-4-cyclohexyl-2-hydroxybutanohydrazide;
(2RS,3R)-3-amino-4-cyclohexyl-2-hydroxy-N'-(3-methoxyphenyl)butanohydrazide;
(2RS,3R)-3-amino-4-cyclohexyl-N'-(3,5-dichlorophenyl)-2-hydroxybutanohydrazide;
(2RS,3R)-3-amino-N'-(3-bromophenyl)-4-cyclohexyl-2-hydroxybutanohydrazide;
(2RS,3R)-3-amino-4-cyclohexyl-2-hydroxy-N'-(4-isopropylphenyl)butanohydrazide;
(2RS,3R)-3-amino-N'-(3-chloro-4-methylphenyl)-4-cyclohexyl-2-hydroxybutanohydrazide;
(2RS,3R)-3-amino-4-cyclohexyl-2-hydroxy-N'-(4-(trifluoromethoxy)phenyl)butanohydrazide;
(2RS,3R)-3-amino-4-cyclohexyl-N'-(4-fluorophenyl)-2-hydroxybutanohydrazide;
(2RS,3R)-3-amino-N'-(4-chlorophenyl)-4-cyclohexyl-2-hydroxybutanohydrazide;
(2RS,3R)-3-amino-4-cyclohexyl-N'-(2-ethylphenyl)-2-hydroxybutanohydrazide;
(2RS,3R)-3-amino-4-cyclohexyl-N'-(3-fluorophenyl)-2-hydroxybutanohydrazide;
(2RS,3R)-3-amino-N'-(4-chloro-2-methylphenyl)-4-cyclohexyl-2-hydroxybutanohydrazide;
(2RS,3R)-3-amino-4-cyclohexyl-2-hydroxy-N'-mesitylbutanohydrazide;
(2RS,3R)-3-amino-4-cyclohexyl-2-hydroxy-N'-(4-((E)-2-(2-pyridinyl)ethenyl)phenyl)butanohydrazide;
(2RS,3R)-3-amino-4-cyclohexyl-N'-(2-fluorophenyl)-2-hydroxybutanohydrazide;
(2RS,3R)-3-amino-4-cyclohexyl-2-hydroxy-N'-(4-(trifluoromethyl)phenyl)butanohydrazide;
(2RS,3R)-3-amino-N'-(2-chloro-6-fluorophenyl)-4-cyclohexyl-2-hydroxybutanohydrazide;
(2RS,3R)-3-amino-4-cyclohexyl-N'-(2,5-difluorophenyl)-2-hydroxybutanohydrazide;
(2RS,3R)-3-amino-N'-(3-chloro-4-fluorophenyl)-4-cyclohexyl-2-hydroxybutanohydrazide;
(2RS,3R)-3-amino-N'-(2-chlorobenzyl)-4-cyclohexyl-2-hydroxybutanohydrazide;
(2RS,3R)-3-amino-4-cyclohexyl-2-hydroxy-N'-phenyl-N'-(3-phenylpropyl)butanohydrazide;
(2RS,3R)-3-amino-4-cyclohexyl-2-hydroxy-N'-isobutyl-N'-phenylbutanohydrazide;
(2RS,3R)-3-amino-4-cyclohexyl-2-hydroxy-N'-pentyl-N'-phenylbutanohydrazide;
(2RS,3R)-3-amino-4-cyclohexyl-2-hydroxy-N'-((2RS)-2-methylbutyl)-N'-phenylbutanohydrazide;
(2RS,3R)-3-amino-4-cyclohexyl-2-hydroxy-N'-isopentyl-N'-phenylbutanohydrazide;
(2RS,3R)-3-amino-4-cyclohexyl-N'-hexyl-2-hydroxy-N'-phenylbutanohydrazide;
(2RS,3R)-3-amino-4-cyclohexyl-2-hydroxy-N'-((2RS)-2-methylpentyl)-N'-phenylbutanohydrazide;
(2RS,3R)-3-amino-4-cyclohexyl-2-hydroxy-N'-((3RS)-3-methylpentyl)-N'-phenylbutanohydrazide;
(2RS,3R)-3-amino-4-cyclohexyl-N'-(3,3-dimethylbutyl)-2-hydroxy-N'-phenylbutanohydrazide;
(2RS,3R)-3-amino-4-cyclohexyl-N'-(2-ethylbutyl)-2-hydroxy-N'-phenylbutanohydrazide;
(2RS,3R)-3-amino-4-cyclohexyl-N'-dodecyl-2-hydroxy-N'-phenylbutanohydrazide;
(2RS,3R)-3-amino-4-cyclohexyl-2-hydroxy-N'-phenyl-N'-((3RS)-3,5,5-trimethylhexyl)butanohydrazide;
(2RS,3R)-3-amino-4-cyclohexyl-2-hydroxy-N'-octyl-N'-phenylbutanohydrazide;
(2RS,3R)-3-amino-4-cyclohexyl-2-hydroxy-N'-phenyl-N'-propylbutanohydrazide;
(2RS,3R)-3-amino-4-cyclohexyl-N'-heptyl-2-hydroxy-N'-phenylbutanohydrazide;
(2RS,3R)-3-amino-4-cyclohexyl-N'-ethyl-2-hydroxy-N'-phenylbutanohydrazide;
(2RS,3R)-3-amino-4-cyclohexyl-2-hydroxy-N'-(2-(4-methylphenyl)ethyl)-N'-phenylbutanohydrazide;
(2RS,3R)-3-amino-4-cyclohexyl-N'-((2RS)-2-ethylhexyl)-2-hydroxy-N'-phenylbutanohydrazide;
(2RS,3R)-3-amino-N'-((2RS)-2-(4-chlorophenyl)-2-cyanoethyl)-4-cyclohexyl-2-hydroxy-N'-phenylbutanohydrazide;
(2RS,3R)-3-amino-4-cyclohexyl-2-hydroxy-N'-phenyl-N'-((2RS)-2-phenylpropyl)butanohydrazide;
(2RS,3R)-3-amino-3-cyclohexyl-2-hydroxy-N'-(4-methylphenyl)propanohydrazide;
(2RS,3R)-3-amino-2-hydroxy-5-phenyl-N'-(4-methylphenyl)pentanohydrazide;
(2S,3R)-3-amino-3-cyclooctyl-2-hydroxy-N'-(4-methylphenyl)propanohydrazide;
(2RS,3S)-3-amino-4-((cyclohexylmethyl)sulfanyl)-2-hydroxy-N'-(4-methylphenyl)butanohydrazide;
(2RS,3R)-3-amino-3-cyclohexyl-2-hydroxy-N'-(1-naphthyl)propanohydrazide;
(2RS,3R)-3-amino-2-hydroxy-5-phenyl-N'-(1-naphthyl)pentanohydrazide;
(2RS,3R)-3-amino-3-cyclooctyl-2-hydroxy-N'-(1-naphthyl)propanohydrazide;
(2RS,3R)-3-amino-5-cyclohexyl-2-hydroxy-N'-(4-methylphenyl)pentanohydrazide;

(2RS,3R)-3-amino-5-cyclohexyl-2-hydroxy-N'-(1-naphthyl)pentanohydrazide; and (2S,3R)-3-amino-4-cyclohexyl-2-hydroxybutanohydrazide.

10. A compound according to claim 5 wherein one of $R^6$ and $R^7$ is selected from the group consisting of hydrogen, alkyl, and aryl; and the other is selected from the group consisting of alkanoyl, alkenyl, alkenyloxyalkyl, alkoxyalkyl, alkoxycarbonylalkyl, alkylsulfanylalkyl, aryloxyalkyl, arylalkoxycarbonyl, arylsulfonyl, carboxyalkyl, —C(O)$R^9R^{10}$, cycloalkyl, (cycloalkyl)alkyl, haloalkanoyl, haloalkyl, heterocycle, (heterocycle)oyl, and hydroxyalkyl.

11. A compound according to claim 10 selected from the group consisting of (2RS,3R)-3-amino-N'-(7-chloro-4-quinolinyl)-4-cyclohexyl-2-hydroxybutanohydrazide;

2-((2RS,3R)-3-amino-4-cyclohexyl-2-hydroxybutanoyl)-N-(4-iodophenyl)hydrazinecarboxamide;

N'-((2RS,3R)-3-amino-4-cyclohexyl-2-hydroxybutanoyl)-2,4,6-trimethylbenzenesulfonohydrazide;

ethyl (2-((2RS,3R)-3-amino-4-cyclohexyl-2-hydroxybutanoyl)hydrazino)acetate trifluoroacetate;

benzyl 2-((2RS,3R)-3-amino-4-cyclohexyl-2-hydroxybutanoyl)hydrazinecarboxylate;

ethyl 3-(2-((2RS,3R)-3-amino-4-cyclohexyl-2-hydroxybutanoyl)hydrazino)-3-oxopropanoate;

(2RS,3R)-3-amino-4-cyclohexyl-2-hydroxy-N'-(2,2,2-trifluoroethyl)butanohydrazide;

(2RS,3R)-3-amino-4-cyclohexyl-2-hydroxy-N'-methyl-N'-(3-nitro-2-pyridinyl)butanohydrazide;

(2RS,3R)-3-amino-N',4-dicyclohexyl-2-hydroxybutanohydrazide;

(2RS,3R)-3-amino-4-cyclohexyl-2-hydroxy-N'-(2-pyridinyl)butanohydrazide;

(2RS,3R)-3-amino-N'-(6-chloro-3-pyridazinyl)-4-cyclohexyl-2-hydroxy-N'-methylbutanohydrazide;

(2RS,3R)-3-amino-N'-(5-chloro-1-methyl-6-oxo-1,6-dihydro-4-pyridazinyl)-4-cyclohexyl-2-hydroxy-N'-methylbutanohydrazide;

N'-((2RS,3R)-3-amino-4-cyclohexyl-2-hydroxybutanoyl)-1,3-benzodioxole-5-carbohydrazide;

methyl 2-(2-((2RS,3R)-3-amino-4-cyclohexyl-2-hydroxybutanoyl)hydrazino)-4-(trifluoromethyl)-5-pyrimidinecarboxylate;

(2RS,3R)-3-amino-4-cyclohexyl-2-hydroxy-N'-((2RS)-2-hydroxy-3-(3-(trifluoromethyl)phenoxy)propyl)-N'-methylbutanohydrazide;

methyl 3-(2-((2RS,3R)-3-amino-4-cyclohexyl-2-hydroxybutanoyl)hydrazino)-2-thiophenecarboxylate;

(2RS,3R)-3-amino-4-cyclohexyl-2-hydroxy-N'-(2-pyridinylcarbonyl)butanohydrazide;

ethyl 3-(2-((2RS,3R)-3-amino-4-cyclohexyl-2-hydroxybutanoyl)hydrazino)-6,6-dimethyl-4-oxo-4,5,6,7-tetrahydro-2-benzothiophene-1-carboxylate;

(2RS,3R)-3-amino-N'-(1,3-benzothiazol-2-yl)-4-cyclohexyl-2-hydroxybutanohydrazide;

(2RS,3R)-3-amino-4-cyclohexyl-2-hydroxy-N'-(trifluoroacetyl)butanohydrazide;

N'-((2RS,3R)-3-amino-4-cyclohexyl-2-hydroxybutanoyl)-3-chloro-1-benzothiophene-2-carbohydrazide;

(2RS,3R)-3-amino-4-cyclohexyl-2-hydroxy-N'-(2-quinoxalinyl)butanohydrazide;

(2RS,3R)-3-amino-4-cyclohexyl-2-hydroxy-N'-methyl-N'-(5-(trifluoromethyl)-2-pyridinyl)butanohydrazide;

(2RS,3R)-3-amino-4-cyclohexyl-N'-(1,3-dimethyl-4-nitro-1H-pyrazol-5-yl)-2-hydroxybutanohydrazide;

2-((2RS,3R)-3-amino-4-cyclohexyl-2-hydroxybutanoyl)-N-phenylhydrazinecarboxamide;

2-((2RS,3R)-3-amino-4-cyclohexyl-2-hydroxybutanoyl)-N-(4-chloro-2-methoxyphenyl)hydrazinecarboxamide;

2-((2RS,3R)-3-amino-4-cyclohexyl-2-hydroxybutanoyl)-N-(3-fluorophenyl)hydrazinecarboxamide;

N-((1R)-1-((2RS,3R)-3-amino-4-cyclohexyl-2-hydroxybutanoyl)hydrazino)carbonyl)-3-(methylsulfanyl)propyl)-4-(trifluoromethyl)benzamide;

(2RS,3R)-3-amino-4-cyclohexyl-2-hydroxy-N'-(2-thienylcarbonyl)butanohydrazide;

4-chlorobenzyl 2-(2-((2RS,3R)-3-amino-4-cyclohexyl-2-hydroxybutanoyl)hydrazino)-4-(trifluoromethyl)-5-pyrimidinecarboxylate;

(2RS,3R)-3-amino-N'-(6-chloro-3-pyridazinyl)-4-cyclohexyl-2-hydroxybutanohydrazide;

(2RS,3R)-3-amino-4-cyclohexyl-2-hydroxy-N'-((3RS)-3-(methylsulfanyl)butyl)-N'-phenylbutanohydrazide;

(2RS,3R)-3-amino-4-cyclohexyl-N'-(cyclopropylmethyl)-2-hydroxy-N'-phenylbutanohydrazide;

(2RS,3R)-3-amino-N'-(2-(benzyloxy)ethyl)-4-cyclohexyl-2-hydroxy-N'-phenylbutanohydrazide;

(2RS,3R)-3-amino-4-cyclohexyl-2-hydroxy-N'-phenyl-N'-(2,2,5-trichloropentyl)butanohydrazide;

(2RS,3R)-3-amino-4-cyclohexyl-2-hydroxy-N'-(3-(methylsulfanyl)propyl)-N'-phenylbutanohydrazide;

(2RS,3R)-3-amino-4-cyclohexyl-N'-(cyclopentylmethyl)-2-hydroxy-N'-phenylbutanohydrazide;

(2RS,3R)-3-amino-4-cyclohexyl-2-hydroxy-N'-(5-hydroxypentyl)-N'-phenylbutanohydrazide;

(2RS,3R)-3-amino-4-cyclohexyl-N'-((2R)-2,3-dihydroxypropyl)-2-hydroxy-N'-phenylbutanohydrazide;

(2RS,3R)-3-amino-4-cyclohexyl-N'-(2,2-dichlorohexyl)-2-hydroxy-N'-phenylbutanohydrazide;

(2RS,3R)-3-amino-4-cyclohexyl-2-hydroxy-N'-((3RS)-7-methoxy-3,7-dimethyloctyl)-N'-phenylbutanohydrazide;

(2RS,3R)-3-amino-4-cyclohexyl-N'-(cyclooctylmethyl)-2-hydroxy-N'-phenylbutanohydrazide;

(2RS,3R)-3-amino-4-cyclohexyl-N'-((11Z)-11-hexadecenyl)-2-hydroxy-N'-phenylbutanohydrazide;

(2RS,3R)-3-amino-4-cyclohexyl-2-hydroxy-N'-phenyl-N'-tridecylbutanohydrazide;

4-(2-((2RS,3R)-3-amino-4-cyclohexyl-2-hydroxybutanoyl)-1-phenylhydrazino)butanoic acid;

(2RS,3R)-3-amino-4-cyclohexyl-2-hydroxy-N'-((6Z)-6-nonenyl)-N'-phenylbutanohydrazide;

(2RS,3R)-3-amino-4-cyclohexyl-N'-((4Z)-4-decenyl)-2-hydroxy-N'-phenylbutanohydrazide;

(2RS,3R)-3-amino-4-cyclohexyl-2-hydroxy-N'-(4-pentenyl)-N'-phenylbutanohydrazide;

(2RS,3R)-3-amino-4-cyclohexyl-N'-((3RS)-3,7-dimethyl-6-octenyl)-2-hydroxy-N'-phenylbutanohydrazide;

(2RS,3R)-3-amino-4-cyclohexyl-2-hydroxy-N'-phenyl-N'-(4,4,4-trifluorobutyl)butanohydrazide;

(2RS,3R)-3-amino-4-cyclohexyl-2-hydroxy-N'-((3RS)-3-hydroxybutyl)-N'-phenylbutanohydrazide;

(2RS,3R)-3-amino-4-cyclohexyl-N'-(2-(((3RS)-3,7-dimethyl-6-octenyl)oxy)ethyl)-2-hydroxy-N'-phenylbutanohydrazide;

(2RS,3R)-3-amino-4-cyclohexyl-N'-(2-((1RS)-3,3-dimethylcyclohexyl)ethyl)-2-hydroxy-N'-phenylbutanohydrazide;

(2RS,3R)-3-amino-N'-((4S)-6-bromo-4-methylhexyl)-4-cyclohexyl-2-hydroxy-N'-phenylbutanohydrazide; and (2RS,3R)-3-amino-4-cyclohexyl-N'-(cyclohexylmethyl)-2-hydroxy-N'-phenylbutanohydrazide.

12. A compound according to claim 5 wherein $R^6$ and $R^7$ together are arylalkylidene.

13. A compound according to claim 12 which is (2RS,3R)-3-amino-N'-((E)-(4-chlorophenyl)methylidene)-4-cyclohexyl-2-hydroxybutanohydrazide.

14. A compound according to claim 5 wherein $R^6$ and $R^7$, together with the nitrogen atom to which they are attached, form a heterocycle.

15. A compound according to claim 14 selected from the group consisting of (2RS,3R)-3-amino-4-cyclohexyl-2-hydroxy-N-((2S)-2-(methoxymethyl)pyrrolidinyl)butanamide;

(2RS,3R)-3-amino-4-cyclohexyl-2-hydroxy-N-(1-pyrrolidinyl)butanamide;

(2RS,3R)-3-amino-4-cyclohexyl-2-hydroxy-N-(4-oxo-2-thioxo-1,3-thiazolidin-3-yl)butanamide;

(2RS,3R)-3-amino-4-cyclohexyl-2-hydroxy-N-(1-piperidinyl)butanamide; and (2RS,3R)-3-amino-4-cyclohexyl-2-hydroxy-N-((2R)-2-(methoxymethyl)pyrrolidinyl)butanamide.

16. A compound according to claim 1 wherein $R^1$ is $R^5$S-(alkylene)-.

17. A compound according to claim 16 wherein $R^4$ is —OR$^8$.

18. A compound according to claim 17 selected from the group consisting of (2RS,3R)-3-amino-5-(ethylsulfanyl)-2-hydroxy-N-phenoxypentamide;

(2RS,3S)-3-amino-4-(ethylsulfanyl)-2-hydroxy-N-phenoxybutanamide;

(2RS,3S)-3-amino-2-hydroxy-N-phenoxy-4-(propylsulfanyl)butanamide;

(2RS,3R)-3-amino-2-hydroxy-5-(isopropylsulfanyl)-N-phenoxypentanamide;

(2RS,3S)-3-amino-2-hydroxy-4-(isobutylsulfanyl)-N-phenoxybutanamide;

(2RS,3S)-3-amino-4-((cyclohexylmethyl)sulfanyl)-2-hydroxy-N-phenoxybutanamide;

(2RS,3R)-3-amino-5-(ethylsulfanyl)-2-hydroxy-N-benzyloxypentanamide;

(2RS,3R)-3-amino-N-(benzyloxy)-2-hydroxy-5-(isopropylsulfanyl)pentanamide;

(2RS,3S)-3-amino-N-(benzyloxy)-2-hydroxy-4-(isobutylsulfanyl)butanamide;

(2S,3S)-3-amino-N-(cyclohexylmethoxy)-2-hydroxy-4-(isobutylsulfanyl)butanamide;

(2S,3S)-3-amino-2-hydroxy-4-(isobutylsulfanyl)-N-(mesitylmethoxy)butanamide;

(2RS,3R)-3-amino-2-hydroxy-5-(ethylsulfanyl)-N-((1RS)-1-phenylethoxy)pentanamide;

(2S,3S)-3-amino-N-(benzyloxy)-2-hydroxy-4-(isobutylsulfanyl)-N-methylbutanamide;

(2RS,3S)-3-amino-N-(benzyloxy)-2-hydroxy-5-(isopropylsulfanyl)-N-methylpentanamide; and (2RS,3R)-3-amino-2-hydroxy-5-(isopropylsulfanyl)-N-((1RS)-1-phenylethoxy)pentanamide.

19. A compound according to claim 18 wherein $R^4$ is —NR$^6$R$^7$.

20. A compound according to claim 19 wherein one of $R^6$ and $R^7$ is hydrogen and the other is (aryl)oyl.

21. A compound according to claim 20 wherein the aryl(oyl) is unsubstituted.

22. A compound according to claim 21 selected from the group consisting of

N'-((2RS,3R)-3-amino-5-(ethylsulfanyl)-2-hydroxypentanoyl)-2-naphthohydrazide;

N'-((2RS,3R)-3-amino-5-(ethylsulfanyl)-2-hydroxypentanoyl)benzohydrazide;

N'-((2RS,3R)-3-amino-2-hydroxy-5-isopropylsulfanylpentanoyl)-2-naphthohydrazide;

N'-((2RS,3S)-3-amino-2-hydroxy-4-(isobutylsulfanyl)butanoyl)-2-naphthohydrazide;

N'-((2RS,3R)-3-amino-5-(ethylsulfanyl)-2-hydroxypentanoyl)-1-naphthohydrazide; and N'-((2RS,3R)-3-amino-2-hydroxy-5-(isopropylsulfanyl)pentanoyl)-1-naphthohydrazide.

23. A compound according to claim 20 wherein the aryl(oyl) is substituted with one substituent.

24. A compound according to claim 23 wherein the substituent is at the 2-position.

25. A compound according to claim 24 selected from the group consisting of

N'-((2RS,3R)-3-amino-5-(ethylsulfanyl)-2-hydroxypentanoyl)-2-chlorobenzohydrazide;

N'-((2RS,3R)-3-amino-5-(ethylsulfanyl)-2-hydroxypentanoyl)-3-hydroxy-2-naphthohydrazide;

N'-((2RS,3R)-3-amino-5-(ethylsulfanyl)-2-hydroxypentanoyl)-2-methylbenzohydrazide;

N'-((2RS,3R)-3-amino-5-(ethylsulfanyl)-2-hydroxypentanoyl)-2-aminobenzohydrazide;

N'-((2RS,3R)-3-amino-5-(ethylsulfanyl)-2-hydroxypentanoyl)-2-hydroxybenzohydrazide;

N'-((2RS,3R)-3-amino-5-(ethylsulfanyl)-2-hydroxypentanoyl)-2-fluorobenzohydrazide;

N'-((2RS,3R)-3-amino-5-(ethylsulfanyl)-2-hydroxypentanoyl)-2-bromobenzohydrazide;

N'-((2RS,3R)-3-amino-2-hydroxy-5-(isopropylsulfanyl)pentanoyl)-2-methylbenzohydrazide;

N'-((2RS,3R)-3-amino-2-hydroxy-5-(isopropylsulfanyl)pentanoyl)-2-methoxybenzohydrazide;

N'-((2RS,3R)-3-amino-2-hydroxy-5-(isopropylsulfanyl)pentanoyl)-2-fluorobenzohydrazide;

N'-((2RS,3R)-3-amino-2-hydroxy-5-(isopropylsulfanyl)pentanoyl)-2-chlorobenzohydrazide;

N'-((2RS,3R)-3-amino-2-hydroxy-5-(isopropylsulfanyl)pentanoyl)-2-bromobenzohydrazide;

N'-((2RS,3R)-3-amino-2-hydroxy-5-(isopropylsulfanyl)pentanoyl)-2-ethoxybenzohydrazide;

N'-((2RS,3R)-3-amino-2-hydroxy-5-(isopropylsulfanyl)pentanoyl)-2-benzylbenzohydrazide;

N'-((2RS,3R)-3-amino-2-hydroxy-5-(isopropylsulfanyl)pentanoyl)-2-anilinobenzohydrazide; and N'-((2RS,3R)-3-amino-2-hydroxy-5-(isopropylsulfanyl) pentanoyl)-2-(2-phenylethyl)benzohydrazide.

26. A compound according to claim 23 wherein the substituent is at the 3-position.

27. A compound according to claim 23 selected from the group consisting of

N'-((2RS,3R)-3-amino-5-(ethylsulfanyl)-2-hydroxypentanoyl)-3-chlorobenzohydrazide;

N'-((2RS,3S)-3-amino-4-(ethylsulfanyl)-2-hydroxybutanoyl)-3-chlorobenzohydrazide;

N'-((2RS,3S)-3-amino-2-hydroxy-4-(propylsulfanyl) butanoyl)-3-chlorobenzohydrazide;

N'-((2RS,3R)-3-amino-2-hydroxy-5-(isopropylsulfanyl) pentanoyl)-3-chlorobenzohydrazide;

N'-((2RS,3S)-3-amino-2-hydroxy-4-(isobutylsulfanyl) butanoyl)-3-chlorobenzohydrazide;

N'-((2RS,3S)-3-amino-4-((cyclohexylmethyl)sulfanyl)-2-hydroxybutanoyl)-3-chlorobenzohydrazide;

N'-((2S,3R)-3-amino-2-hydroxy-5-(isopropylsulfanyl) pentanoyl-3-chlorobenzohydrazide N'-((2S,3R)-3-amino-5-(ethylsulfanyl)-2-hydroxypentanoyl)-3-chlorobenzohydrazide;

N'-((2R,3R)-3-amino-5-(ethylsulfanyl)-2-hydroxypentanoyl)-3-chlorobenzohydrazide;

N'-((2R,3R)-3-amino-2-hydroxy-5-(isopropylsulfanyl) pentanoyl)-3-chlorobenzohydrazide;

3-(2-aminoethyl)-N'-((2S,3S)-3-amino-2-hydroxy-4-(isobutylsulfanyl)butanoyl)benzohydrazide;

N'-((2S,3S)-3-amino-2-hydroxy-4-(isobutylsulfanyl) butanoyl)-3-propoxybenzohydrazide;

N'-((2RS,3R)-3-amino-5-(ethylsulfanyl)-2-hydroxypentanoyl)-3-trifluoromethylsulfanylbenzohydrazide;

N'-((2RS,3R)-3-amino-5-(ethylsulfanyl)-2-hydroxypentanoyl)-3-methylbenzohydrazide;

N'-((2RS,3R)-3-amino-5-(ethylsulfanyl)-2-hydroxypentanoyl)-3-aminobenzohydrazide;

N'-((2RS,3R)-3-amino-5-(ethylsulfanyl)-2-hydroxypentanoyl)-3-hydroxybenzohydrazide;

N'-((2RS,3R)-3-amino-5-(ethylsulfanyl)-2-hydroxypentanoyl)-3-methoxybenzohydrazide;

N'-((2RS,3R)-3-amino-5-(ethylsulfanyl)-2-hydroxypentanoyl)-3-fluorobenzohydrazide;

N'-((2RS,3R)-3-amino-5-(ethylsulfanyl)-2-hydroxypentanoyl)-3-(dimethylamino)benzohydrazide;

N'-((2RS,3R)-3-amino-5-(ethylsulfanyl)-2-hydroxypentanoyl)-3-(trifluoromethyl)benzohydrazide;

N'-((2RS,3R)-3-amino-5-(ethylsulfanyl)-2-hydroxypentanoyl)-3-(trifluoromethoxy)benzohydrazide;

(2RS,3R)-3-amino-N'-(3-(2-aminoethoxy)phenyl)-2-hydroxy-5-(isopropylsulfanyl)pentanohydrazide;

N'-((2RS,3R)-3-amino-5-(ethylsulfanyl)-2-hydroxypentanoyl)-3-bromobenzohydrazide;

N'-((2RS,3R)-3-amino-5-(ethylsulfanyl)-2-hydroxypentanoyl)-3-cyanobenzohydrazide;

N'-((2RS,3R)-3-amino-2-hydroxy-5-(isopropylsulfanyl) pentanoyl)-3-hydroxybenzohydrazide;

N'-((2RS,3R)-3-amino-2-hydroxy-5-(isopropylsulfanyl) pentanoyl)-3-methylbenzohydrazide;

N'-((2RS,3R)-3-amino-2-hydroxy-5-(isopropylsulfanyl) pentanoyl)-3-methoxybenzohydrazide;

N'-((2RS,3R)-3-amino-2-hydroxy-5-(isopropylsulfanyl) pentanoyl)-3-fluorobenzohydrazide;

N'-((2RS,3R)-3-amino-2-hydroxy-5-(isopropylsulfanyl) pentanoyl)-3-bromobenzohydrazide;

N'-((2RS,3R)-3-amino-2-hydroxy-5-(isopropylsulfanyl) pentanoyl)-3-(methylsulfanyl)benzohydrazide;

N'-((2RS,3R)-3-amino-2-hydroxy-5-(isopropylsulfanyl) pentanoyl)-3-(ethylsulfanyl)benzohydrazide;

N'-((2RS,3R)-3-amino-2-hydroxy-5-(isopropylsulfanyl) pentanoyl)-3-(propylsulfanyl)benzohydrazide;

N'-((2RS,3R)-3-amino-2-hydroxy-5-(isopropylsulfanyl) pentanoyl)-3-(butylsulfanyl)benzohydrazide;

N'-((2RS,3R)-3-amino-2-hydroxy-5-(isopropylsulfanyl) pentanoyl)-3-(hexylsulfanyl)benzohydrazide;

N'-((2RS,3R)-3-amino-2-hydroxy-5-(isopropylsulfanyl) pentanoyl)-3-(isopropylsulfanyl)benzohydrazide;

N'-((2RS,3R)-3-amino-2-hydroxy-5-(isopropylsulfanyl) pentanoyl)-3-(isobutylsulfanyl)benzohydrazide;

N'-((2RS,3R)-3-amino-2-hydroxy-5-(isopropylsulfanyl) pentnoyl)-3-((4-methylpentyl)sulfanyl)benzohydrazide;

N'-((2RS,3R)-3-amino-2-hydroxy-5-(isopropylsulfanyl) pentanoyl)-3-(sec-butylsulfanyl)benzohydrazide;

N'-((2RS,3R)-3-amino-2-hydroxy-5-(isopropylsulfanyl) pentanoyl)-3-(neopentylsulfanyl)benzohydrazide;

N'-((2RS,3R)-3-amino-2-hydroxy-5-(isopropylsulfanyl) pentanoyl)-3-(cyclohexylsulfanyl)benzohydrazide;

N'-((2RS,3R)-3-amino-2-hydroxy-5-(isopropylsulfanyl) pentanoyl)-3-((cyclohexylmethyl)sulfanyl)benzohydrazide;

N'-((2RS,3R)-3-amino-2-hydroxy-5-(isopropylsulfanyl) pentanoyl)-3-(benzylsulfanyl)benzohydrazide;

N'-((2RS,3R)-3-amino-2-hydroxy-5-(isopropylsulfanyl) pentanoyl)-3-((2-phenylethyl)sulfanyl)benzohydrazide;

N'-((2RS,3R)-3-amino-2-hydroxy-5-(isopropylsulfanyl) pentanoyl)-3-((3-phenylpropyl)sulfanyl)benzohydrazide;

N'-((2RS,3R)-3-amino-2-hydroxy-5-(isopropylsulfanyl) pentanoyl)-3-(((1,1'-biphenyl)-4-ylmethyl)sulfanyl)benzohydrazide; and (2RS,3R)-3-amino-N'-(3-(2,3-dihydroxypropoxy)benzoyl)-2-hydroxy-5-(isopropylsulfanyl)pentanohydrazide.

28. A compound according to claim 23 wherein the substituent is at the 4-position.

29. A compound according to claim 28 selected from the group consisting of

N'-((2RS,3R)-3-amino-5-(ethylsulfanyl)-2-hydroxypentanoyl)-4-methylbenzohydrazide;

N'-((2RS,3R)-3-amino-5-(ethylsulfanyl)-2-hydroxypentanoyl)-4-aminobenzohydrazide;

N'-((2RS,3R)-3-amino-5-(ethylsulfanyl)-2-hydroxypentanoyl)-4-hydroxybenzohydrazide;

N'-((2RS,3R)-3-amino-5-(ethylsulfanyl)-2-hydroxypentanoyl)-4-methoxybenzohydrazide;

N'-((2RS,3R)-3-amino-5-(ethylsulfanyl)-2-hydroxypentanoyl)-4-fluorobenzohydrazide;

N'-((2RS,3R)-3-amino-5-(ethylsulfanyl)-2-hydroxypentanoyl)-4-bromobenzohydrazide; N'-

((2RS,3R)-3-amino-5-(ethylsulfanyl)-2-hydroxypentanoyl)-4-isopropylbenzohydrazide;
N'-((2RS,3R)-3-amino-5-(ethylsulfanyl)-2-hydroxypentanoyl)-4-propoxybenzohydrazide;
N'-((2RS,3R)-3-amino-5-(ethylsulfanyl)-2-hydroxypentanoyl)-4-(methylsulfanyl)benzohydrazide;
N'-((2RS,3R)-3-amino-5-(ethylsulfanyl)-2-hydroxypentanoyl)-4-isopropoxybenzohydrazide;
N'-((2RS,3R)-3-amino-5-(ethylsulfanyl)-2-hydroxypentanoyl)-4-(diethylamino)benzohydrazide;
N'-((2RS,3R)-3-amino-5-(ethylsulfanyl)-2-hydroxypentanoyl)-4-butoxybenzohydrazide;
N'-((2RS,3R)-3-amino-5-(ethylsulfanyl)-2-hydroxypentanoyl)-4-chlorobenzohydrazide;
N'-((2RS,3R)-3-amino-5-(ethylsulfanyl)-2-hydroxypentanoyl)-4-(dimethylamino)benzohydrazide;
N'-((2RS,3R)-3-amino-5-(ethylsulfanyl)-2-hydroxypentanoyl)-4-(trifluoromethyl)benzohydrazide;
N'-((2RS,3R)-3-amino-5-(ethylsulfanyl)-2-hydroxypentanoyl)-4-phenoxybenzohydrazide;
N'-((2RS,3R)-3-amino-5-(ethylsulfanyl)-2-hydroxypentanoyl)-4-(phenoxymethyl)benzohydrazide;
N'-((2RS,3R)-3-amino-5-(ethylsulfanyl)-2-hydroxypentanoyl)-4-cyanobenzohydrazide;
N'-((2RS,3R)-3-amino-2-hydroxy-5-(isopropylsulfanyl)pentanoyl)-4-methylbenzohydrazide;
N'-((2RS,3R)-3-amino-2-hydroxy-5-(isopropylsulfanyl)pentanoyl)-4-methoxybenzohydrazide;
N'-((2RS,3R)-3-amino-2-hydroxy-5-(isopropylsulfanyl)pentanoyl)-4-fluorobenzohydrazide;
N'-((2RS,3R)-3-amino-2-hydroxy-5-(isopropylsulfanyl)pentanoyl)-4-chlorobenzohydrazide;
N'-((2RS,3R)-3-amino-2-hydroxy-5-(isopropylsulfanyl)pentanoyl)-4-bromobenzohydrazide;
N'-((2RS,3R)-3-amino-2-hydroxy-5-(isopropylsulfanyl)pentanoyl)-4-ethylbenzohydrazide;
N'-((2RS,3R)-3-amino-2-hydroxy-5-(isopropylsulfanyl)pentanoyl)-4-propylbenzohydrazide;
N'-((2RS,3R)-3-amino-2-hydroxy-5-(isopropylsulfanyl)pentanoyl)-4-isopropylbenzohydrazide;
N'-((2RS,3R)-3-amino-2-hydroxy-5-(isopropylsulfanyl)pentanoyl)-4-ethoxybenzohydrazide;
N'-((2RS,3R)-3-amino-2-hydroxy-5-(isopropylsulfanyl)pentanoyl)-4-tert-butylbenzohydrazide;
N'-((2RS,3R)-3-amino-2-hydroxy-5-(isopropylsulfanyl)pentanoyl)-4-propoxybenzohydrazide;
N'-((2RS,3R)-3-amino-2-hydroxy-5-(isopropylsulfanyl)pentanoyl)-4-isopropoxybenzohydrazide;
N'-((2RS,3R)-3-amino-2-hydroxy-5-(isopropylsulfanyl)pentanoyl)-4-(methylsulfonyl)benzohydrazide;
N'-((2RS,3R)-3-amino-2-hydroxy-5-(isopropylsulfanyl)pentanoyl)-4-(methylsulfanyl)benzohydrazide;
N'-((2RS,3R)-3-amino-2-hydroxy-5-(isopropylsulfanyl)pentanoyl)-4-(ethylsulfanyl)benzohydrazide;
N'-((2RS,3R)-3-amino-2-hydroxy-5-(isopropylsulfanyl)pentanoyl)-4-(propylsulfanyl)benzohydrazide;
N'-((2RS,3R)-3-amino-2-hydroxy-5-(isopropylsulfanyl)pentanoyl)-4-(butylsulfanyl)benzohydrazide;
N'-((2RS,3R)-3-amino-2-hydroxy-5-(isopropylsulfanyl)pentanoyl)-4-(hexylsulfanyl)benzohydrazide;
N'-((2RS,3R)-3-amino-2-hydroxy-5-(isopropylsulfanyl)pentanoyl)-4-(isopropylsulfanyl)benzohydrazide;
N'-((2RS,3R)-3-amino-2-hydroxy-5-(isopropylsulfanyl)pentanoyl)-4-(isobutylsulfanyl)benzohydrazide;
N'-((2RS,3R)-3-amino-2-hydroxy-5-(isopropylsulfanyl)pentanoyl)-4-((4-methylpentyl)sulfanyl)benzohydrazide;
N'-((2RS,3R)-3-amino-2-hydroxy-5-(isopropylsulfanyl)pentanoyl)-4-(sec-butylsulfanyl)benzohydrazide;
N'-((2RS,3R)-3-amino-2-hydroxy-5-(isopropylsulfanyl)pentanoyl)-4-(neopentylsulfanyl)benzohydrazide;
N'-((2RS,3R)-3-amino-2-hydroxy-5-(isopropylsulfanyl)pentanoyl)-4-(cyclohexylsulfanyl)benzohydrazide;
N'-((2RS,3R)-3-amino-2-hydroxy-5-(isopropylsulfanyl)pentanoyl)-4-((cyclohexylmethyl)sulfanyl)benzohydrazide;
N'-((2RS,3R)-3-amino-2-hydroxy-5-(isopropylsulfanyl)pentanoyl)-4-(benzylsulfanyl)benzohydrazide;
N'-((2RS,3R)-3-amino-2-hydroxy-5-(isopropylsulfanyl)pentanoyl)-4-((2-phenylethyl)sulfanyl)benzohydrazide;
N'-((2RS,3R)-3-amino-2-hydroxy-5-(isopropylsulfanyl)pentanoyl)-4-((3-phenylpropyl)sulfanyl)benzohydrazide; and
N'-((2RS,3R)-3-amino-2-hydroxy-5-(isopropylsulfanyl)pentanoyl)-4-(((1,1'-biphenyl)-4-ylmethyl)sulfanyl)benzohydrazide.

30. A compound according to claim 20 wherein the aryl(oyl) is substituted with two or three substituents.

31. A compound according to claim 30 selected from the group consisting of

N'-((2RS,3R)-3-amino-5-(ethylsulfanyl)-2-hydroxypentanoyl)-3,4-diethoxybenzohydrazide;
N'-((2RS,3R)-3-amino-5-(ethylsulfanyl)-2-hydroxypentanoyl)-2,3-dimethylbenzohydrazide;
N'-((2RS,3R)-3-amino-5-(ethylsulfanyl)-2-hydroxypentanoyl)-2,4-dimethylbenzohydrazide;
N'-((2RS,3R)-3-amino-5-(ethylsulfanyl)-2-hydroxypentanoyl)-2,5-dimethylbenzohydrazide;
N'-((2RS,3R)-3-amino-5-(ethylsulfanyl)-2-hydroxypentanoyl)-4,5-dimethylbenzohydrazide;
N'-((2RS,3R)-3-amino-5-(ethylsulfanyl)-2-hydroxypentanoyl)-3,5-dimethylbenzohydrazide;
N'-((2RS,3R)-3-amino-5-(ethylsulfanyl)-2-hydroxypentanoyl)-2,3-dimethoxybenzohydrazide;
N'-((2RS,3R)-3-amino-5-(ethylsulfanyl)-2-hydroxypentanoyl)-2,4-dimethoxybenzohydrazide;
N'-((2RS,3R)-3-amino-5-(ethylsulfanyl)-2-hydroxypentanoyl)-2,5-dimethoxybenzohydrazide;
N'-((2RS,3R)-3-amino-5-(ethylsulfanyl)-2-hydroxypentanoyl)-3,4-dimethoxybenzohydrazide;
N'-((2RS,3R)-3-amino-5-(ethylsulfanyl)-2-hydroxypentanoyl)-3,5-dimethoxybenzohydrazide;
N'-((2RS,3R)-3-amino-5-(ethylsulfanyl)-2-hydroxypentanoyl)-3,4,5-trimethoxybenzohydrazide;
N'-((2RS,3R)-3-amino-5-(ethylsulfanyl)-2-hydroxypentanoyl)-2,3-dichlorobenzohydrazide;
N'-((2RS,3R)-3-amino-5-(ethylsulfanyl)-2-hydroxypentanoyl)-2,4-dichlorobenzohydrazide;
N'-((2RS,3R)-3-amino-5-(ethylsulfanyl)-2-hydroxypentanoyl)-2,5-dichlorobenzohydrazide;

N'-((2RS,3R)-3-amino-5-(ethylsulfanyl)-2-hydroxypentanoyl)-3,4-dichlorobenzohydrazide;
N'-((2RS,3R)-3-amino-5-(ethylsulfanyl)-2-hydroxypentanoyl)-3,5-dichlorobenzohydrazide;
N'-((2RS,3R)-3-amino-2-hydroxy-5-(isopropylsulfanyl)pentanoyl)-2,3-dichlorobenzohydrazide; N'-((2RS,3R)-3-amino-2-hydroxy-5-(isopropylsulfanyl)pentanoyl)-3-fluoro-2-methylbenzohydrazide;
N'-((2RS,3R)-3-amino-2-hydroxy-5-(isopropylsulfanyl)pentanoyl)-2,3-difluorobenzohydrazide;
N'-((2RS,3R)-3-amino-2-hydroxy-5-(isopropylsulfanyl)pentanoyl)-5-chloro-2-methoxybenzohydrazide;
N'-((2RS,3R)-3-amino-2-hydroxy-5-(isopropylsulfanyl)pentanoyl)-2-chloro-5-(methylsulfanyl)benzohydrazide; and
N'-((2RS,3R)-3-amino-2-hydroxy-5-(isopropylsulfanyl)pentanoyl)-3,4-diethoxybenzohydrazide.

32. A compound according to claim 19 wherein one of $R^6$ and $R^7$ is hydrogen; and the other is selected from the group consisting of aryl, arylalkanoyl, arylalkoxycarbonyl, and arylsulfonyl.

33. A compound according to claim 32 selected from the group consisting of
benzyl 2-((2RS,3S)-3-amino-4-((cyclohexylmethyl)sulfanyl)-2-hydroxybutanoyl)hydrazinecarboxylate;
benzyl 2-((2RS,3S)-3-amino-2-hydroxy-4-(propylsulfanyl)butanoyl)hydrazinecarboxylate;
(2RS,3R)-3-amino-5-(ethylsulfanyl)-2-hydroxy-N'-(4-methylphenyl)pentanohydrazide;
(2RS,3R)-3-amino-5-(ethylsulfanyl)-2-hydroxy-N'-(4-methoxyphenyl)pentanohydrazide;
(2RS,3R)-3-amino-5-(ethylsulfanyl)-2-hydroxy-N'-(1-naphthyl)pentanohydrazide;
(2RS,3R)-3-amino-5-(ethylsulfanyl)-2-hydroxy-N'-(4-iodophenyl)pentanohydrazide;
(2RS,3R)-3-amino-5-(ethylsulfanyl)-2-hydroxy-N'-(3-chlorophenyl)pentanohydrazide;
(2RS,3R)-3-amino-5-(ethylsulfanyl)-2-hydroxy-N'-(3-methoxyphenyl)pentanohydrazide;
(2RS,3R)-3-amino-5-(ethylsulfanyl)-2-hydroxy-N'-(2-chlorophenyl)pentanohydrazide;
(2RS,3R)-3-amino-5-(ethylsulfanyl)-2-hydroxy-N'-(3-trifluoromethylphenyl)pentanohydrazide;
(2RS,3R)-3-amino-5-(ethylsulfanyl)-2-hydroxy-N'-(4-isopropyl)pentanohydrazide;
(2RS,3R)-3-amino-5-(ethylsulfanyl)-2-hydroxy-N'-(3-chloro-4-methylphenyl)pentanohydrazide;
(2RS,3R)-3-amino-5-(ethylsulfanyl)-2-hydroxy-N'-(3-fluorophenyl)pentanohydrazide;
(2RS,3R)-3-amino-5-(ethylsulfanyl)-2-hydroxy-N'-(2-ethylphenyl)pentanohydrazide;
(2RS,3R)-3-amino-5-(ethylsulfanyl)-2-hydroxy-N'-(4-fluorophenyl)pentanohydrazide;
(2RS,3R)-3-amino-5-(ethylsulfanyl)-2-hydroxy-N'-(4-trifluoromethoxyphenyl)pentanohydrazide;
(2RS,3S)-3-amino-4-(ethylsulfanyl)-2-hydroxy-N'-(4-methylphenyl)butanohydrazide;
(2RS,3S)-3-amino-2-hydroxy-N'-(4-methylphenyl)-4-(propylsulfanyl)butanohydrazide;
(2RS,3R)-3-amino-2-hydroxy-5-(isopropylsulfanyl)-N'-(4-methylphenyl)pentanohydrazide;
(2RS,3S)-3-amino-2-hydroxy-4-(isobutylsulfanyl)-N'-(4-methylphenyl)butanohydrazide;
(2RS,3S)-3-amino-4-(ethylsulfanyl)-2-hydroxy-N'-(1-naphthyl)butanohydrazide;
(2RS,3R)-3-amino-2-hydroxy-5-(isopropylsulfanyl)-N'-(1-naphthyl)pentanohydrazide;
(2RS,3S)-3-amino-2-hydroxy-4-(isobutylsulfanyl)-N'-(1-naphthyl)butanohydrazide;
(2RS,3S)-3-amino-2-hydroxy-N'-(1-naphthyl)-4-(propylsulfanyl)butanohydrazide;
(2RS,3S)-3-amino-4-((cyclohexylmethyl)sulfanyl)-2-hydroxy-N'-(1-naphthyl)butanohydrazide;
(2RS,3R)-3-amino-5-(ethylsulfanyl)-2-hydroxy-N'-(phenylacetyl)pentanohydrazide;
(2RS,3R)-3-amino-5-(ethylsulfanyl)-2-hydroxy-N'-((2-methoxyphenyl)acetyl)pentanohydrazide;
(2RS,3R)-3-amino-5-(ethylsulfanyl)-2-hydroxy-N'-((3-methoxyphenyl)acetyl)pentanohydrazide;
(2RS,3R)-3-amino-5-(ethylsulfanyl)-2-hydroxy-N'-((4-methoxyphenyl)acetyl)pentanohydrazide;
(2RS,3R)-3-amino-5-(ethylsulfanyl)-2-hydroxy-N'-((2-chlorophenyl)acetyl)pentanohydrazide;
(2RS,3R)-3-amino-5-(ethylsulfanyl)-2-hydroxy-N'-((3-chlorophenyl)acetyl)pentanohydrazide;
(2RS,3R)-3-amino-5-(ethylsulfanyl)-2-hydroxy-N'-((4-chlorophenyl)acetyl)pentanohydrazide;
N'-((2RS,3R)-3-amino-5-(ethylsulfanyl)-2-hydroxypentanoyl)-2-(1,1'-biphenyl)-4-ylacetohydrazide;
N'-((2RS,3R)-3-amino-5-(ethylsulfanyl)-2-hydroxypentanoyl)-2-(4-dimethylaminophenyl)acetohydrazide;
N'-((2RS,3R)-3-amino-5-(ethylsulfanyl)-2-hydroxypentanoyl)-2-(1-naphthyl)acetohydrazide;
N'-((2RS,3R)-3-amino-5-(ethylsulfanyl)-2-hydroxypentanoyl)-2-(2-naphthyl)acetohydrazide;
N'-((2RS,3R)-3-amino-5-(ethylsulfanyl)-2-hydroxypentanoyl)benzenesulfonohydrazide;
N'-((2RS,3R)-3-amino-5-(ethylsulfanyl)-2-hydroxypentanoyl)-3-chlorobenzenesulfonohydrazide;
N'-((2RS,3R)-3-amino-5-(ethylsulfanyl)-2-hydroxypentanoyl)-1-naphthalenesulfonohydrazide; and
N'-((2RS,3R)-3-amino-5-(ethylsulfanyl)-2-hydroxypentanoyl)-4-methylbenzenesulfonohydrazide.

34. A compound according to claim 19 wherein one of $R^6$ and $R^7$ is hydrogen; and the other is selected from the group consisting of alkanoyl, cycloalkyl, cycloalkylalkanoyl, (cycloalkyl)oyl, (heterocycle)alkanoyl, and (heterocycle)oyl.

35. A compound according to claim 34 selected from the group consisting of
(2RS,3R)-3-amino-5-(ethylsulfanyl)-2-hydroxy-N'-cyclopentylpentanohydrazide;
(2RS,3R)-N'-acetyl-3-amino-5-(ethylsulfanyl)-2-hydroxypentanohydrazide;
(2RS,3R)-3-amino-5-(ethylsulfanyl)-2-hydroxy-N'-isobutyrylpentanohydrazide;
(2RS,3R)-3-amino-5-(ethylsulfanyl)-2-hydroxy-N'-(3-methylbutanoyl)pentanohydrazide;
(2RS,3R)-3-amino-5-(ethylsulfanyl)-N'-heptanoyl-2-hydroxypentanohydrazide;
(2RS,3R)-3-amino-5-(ethylsulfanyl)-2-hydroxy-N'-(tetrahydro-2-furanylcarbonyl)pentanohydrazide;

(2RS,3R)-3-amino-N'-(cyclohexylacetyl)-5-(ethylsulfanyl)-2-hydroxyheptanohydrazide;

N'-((2RS,3R)-3-amino-5-(ethylsulfanyl)-2-hydroxypentanoyl)-2-furohydrazide;

N'-((2RS,3R)-3-amino-5-(ethylsulfanyl)-2-hydroxypentanoyl)-3-furohydrazide;

N'-((2RS,3R)-3-amino-5-(ethylsulfanyl)-2-hydroxypentanoyl)-2-thiophenecarbohydrazide;

N'-((2RS,3R)-3-amino-5-(ethylsulfanyl)-2-hydroxypentanoyl)-3-thiophenecarbohydrazide;

N'-((2RS,3R)-3-amino-5-(ethylsulfanyl)-2-hydroxypentanoyl)-1H-pyrrole-2-carbohydrazide;

N'-((2RS,3R)-3-amino-5-(ethylsulfanyl)-2-hydroxypentanoyl)-1,3-thiazole-2-carbohydrazide;

N'-((2RS,3R)-3-amino-5-(ethylsulfanyl)-2-hydroxypentanoyl)-1,3-thiazole-4-carbohydrazide;

N'-((2RS,3R)-3-amino-5-(ethylsulfanyl)-2-hydroxypentanoyl)-1,3-thiazole-5-carbohydrazide;

N'-((2RS,3R)-3-amino-5-(ethylsulfanyl)-2-hydroxypentanoyl)-1H-pyrazole-5-carbohydrazide;

N'-((2RS,3R)-3-amino-5-(ethylsulfanyl)-2-hydroxypentanoyl)-1H-pyrazole-4-carbohydrazide;

N'-((2RS,3R)-3-amino-5-(ethylsulfanyl)-2-hydroxypentanoyl)-5-isoxazolecarbohydrazide;

N'-((2RS,3R)-3-amino-5-(ethylsulfanyl)-2-hydroxypentanoyl)-2-pyridinecarbohydrazide;

N'-((2RS,3R)-3-amino-5-(ethylsulfanyl)-2-hydroxypentanoyl)-2-(2-pyridinyl)acetohydrazide;

N'-((2RS,3R)-3-amino-5-(ethylsulfanyl)-2-hydroxypentanoyl)-3-pyridinecarbohydrazide;

N'-((2RS,3R)-3-amino-5-(ethylsulfanyl)-2-hydroxypentanoyl)-2-(3-pyridinyl)acetohydrazide;

N'-((2RS,3R)-3-amino-5-(ethylsulfanyl)-2-hydroxypentanoyl)-4-pyridinecarbohydrazide;

N'-((2RS,3R)-3-amino-5-(ethylsulfanyl)-2-hydroxypentanoyl)-2-(4-pyridinyl)acetohydrazide;

N'-((2RS,3R)-3-amino-5-(ethylsulfanyl)-2-hydroxypentanoyl)-3-pyridazinecarbohydrazide;

N'-((2RS,3R)-3-amino-5-(ethylsulfanyl)-2-hydroxypentanoyl)-4-pyrimidinecarbohydrazide;

N'-((2RS,3R)-3-amino-5-(ethylsulfanyl)-2-hydroxypentanoyl)-2-pyrazinecarbohydrazide;

(2RS,3R)-3-amino-N'-((2RS,3S)-3-amino-2-hydroxy-5-(isopropylsulfanyl)pentanoyl)-2-hydroxy-5-(isopropylsulfanyl)pentanohydrazide; N'-((2RS,3R)-3-amino-5-(ethylsulfanyl)-2-hydroxypentanoyl)-1,3-benzodioxole-5-carbohydrazide;(2RS,3R)-3-amino-2-hydroxy-5-(isopropylsulfanyl)-N'-(tetrahydro-2-furanylcarbonyl)pentanohydrazide;

(2RS,3R)-3-amino-2-hydroxy-5-(isopropylsulfanyl)-N'-(tetrahydro-3-furanylcarbonyl)pentanohydrazide;

(2RS,3R)-3-amino-2-hydroxy-5-(isopropylsulfanyl)-N'-cyclopentylpentanohydrazide;

N'-((2RS,3R)-3-amino-2-hydroxy-5-(isopropylsulfanyl)pentanoyl)-2-cyclopentylacetohydrazide;

(2RS,3R)-3-amino-2-hydroxy-5-(isopropylsulfanyl)-N'-cyclohexylpentanohydrazide;

N'-((2RS,3R)-3-amino-2-hydroxy-5-(isopropylsulfanyl)pentanoyl)-2-cyclohexylacetohydrazide;

N'-((2RS,3R)-3-amino-2-hydroxy-5-(isopropylsulfanyl)pentanoyl)-2-furohydrazide;

N'-((2RS,3R)-3-amino-2-hydroxy-5-(isopropylsulfanyl)pentanoyl)-3-furohydrazide;

N'-((2RS,3R)-3-amino-2-hydroxy-5-(isopropylsulfanyl)pentanoyl)-2,5-dimethyl-3-furohydrazide;

N'-((2RS,3R)-3-amino-2-hydroxy-5-(isopropylsulfanyl)pentanoyl)-2-thiophenecarbohydrazide;

N'-((2RS,3R)-3-amino-2-hydroxy-5-(isopropylsulfanyl)pentanoyl)-3-thiophenecarbohydrazide;

N'-((2RS,3R)-3-amino-2-hydroxy-5-(isopropylsulfanyl)pentanoyl)-3-methyl-2-thiophenecarbohydrazide;

N'-((2RS,3R)-3-amino-2-hydroxy-5-(isopropylsulfanyl)pentanoyl)-5-methyl-2-thiophenecarbohydrazide;

N'-((2RS,3R)-3-amino-2-hydroxy-5-(isopropylsulfanyl)pentanoyl)-1H-pyrrole-2-carbohydrazide;

N'-((2RS,3R)-3-amino-2-hydroxy-5-(isopropylsulfanyl)pentanoyl)-1-methyl-1H-pyrrole-2-carbohydrazide;

N'-((2RS,3R)-3-amino-2-hydroxy-5-(isopropylsulfanyl)pentanoyl)-1,3-thiazole-2-carbohydrazide;

N'-((2RS,3R)-3-amino-2-hydroxy-5-(isopropylsulfanyl)pentanoyl)-1,3-thiazole-4-carbohydrazide;

N'-((2RS,3R)-3-amino-2-hydroxy-5-isopropylpentanoyl)-2-pyridinecarbohydrazide;

N'-((2RS,3R)-3-amino-2-hydroxy-5-(isopropylsulfanyl)pentanoyl)-6-chloro-2H-chromene-3-carbohydrazide;

N'-((2RS,3R)-3-amino-2-hydroxy-5-(isopropylsulfanyl)pentanoyl)-2-(4-morpholinyl)acetohydrazide;

N'-((2RS,3R)-3-amino-2-hydroxy-5-(isopropylsulfanyl)pentanoyl)-2-(4-methyl-1-piperazinyl)acetohydrazide; and 1-acetyl-N'-((2RS,3R)-3-amino-2-hydroxy-5-(isopropylsulfanyl)pentanoyl)-4-piperidinecarbohydrazide.

36. A compound according to claim 19 wherein $R^6$ and $R^7$, together with the nitrogen atom to which they are attached, form a heterocycle.

37. A compound according to claim 36 which is (2RS,3R)-3-amino-5-(ethylsulfanyl)-2-hydroxy-N-(1-piperidinyl)pentanamide.

38. A pharmaceutical composition comprising a compound of claim 1 or a therapeutically acceptable salt or prodrug thereof, in combination with a therapeutically acceptable carrier.

39. A method of inhibiting angiogenesis in a mammal in recognized need of such treatment comprising administering to the mammal a therapeutically acceptable amount of a compound of claim 1.

40. A compound which is
N'-((2S,3R)-3-amino-2-hydroxy-5-(isopropylsulfanyl)pentanoyl)-3-chlorobenzoyl hydrazide.

* * * * *